(12) United States Patent
Conklin et al.

(10) Patent No.: US 12,390,332 B2
(45) Date of Patent: Aug. 19, 2025

(54) METHODS AND DEVICES FOR VENTRICULAR RESHAPING AND HEART VALVE RESHAPING

(71) Applicant: Edwards Lifesciences Corporation, Irvine, CA (US)

(72) Inventors: Brian S. Conklin, Orange, CA (US); Maria L. Saravia, Irvine, CA (US); Adam J. Yestrepsky, Costa Mesa, CA (US); Derrick Johnson, Orange, CA (US); Rodolfo Rodriguez, Costa Mesa, CA (US); Sai Prasad Uppalapati, Plano, TX (US); Louis A. Campbell, Santa Ana, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1039 days.

(21) Appl. No.: 16/549,957

(22) Filed: Aug. 23, 2019

(65) Prior Publication Data
US 2020/0069426 A1 Mar. 5, 2020

Related U.S. Application Data

(60) Provisional application No. 62/839,298, filed on Apr. 26, 2019, provisional application No. 62/723,924, filed on Aug. 28, 2018.

(51) Int. Cl.
*A61F 2/24* (2006.01)
(52) U.S. Cl.
CPC .... *A61F 2/2487* (2013.01); *A61F 2002/2484* (2013.01); *A61F 2210/0014* (2013.01); *A61F 2220/0075* (2013.01); *A61F 2230/0039* (2013.01); *A61F 2230/0065* (2013.01)

(58) Field of Classification Search
CPC ..................................................... A61F 2/2487
See application file for complete search history.

(56) References Cited

U.S. PATENT DOCUMENTS

| 2004/0015232 A1* | 1/2004 | Shu | A61F 2/2409 623/2.11 |
|---|---|---|---|
| 2004/0049211 A1* | 3/2004 | Tremulis | A61F 2/2487 623/1.36 |
| 2004/0167620 A1 | 8/2004 | Ortiz et al. | |

(Continued)

*Primary Examiner* — Leslie A Lopez
(74) *Attorney, Agent, or Firm* — Snell & Wilmer

(57) ABSTRACT

Systems, apparatuses, and methods disclosed herein are provided for medical treatment, including transcatheter medical treatments and/or for treatment of dilated hearts (e.g., dilated left ventricle) or functional mitral valve regurgitation within a human heart. The systems, apparatuses, and methods disclosed herein may include applying one or more heart splints to the patient's heart to apply pressure to the heart to reshape the heart. Anchors disclosed herein may be utilized in plugs for treating openings in a septum between two chambers of a heart, e.g., ventricular septal defects (VSD), atrial septal defects (ASD), and patent foramen ovale (PFO). In addition, the anchors disclosed herein may be utilized to reshape an annulus of a patient's heart valve, including a tricuspid valve of a patient's heart. The anchors disclosed herein may also be utilized to reposition a heart valve leaflet to reduce heart valve leaflet prolapse.

20 Claims, 94 Drawing Sheets

(56) References Cited

U.S. PATENT DOCUMENTS

| | | | |
|---|---|---|---|
| 2010/0280607 A1* | 11/2010 | Milo | A61F 2/2448 623/2.37 |
| 2015/0127093 A1* | 5/2015 | Hosmer | A61F 2/2418 623/2.11 |
| 2017/0135817 A1 | 5/2017 | Tylis et al. | |
| 2020/0060827 A1* | 2/2020 | Tylis | A61F 2/2487 |

* cited by examiner

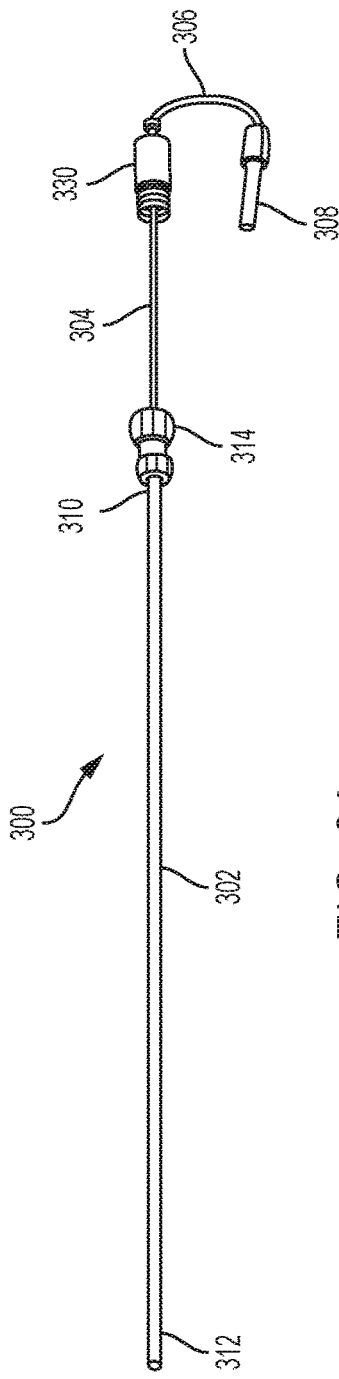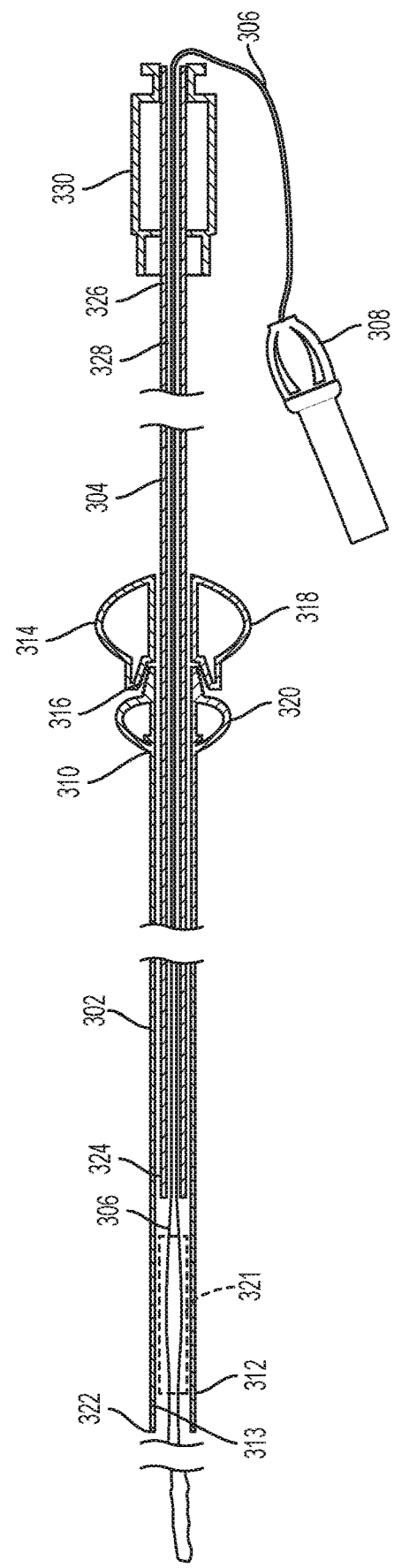
FIG. 3A
FIG. 3B

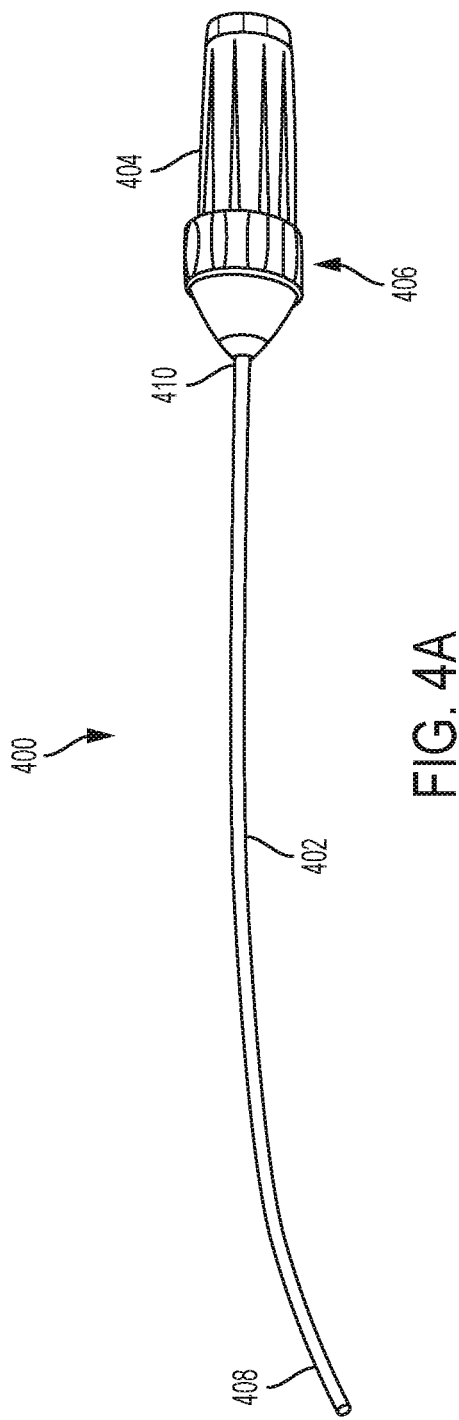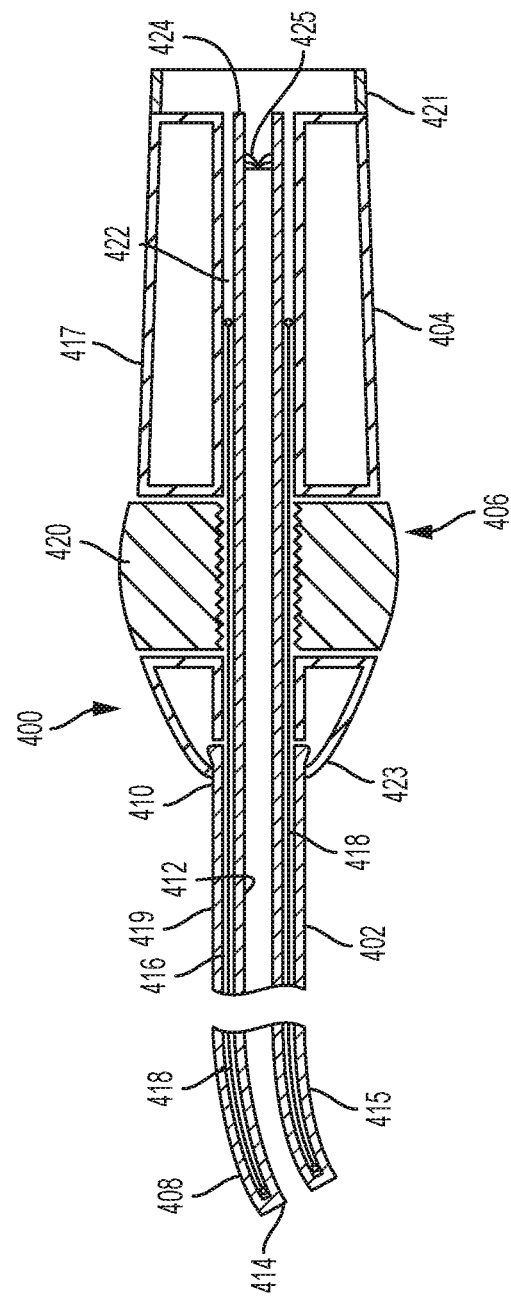
FIG. 4A
FIG. 4B

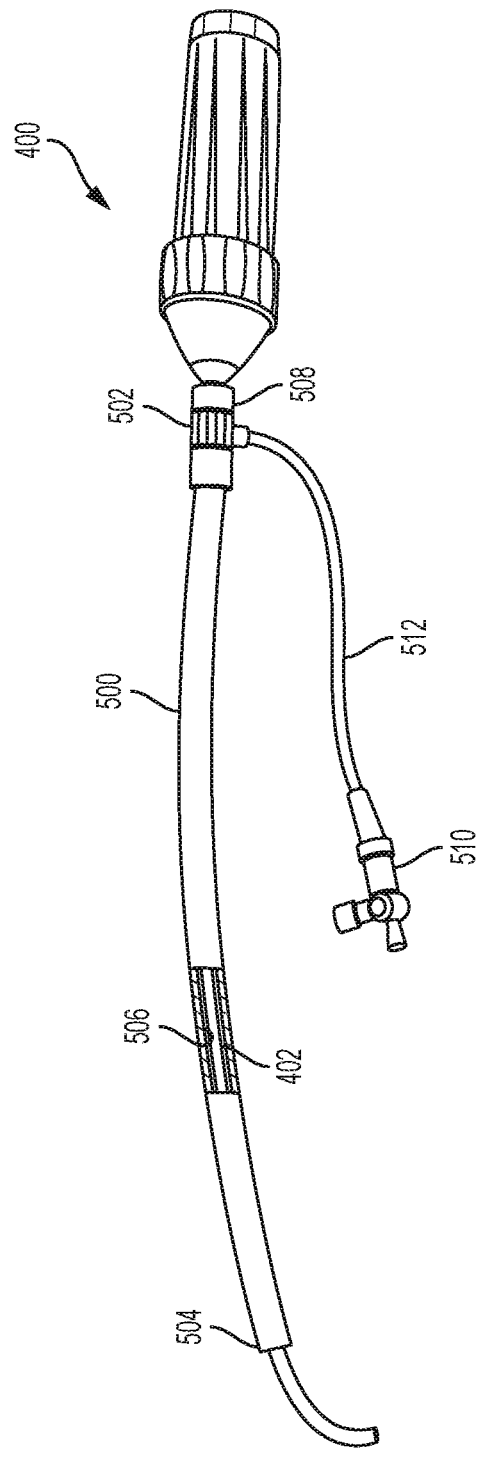
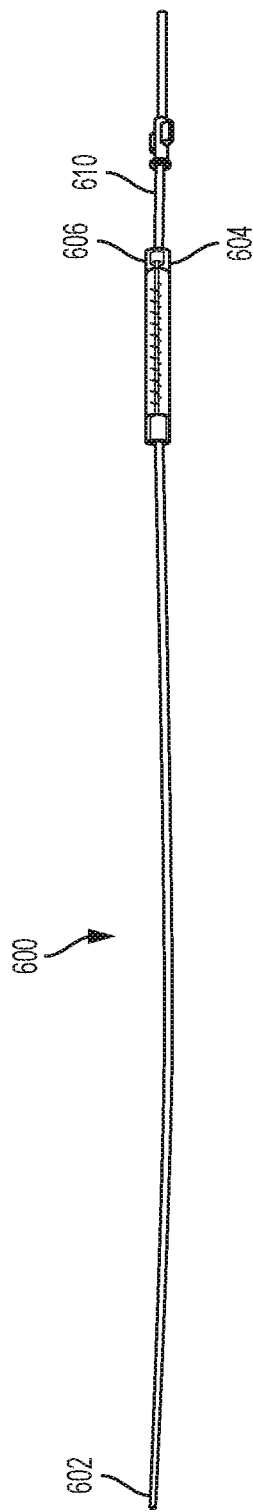
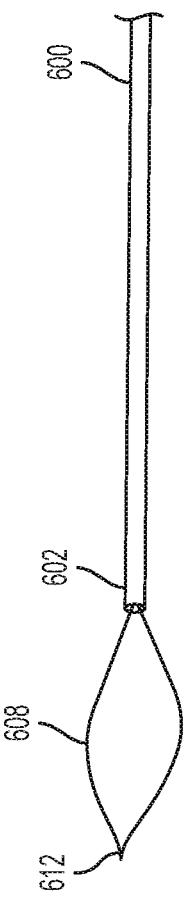
FIG. 5
FIG. 6A
FIG. 6B

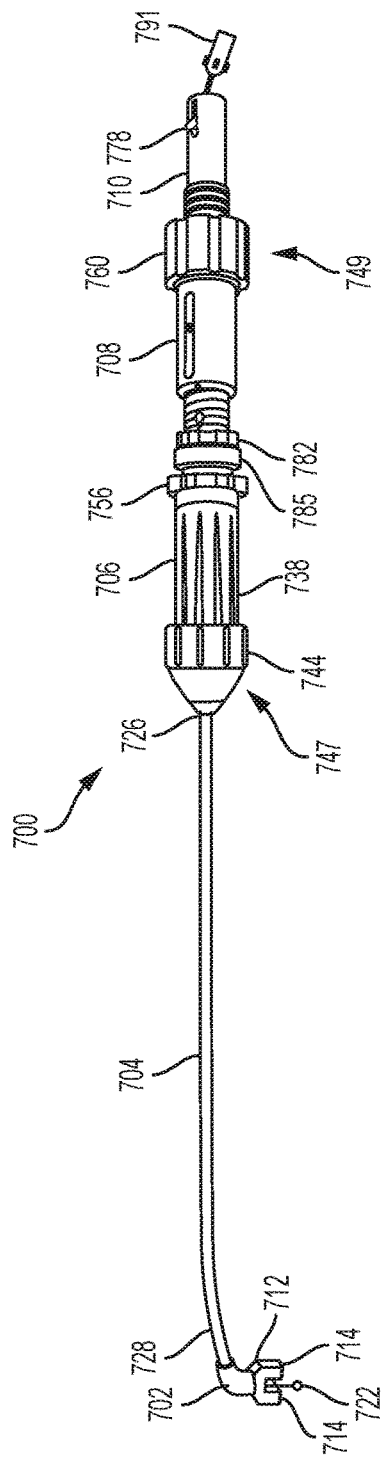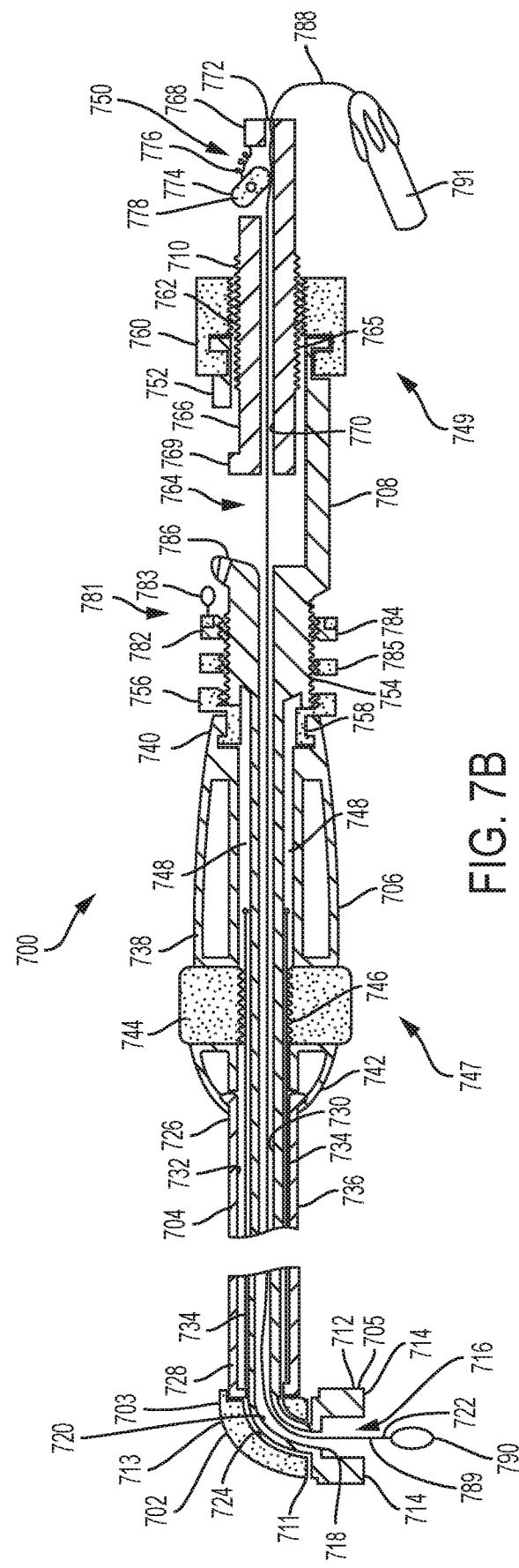
FIG. 7A
FIG. 7B

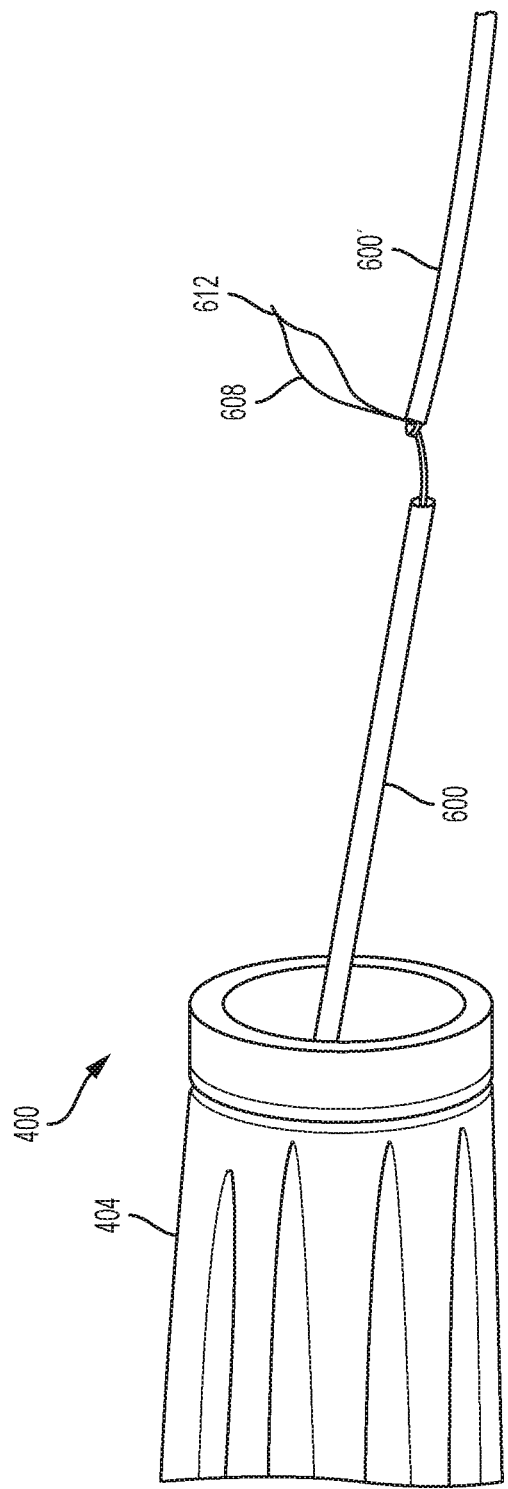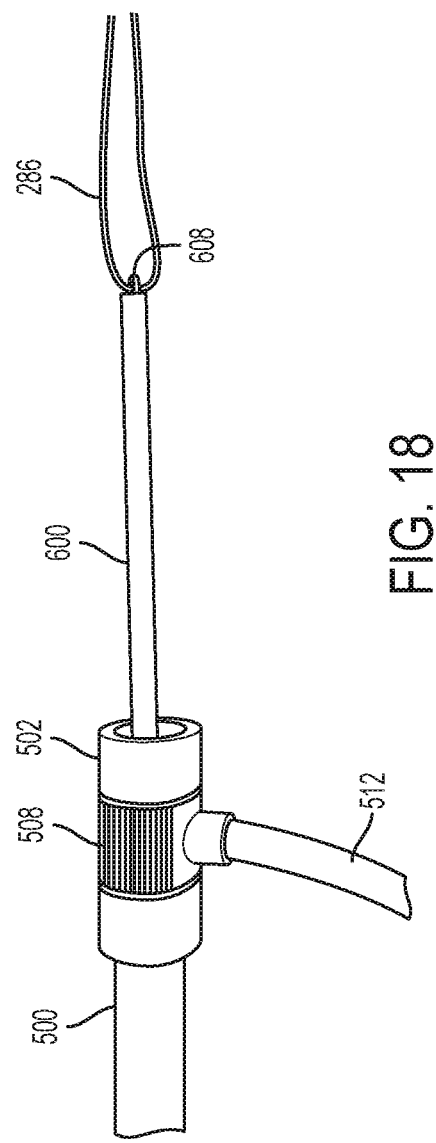
FIG. 17
FIG. 18

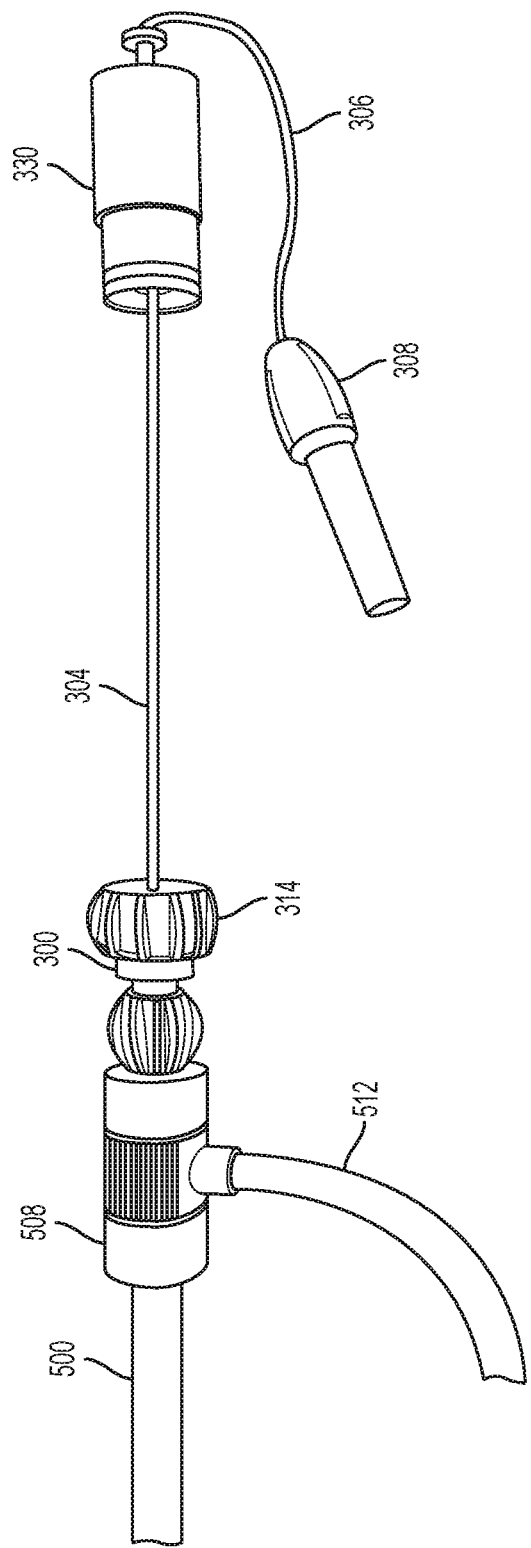
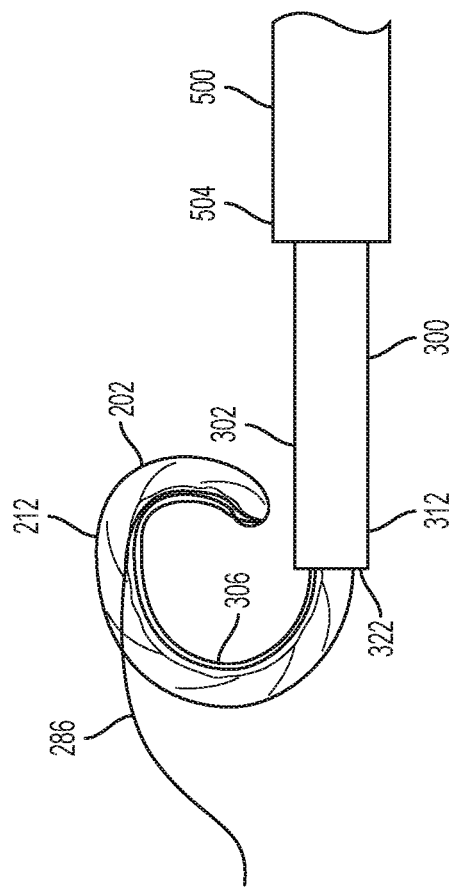
FIG. 20
FIG. 21

METHODS AND DEVICES FOR VENTRICULAR RESHAPING AND HEART VALVE RESHAPING

CROSS REFERENCE TO RELATED APPLICATIONS

This application claims the benefit of U.S. Patent Application No. 62/723,924, filed Aug. 28, 2018, and U.S. Patent No. 62/839,298, filed Apr. 26, 2019, the entire disclosures which are incorporated by reference herein.

BACKGROUND

Heart failure can occur when the left ventricle of the heart becomes enlarged and dilated as a result of one or more of various etiologies. Initial causes of heart failure can include chronic hypertension, myocardial infarction, mitral valve incompetency, and other dilated cardiomyopathies. With each of these conditions, the heart is forced to overexert itself in order to provide a cardiac output demanded by the body during various demand states. The result can be an enlarged left ventricle.

A dilated or enlarged heart, and particularly a dilated or enlarged left ventricle, can significantly increase tension and stress in heart walls both during diastolic filling and systolic contraction, which contributes to further dilatation or enlargement of chambers of the heart. In addition, mitral valve incompetency or mitral valve regurgitation is a common comorbidity of congestive heart failure. As the dilation of the ventricle increases, valve function generally worsens, which results in a volume overload condition. The volume overload condition further increases ventricular wall stress, thereby advancing the dilation process, which further worsens valve dysfunction.

In heart failure, the size of the valve annulus (particularly the mitral valve annulus) increases while the area of the leaflets of the valve remains constant. This may lead to reduced coaptation area between the valve leaflets, and, as a result, eventually to valve leakage or regurgitation. Moreover, in normal hearts, the annular size contracts during systole, aiding in valve coaptation. In heart failure, there is poor ventricular function and elevated wall stress. These conditions tend to reduce annular contraction and distort annular size, often exacerbating mitral valve regurgitation. In addition, as the chamber dilates, the papillary muscles (to which the leaflets are connected via the chordae tendineae) may move radially outward and downward relative to the valve, and relative to their normal positions. During this movement of the papillary muscles, however, the various chordae lengths remain substantially constant, which limits the full closure ability of the leaflets by exerting tension prematurely on the leaflets. This condition is commonly referred to as "chordal tethering." The combination of annular changes and papillary changes results in a poorly functioning valve.

A concept for treating heart failure includes applying one or more splints onto the heart, to reduce myocardial muscular stresses encountered during pumping. One example includes a transventricular splint placed across the left ventricle. The splint may include a tension member extending across the ventricle with anchors disposed on opposite ends of the tension member and placed on the external surface of the heart.

However, currently available methods of applying a splint, or performing mitral valve repair or replacement typically require opening the chest and/or heart, e.g., to gain direct access to the valve and its annulus or another portion of the heart. This type of access typically necessitates a use of cardiopulmonary bypass, which can introduce additional complications to the surgical procedure. Since the implantation of the splints themselves do not require the patient to be on cardiopulmonary bypass, it would be advantageous to devise a technique that could improve the mitral valve function without any need for cardiopulmonary bypass. The ability to improve the mitral valve function without the need for cardiopulmonary bypass would be an advantage. In addition, a splint may be utilized to reduce stresses on the ventricular wall, thereby relieving load from the ventricle (including the left ventricle). Indeed, it would be desirable to have systems, apparatuses, and methods capable of a deploying a splint using a less invasive, or minimally invasive procedure.

Other maladies of the heart include expansion of a heart valve annulus, including a tricuspid valve annulus. Expansion of the heart valve annulus may lead to functional heart valve regurgitation, including tricuspid regurgitation (TR). Current methods for addressing expansion of a heart valve annulus are invasive and typically involve an annuloplasty process. Other conditions affecting a heart valve may include prolapse of a heart valve leaflet such as a mitral valve leaflet. Such a condition, if left untreated may lead to functional heart valve regurgitation, including mitral regurgitation. Current methods for addressing mitral valve leaflet prolapse may include providing anchors for the prolapsing leaflet. However, such current methods are often complicated to perform and may damage the prolapsing leaflet.

SUMMARY

Systems, apparatuses, and methods disclosed herein are provided for medical treatment, including transcatheter medical treatments and/or for treatment of dilated hearts (e.g., dilated left ventricle) or functional mitral valve regurgitation within a human heart. The treatments may include reshaping a ventricle of the heart, including the left ventricle of the heart. The portion of the patient's heart may be dilated due to a myocardial infarction or other cardiomyopathy. The treatment may comprise beating-heart repair of left ventricles with ischemic cardiomyopathy.

The systems, apparatuses, and methods disclosed herein may include applying one or more heart splints to the patient's heart to apply pressure to the heart to reshape the heart. The heart splints may include anchors connected by a tension member that is tensioned to apply pressure to the patient's heart. The anchors may be positioned in desired locations to reshape the heart at particular locations (e.g., the mitral annulus, or the papillary heads of the left ventricle, among other locations).

Preferably, the systems, apparatuses, and methods disclosed herein may be utilized in a minimally invasive procedure, to access the heart and apply the heart splint without requiring a full sternotomy.

The anchors disclosed herein may not only be utilized in heart splints, but may also be utilized in plugs for treating openings in a septum between two chambers of a heart, e.g., ventricular septal defects (VSD), atrial septal defects (ASD), and patent foramen ovale (PFO). In addition, the anchors disclosed herein may be utilized to reshape an annulus of a patient's heart valve, including a tricuspid valve of a patient's heart. The anchors disclosed herein may also be utilized to reposition a heart valve leaflet to reduce heart valve leaflet prolapse. The anchors disclosed herein may also be utilized to reposition one or more papillary muscles of a patient's heart, to draw the papillary muscles towards the mitral valve. The anchors disclosed herein may be utilized with a heart valve implant, which may comprise a heart valve prosthetic or a heart valve repair implant.

Any or all of the treatment methods, operations, or steps described herein may be performed on a living human or non-human subject, or on a human or non-human cadaver or portion(s) thereof (e.g., heart, body part, tissue, etc.), simulator, or anthropomorphic ghost, for example, for educational or training purposes.

A heart anchor of the present disclosure may include a ring having two ends and configured to move from a linearized configuration to a ring-shaped configuration, a first portion of the ring overlapping a second portion of the ring in the ring-shaped configuration. The heart anchor may include a cover coupled to the ring and extending inward from the ring in the ring-shaped configuration.

A heart anchor of the present disclosure may be for a heart splint, and may include a first support pad and a second support pad. A bridge may couple the first support pad to the second support pad. A receiver may couple to the bridge and be configured to receive a tension member. A lock may couple to the bridge and be configured to vary from an unlocked state in which the tension member is unlocked in the receiver to a locked state in which tension member is locked in the receiver.

An access apparatus of the present disclosure may be for gripping an external surface of a patient's heart. The access apparatus may include a housing and a head configured to contact the external surface of the patient's heart and including one or more lumens configured to apply vacuum suction to the external surface of the patient's heart to grip the external surface of the patient's heart, the one or more lumens configured to pass a puncture device from the head through the external surface of the patient's heart. An elongate neck may couple the head to the housing and may include one or more lumens for passing the vacuum suction therethrough and for passing the puncture device therethrough to the head, the elongate neck being configured to deflect to move the head. A control mechanism may be configured to deflect the elongate neck to move the head.

A deployment apparatus of the present disclosure may be for deploying a heart anchor to an external surface of a patient's heart. The deployment apparatus may include a housing and a head configured to retain the heart anchor. An elongate neck may couple the head to the housing, the elongate neck being configured to deflect to move the head. A control mechanism may be configured to deflect the elongate neck to move the head.

A system of the present disclosure may comprise a heart splint system. The system may include a first heart anchor including a first support pad, a second support pad, and a bridge coupling the first support pad to the second support pad. A second heart anchor may be configured to move from an unexpanded configuration to an expanded configuration. A tension member may be configured to couple the first heart anchor to the second heart anchor.

A system of the present disclosure may comprise a heart splint system. The system may include a first heart anchor including a ring having two ends and configured to move from a linearized configuration to a ring-shaped configuration, and a cover coupled to the ring and extending inward from the ring in the ring-shaped configuration. The system may include a second heart anchor including a ring having two ends and configured to move from a linearized configuration to a ring-shaped configuration, and a cover coupled to the ring of the second heart anchor and extending inward from the ring of the second heart anchor in the ring-shaped configuration. The system may include a third heart anchor, and a first tension member for coupling the first heart anchor to the third heart anchor, and a second tension member for coupling to the second heart anchor to the third heart anchor.

A system of the present disclosure may be for treating a dilated heart condition or functional heart valve regurgitation of a patient. The system may include an access apparatus for penetrating through an external surface of the patient's heart and into an interior chamber of the patient's heart. The system may include a first heart anchor including a first support pad, a second support pad, and a bridge coupling the first support pad to the second support pad. The system may include a second heart anchor, a tension member configured to couple the first heart anchor to the second heart anchor, and a deployment apparatus configured to deploy the second heart anchor in an interior chamber of the patient's heart.

A method of the present disclosure may include a method for treating a dilated heart condition or functional heart valve regurgitation of a patient. The method may include deploying a first heart anchor to a position on an external surface of the patient's heart, the first heart anchor including a first support pad, a second support pad, and a bridge coupling the first support pad to the second support pad. The method may include deploying a second heart anchor to a position on an interventricular septum of the patient's heart. The method may include tensioning a tension member for coupling the first heart anchor to the second heart anchor. The method may include locking the tension member in tension between the first heart anchor and the second heart anchor.

A method of the present disclosure may include a method for treating a dilated heart condition or functional heart valve regurgitation of a patient. The method may include deploying a first heart anchor to a position on an external surface of the patient's heart and adjacent the left ventricle. The first heart anchor may include a ring having two ends and configured to move from a linearized configuration to a ring-shaped configuration, and a cover coupled to the ring and extending inward from the ring in the ring-shaped configuration. The method may include deploying a second heart anchor to a position on an external surface of the patient's heart and adjacent the left ventricle. The second heart anchor may include a ring having two ends and configured to move from a linearized configuration to a ring-shaped configuration, and a cover coupled to the ring of the second heart anchor and extending inward from the ring of the second heart anchor. The method may include deploying a third heart anchor to a position that is on an external surface of the patient's heart and adjacent the right ventricle or to a position that is on the interventricular septum of the patient's heart. The method may include tensioning a first tension member for coupling the first heart anchor to the third heart anchor. The method may include locking the first tension member in tension between the first heart anchor and the third heart anchor. The method may include tensioning a second tension member for coupling the second heart anchor to the third heart anchor. The method may include locking the second tension member in tension between the second heart anchor and the third heart anchor.

A method of the present disclosure may include a method for treating an opening in a septum of a patient's heart. The method may include deploying a first heart anchor to a position on the septum adjacent the opening and in a chamber of the heart. The first heart anchor may include a ring having two ends and configured to move from a linearized configuration to a ring-shaped configuration, and a cover coupled to the ring and extending inward from the ring in the ring-shaped configuration. The method may include deploying a second heart anchor to a position on the septum and in a chamber of the heart on an opposite side of the septum and adjacent the opening, the second heart anchor being coupled to the first heart anchor with a tension member extending through the opening. The second heart anchor may include a ring having two ends and configured to move from a linearized configuration to a ring-shaped configuration, and a cover coupled to the ring of the second heart anchor and extending inward from the ring of the second heart anchor in the ring-shaped configuration.

A system of the present disclosure may include a system for reshaping an annulus of a tricuspid valve of a patient's heart. The system may include a first heart anchor configured to be positioned on a free wall of a right atrium of the patient's heart, a second heart anchor configured to be positioned on an interatrial septum of the patient's heart, and a tension member configured to couple the first heart anchor to the second heart anchor and extend within the right atrium.

A system of the present disclosure may include a system for reshaping an annulus of a tricuspid valve of a patient's heart. The system may include a first heart anchor configured to be positioned on a free wall of a right atrium of the patient's heart, a second heart anchor configured to be positioned within a coronary sinus of the patient's heart, and a tension member configured to couple the first heart anchor to the second heart anchor and extend within the right atrium.

A method of the present disclosure may include a method for reshaping an annulus of a tricuspid valve of a patient's heart. The method may include deploying a first heart anchor to an interatrial septum or a coronary sinus of the patient's heart. The method may include deploying a second heart anchor to a free wall of a right atrium of the patient's heart. The method may include tensioning a tension member for coupling the first heart anchor to the second heart anchor. The method may include locking the tension member in tension between the first heart anchor and the second heart anchor.

A system of the present disclosure may include a system for repositioning a leaflet of a valve of a patient's heart. The system may include a first heart anchor configured to be positioned on a leaflet of a valve in a patient's heart. The first heart anchor may include a ring having two ends and configured to move from a linearized configuration to a ring-shaped configuration, and a cover coupled to the ring and extending inward from the ring in the ring-shaped configuration. A second heart anchor may be configured to be positioned on a portion of the patient's heart. A tension member may be configured to couple the first heart anchor to the second heart anchor and provide a tension that repositions the leaflet.

A method of the present disclosure may include a method for repositioning a leaflet of a valve of a patient's heart. The method may include deploying a first heart anchor to a leaflet of a valve in a patient's heart. The first heart anchor may include a ring having two ends and configured to move from a linearized configuration to a ring-shaped configuration, and a cover coupled to the ring and extending inward from the ring in the ring-shaped configuration. The method may include deploying a second heart anchor to a portion of the patient's heart. The method may include tensioning a tension member for coupling the first heart anchor to the second heart anchor to reposition the leaflet. The method may include locking the tension member between the first heart anchor and the second heart anchor.

A system of the present disclosure may include a system for repositioning one or more papillary muscles of a left ventricle of a patient's heart. The system may include a first heart anchor configured to be positioned on a mitral annulus of a patient's heart and including two or more lobes extending outward from a central portion of the first heart anchor. The system may include a second heart anchor configured to apply a force to the one or more papillary muscles of the left ventricle of the patient's heart. The system may include a tension member configured to couple the first heart anchor to the second heart anchor and extend within the left ventricle.

A system of the present disclosure may include a system for repositioning one or more papillary muscles of a left ventricle of a patient's heart. The system may include a first heart anchor configured to be positioned on a mitral annulus of a patient's heart and including a ring having two ends and configured to move from a linearized configuration to a ring-shaped configuration, and a cover coupled to the ring and extending inward from the ring in the ring-shaped configuration. The system may include a second heart anchor configured to apply a force to the one or more papillary muscles of the left ventricle of the patient's heart. The system may include a tension member configured to couple the first heart anchor to the second heart anchor and extend within the left ventricle.

A method of the present disclosure may include a method for repositioning one or more papillary muscles of a left ventricle of a patient's heart. The method may include deploying a first heart anchor to a mitral annulus in the patient's heart, the first heart anchor including a ring having two ends and configured to move from a linearized configuration to a ring-shaped configuration, and a cover coupled to the ring and extending inward from the ring in the ring-shaped configuration. The method may include deploying a second heart anchor to a portion of the patient's heart such that the second heart anchor is configured to apply a force to the one or more papillary muscles. The method may include tensioning a tension member for coupling the first heart anchor to the second heart anchor to reposition the one or more papillary muscles. The method may include locking the tension member between the first heart anchor and the second heart anchor.

A method of the present disclosure may include a method for repositioning one or more papillary muscles of a left ventricle of a patient's heart. The method may include deploying a first heart anchor to a mitral annulus in the patient's heart, the first heart anchor including two or more lobes extending outward from a central portion of the first heart anchor. The method may include deploying a second heart anchor to a portion of the patient's heart such that the second heart anchor is configured to apply a force to the one or more papillary muscles. The method may include tensioning a tension member for coupling the first heart anchor to the second heart anchor to reposition the one or more papillary muscles. The method may include locking the tension member between the first heart anchor and the second heart anchor.

A system of the present disclosure may include one or more of a heart valve prosthetic or a heart valve repair implant. The system may include a heart anchor configured to be positioned on a ventricular wall of a patient's heart. The system may include a tension member configured to couple the one or more of the heart valve prosthetic or the heart valve repair implant to the heart anchor.

A method of the present disclosure may include deploying one or more of a heart valve prosthetic or a heart valve repair implant to a heart valve of a patient's heart. The method may include anchoring, with a tension member, the one or more of the heart valve prosthetic or the heart valve repair implant to a heart anchor positioned on a ventricular wall of the patient's heart.

BRIEF DESCRIPTION OF THE DRAWINGS

Features and advantages of the systems, apparatuses, and methods as disclosed herein will become appreciated as the same become better understood with reference to the specification, claims, and appended drawings wherein:

FIG. 3A illustrates a side view of a deployment apparatus according to an embodiment of the present disclosure.

FIG. 3B illustrates a cross sectional view of the deployment apparatus shown in FIG. 3A.

FIG. 4A illustrates a side view of a delivery apparatus according to an embodiment of the present disclosure.

FIG. 4B illustrates a cross sectional view of the delivery apparatus shown in FIG. 4A.

FIG. 5 illustrates a side view of a delivery apparatus positioned within an introducer sheath according to an embodiment of the present disclosure.

FIG. 6A illustrates a side view of a snare according to an embodiment of the present disclosure.

FIG. 6B illustrates a close up view of the end of the snare shown in FIG. 6A with a snare device expanded.

FIG. 7A illustrates a side view of a deployment apparatus according to an embodiment of the present disclosure.

FIG. 7B illustrates a cross sectional view of the deployment apparatus shown in FIG. 7A.

FIG. 17 illustrates a side view of a proximal end of a delivery apparatus according to an embodiment of the present disclosure.

FIG. 18 illustrates a side view of a proximal end of an introducer sheath according to an embodiment of the present disclosure.

FIG. 20 illustrates a side view of a deployment apparatus positioned within an introducer sheath according to an embodiment of the present disclosure.

FIG. 21 illustrates a side view of a heart anchor being passed out of a deployment apparatus according to an embodiment of the present disclosure.

FIG. 95 illustrates a perspective view of a head of an access apparatus according to an embodiment of the present disclosure.

FIG. 96 illustrates a bottom view of the head shown in FIG. 95.

FIG. 97 illustrates a top perspective cross sectional view of the head shown in FIG. 95.

FIG. 98 illustrates a side cross sectional view along a mid-line of the head shown in FIG. 95.

FIG. 99 illustrates a front view of the head shown in FIG. 95.

FIG. 100 illustrates the head shown in FIG. 95 in position on a portion of a patient's heart.

FIG. 101 illustrates a side view of an apparatus according to an embodiment of the present disclosure, with a portion of a shaft cut away.

FIG. 102 illustrates a bottom perspective view of the apparatus shown in FIG. 101.

FIG. 103 illustrates a side perspective view of the apparatus shown in FIG. 101 in position on a portion of a patient's heart.

FIG. 104 illustrates a side view of an apparatus according to an embodiment of the present disclosure.

FIG. 105 illustrates a side view of the apparatus shown in FIG. 104 with a heart anchor shown in cross section.

FIG. 106 illustrates a bottom perspective view of the apparatus shown in FIG. 104.

Figure 104:
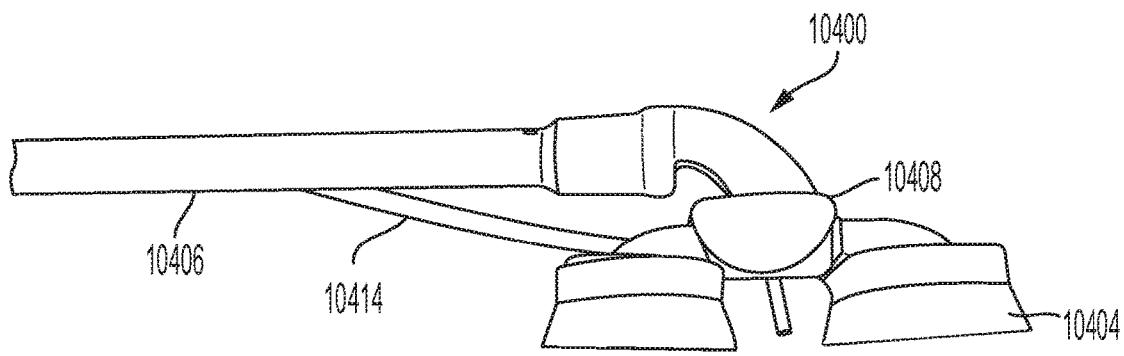
Figure 105:
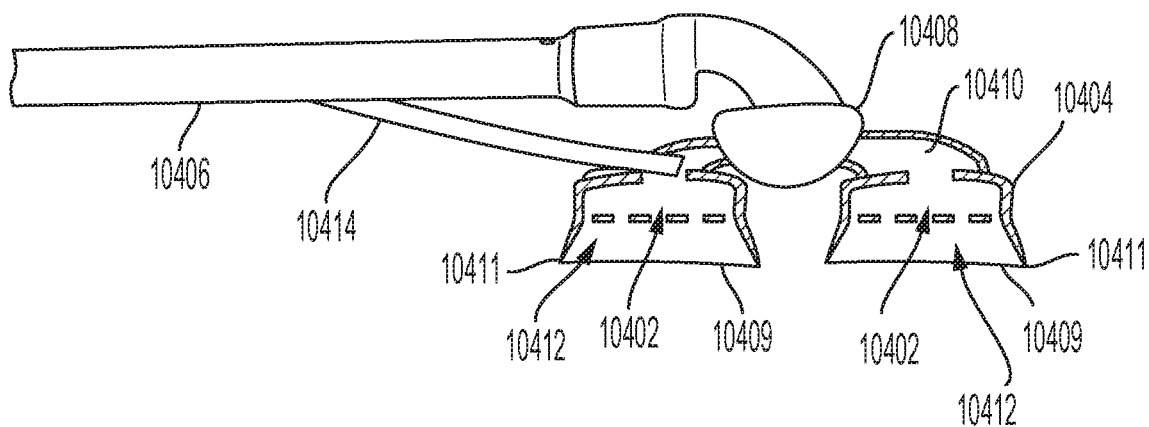
Figure 107:
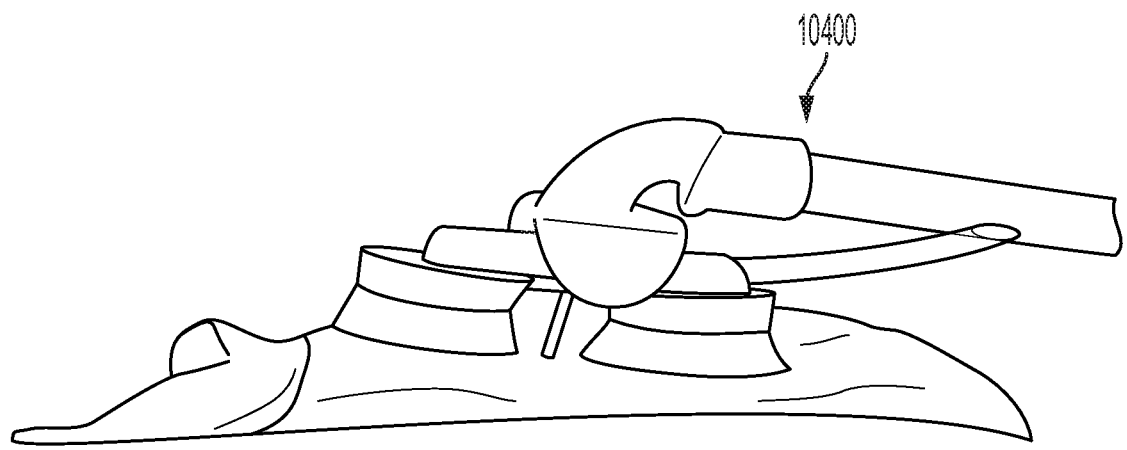

FIG. 107 illustrates a side perspective view of the apparatus shown in FIG. 104 in position on a portion of a patient's heart.

Figure 108:
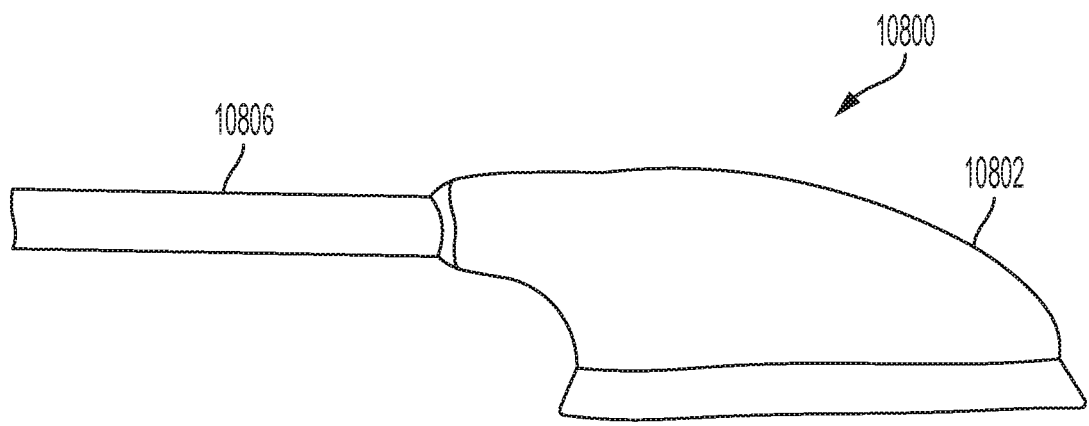

FIG. 108 illustrates a side view of an apparatus according to an embodiment of the present disclosure.

Figure 109:
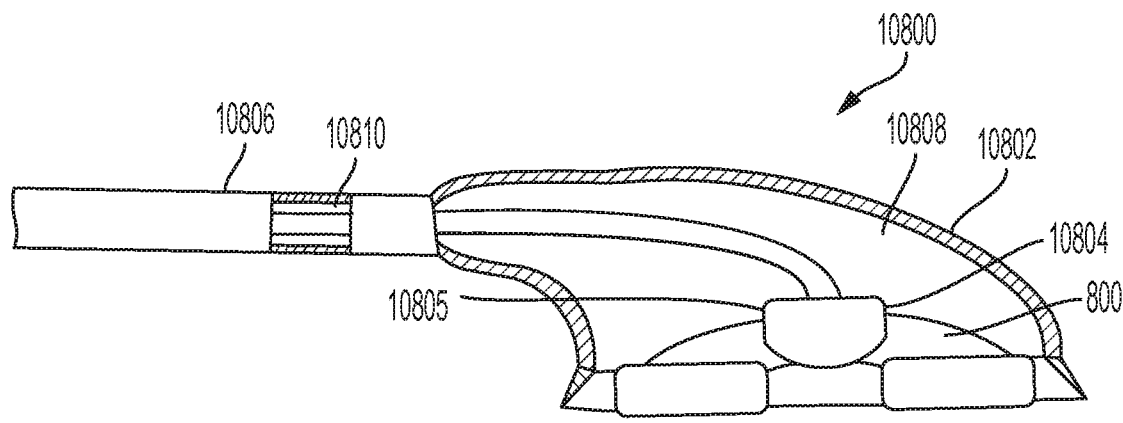

FIG. 109 illustrate a side view of the apparatus shown in FIG. 108 with a hood shown in cross section.

Figure 110:
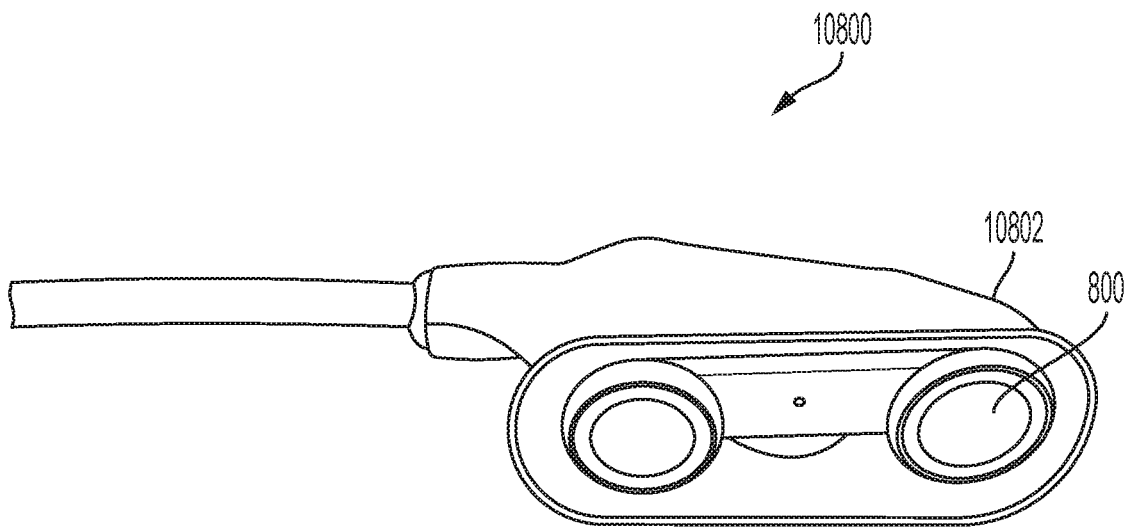

FIG. 110 illustrates a bottom perspective view of the apparatus shown in FIG. 108.

Figure 111:
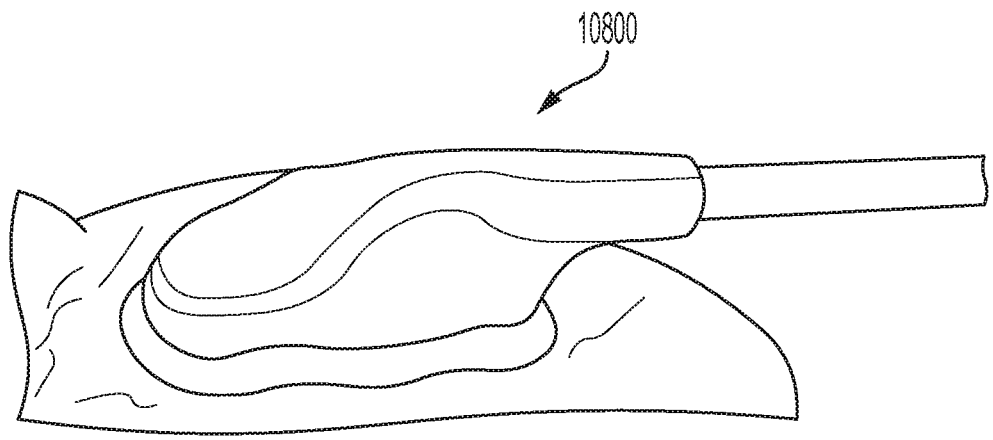

FIG. 111 illustrates a side perspective view of the apparatus shown in FIG. 108 in position on a portion of a patient's heart.

Figure 112:
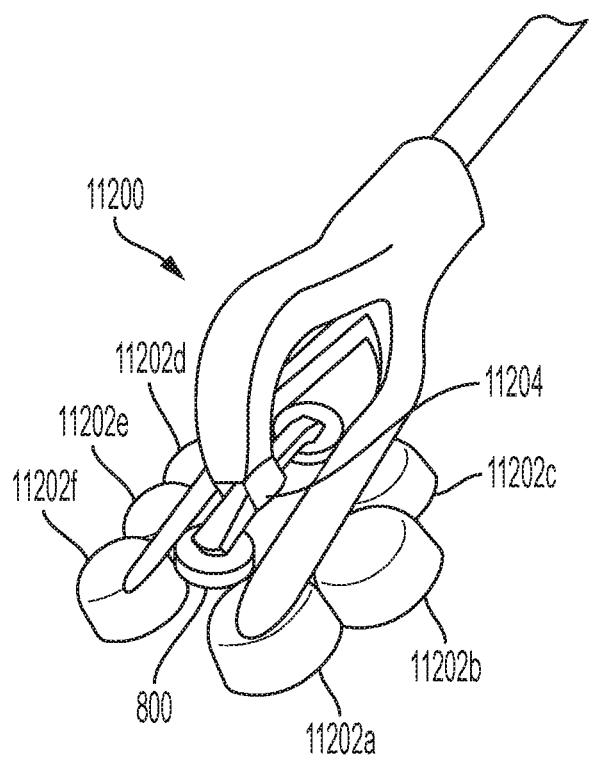

FIG. 112 illustrates a side perspective view of an apparatus according to an embodiment of the present disclosure.

Figure 113:
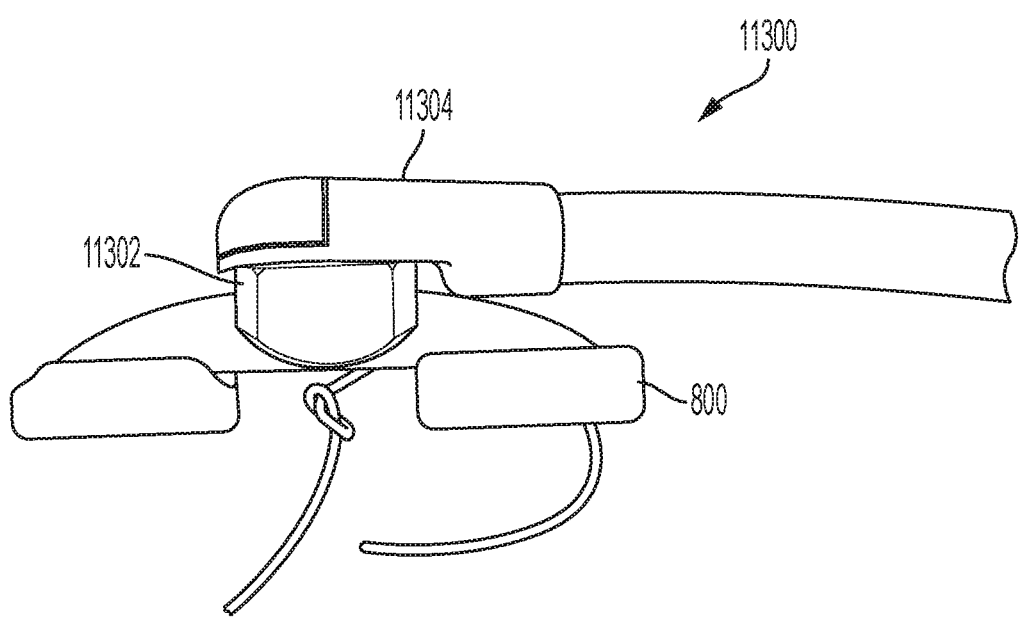

FIG. 113 illustrates a side view of a deployment apparatus according to an embodiment of the present disclosure.

Figure 114:
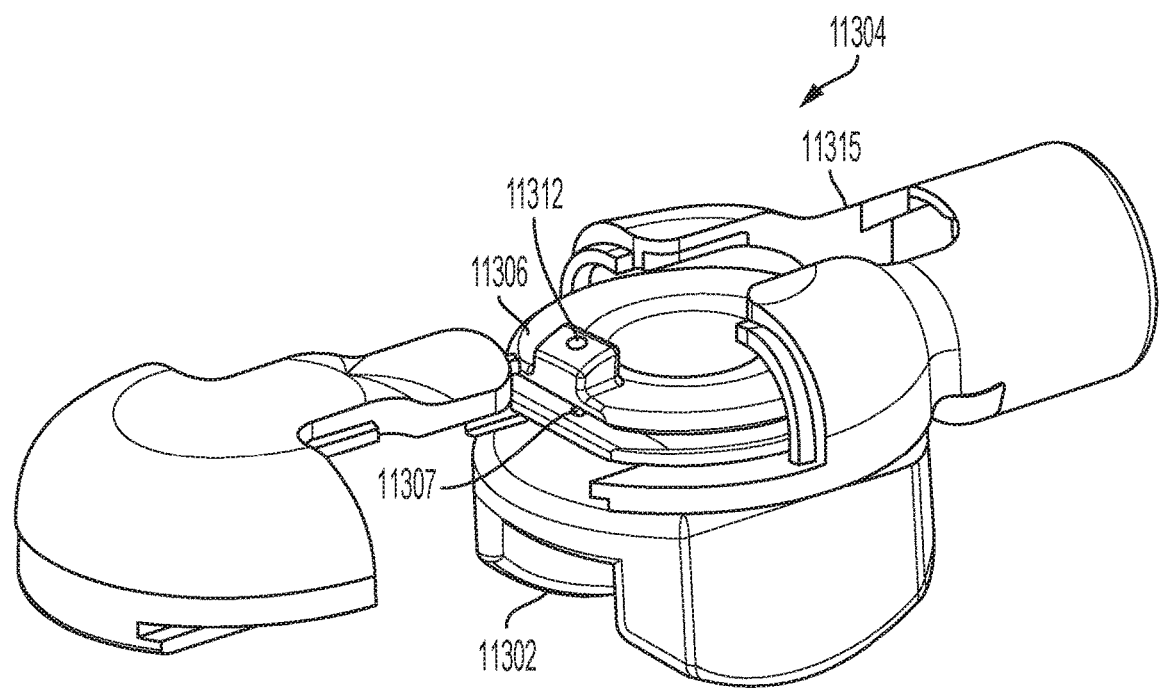

FIG. 114 illustrates an exploded perspective view of the head of the deployment apparatus shown in FIG. 113.

Figure 115:
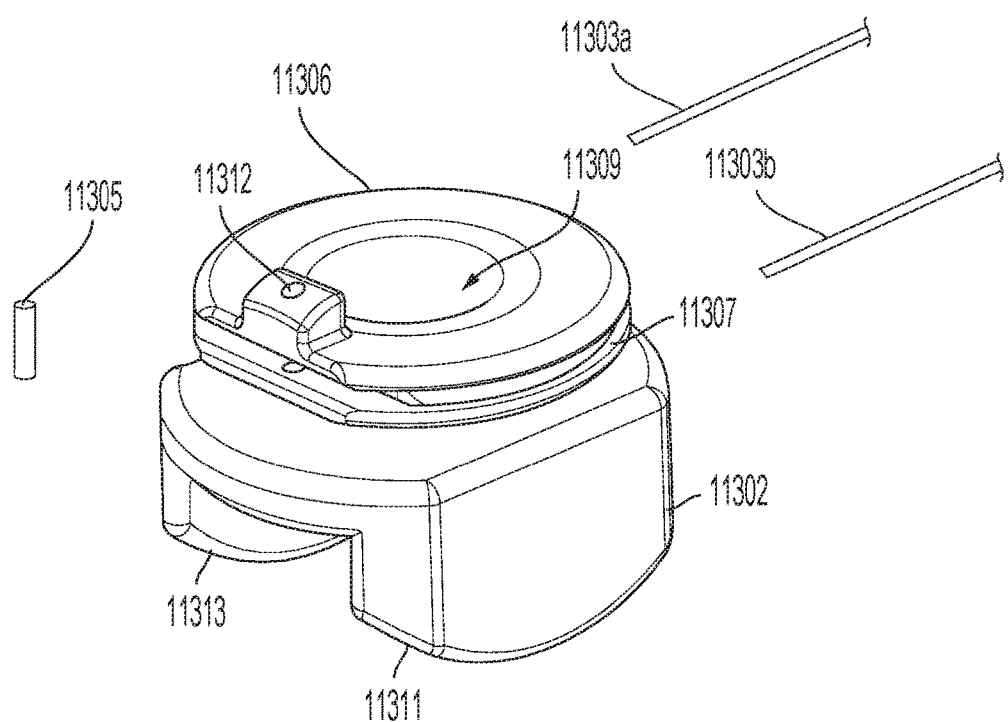

FIG. 115 illustrates an exploded perspective view of components of a pulley system of the deployment apparatus shown in FIG. 113.

Figure 116:
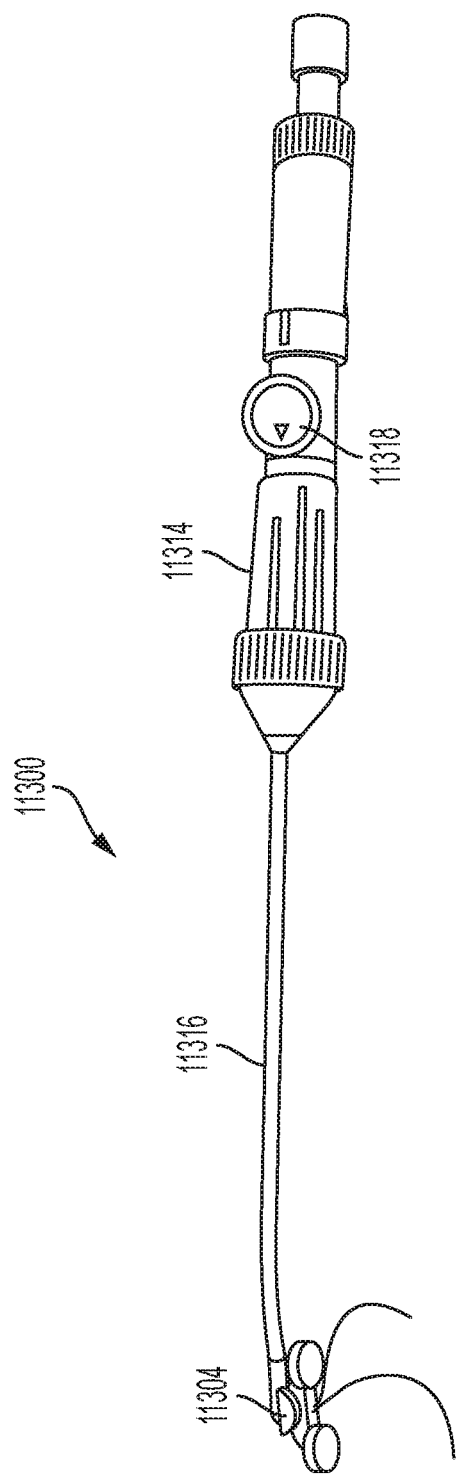

FIG. 116 illustrates a side view of the deployment apparatus shown in FIG. 113.

Figure 117:
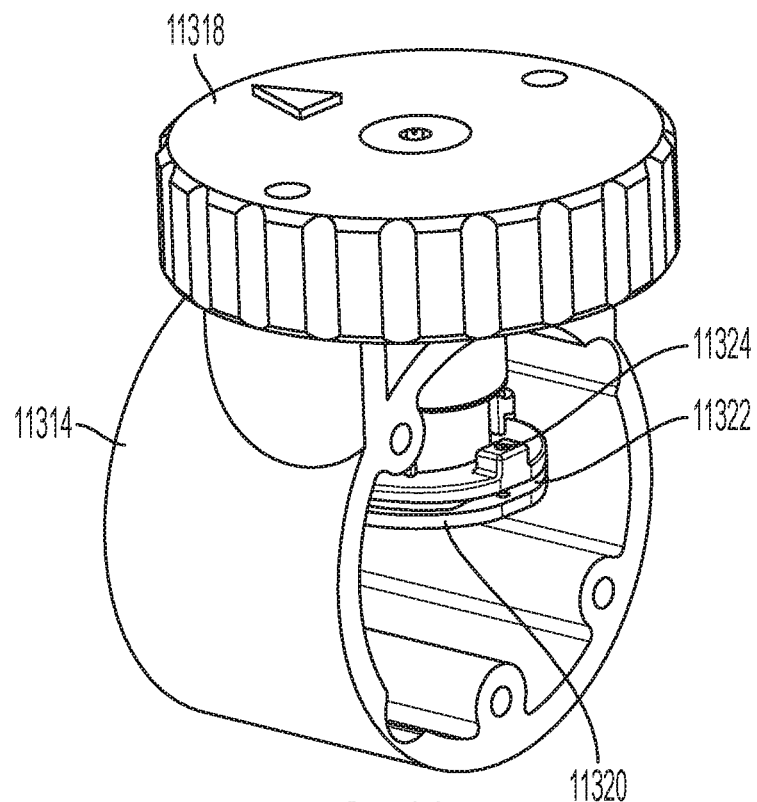

FIG. 117 illustrates a perspective close up view of a proximal portion of a pulley system of the deployment apparatus shown in FIG. 113.

Figure 118:
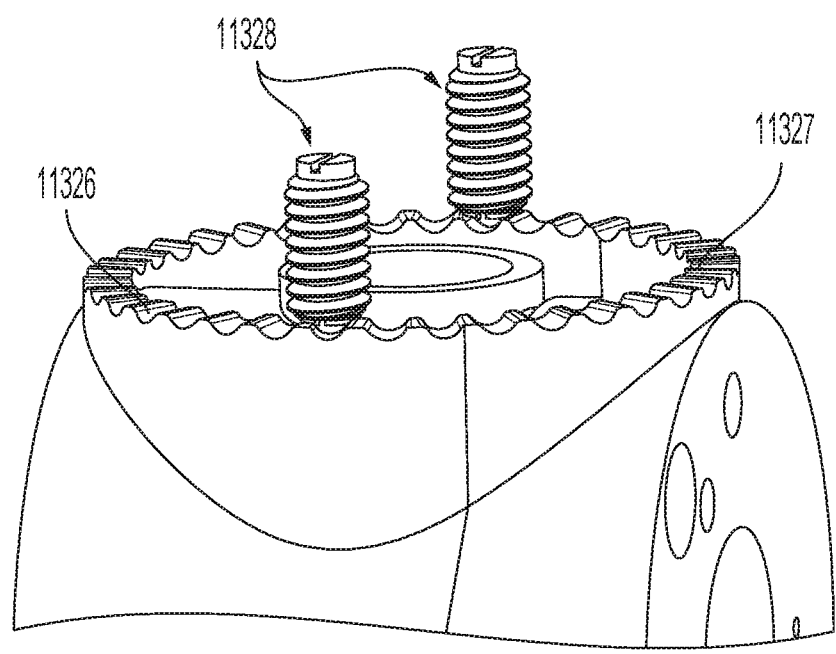

FIG. 118 illustrates a close-up perspective view of the components of FIG. 117 with the control knob excluded from view.

Figure 119:
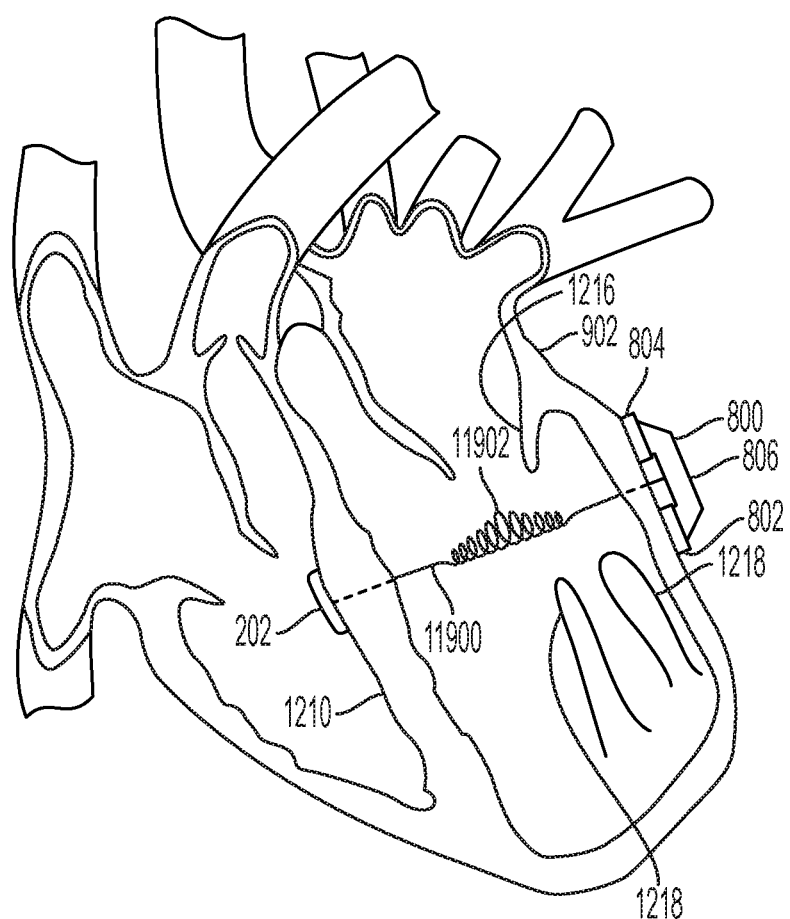

FIG. 119 illustrates a schematic view of a patient's heart having a heart splint with a tension member therein according to an embodiment of the present disclosure.

Figure 120:
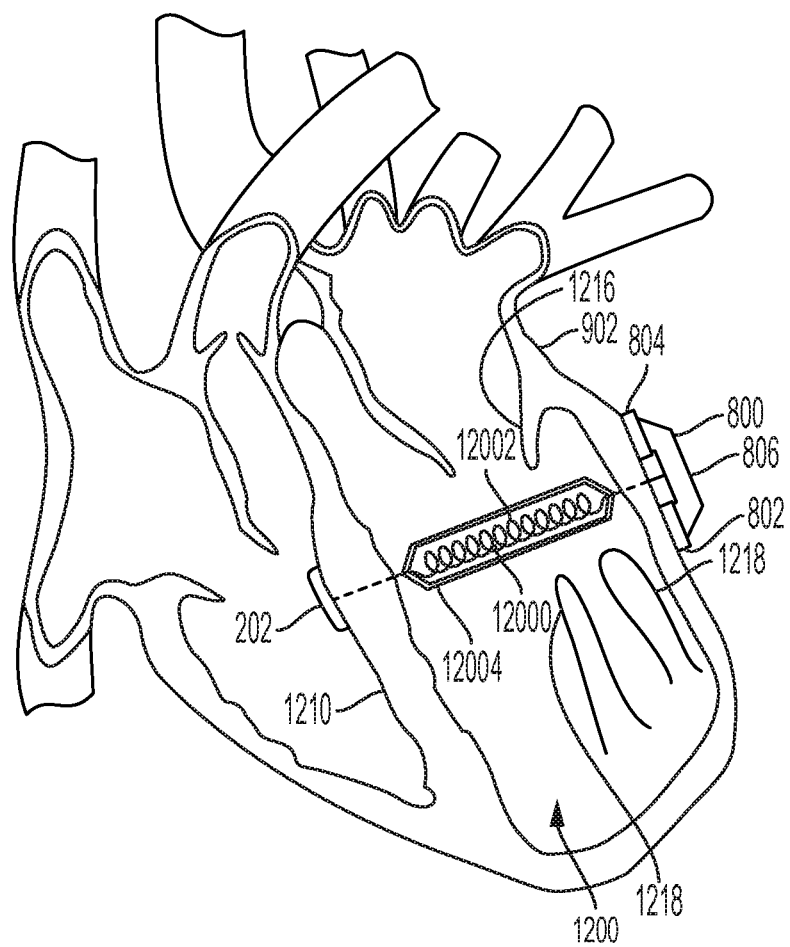

FIG. 120 illustrates a schematic view of a patient's heart having a heart splint with a tension member therein according to an embodiment of the present disclosure.

Figure 121:
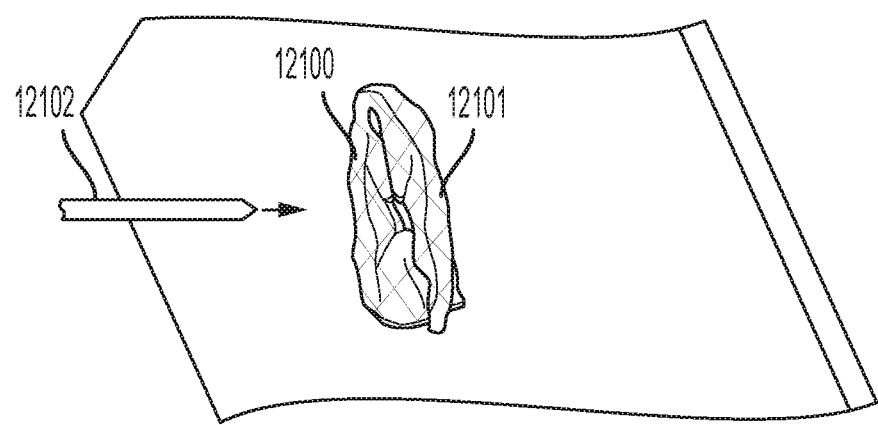

FIG. 121 illustrates a perspective view of a heart anchor that is puncturable by a puncture device according to an embodiment of the present disclosure.

Figure 122:
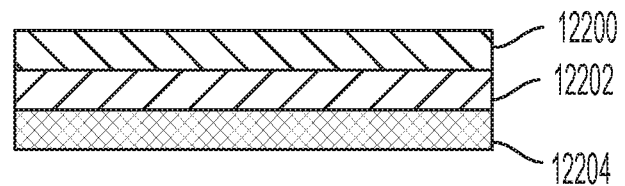

FIG. 122 illustrates a cross sectional schematic view of layers of a heart anchor according to an embodiment of the present disclosure.

Figure 123:
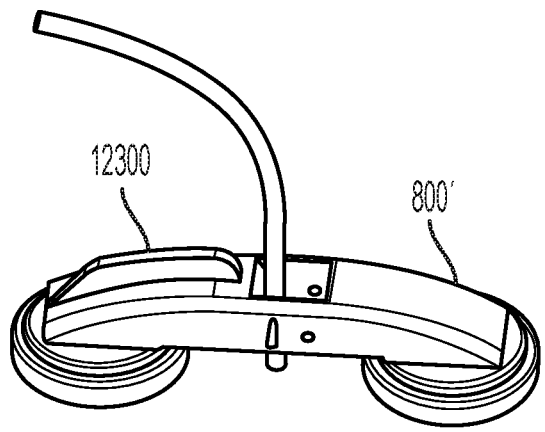

FIG. 123 illustrates a perspective view of a heart anchor according to an embodiment of the present disclosure.

Figure 124:
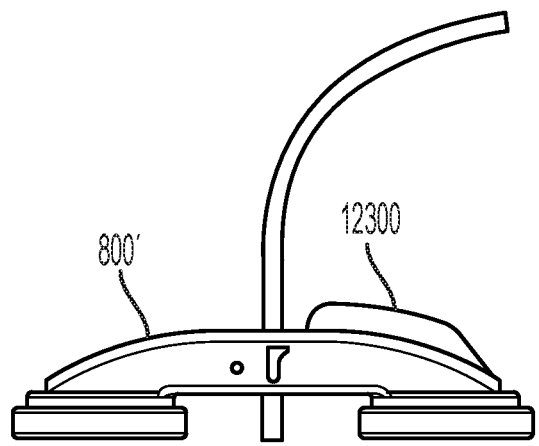

FIG. 124 illustrates a side view of the heart anchor shown in FIG. 123 according to an embodiment of the present disclosure.

Figure 125:
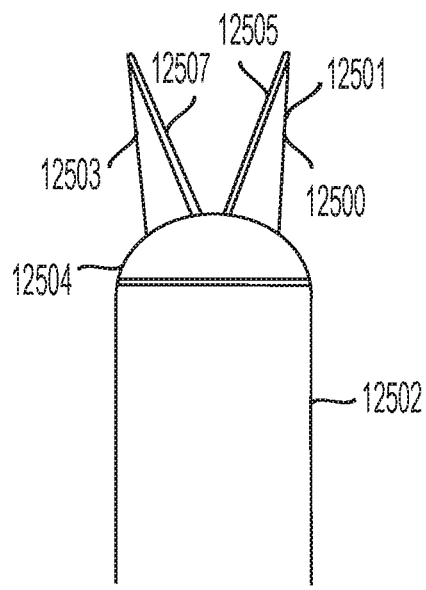

FIG. 125 illustrates a side schematic view of a robotic grasper according to an embodiment of the present disclosure.

Figure 126:
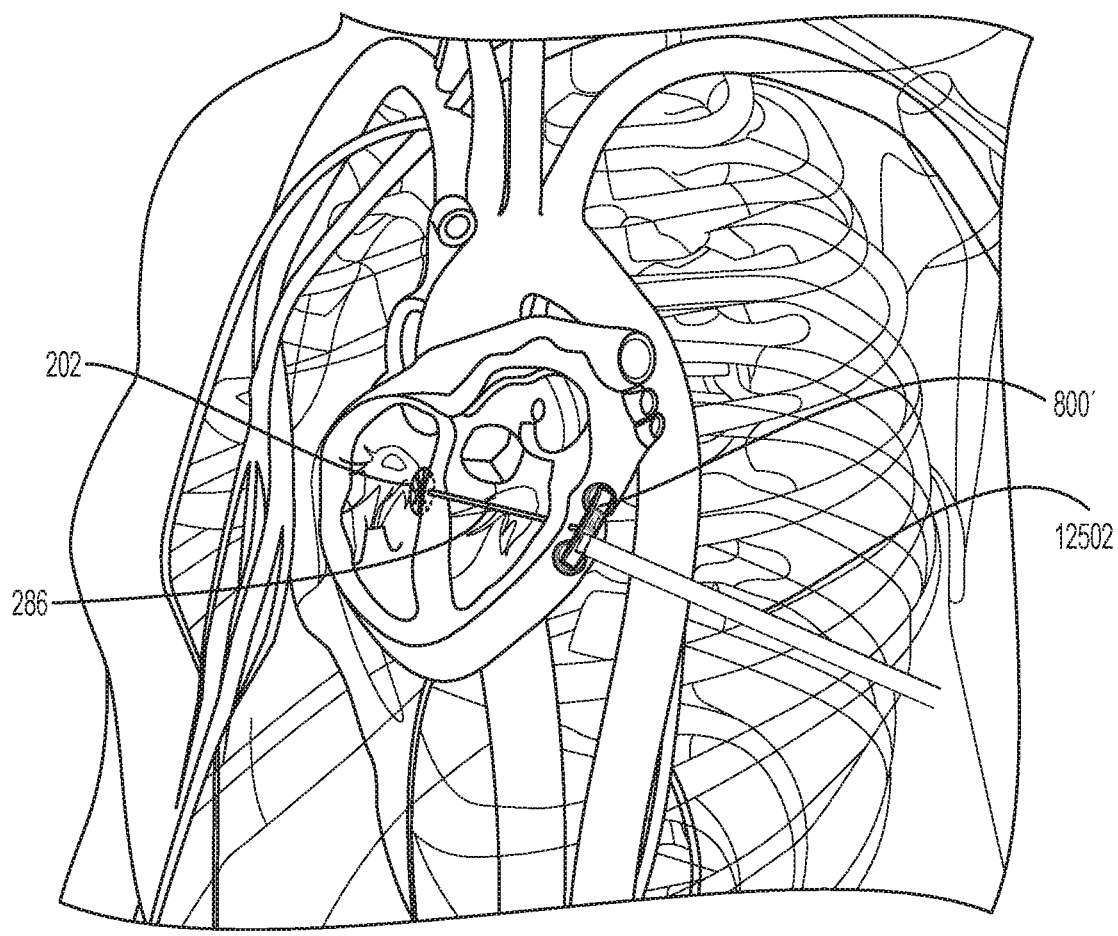

FIG. 126 illustrates a representation of a heart anchor upon a portion of a patient's heart applied by a robotic arm, according to an embodiment of the present disclosure.

Figure 127:
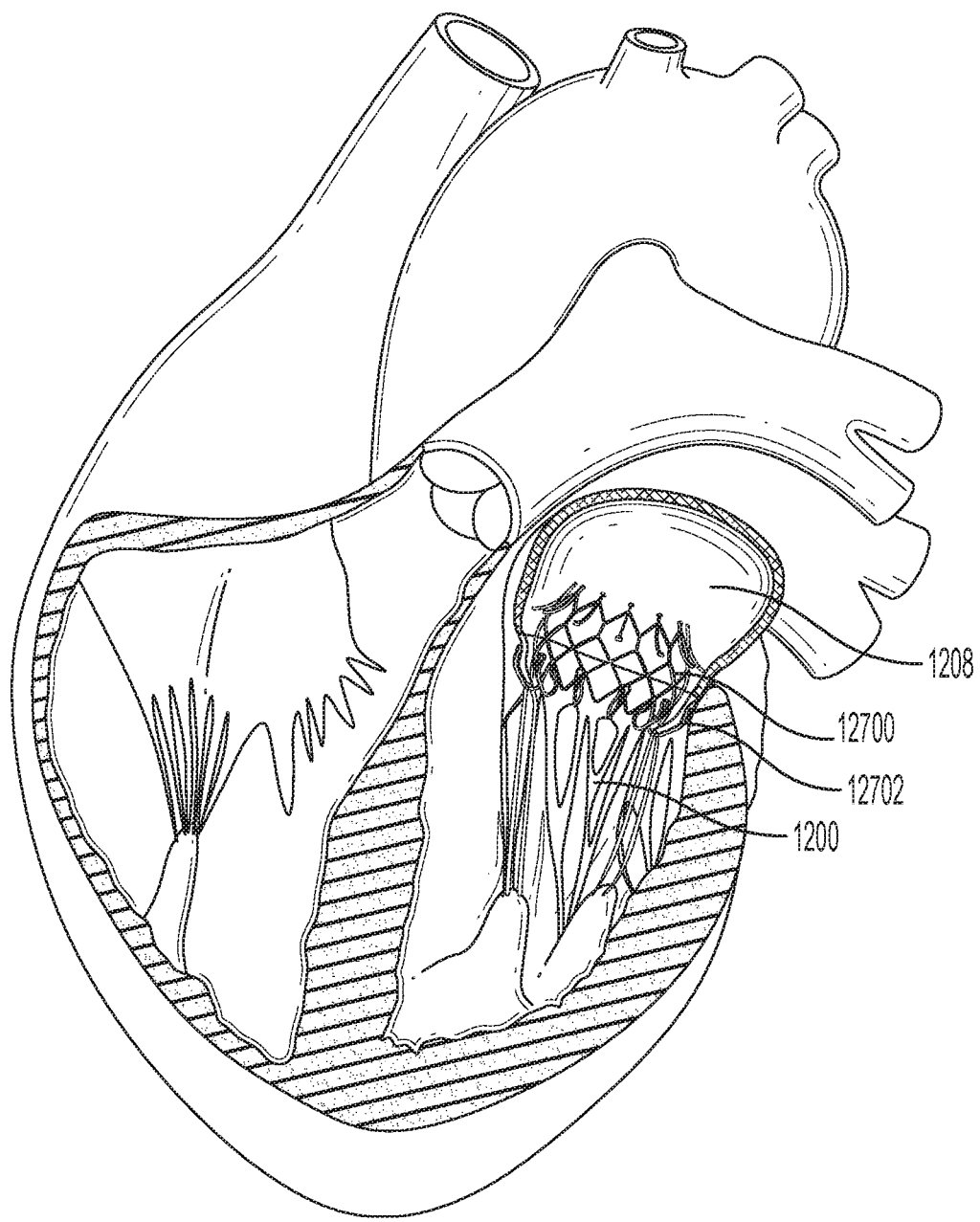

FIG. 127 illustrates a perspective cross sectional view of a patient's heart including a heart implant positioned therein.

Figure 128:
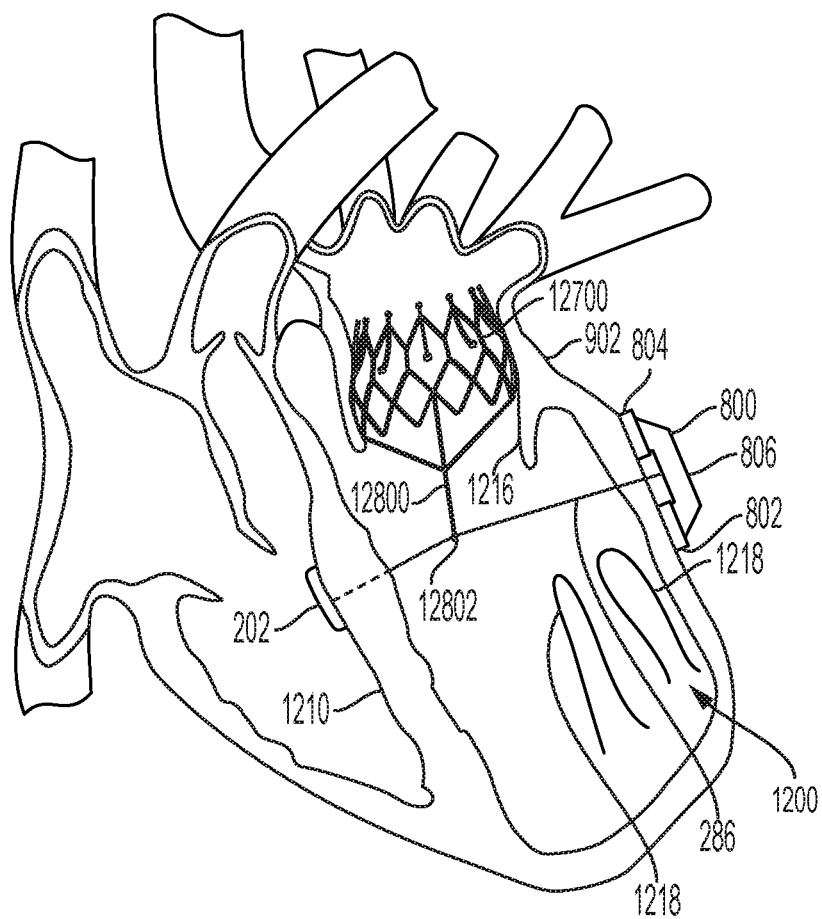

FIG. 128 illustrates a cross sectional view of a patient's heart with a heart implant positioned therein and anchored to a heart splint according to an embodiment of the present disclosure.

Figure 129:
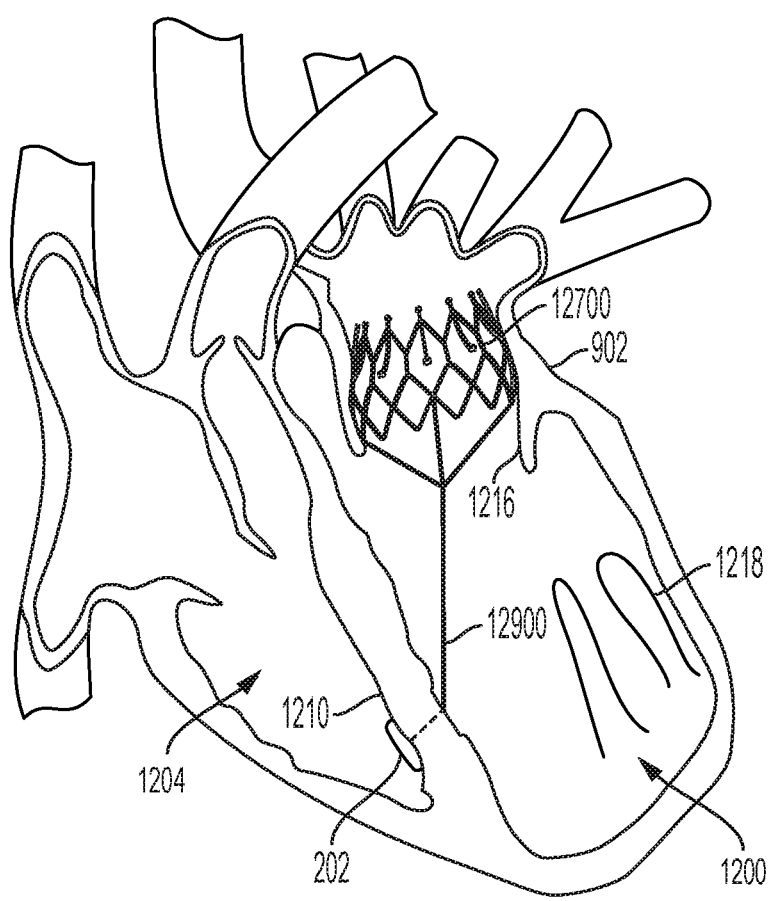

FIG. 129 illustrates a cross sectional view of a patient's heart with a heart implant positioned therein and anchored to a heart anchor according to an embodiment of the present disclosure.

Figure 130:
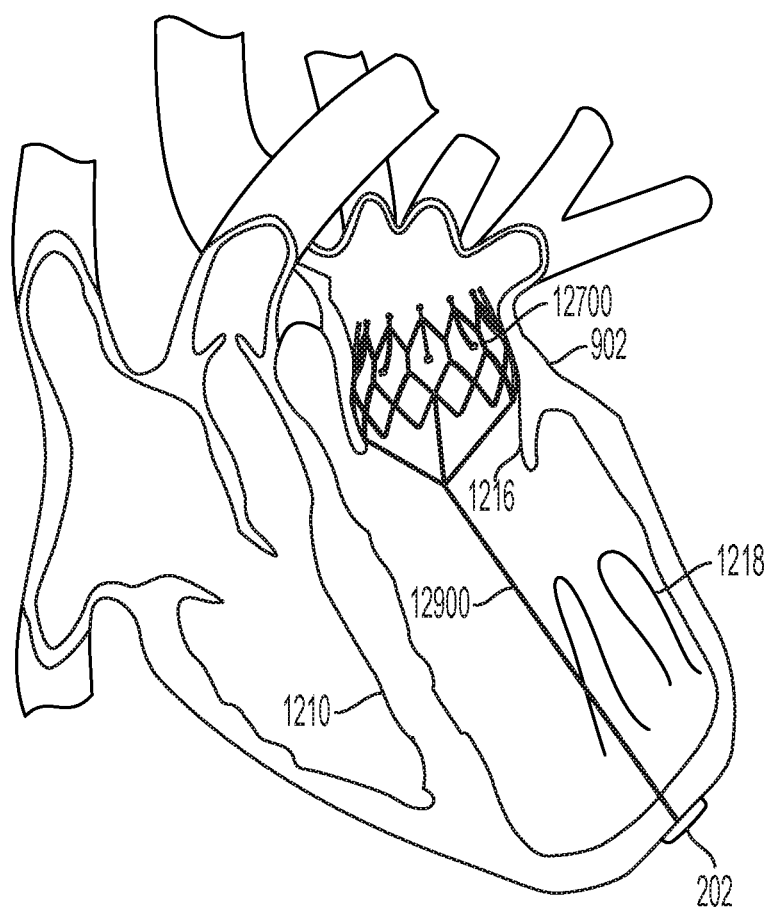

FIG. 130 illustrates a cross sectional view of a patient's heart with a heart implant positioned therein and anchored to a heart anchor according to an embodiment of the present disclosure.

Figure 131:
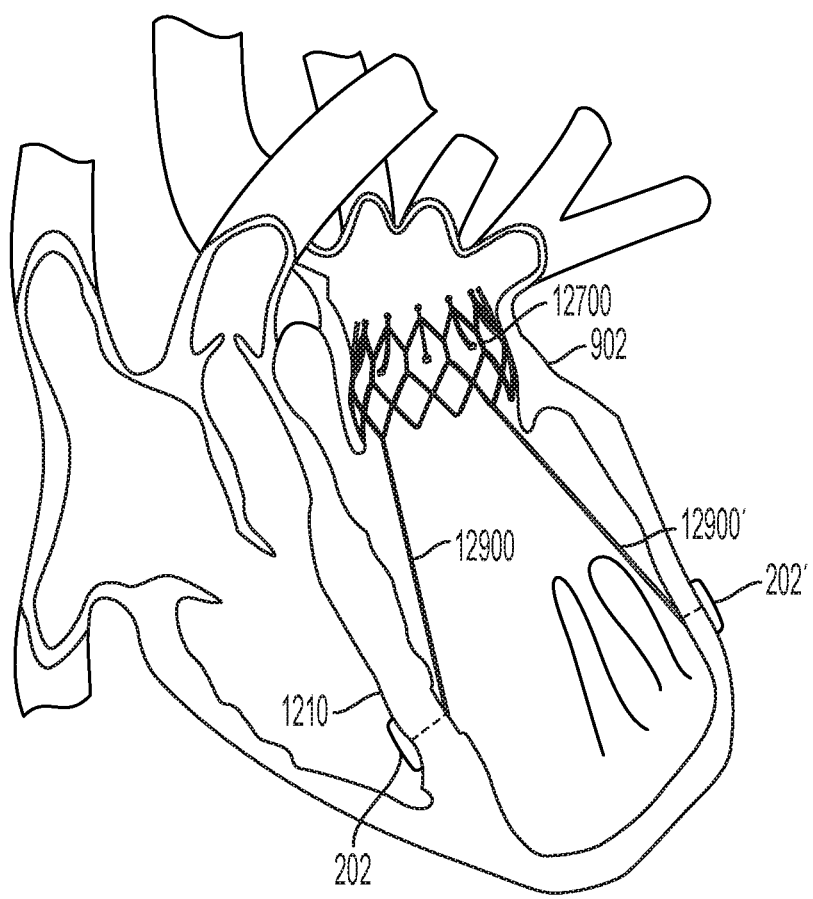

FIG. 131 illustrates a cross sectional view of a patient's heart with a heart implant positioned therein and anchored to multiple heart anchors according to an embodiment of the present disclosure.

DETAILED DESCRIPTION

Various aspects of the present disclosure generally relate to systems, apparatuses, and methods for medical treatment and/or treating heart conditions, including, by way of example, treating dilation/dilatation (including a dilated left ventricle), valve incompetencies (including mitral valve regurgitation), one or more openings in one or more septums of the heart, and other similar heart conditions. The systems, apparatuses, and methods may be adapted for transcatheter medical treatments that may not require full, open surgery, and can be minimally invasive. The systems, apparatus, and methods may be utilized to reshape a heart valve annulus, including a tricuspid valve annulus. The systems, apparatus, and methods may be utilized to reposition a heart valve leaflet to reduce heart valve leaflet prolapse. The systems, apparatus, and methods may be utilized to reposition one or more papillary muscles of a patient's heart, to draw the papillary muscles towards the mitral valve. The systems, apparatus, and methods may include use of a heart valve implant, which may comprise a heart valve prosthetic or a heart valve repair implant.

In certain embodiments, the present disclosure involves geometric reshaping of the heart and treating valve incompetencies. In certain aspects of the present disclosure, substantially an entire chamber geometry is altered so as to return the heart to a more normal state of stress. Geometric reshaping according to the present disclosure may reduce the stress in the walls of the heart chamber to increase the heart's pumping efficiency, as well as to stop further dilatation of the heart.

Figure 1A:
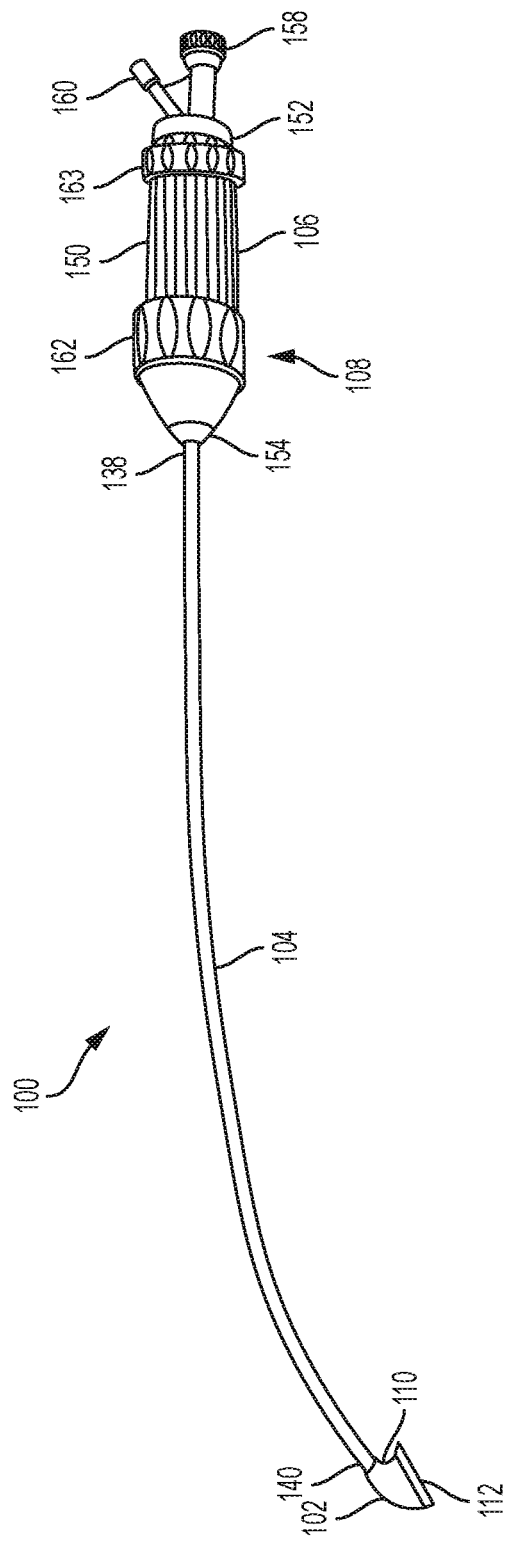
FIG. 1A illustrates a side view of an access apparatus according to an embodiment of the present disclosure.

FIG. 1A illustrates an embodiment of an access apparatus 100 that may be used in the systems and methods disclosed herein. The access apparatus 100 may include a head 102, an elongate neck 104, and a housing 106. The access apparatus 100 may include a control mechanism 108 for controlling movement of the elongate neck 104 and movement of the head 102. The access apparatus 100 may be configured for gripping an external surface of a patient's heart. The access apparatus 100 may be configured to penetrate through an external surface of a patient's heart and into an interior chamber of the patient's heart.

Figure 1B:
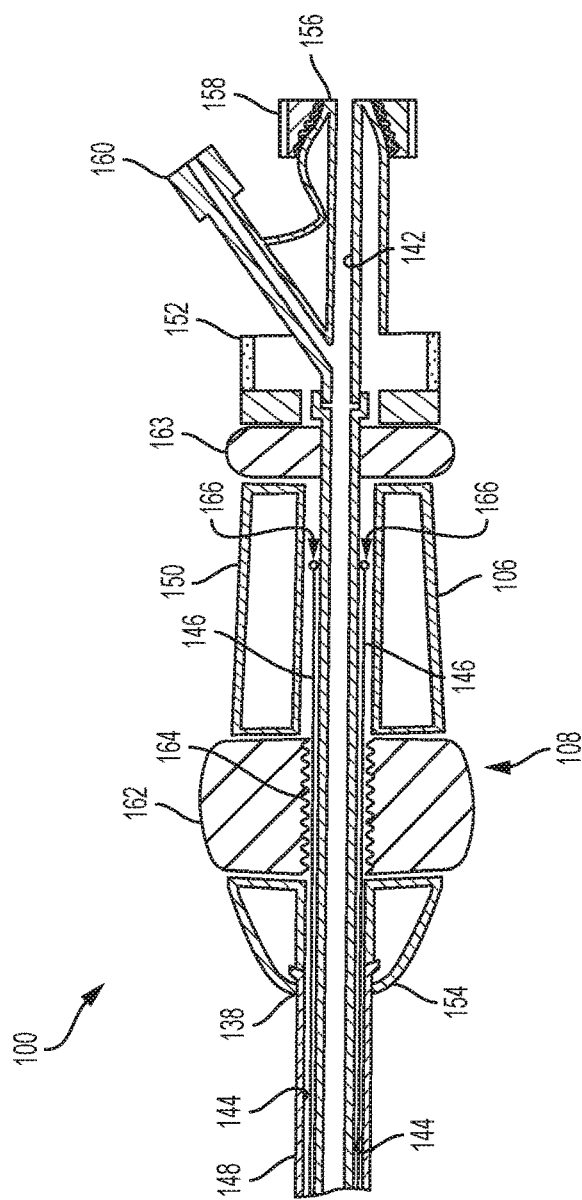
FIG. 1B illustrates a cross sectional view of the access apparatus shown in FIG. 1A.
Figure 1B:
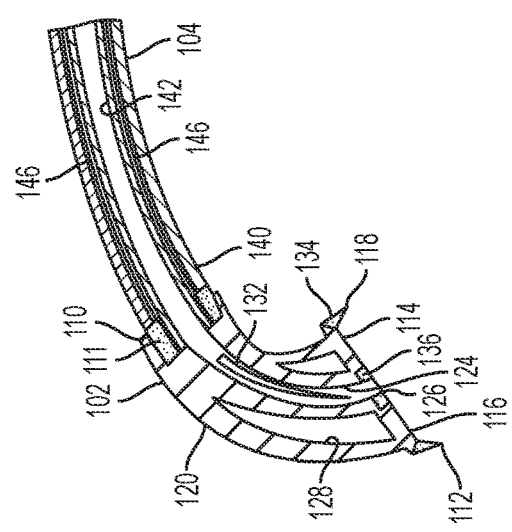
Figures 1C, 1D:
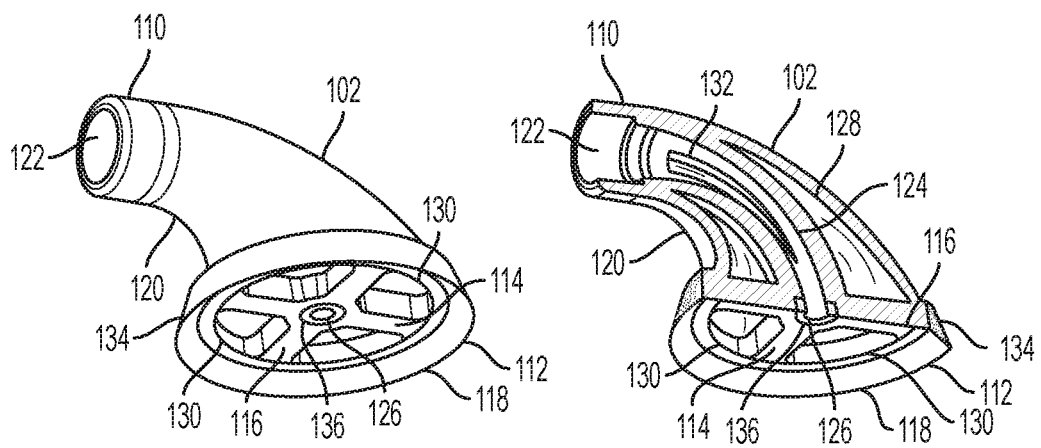
FIG. 1C illustrates a perspective view of the head of the access apparatus shown in FIG. 1A.
FIG. 1D illustrates a cross sectional view of the head of the access apparatus shown in FIG. 1A.

FIG. 1B illustrates a cross sectional view of the access apparatus 100 shown in FIG. 1A. FIG. 1C illustrates a close-up perspective view of the head 102, and FIG. 1D illustrates a cross sectional perspective view of the head 102.

Referring to FIGS. 1A, 1B, 1C, and 1D, the head 102 may include a proximal end 110 and a distal end 112. The head 102 may be configured to contact an external surface of the patient's heart. The head 102 may include an application portion 114 for being applied to a portion of a patient's heart. The application portion 114 may include a planar face 116 and a contact surface 118. The contact surface 118 may extend around the periphery of the planar face 116. The contact surface 118 may be configured to contact the portion of the patient's heart, and the planar face 116 may also be configured to contact the portion of the patient's heart depending on the amount of pressure applied by the head 102 to the patient's heart.

The head 102 may include a connector portion 120 that extends from the application portion 114 to the proximal end 110 of the head 102. The connector portion 120 may comprise a curved body extending from the application portion 114. The body may curve at an angle of about 90 degrees from the planar face 116 of the head 102 to an opening 122 at the proximal end 110 of the head 102, or may curve for a different amount as desired.

The head 102 may include a lumen 124 for devices to pass through. The lumen 124 may be disposed centrally in the application portion 114 and may end at an opening 126 in the planar face 116 of the head 102. The lumen 124 may extend from the opening 126 and through the connector portion 120, to the opening 122 at the proximal end 110 of the head 102. The devices that may pass through the lumen 124 may include a puncture device or other devices that may be disclosed herein.

The head 102 may include a lumen 128 for applying vacuum suction to the portion of the patient's heart to grip the portion of the patient's heart. The lumen 128 may end at multiple openings 130 that allow the vacuum suction to be applied to the portion of the heart. The openings 130 may extend through the planar face 116 at the application portion 114 of the head 102 and may comprise a pattern of cut-outs in the planar face 116. The four openings 130 shown in FIG. 1C, for example, include four wedge shaped cut-outs spaced about the central opening 126 such that the remaining portion of the planar face 116 has a cross-shape.

The lumen 128 may extend through the connector portion 120 of the head. The lumen 128 may be positioned around the central lumen 124. The lumen 128 may couple to the opening 122 at the proximal end 110 of the head 102 through an opening 132 (shown in FIG. 1D) in the lumen 124 that allows the vacuum suction to pass therethrough. The lumen 124 and vacuum lumen 128 may connect to each other through the opening 132 in the lumen 124. In other embodiments, the lumen 128 may remain separate from the lumen 124. For example, the lumen 128 may remain a separate channel that extends along the head 102 and the elongate neck 104 to couple to a port for receiving vacuum suction. One or more lumens may be utilized to apply the vacuum suction to the external surface of the patient's heart to grip the external surface of the patient's heart, and to pass a puncture device from the head through the external surface of the patient's heart.

The contact surface 118 may comprise a seal 134 that extends around the outer periphery of the head 102. The seal 134 may comprise a skirt that is configured to seal the connection with a portion of the patient's heart upon the vacuum suction being applied. The seal 134 may be flexible, and may be made of a rubberized or elastomeric material to allow the seal 134 to conform to the shape of the patient's heart and form a sealed connection with the patient's heart. In other embodiments, the seal 134 may have a different form than shown. The sealed connection may be sufficient to maintain the vacuum suction that may be sufficient to secure the head 102 to the desired portion of the patient's heart and resist the force of a puncture device being passed through a surface of the patient's heart.

The head 102 may include a location marker 136. The location marker 136 may be positioned in the application portion 114 of the head 102 and may be positioned in the planar face 116 of the head 102. The location marker 136 may be positioned adjacent and around the opening 126 in the planar face 116 of the head 102. The location marker 136 may be configured for a user to determine the location of the head 102 and particularly the opening 126. The location marker 136 may be a radio-opaque marker that forms a target for a user to visualize to determine the location of the head 102 and particularly the opening 126. In other embodiments, the location marker 136 may have a different configuration than shown.

Referring to FIGS. 1A and 1B, the elongate neck 104 may have a proximal end 138 and distal end 140 and a body extending from the proximal end 138 to the distal end 140. The distal end 140 of the elongate neck 104 may couple to the proximal end 110 of the head 102. One or more bearing surfaces 111 may be positioned between the head 102 and the elongate neck 104 so that the head 102 may rotate relative to the elongate neck 104 and about an axis of the elongate neck 104.

The elongate neck 104 may include a lumen 142 that may extend the length of the elongate neck 104. The lumen 142 may be configured for devices to pass through, and may be configured to pass the vacuum suction from the head 102. The lumen 142 may couple to the opening 122 of the head 102 shown in FIGS. 1C and 1D and may be configured to pass the vacuum suction from the lumen 128, and may be configured to pass devices through the lumen 124. The devices may be puncture devices or other devices for passing through the lumen 124 and the opening 126. The elongate neck 104 may include one or more lumens that may be utilized to pass the vacuum suction therethrough and to a puncture device therethrough.

The elongate neck 104 may include a lumen 144 that one or more control members 146 may pass through. The lumen 144 may be positioned exterior of the lumen 142 and may surround the lumen 142. The elongate neck 104 may include an outer sheath 148 that extends around the lumens 142, 144 and forms the outer surface of the elongate neck 104. The outer surface may be smooth to allow for a smooth entry into the patient's body.

The one or more control members 146 may be elongate members that extend along the length of the elongate neck 104. The control members 146 may comprise wires or rods, or other forms of control members. The control members 146 may couple to a portion of the elongate neck 104 or head 102. The control members 146 may be configured to deflect the elongate neck 104. For example, the control members 146 may be configured such that one control member is pulled along the elongate neck 104. The movement of the control member 146 may cause the elongate neck 104 to deflect along its length. In other embodiments, other forms of control may be applied, for example, one or more control members 146 may be configured to rotate to cause the elongate neck 104 to deflect, or other forms of control may be utilized. In one embodiment, one control member 146 may be configured to be pushed while the other control member is pulled along the elongate neck 104, to cause the elongate neck 104 to deflect. In one embodiment, only one control member 146 may be pushed or pulled along the length of the elongate neck 104 to control deflection of the elongate neck 104.

Figure 1E:
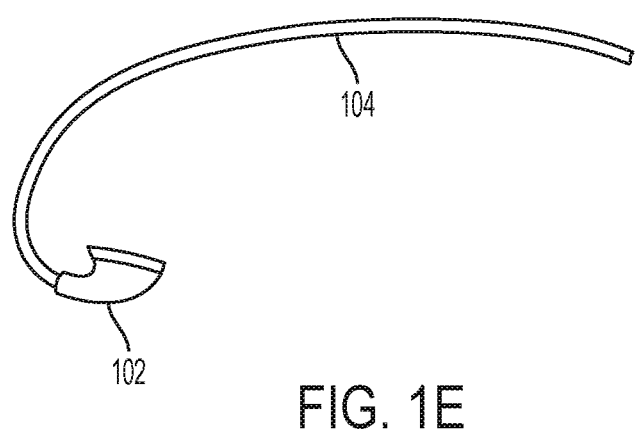
FIG. 1E illustrates a side view of the elongate neck of the access apparatus shown in FIG. 1A.

The elongate neck 104 may be flexible and configured to deflect along its length. The deflection may comprise a curvature of the elongate neck 104. Referring to FIG. 1E, the elongate neck 104 is shown deflecting along its length, and curving to vary the orientation of the head 102. The elongate neck 104 may be configured to curve such that the head 102 rotates by approximately 180 degrees, and the planar face 116 may face the elongate neck 104. The elongate neck 104 may be configured to curve at only a portion of the elongate neck 104, for example a distal portion of the elongate neck 104, or a portion proximate to the head 102. The elongate neck 104 may include a first portion and a second portion that is more proximate to the head 102 than the first portion, with the second portion configured to curve to a greater extent than the first portion. As such, a desired portion of the elongate neck 104 (proximal the head 102) may curve. The amount of deflection, or curvature, may vary as desired. The deflection may occur in multiple planes of the elongate neck 104, for example, if multiple control members 146 are pulled at various orientations along the lumen 142. The elongate neck 104 may deflect in a downward direction as shown in FIG. 1E, or may deflect in a relative upward direction or right direction (into the page in FIG. 1E) or left direction (out of the page in FIG. 1E). Combinations of directions of movement may occur based on the orientation and movement of the control members 146.

Referring to FIGS. 1A and 1B, the housing 106 may be positioned at the proximal end 138 of the elongate neck 104. The housing 106 may couple to the elongate neck 104 and may be configured for a user to grip. The housing 106 may be configured as a handle including an outer surface 150 for the user to grip. The housing 106 may have a proximal end 152 and a distal end 154.

The lumen 142 may extend through the housing 106. The lumen 142 in the housing 106 may comprise a separate and distinct lumen, or may comprise the lumen 142 that extends through the elongate neck 104. The housing 106 may include a port 156 at the proximal end 152 of the housing 106. The port 156 may be configured for devices, such as a puncture device or other devices for passing through the lumen 142 and the lumen 124 and the opening 126 of the head 102. The housing 106 may include a lock 158 at the port 156 that may lock the devices passing therethrough in position. The lock 158 may comprise a lock-knob or other form of lock.

The housing 106 may include a vacuum port 160 at the proximal end 152 of the housing 106. The vacuum port 160 may be configured to couple to a vacuum device for producing the vacuum suction at the head 102 and may pass the vacuum suction from the lumen 128. The lumen of the vacuum port 160 may be coupled to the lumen 142 of the port 156. At least one port may be utilized to pass vacuum suction therethrough and for passing a puncture device or other device therethrough to the head 102.

The housing 106 may include a control device 162. The control device 162 may be configured for a user to manipulate or otherwise control the deflection of the elongate neck 104 to move the head 102. The control device 162 may comprise a rotatable body (as shown in FIGS. 1A and 1B) and may be rotated to control the deflection of the elongate neck 104 and resulting orientation of the head 102. In other embodiments, other forms of control devices may be utilized. The control device 162 may be coupled to the one or more control members 146. The control device 162 may be configured to control the one or more control members 146 to control the elongate neck 104 and head 102 in a manner discussed herein. For example, the control device 162 may pull or otherwise tension one or more control members 146 to deflect the elongate neck 104. The control device 162 may be configured to engage the one or more control members 146. The control device 162 may include a gear drive 164 or other form of engagement, for engaging and moving the one or more control members 146. The gear drive 164 may pull the control member 146 to deflect the elongate neck, and to result in the curve shown for example in FIG. 1E. In other embodiments, other forms of control may be utilized. For example, the gear drive 164 may be configured to push one of the control members 146 while another control member 146 is being pulled, to deflect the neck.

Figure 1F:
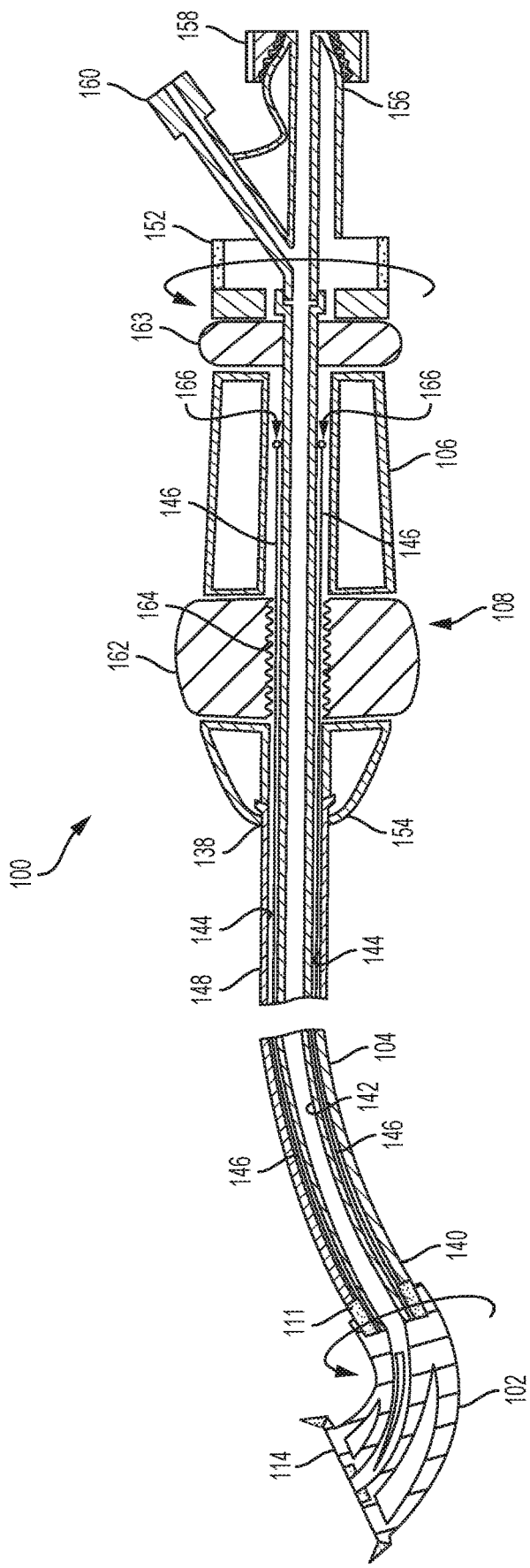
FIG. 1F illustrates a cross sectional view of the access apparatus shown in FIG. 1A with the head of the access apparatus rotated from the position shown in FIG. 1A.

The housing 106 may include a control device 163. The control device 163 may be configured to control a rotation of the head 102. The head 102 may be configured to rotate in position relative to the bearing surface 111. FIG. 1F for example, illustrates the head 102 rotating in position relative to the bearing surface 111 and accordingly relative to the elongate neck 104. The application portion 114 accordingly rotates in position as well. The rotation of the head 102 may allow for a variety of orientations of the application portion 114, and may be utilized in combination with the deflection of the elongate neck 104. The head 102 may rotate for 360 degrees, or a different amount as desired.

The control device 163 may be coupled to the lumen 142 of the elongate neck 104 such that rotation of the control device 163 and accordingly the lumen 142 may cause the head 102 to rotate relative to the elongate neck 104. In other embodiments, a separate control member may extend from the control device 163 to the head 102 to rotate the head 102 relative to the elongate neck 104. The control device 163 may comprise a rotatable body, similar to the control device 162.

The housing may include a cavity 166 for the one or more control members 146 to extend in. The cavity 166 may extend around the lumen 142.

The control devices 162, 163 and one or more control members 146 may comprise a control mechanism 108 for deflecting the elongate neck 104 to move the head 102 (which may include curving the elongate neck 104), and for rotating the head 102 as discussed. In other embodiments, other forms of control mechanisms may be used.

Figure 11:
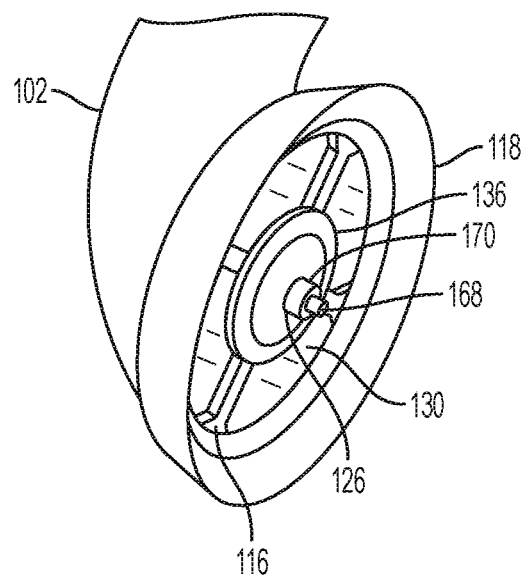
FIG. 11 illustrates a perspective view of the head of the access apparatus shown in FIG. 1A.

The access apparatus 100 may include a puncture device 168 as shown in FIG. 11. The puncture device 168 may be configured to pass through the lumen 124 and the opening 126 of the head 102 and puncture a surface of the patient's heart. The puncture device 168 may comprise a needle or other form of puncture device. The access apparatus 100 may include a sheath 170 (shown in FIG. 11) that extends around the puncture device 168. The puncture device 168 may extend within the lumen of the sheath 170. The sheath 170 may be a relatively small sized sheath, for example, the sheath may be an about 5 Fr (French) sized sheath, or other sizes as desired.

The access apparatus 100 may be utilized to control the orientation of the head 102 to move into a desired position. The access apparatus 100 as used in the systems and methods herein may be configured to be inserted into the patient's body from the front of the patient with the head 102 directed to a posterior portion of the patient's heart. Percutaneous entry of the patient's body may be utilized. The housing 106 may remain exterior to the insertion point of the access apparatus 100. The elongate neck 104 may be deflected to vary the orientation of the head 102 and the head 102 may be rotated such that the application portion 114 and contact surface 118 contact the desired posterior portion of the patient's heart. The elongate neck 104 in this configuration may have a curvature that is similar or less than the curvature shown in FIG. 1E, with the remainder of the elongate neck 104 extending around or along or curling around the patient's heart. The access apparatus 100 may accordingly allow for access to a posterior portion of the patient's heart from an anterior access location such as a sub xiphoid incision or anterior thoracotomy.

The user may operate the control mechanism 108 to vary the position of the head 102 until the head is in the desired position. The head 102 may also be rotated to a desired orientation. The location marker 136 may be utilized to determine that the head 102 is in the desired position. Vacuum suction may be applied by the head 102 to grip the head 102 to the desired portion of the patient's heart. The vacuum suction may be applied though the lumen 128 of the head 102 and passed by the lumen 142 and vacuum port 160. The vacuum suction may be released if the user determines the head 102 is in the incorrect position, and then reapplied upon the head 102 being moved to the desired position. Upon the vacuum suction gripping the head 102 to the patient's heart, the puncture device 168 may be passed through the lumen 124 and opening 126 to puncture the patient's heart. The puncture device 168, or the sheath 170, or other devices may be passed through the lumen 124 and opening 126 and into the patient's heart.

Upon the desired procedure being applied to the patient's heart, the vacuum suction of the head 102 may be released to release the access apparatus 100 from the patient's heart. The access apparatus 100 may be withdrawn from the patient's body, and the elongate neck 104 may be deflected to vary the orientation of the head 102 in a reverse operation as the entry procedure.

The access apparatus 100 may beneficially provide a minimally invasive manner to access the posterior portion of the patient's heart, without requiring a full sternotomy to be performed. The deflection of the elongate neck may allow the head 102 to reach the posterior portion of the patient's heart with a frontal entry of the patient's body. The rotation of the head 102 may also increase the variety of positions on the heart that the access apparatus 100 may access. The access apparatus 100 may beneficially allow for the vacuum suction to be applied and released, to allow the user to secure and release the head 102 to the patient's heart until the head 102 is in the desired position. The vacuum suction may also provide an effective manner to release the head 102 from the patient's heart when the desired procedure is complete. In other embodiments, the access apparatus 100 may have a different configuration than the configuration shown in FIGS. 1A-1F.

Figure 2A:
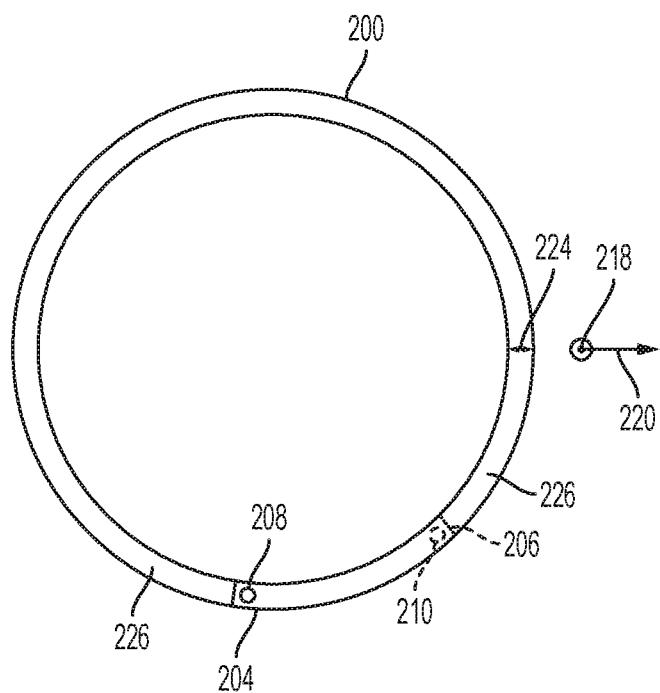
FIG. 2A illustrates a front view of a ring of a heart anchor according to an embodiment of the present disclosure.

FIG. 2A illustrates an embodiment of a ring 200 that may be used in a heart anchor, as may be used in the systems and methods disclosed herein. A heart anchor 202 as may be used in the systems and methods disclosed herein is illustrated in FIG. 2G. The heart anchor 202 may be utilized in a heart splint (for example the splint 3100 shown in FIG. 31, or other splints) or utilized in a plug (for example the plug 4100 shown in FIG. 44) among other uses.

Figure 2B:
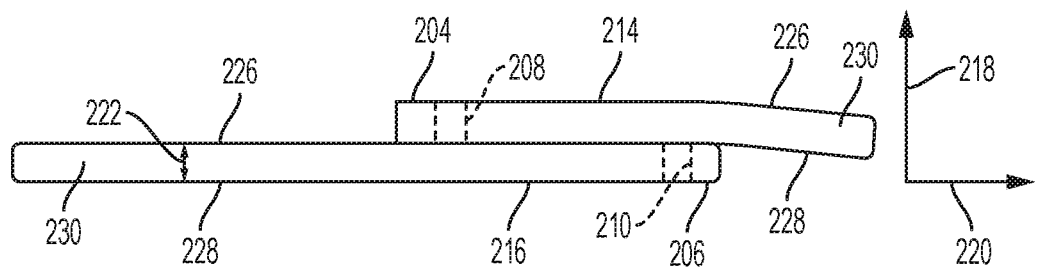
FIG. 2B illustrates a side view of the ring of a heart anchor shown in FIG. 2A.

The ring 200 may include a body having a first end 204 and a second end 206 (shown in FIG. 2A in dashed lines, and shown in FIG. 2B). The ring 200 may be configured to move from a linearized configuration (as shown in FIG. 2H) to a ring-shaped configuration, as shown in FIG. 2A. The first end 204 may include an opening 208 extending through the ring 200 at or proximal the first end 204 and an opening 210 (shown in FIGS. 2A and 2B in dashed lines) extending through the ring 200 at or proximal the second end 206. The openings 208, 210 may comprise couplers for coupling to the cover 212 (shown in FIGS. 2G and 2H).

FIG. 2B illustrates a side view of the ring 200 in the ring-shaped configuration shown in FIG. 2A. Portions 214, 216 of the ring 200 may overlap when the ring 200 is in the ring-shaped configuration. The portions 214, 216 may overlap in the axial dimension 218, as opposed to the radial dimension 220. The portions 214, 216 may overlap such that the portions 214, 216 that overlap include the ends 204, 206. From a top view (as shown in FIG. 2A), the portions may overlap such that the edges of the body of the ring 200 have a matching profile as viewed from the top. The edges of the body of the ring 200 may be aligned with each other in the radial dimension 220. The edges of the body of the ring are not offset from each other at the overlapping portions in the radial dimension 220. Thus, the ring 200 may appear as a continuous ring, which may have a circular shape or other shape as desired. Some examples of the ring include any suitable closed shape, which can be generally flat, as illustrated in FIGS. 2A and 2B, or can have a three-dimensional shape, for example, that accommodates one or more anatomical features.

In some examples, a first end portion of the ring can overlap a second end portion of the ring where at least one of the first end portion or the second portion is adjacent to or spaced from the respective end. For example, in some rings, at least one edge of the first end portion is offset or at an angle to at least one edge of the second end portion at the overlap. In other examples, the overlapping portions can include both ends of the first and second end portions where at least one edge of the first end portion is offset from an edge of the second end portion.

The overlapping portions 214, 216 may contact each other, and one of the overlapping portions may provide a support against force for the other overlapping portion. For example, a force applied to portion 214 may be resisted by portion 216 at the overlap, and a force applied to portion 216 may be resisted by portion 214 at the overlap. The overlapping portions 214, 216 may provide support for the ring 200 upon a force being applied in the axial dimension.

The overlapping portions 214, 216 may overlap to a desired amount. In one embodiment, the overlapping portions 214, 216 may overlap to at least about 5 degrees of the ring 200. In one embodiment, the overlapping portions 214, 216 may overlap to at least about 10 degrees, to at least about 20 degrees, to at least about 40 degrees, or to at least about 60 degrees of the ring 200, or to a different amount as desired. In one embodiment, the entirety of the ring 200 may overlap such that the overlapping portions 214, 216 comprise the entirety of the ring, for example, about 360 degrees, or even greater than 360 degrees. In one embodiment, the ring 200 may be configured to have a single overlap, as shown in FIG. 2A, which may reduce the amount of material comprising the ring 200 and may ease the transition between the linearized configuration and the ring-shaped configuration. As will be apparent in the discussion below, the degree of overlap can change when the ring is in use. For example, tensioning and/or applying a load to the cover can reduce a diameter/circumference of the ring, thereby increasing the overlap in some examples.

The ring 200 may have a thickness 222 (in the axial dimension 218) and may have a width 224 (in the radial dimension 220) (as marked in FIG. 2A). The thickness 222 may be between about 0.2 and about 0.4 millimeters, although in other embodiments other thicknesses 222 may be utilized. In one embodiment, the thickness 222 may be about 0.3 millimeters. In some examples, the thickness can be non-uniform along a length/circumference of the ring. For example, in some rings, at least one of the overlapping portions can be thinner than a non-overlapping portion of the ring. The width 224 may be between about 0.3 and about 0.5 millimeters, although in other embodiments other widths 224 may be utilized. In one embodiment, the width 224 may be about 0.4 millimeters. In some examples, the width is non-uniform along a length/circumference of the ring, for example, wider at at least one of the overlapping portions. The ring 200 may be sized as desired, and may be configured to be a relatively thin ring that is flexible to allow for ease of movement of the ring 200.

Referring to FIG. 2B, the ring 200 may have a flattened shape with a substantially planar top surface 226 and a substantially planar bottom surface 228 facing opposite the top surface 226. The ring 200 at the overlapping portions 214, 216 may have the top surface 226 of portion 216 face towards the bottom surface 228 of portion 214. The terms "top" and "bottom" may be used interchangeably. Side surfaces 230 may connect the top surface 226 to the bottom surface 228. The body of the ring 200 may have a rectangular profile when viewed in cross section.

The ring 200 may be made of a material that is flexible, such that the ring may move from the linearized configuration (as shown in FIG. 2H) to the ring-shaped configuration (as shown in FIG. 2A). The ring 200 may be made of an elastic material to move from one configuration to the other relaxed or default configuration. In one embodiment, the ring 200 may be made of a super elastic or shape-memory material, which may include a shape-memory alloy, to allow the ring to move from the linearized configuration to the ring-shaped configuration. The shape-memory material may be a material such as nitinol or another shape-memory material. The ring 200 may be configured to automatically move from the linearized configuration to the ring-shaped configuration, as the shape-memory material may automatically move to the shape-set ring-shaped configuration.

A linearized configuration is shown in FIG. 2H. In this configuration, the portions 214, 216 of the ring 200 may be separated from each other and do not overlap. The ends 204, 206 of the ring 200 do not overlap. The ring 200 in FIG. 2H may be in one form of linearized configuration, however, other forms may be utilized. For example, two opposite portions of the ring 200 in the ring-shaped configuration may be squeezed together towards a center portion of the ring such that the opposite portions of the ring-shaped body come together at the center portion and the ring 200 is linearized. Other forms of linearization may be utilized. The ring 200 in the linearized configuration may not be entirely straightened, although in other embodiments, the ring 200 may be entirely straightened (as shown in FIG. 2H). As such, the term "linearized" refers to any configuration that is suitable for delivery and deployment through a catheter or other minimally invasive or percutaneous delivery system, and does not require that the ring or any portion thereof is substantially straight or linear. In some examples, no portion of the ring is substantially straight or linear in the linearized configuration. For example, all or a portion of a ring can adopt a helical, sinusoidal, and/or other curved shape in the linearized configuration. Consequently, the terms "delivery configuration" and "open configuration" can also be used to describe some examples. The ring 200 in the linearized configuration may be configured to fit within the lumen of a deployment apparatus 300, as marked in FIG. 2H.

Figure 2C:
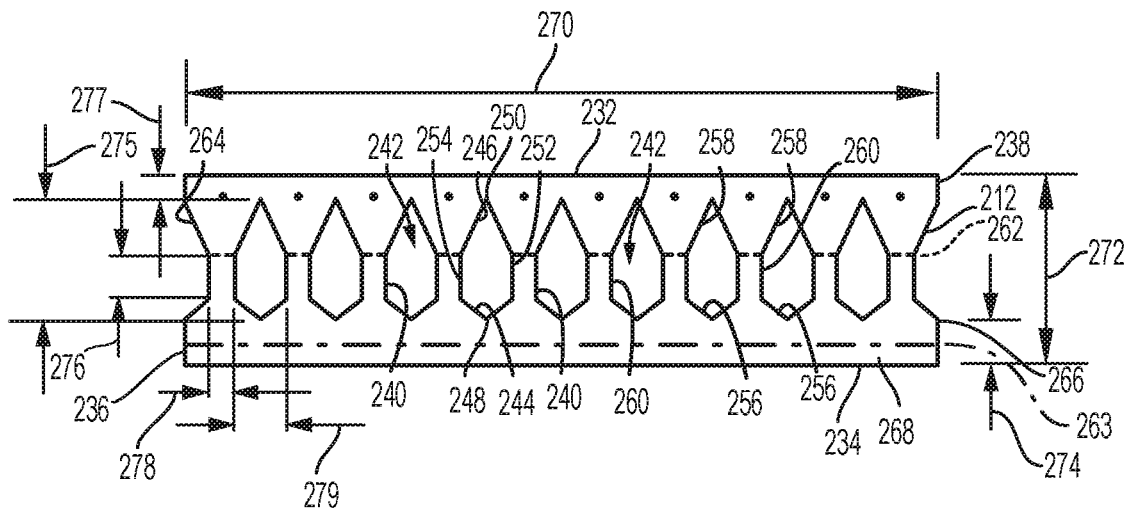
FIG. 2C illustrates a top view of an unfolded cover of a heart anchor according to an embodiment of the present disclosure.

FIG. 2C illustrates a top view of the cover 212 unfolded. The cover 212 may include a top edge 232 and an opposite bottom edge 234. Side edges 236, 238 may extend from the top edge 232 to the bottom edge 234. The terms "top" and "bottom" may be used interchangeably.

The cover 212 may include a plurality of cut-outs 240 defining openings 242 in the cover 212. The cut-outs 240 may be in the form of a pattern of shapes. The shapes, as shown in FIG. 2C, may be asymmetric diamonds. The asymmetric diamonds may include opposite triangular portions 244, 246. The triangular portions 244 may have an angle and side lengths from the central vertex 248 that is different than the angle and side lengths from the central vertex 250 of the triangular portion 246. The angle from the central vertex 248 is greater than the angle from the central vertex 250, and the side lengths from the central vertex 248 are shorter than the side lengths from the central vertex 250. The side lengths of the triangular portions 244, 246 extend to straight side portions 252, 254.

The cut-outs 240 may leave the remaining portion of the cover 212 with trapezoidal portions 256, 258 having differing heights and side lengths. The height and side lengths of the trapezoidal portions 256 may be less than the height and side lengths of the trapezoidal portions 258. The trapezoidal portions 256, 258 may be connected with rectangular portions 260.

The pattern of cut-outs 240 may be repeated along the length of the cover 212. The shape and pattern of cut-outs 240 and shape and pattern of the remaining portions of the cover 212 may be varied from the shapes and pattern shown in FIG. 2C as desired. In examples in which the ring has a non-circular ring-shaped or closed configuration, the particular details of the cover can differ, for example, the patterns of shapes defined by the cut-outs and/or their dimensions.

The cover 212 may include a fold portion 262 marked in dashed lines in FIG. 2C. The cover 212 may be configured to fold at the fold portion 262. The portion of the cover 212 shown above the fold portion 262 may comprise an overlapping portion 264 and the portion of the cover 212 shown below the fold portion 262 and above the dot-dashed line may comprise an overlapping portion 266. The overlapping portion 266 may overlap the overlapping portion 264 when the cover 212 is folded at the fold portion 262. The cover 212 may include a fold portion 263 marked in dot-dashed lines in FIG. 2C. The cover 212 may include an overlapping portion 268 indicated below the dot-dashed line in FIG. 2C. The overlapping portion 268 may be configured to overlap the top edge 232 of the cover 212 and a portion of overlapping portion 264 when the cover 212 is folded upon the fold portion 262.

The dimensions of the cover 212 may be set as desired. The dimensions may include a length 270. The length 270 may extend from the side edge 236 to the side edge 238. The length 270 may be between about 100 millimeters and about 70 millimeters, and in other embodiments, may have a greater or lesser size as desired. In one embodiment, the length 270 may be about 88 millimeters. The dimensions may include a width 272 of the unfolded cover 212. The width 272 may extend from the top edge 232 to the bottom edge 234. The width 272 may be between about 20 millimeters and about 30 millimeters, and in other embodiments, may have a greater or lesser size as desired. In one embodiment, the width 272 may be about 22 millimeters.

The dimensions may include a width 274 of the cover 212 from the bottom edge 234 to the lower end of the cut-outs 240. The width 274 may be between about 4 millimeters and about 7 millimeters, and in other embodiments, may have a greater or lesser size as desired. In one embodiment, the width 274 may be about 5.5 millimeters. The dimensions may include a width 275 of the cut-outs 240. The width 275 may be between 10 about millimeters and about 15 millimeters, and in other embodiments, may have a greater or lesser size as desired. In one embodiment, the width 275 may be about 13.5 millimeters. The dimensions may include a width 276 of the rectangular portions 260. The width 276 may be between about 3 millimeters and about 7 millimeters, and in other embodiments, may have a greater or lesser size as desired. In one embodiment, the width 276 may be about 5 millimeters. The dimensions may include a width 277 of the cover 212 from the top edge 232 to the upper end of the cut-outs 240. The width 277 may be between about 1 millimeter and about 5 millimeters, and in other embodiments, may have a greater or lesser size as desired. In one embodiment, the width 277 may be about 3 millimeters.

The dimensions may include a thickness 278 of the rectangular portions 260. The thickness 278 may be between about 1 millimeter and about 5 millimeters, and in other embodiments, may have a greater or lesser size as desired. In one embodiment, the thickness 278 may be about 3 millimeters. The dimensions may include a thickness 279 of the cut-outs 240. The thickness 279 may be between about 3 millimeters and about 8 millimeters, and in other embodiments, may have a greater or lesser size as desired. In one embodiment, the thickness 279 may be about 6 millimeters.

Figure 2D:
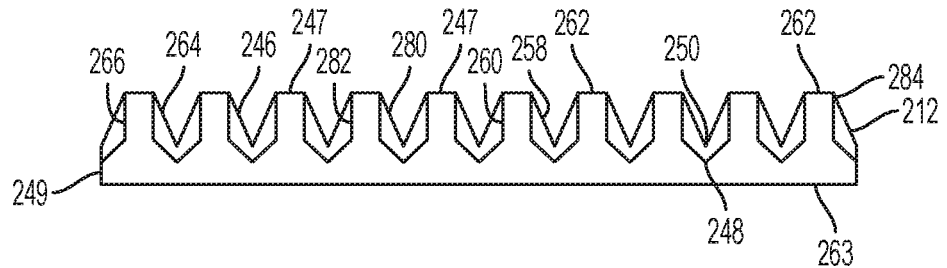
FIG. 2D illustrates a top view of the cover shown in FIG. 2C folded.

FIG. 2D illustrates the cover 212 having been folded at the fold portion 262. The overlapping portion 266 overlaps the overlapping portion 264 (and the overlapping portion 264 overlaps the overlapping portion 266). The overlapping portions 264, 266 form respective layers, including a first layer 280 and a second layer 282 that overlap and may be in contact with each other. The cover 212 may be folded such that the central vertices 250 may be brought towards the central vertices 248, and the trapezoidal portions 258 overlap the rectangular portions 260. The triangular portions 246 of the cut-outs may form triangular-shaped gaps between the trapezoidal portions 258. The cover 212 in this configuration includes a plurality of protrusions 247 extending from a connecting portion 249 of the cover 212.

The cover 212 at the fold portion 262 may form a coupler 284 for coupling the cover 212 to a tension member 286 (as shown in FIG. 2G). The cover 212 at the fold portion 263 may form a coupler 287 (marked in FIG. 2E) for coupling to the ring 200. The couplers 284, 287 may comprise folded material at the fold portions 262, 263 that the respective tension member 286 and ring 200 may be passed through.

Figure 2E:
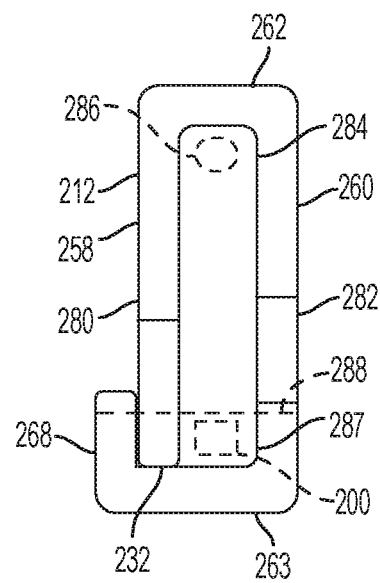
FIG. 2E illustrates a side view of the folded cover shown in FIG. 2D.

FIG. 2E illustrates a side view of the cover 212 in the configuration shown in FIG. 2D. The position of the tension member 286 (if coupled to the cover 212) is shown in dashed lines at the top of the cover 212 and the position of the ring 200 (if coupled to the cover 212) is shown in dashed lines at the bottom of the cover. The overlapping layers 280, 282 are visible. The overlapping portion 268 overlaps the edge 232 of the cover 212. The overlap of the overlapping portion 268 forms the coupler 287 in the form of a loop at a bottom end of the cover 212. The bottom end, when the ring 200 is in the ring-shaped configuration, may comprise a peripheral portion of the cover 212. Connectors 288 may extend through the layers 280, 282 and overlapping portion 268 to secure the loop in position at the bottom end of the cover 212. The connectors 288 may comprise sutures or other form of stitching, or another form of connector that connects the overlapping layers 280, 282 and overlapping portion 268. The connectors 288 may pass through the openings 208, 210 in the ring 200 to securely connect the ring 200 to the cover 212. The ring 200 may be positioned between the connectors 288 and the fold portion 263, and sandwiched between the layers 280, 282.

The cover 212 at the fold portion 262 forms a coupler 284 in the form of a loop at the top end of the cover 212. The top end, when the ring 200 is in the ring-shaped configuration, may comprise a central portion of the cover 212. The tension member 286 may pass through the coupler 284 and may be sandwiched between the layers 280, 282.

Figure 2F:
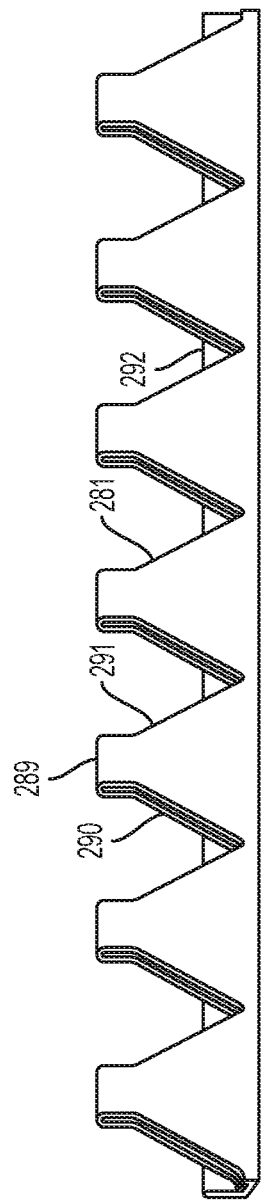
FIG. 2F illustrates an alternate configuration of a cover of a heart anchor according to an embodiment of the present disclosure.
Figure 2G:
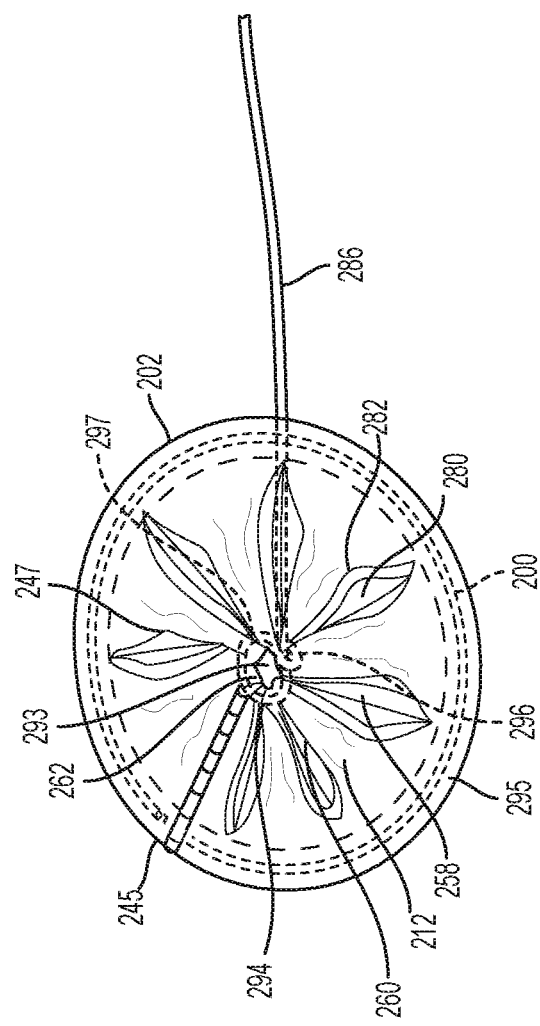
FIG. 2G illustrates a heart anchor according to an embodiment of the present disclosure.
Figure 2H:
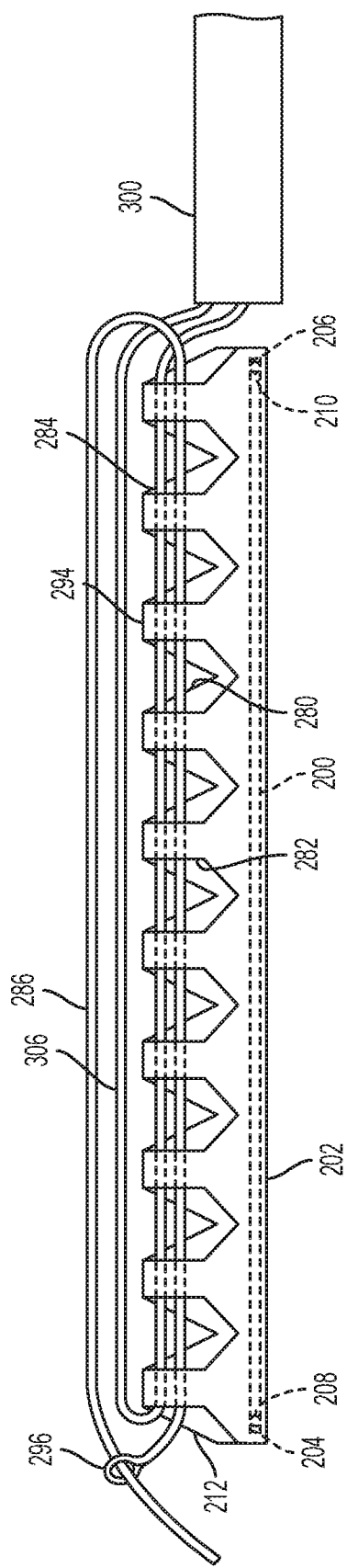
FIG. 2H illustrates the heart anchor shown in FIG. 2G in a linearized configuration.

FIG. 2F illustrates an embodiment of a cover 281 having a different configuration of cut-outs than shown in the embodiment of FIGS. 2C-2E, 2G and 2H. The cut-outs in the embodiment of FIG. 2F are symmetrical as folded upon the fold portion 289. The remaining portions of the cover 281 include a first layer 290 and a second layer 291 that have the same symmetrical shapes of trapezoidal portions coupled to rectangular portions (that include the fold portion 289). An overlapping portion 292 may overlap the layers 290, 291 and may form a coupler for coupling to the ring 200, in a similar manner as the embodiment of FIGS. 2C-2E, 2G and 2H. The fold portion 289 may form a coupler for coupling to the tension member 286, in a similar manner as the embodiment of FIGS. 2C-2E, 2G and 2H. The configuration of cover 281 may be utilized with the systems and methods disclosed herein, in a similar manner as cover 212. The shape and configuration of the covers 212, 281 shown in FIGS. 2C-2H may be varied as desired.

The covers 212, 281 may be flexible and configured to move with the ring 200 as it moves from the linearized configuration to the ring-shaped configuration. The covers 212, 281 may be made of a flexible material, which may include, for example, a cloth or fabric. The flexible material may be woven or non-woven. The flexible material may include materials such as ultra-high-molecular-weight polyethylene (UHMwPE) (for example, DYNEEMA® fabric or laminate, Koninklijke DSM, the Netherlands) or polyethylene terephthalate (PET, for example, DACRON® fabric, Invista, Wilmington, Delaware). In other embodiments, other flexible materials may be utilized.

FIG. 2G illustrates the ring 200 in a ring-shaped configuration, with the ring 200 coupled to the cover 212, and the tension member 286 coupled to the cover 212. Portions of the ring 200 coupled to the cover 212 may overlap, in a manner discussed previously. Portion 245 comprises an overlapping portion of the ring 200 and the cover 212. The cover 212 extends inward from the ring 200 in the ring-shaped configuration.

The tension member 286 is coupled to the cover 212 at the fold portions 262. The tension member 286 is drawn away from the cover 212 such that the cover 212 is drawn towards a central opening 293 of the cover 212. The tension member 286 accordingly may cinch the cover 212 towards the central opening 283. In some examples, the cover 212 can in turn pull on the ring 200, reducing a diameter/circumference thereof. The cover 212 is in a disc-shaped configuration. The cover 212 in this configuration includes a central portion 294 and a peripheral portion 295. The overlapping layers of material of the cover 212 (the layers 280, 282) extend from the peripheral portion 295 to the central portion 294. The fold portions 262 are positioned at the central portion 294, and the ring 200 is positioned in the peripheral portion 295.

The trapezoidal portions 258 of the layer 280 may be placed adjacent each other such that the gaps between the trapezoidal portions 258 shown in FIG. 2D are closed. The cover 212 accordingly may comprise a closed surface extending from the peripheral portion 295 to the central portion 294. The protrusions 247 are adjacent each other and extend from the peripheral portion 295 to the central portion 294.

The tension member 286 may comprise a portion of a heart splint, and may be configured to provide tension between the anchors of a heart splint. The tension member 286 may comprise a tether, and may be in the form of a cord, or other form of tension member. The tension member 286 may be made of a flexible material, which may include ultra-high-molecular-weight polyethylene (UHMwPE) (for example, FORCE FIBER® suture, Teleflex, Wayne, Pennsylvania or DYNEEMA® fiber, Koninklijke DSM, the Netherlands), among other flexible materials. The tension member 286 may include a body, and may include a coupling device 296 at its end that may couple the tension member 286 to itself. The coupling device 296 may comprise a loop that the body of the tension member 286 passes through, such that as the body of the tension member 286 is pulled, a size of a loop 297 formed by the tension member 286 being threaded through the fold portions 289 of the cover 212 reduces in size. The portion of the tension member 286 forming the loop 297 passes through the coupler 284 (marked in FIG. 2D) positioned at the central portion 294 of the cover 212. Thus, as the tension member 286 is pulled, the size of the loop 297 reduces, and accordingly the cover 212 is cinched and pulled radially towards the central opening 293 of the cover 212. The anchor 202 in the configuration shown in FIG. 2G may have a diameter of between about 20 millimeters and about 25 millimeters, although other diameters may be utilized as desired. In one embodiment, the anchor 202 may have a diameter of about 22 millimeters.

The cover 212 may be configured to be drawn towards the central opening 293 such that the central opening 293 entirely closes. The tension member 286 may extend from the cover 212 at the central portion 294 of the cover 212.

FIG. 2H illustrates the ring 200 in a linearized configuration. The ring 200 is extended such that the ends 204, 206 are separated from each other. The tension member 286 is visible extending through the coupler 284 of the central portion 294. The anchor 202 is in a linearized configuration.

A deployment member 306 may be utilized to deploy the cover 212 of the anchor 202. The deployment member 306 may comprise a tether, and may be in the form of a cord, or other form of deployment member. The deployment member 306 may be looped, and may be coupled to the cover 212 at the coupler 284. The deployment member 306 may be looped through the coupler 284 in a manner shown in FIG. 2H. The deployment member 306 may be pulled to cinch or draw the cover 212 towards the central opening 293 of the cover 212 in a similar manner as discussed above regarding the tension member 286. The anchor 202, upon being positioned in the lumen of a deployment apparatus, may have the cover 212 flattened, as shown in FIG. 2I. The deployment member 306 may close or otherwise cinch the cover 212. The anchor 202 may be held against the end of the deployment apparatus 300 when the deployment member 306 is pulled, to support the anchor 202 in position. The ring 202, however, may also be configured to automatically move to or towards the ring-shaped configuration.

The anchor 202 may accordingly be configured to move from an unexpanded configuration to an expanded configuration. The unexpanded configuration may comprise the configuration in which the ring 202 is in the linearized configuration, and the anchor 202 is accordingly linearized. The expanded configuration may be the configuration in which the ring 202 is in the ring-shaped configuration and the cover 212 is in a disc-shaped configuration. In other embodiments, other unexpanded and expanded configurations may be utilized. In an expanded configuration, an anchor may have a larger diameter or other dimensions. In unexpanded configuration, the anchor may have a smaller diameter or other dimensions and may be configured to fit within the lumen of a deployment apparatus. The configurations of anchor may vary from that shown in FIGS. 2G and 2H.

The anchor 202 may beneficially be configured such that the cover 212 bears the majority of the force against the anchor 202 when the tension member 286 is tensioned. The ring 200 may be configured to provide support for the shape of the cover 212, but otherwise may bear a lesser portion of the force against the anchor 202. The overlapping portions of the ring 200 may beneficially provide enhanced strength for the ring 200.

The relatively thin shape of the ring 200 may allow the ring 200 to be flexible to fit within the lumen of a deployment apparatus. The ring 200 may be able to be positioned within the lumen of a deployment apparatus with a relatively low force, and may be positioned within the lumen manually. The ring 200 may be sufficiently flexible to be hand-loaded into a deployment apparatus.

The anchor 202 may have a variety of uses, including use as a portion of a heart splint as may be disclosed herein. The anchor 202 may also be used as a portion of a plug to seal an opening in a patient's heart septum, among other uses.

FIG. 3A illustrates an embodiment of a deployment apparatus 300 that may be used in the systems and methods disclosed herein. The deployment apparatus 300 may include a deployment catheter 302, a push device 304, and a deployment member 306. The deployment apparatus 300 may be configured to deploy an anchor, such as the anchor 202 shown in FIGS. 2G and 2H, in an interior chamber of the patient's heart.

FIG. 3B illustrates a cross sectional view of the deployment apparatus 300 (with the pull device 308 not shown in cross section).

Referring to FIGS. 3A and 3B, the deployment catheter 302 may include a proximal end 310, a distal end 312 and a body extending between the proximal end 310 and the distal end 312. The deployment catheter 302 may include a lumen 313 positioned therein. A housing 314 may be positioned at the proximal end 310 of the catheter 302. The housing 314 may be configured to be manipulated by a user. The deployment catheter 302 may have an about 8 Fr size, although other sizes may be utilized as desired.

The housing 314 may include a lock 316 and two portions 318, 320 for controlling the lock 316. The lock 316 may be configured to lock movement of the push device 304 positioned within the lumen 313. The lock 316 may comprise threaded portions of the housing 314 that are pressed as the portions 318, 320 are rotated relative to each other. The portion 320 may be constricted to press against the push device 304 to lock movement of the push device 304 within the lumen 313.

The lumen 313 of the deployment catheter 302 may be configured to hold the anchor 202 in the lumen 313, in a portion 321 marked in dashed lines in FIG. 3B. The lumen 313 may hold the anchor 202 in the unexpanded or linearized configuration in the lumen 313. The deployment catheter 302 may include a tip 322 for the anchor 202 to be pressed against as the deployment member 306 is pulled, in a manner discussed herein.

The push device 304 may include a distal end 324, a proximal end 326, and a body extending between the distal end 324 and the proximal end 326. The push device 304 may include a lumen 328 for the deployment member 306 to extend in.

A housing 330 may be positioned at the proximal end 326 of the push device 304. The housing 330 may be configured to form a grip for a user.

The push device 304 may be sized to fit within the lumen 313 of the deployment catheter 302. The push device 304 may be configured to slide within the lumen 313 of the deployment catheter 302 and may be configured to push the anchor 202 in the linearized configuration out of the lumen 313 and distal end 312 of the deployment catheter 302.

The deployment member 306, as previously discussed, may comprise a tether, and may be in the form of a cord, or other form of deployment member. The deployment member 306 may be looped, with ends of the deployment member coupled to a pull device 308. The deployment member 306 may be looped through a coupler of the anchor 202, as previously discussed. The deployment member 306 may be configured to extend in the lumen 313 of the deployment catheter 302 and the lumen 328 of the push device 304.

The pull device 308 may comprise a handle for being pulled, or may comprise another form of pull device 308. The pull device 308 may be configured for a user to grip and pull. Pulling the pull device 308 may draw the deployment member 306 in a proximal direction through the deployment catheter 302 and the push device 304.

FIG. 4A illustrates an embodiment of a delivery apparatus 400 that may be used in the systems and methods disclosed herein. The delivery apparatus 400 may include an elongate sheath 402 and a housing 404. The delivery apparatus 400 may include a control mechanism 406 for controlling movement of the elongate sheath 402.

FIG. 4B illustrates a cross sectional view of the delivery apparatus 400.

Referring to FIGS. 4A and 4B, the elongate sheath 402 may include a distal end 408 and a proximal end 410 and a body extending between the distal end 408 and the proximal end 410. The elongate sheath 402 may include a lumen 412. The lumen 412 may allow devices to be passed therethrough. The elongate sheath 402 may include an opening 414 at the distal end 408 for devices to be passed through to exit the lumen 412.

The elongate sheath 402 may be flexible and configured to deflect along its length. The elongate sheath 402 may be configured to curve, and may deflect and curve in a similar manner as the elongate neck 104 of the access apparatus 100 discussed in regard to FIGS. 1A-1F.

The elongate sheath 402 may include a lumen 416 that one or more control members 418 may pass through. The lumen 416 may be positioned exterior of the lumen 412 and may surround the lumen 412. The elongate sheath 402 may include an outer sheath 419 that extends around the lumens 412, 416 and forms the outer surface 415 of the elongate sheath 402. The outer surface 415 may be configured to be smooth to allow for a smooth entry into the vessels of the patient's body, including the chambers of the patient's heart. The one or more control members 418 may be configured similarly as the control members 146 discussed in regard to FIGS. 1A-1F.

The housing 404 may be positioned at the proximal end 410 of the elongate sheath 402. The housing 404 may couple to the elongate sheath 402 and may be configured for a user to grip. The housing 404 may be configured as a handle include an outer surface 417 for the user to grip. The housing 404 may have a proximal end 421 and a distal end 423.

The lumen 412 may extend through the housing 404. The lumen 412 in the housing 404 may comprise a separate and distinct lumen, or may comprise the lumen 412 that extends through the elongate sheath 402. The housing 404 may include a port 424 at the proximal end 421 of the housing 404 for a device to be inserted into the lumen 412. A valve 425 may be positioned at the proximal end of the delivery apparatus 400 to prevent fluid such as blood from exiting the lumen 412 in the proximal direction.

The housing 404 may include a control device 420. The control device 420 may be configured for a user to manipulate or otherwise control the elongate sheath 402. The control device 420 may comprise a rotatable body and may be rotated to control the elongate sheath 402. In other embodiments, other forms of control devices may be utilized. The control device 420 may be configured to control the one or more control members 418 in a similar manner as discussed in regard to the control device 162 discussed in regard to FIGS. 1A-1F. The control device 420 may be configured to move the one or more control members 418 to deflect the elongate sheath 402 in a similar manner as discussed regarding elongate neck 104. In other embodiments, other forms of control may be utilized.

The housing 404 may include a cavity 422 for the one or more control members 418 to extend in.

The control device 420 and one or more control members 418 may comprise a control mechanism 406 for deflecting the elongate sheath 402 varying the orientation of the opening 414 at the end 408 of the elongate sheath 402. The control mechanism 406 may operate in a similar manner as the control mechanism 108 discussed in regard to FIGS. 1A-1F. In other embodiments, other forms control mechanisms may be used.

The delivery apparatus 400 may be utilized to control the orientation of the distal end 408 of the elongate sheath 402 to move the distal end 408 into a desired position. A device may then be passed through the opening 414 at the distal end 408 at the desired position. The deflection and curvature of the elongate sheath 402 may be controlled with the control mechanism 406 to place the opening 414 in the desired position. The delivery apparatus 400 may be used in the systems and methods disclosed herein to deliver a device to a desired location, which may include a chamber of the patient's heart and may include a position adjacent the interventricular septum. The delivery apparatus 400 may have other configurations than shown in FIGS. 4A and 4B.

FIG. 5 illustrates an embodiment of an introducer sheath 500 that may be used in the systems and methods disclosed herein. The introducer sheath 500 includes a proximal end 502, a distal end 504 and a body extending between the proximal end 502 and the distal end 504. The sheath 500 may include a lumen 506, as shown in cut-away in FIG. 5. The sheath 500 may include a housing 508 at the proximal end 502 of the sheath 500. A valve 510 may be coupled to the housing 508 via tubing 512, and the valve 510 may control fluid flow through the sheath 500. The sheath 500 may be sized as an about 14 Fr sized sheath, although other sizes may be utilized as desired.

The introducer sheath 500 may be configured to be inserted into the patient's body via an introducer and may be configured to serve as an entry-way into the patient's body, and particularly the vessels of the patient's body leading to the patient's heart. The introducer sheath 500 may be configured for a neckline introduction into the patient's blood vessels, and particularly the patient's superior vena cava. The introducer sheath 500 may be configured to allow devices to pass through the lumen 506, including devices disclosed in this application. Such devices may include the delivery apparatus 400, as shown in FIG. 5 extending through the lumen 506. The introducer sheath 500 may have other configurations than shown in FIG. 5.

FIG. 6A illustrates an embodiment of a snare 600 that may be used in the systems and methods disclosed herein. The snare 600 may include a longitudinal body having a distal end 602 and a proximal end 604. A snare control 606 may be positioned at the proximal end 604 of the snare 600 and may be configured to control the operation of a snare device 608 that may be positioned at the distal end 602 of the snare 600, as shown in FIG. 6B. The snare control 606 may comprise a plunger 610 for being pushed to extend the snare device 608 from the distal end 602 of the snare 600. The plunger 610 may be biased to retract the snare device 608 from the distal end 602 of the snare 600. A force against the bias of the plunger 610 may extend the snare device 608 from the distal end 602 of the snare 600. In other embodiments, other forms of snare control 606 may be utilized.

The snare device 608 may comprise a device for snaring other components of the systems disclosed herein. As shown in FIG. 6B, the snare device 608 may comprise a loop that may extend and retract into the distal end 602 of the snare 600 depending on the operation state of the snare control 606. The snare device 608 may retract into the body of the snare 600 for an unexpanded configuration (as shown in FIG. 6A), and may expand into the expanded configuration shown in FIG. 6B. The snare device 608 may loop around another component of the system and then be retracted to the distal end 602 of the snare 600 to snare the other component. The snare device 608 may include a puncture device 612 at a tip of the snare device 608. The puncture device 612 may comprise a needle or other form of puncture device for puncturing a portion of a patient's heart. The snare device 608 may be configured such that the puncture device 612 extends out from the distal end 602 of the snare 600 without the remainder of the snare device 608 being expanded. In this manner, the snare 600 may be configured to puncture portions of the patient's heart without the remainder of the snare device 608 being fully expanded.

The snare 600 may be configured to be flexible and may be configured to pass through portions of the patient's heart, including the interventricular septum and the exterior wall of the heart. The snare device 608 may be configured to be expanded in chambers of the patient's heart, including the left or right ventricle.

In other embodiments, the configuration of the snare device 608 or puncture device 612 may be varied as desired. Multiple snares may be utilized in the systems and methods disclosed herein. Like snares, and like components of such snares, may be indicated with a prime symbol following a reference number, such as 600'.

FIG. 7A illustrates an embodiment of a deployment apparatus 700 that may be used in the systems and methods disclosed herein. The deployment apparatus 700 may include a head 702, an elongate neck 704, and a housing 706. The deployment apparatus 700 may include housings 708 and 710. The deployment apparatus 700 may be configured to deploy a heart anchor, such as the heart anchor 800 shown in FIGS. 8A-8F to an external surface of a patient's heart.

FIG. 7B illustrates a cross sectional view of the deployment apparatus 700.

Referring to FIGS. 7A and 7B, the head 702 may include a proximal end 703 and a distal end 705. The head 702 may be configured to retain the heart anchor. The head 702 may include a retainer 712 and a connection portion 713.

The retainer 712 may be configured to retain an anchor to the deployment apparatus 700. The retainer 712 may comprise a portion of the head 702. The retainer 712 may include side walls 714 that extend on opposite sides of the anchor to retain the anchor to the deployment apparatus 700. The anchor may be positioned in a gap 716 positioned between the side walls 714. In other embodiments, the retainer 712 may have a different configuration than shown in FIGS. 7A and 7B.

Figure 7C:
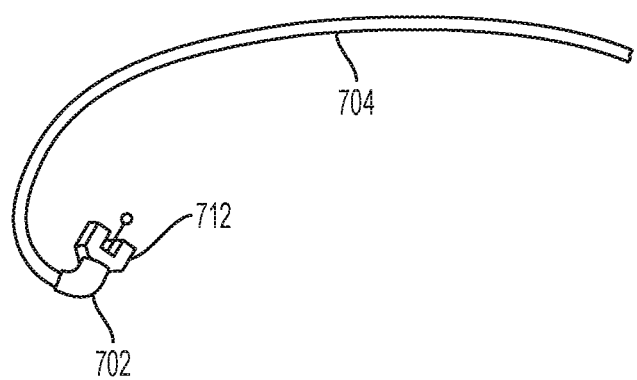
FIG. 7C illustrates a side view of the elongate neck of the deployment apparatus shown in FIG. 7A.
Figure 8A:
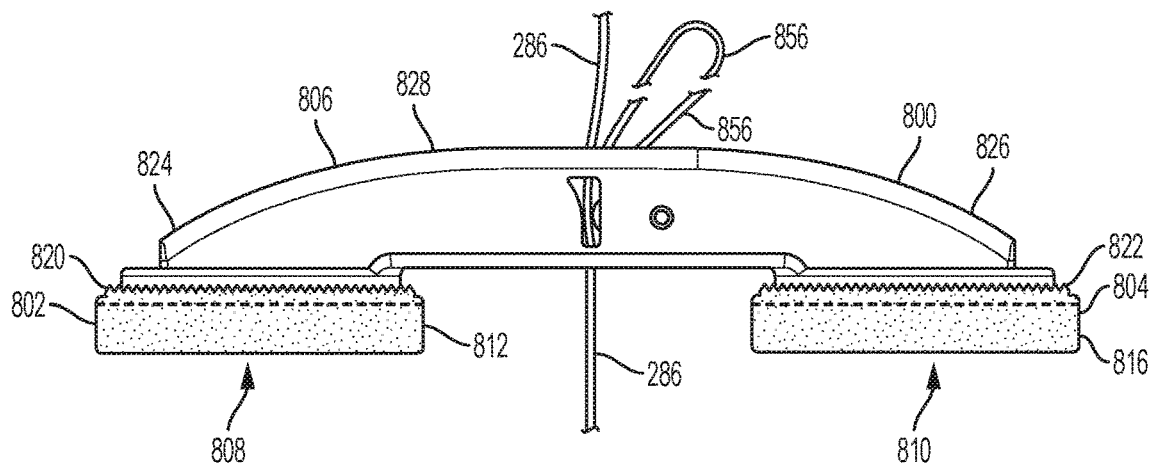
FIG. 8A illustrates a side view of a heart anchor according to an embodiment of the present disclosure.

The retainer 712 may include an opening 718 of a lumen 720. The lumen 720 may be configured to pass a device therethrough, such as a snare 722 or a tension member (such as tension member 286 shown in FIG. 2G), or a lock retainer member 856 as shown in FIG. 8A. The lumen 720 may be configured to receive the snare 722 and the tension member. The body of a snare 722, for example, is shown passing through the lumen 720 and the opening 718 in FIG. 7B.

Figure 7D:
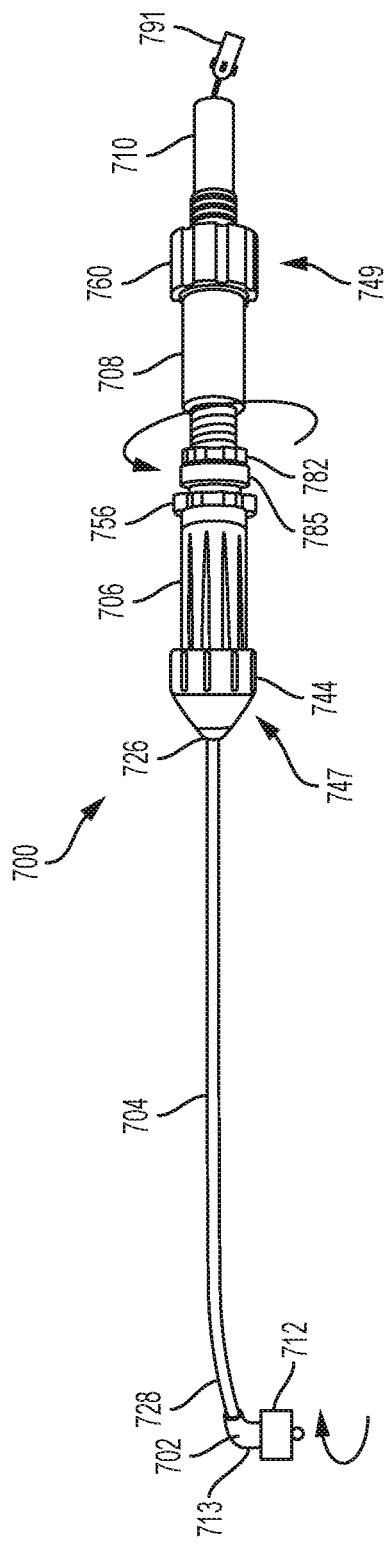
FIG. 7D illustrates a side view of the deployment apparatus shown in FIG. 7A with a retainer rotated from the position shown in FIG. 7A.

The retainer 712 may be configured to rotate in position. A bearing surface 711 may be positioned between the retainer 712 and the remaining portion of the head 702 to allow the retainer 712 to rotate. The retainer 712 may be configured to rotate about the axis of the end of the lumen 720 at the opening 718. The rotation of the retainer 712 may cause the anchor coupled thereto to rotate, to vary the orientation of the anchor relative to a portion of the patient's heart for the anchor to be deployed upon. The retainer 712 may be configured to rotate for 360 degrees, or a different amount as desired. FIG. 7D illustrates the rotation of the retainer 712.

The connection portion 713 of the head 702 may connect the retainer 712 to the elongate neck 704. The connection portion 713 may be angled to angle the position of the retainer 712 relative to the elongate neck 704. The connection portion 713 may be curved, as shown in FIG. 7B. The connection portion 713 may be configured to be angled at about 90 degrees, as shown in FIG. 7B, or may be angled to a greater or lesser amount as desired. The connection portion 713 may include a lumen 724 that the lumen 720 may pass through.

The elongate neck 704 may include a proximal end 726 and distal end 728 and a body extending from the proximal end 726 to the distal end 728. The distal end 728 of the elongate neck 704 may couple to the proximal end 703 of the head 702. The elongate neck 704 may include a lumen 730 that may extend the length of the elongate neck 704. The lumen 730 may be configured for devices to pass through, such as the snare 722 or a tension member (such as tension member 286 shown in FIG. 2G), or a lock retainer member 856 as shown in FIG. 8A. The lumen 730 may couple to the opening 718 and may be configured to pass devices through the lumen 720 and opening 718. The lumen 730 may be separate from the lumen 720 or may be integral with the lumen 720.

The elongate neck 704 may include a lumen 732 that one or more control members 734 may pass through. The lumen 732 may be positioned exterior of the lumen 730 and may surround the lumen 730. The elongate neck 704 may include an outer sheath 736 that extends around the lumens 730, 732 and forms the outer surface of the elongate neck 704. The outer surface may be configured to be smooth to allow for a smooth entry into the patient's body.

The one or more control members 734 may be elongate members that extend along the length of the elongate neck 704. The control members 734 may comprise wires or rods, or other forms of control members. The control members 734 may couple to a portion of the elongate neck 704 or head 702. The control members 734 may be configured to deflect the elongate neck 704 to move the head 702 in a similar manner as discussed in regard to elongate neck 104 of FIGS. 1A-1F. For example, the control members 734 may be configured such that one control member is pulled along the elongate neck 704. The movement of the control member 734 along the elongate neck 704 may cause the elongate neck 704 to deflect or curve along its length. In other embodiments, other forms of control may be applied, for example, one or more control members 734 may be configured to rotate to cause the elongate neck 704 to deflect or curve, or other forms of control may be utilized. In one embodiment, one control member 734 may be configured to be pushed while the other control member is pulled along the elongate neck 704, to cause the elongate neck 704 to deflect or curve. In one embodiment, only one control member 734 may be pushed or pulled along the length of the elongate neck 704 to control deflection of the elongate neck 704.

The elongate neck 704 may be flexible and configured to deflect along its length. The elongate neck 704 may be configured to curve. The deflection of the elongate neck 704 may operate similarly as the deflection of the elongate neck 104 shown in FIG. 1E. FIG. 7C, for example, illustrates the deflection of the elongate neck 704. The elongate neck 704 may be configured to curve such that the head 702 rotates by approximately 180 degrees, and the retainer 712 may face the elongate neck 704. The elongate neck 704 may be configured to curve at only a portion of the elongate neck 704, for example a distal portion of the elongate neck 704, or a portion proximate to the head 702. The amount of deflection, or curvature, may vary as desired. The deflection may occur in multiple planes of the elongate neck 704, for example, if multiple control members 734 are pulled at various orientations along the lumen 730. The elongate neck 704 may deflect in a downward direction as shown in FIG. 7C, or may deflect in a relative upward direction or right direction (into the page in FIG. 7C) or left direction (out of the page in FIG. 7C). Combinations of directions of movement may occur based on the orientation and movement of the control members 734.

The housing 706 may be positioned at the proximal end 726 of the elongate neck 704. The housing 706 may couple to the elongate neck 704 and may be configured for a user to grip. The housing 706 may be configured as a handle including an outer surface 738 for the user to grip. The housing 706 may have a proximal end 740 and a distal end 742.

The lumen 730 may extend through the housing 706. The lumen 730 in the housing 706 may comprise a separate and distinct lumen, or may comprise the lumen 730 that extends through the elongate neck 704.

The housing 706 may include a control device 744. The control device 744 may be configured for a user to manipulate or otherwise control the elongate neck 704. The control device 744 may comprise a rotatable body (as shown in FIGS. 7A and 7B) and may be rotated to control the elongate neck 704. In other embodiments, other forms of control devices may be utilized. The control device 744 may be configured to control the one or more control members 734 to control the elongate neck 704. The control device 744 may operate similarly as control device 162 of FIGS. 1A-1F. For example, the control device 744 may move the one or more control members 734 to deflect the elongate neck 704. The control device 744 may be configured to engage the one or more control members 734. The control device 744 may include a gear drive 746 or other form of engagement, for engaging and moving the one or more control members 734. The gear drive 746 may pull or tension the control members 734 to deflect the elongate neck 704. In embodiment, the gear drive 746 may alternatively move the control members 734 in opposite directions to deflect the elongate neck. In other embodiments, other forms of control may be utilized. In one embodiment, a single control member 734 may be pushed and pulled to deflect the elongate neck 704.

The housing may include a cavity 748 for the one or more control members 734 to extend in.

The control device 744 and one or more control members 734 may comprise a control mechanism 747 for deflecting the elongate neck 704 and varying the orientation of the retainer 712 as discussed. In other embodiments, other forms of control mechanisms may be used.

The deployment apparatus 700 may include a tension mechanism 749. The tension mechanism 749 may be configured to tension a tension member of the anchor (such as tension member 286 shown in FIG. 2G). The tension mechanism 749 may include the housing 708, the housing 710, and the lock 750.

The housing 708 may include a proximal end 752, a distal end 754, and a body extending from the proximal end 752 to the distal end 754. The distal end 754 of the housing 708 is coupled to the proximal end 740 of the housing 706. The housing 708 may include a rotation device 756 at the distal end 754 of the housing 706. The rotation device 756 may comprise a rotation ring that may be inserted into a receiver 758 positioned at the proximal end 740 of the housing 706. The receiver 758 may comprise a slot positioned at the proximal end 740 of the housing 706. The rotation device 756 may be configured to rotate within the slot to rotate relative to the housing 706. A proximal end of the rotation device 756 may be coupled to the housing 708 such that the housing 708 rotates with the rotation device 756. For example, the rotation device 756 may couple to the housing 708 with a threaded coupling or other form of secure coupling. The configuration of the rotation device 756 and receiver 758 may vary from the configuration shown in FIGS. 7A and 7B.

The proximal end 752 of the housing 708 may include a control device 760. The control device 760 may comprise a rotatable body (as shown in FIGS. 7A and 7B) and may be rotated to move the housing 710 relative to the housing 708. The control device 760 may comprise a knob or other form of rotatable body for control by a user. In other embodiments, other forms of control devices may be utilized. The control device 760 may include a gear drive 762 or other form of engagement, for engaging and moving the housing 710. The gear drive 762 may comprise threading on the interior surface of the control device 760. The gear drive 762 may move the housing 710 in a proximal direction when the control device 760 is rotated in one direction, and may move the housing 710 is a distal direction when the control device 760 is rotated in an opposite direction. In other embodiments, other forms of control may be utilized.

The housing 708 may include a cavity 764 for receiving the housing 710. The lumen 730 may extend through the housing 706 and may extend into cavity 764. The lumen 730 in the housing 708 may comprise a separate and distinct lumen, or may comprise the lumen 730 that extends through the elongate neck 704.

The housing 710 may include a distal end 766 and a proximal end 768 and a body extending from the distal end 766 to the proximal end 768. An outer surface of the housing 710 may include a gear drive 765 configured to engage the gear drive 762 of the control device 760. The gear drive 765 may comprise threading on the outer surface of the control device 760. As the gear drive 762 of the control device 760 is rotated, the engagement of the gear drives 762, 765 may cause the housing 710 to slide within the housing 708. The housing 710 may include a lumen 770. The lumen 770 in the housing 710 may comprise a separate and distinct lumen, or may comprise the lumen 730 that extends through the elongate neck 704. The housing 710 may include a port 772 at the proximal end of the housing 710 for devices to pass through the lumen 770 and lumen 730, such as the snare 722 or a tension member (such as tension member 286 shown in FIG. 2G).

A protrusion 769 may extend outward from the housing 710. The protrusion 769 may be configured to contact inner walls of the housing 708 to limit movement of the housing 710 relative to housing 708.

Figure 27:
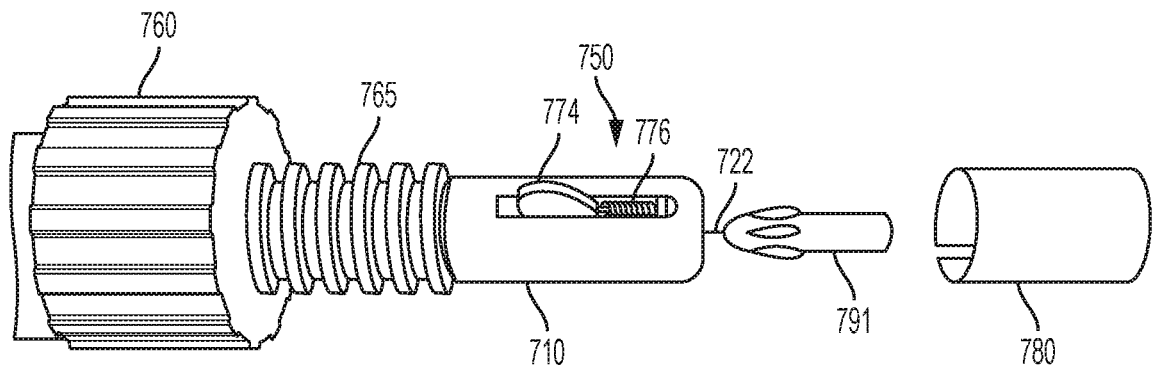
FIG. 27 illustrates a side view of a proximal end of a deployment apparatus according to an embodiment of the present disclosure.

The lock 750 may be coupled to the housing 710. The lock 750 may include a rotatable body 774 and a biasing device 776. The rotatable body 774 may be pivotally coupled to the housing 710 such that the rotatable body 774 may pivot within the lumen 770 and relative to the housing 710. The rotatable body 774 may rotate about a pivot. The biasing device 776 may bias the rotatable body 774 to a locked state, in which the rotatable body 774 is pressed towards a surface of the lumen 770 (as shown in FIG. 7B). The rotatable body 774 in the locked state may press a device against a surface of the lumen 770 to prevent movement of the device. For example, as shown in FIG. 7B, the body of the snare 722 is pressed by the rotatable body 774 and locked in position. Other devices, such as a tension member (such as tension member 286 shown in FIG. 2G) may be locked in position in a similar manner. The opposite end of the rotatable body 774 may comprise a protrusion 778 that extends outward from the outer surface of the housing 710 when the lock 750 is in the locked state. The protrusion 778 may be pressed with an unlock ring 780 (as shown in FIG. 27) that may be slid over the outer surface of the housing 710 to move the lock 750 to the unlocked state. The rotatable body 774 may be rotated away from the surface of the lumen 770 in the unlocked state and a device may be released to slide within the lumen 770. In other embodiments, other forms of locks may be utilized as desired.

The tension mechanism 749 may be configured such that the lock 750 locks a device in position relative to housing 710. As discussed, the device may be a tension member of the anchor (such as tension member 286 shown in FIG. 2G). Upon the lock 750 locking the device in position, the control device 760 may be operated to vary a position of the housing 710 relative to housing 708. The housing 710 may be moved proximally to accordingly draw the device positioned therein proximally. The opposite end of a device passing through the lumens 730, 720 may be drawn proximally. The opposite end may be fixed to another anchor or a portion of the patient's heart. The device may be tensioned by the device being drawn proximally. The tension mechanism 749 may have a different configuration than shown in FIGS. 7A and 7B in other embodiments.

The deployment apparatus 700 may include a lock control mechanism 781. The lock control mechanism 781 may be configured to control a lock of an anchor (such as the lock 838 shown in FIG. 8D) remotely and set a locked or unlocked state of the anchor. The lock control mechanism 781 may include a receiver 782.

The receiver 782 may be configured to receive a lock retainer member 856 of an anchor, such as the lock retainer member 856 shown in FIG. 8A. The receiver 782 may be configured to move along the length of the housing 708 to move the relative position of the lock retainer member 856. The receiver 782 may comprise a ring 783 with an opening that the lock retainer member 856 is passed through and may be looped around. The receiver 782 may include a slide body 784 coupled to the ring 783 for sliding the ring 783 relative to the housing 708. The slide body 784 may be configured such that a portion of the slide body 784 rotates upon the outer surface of the housing 708, while a portion coupled to the ring 783 does not rotate. The slide body 784 may be threaded to threading on the outer surface of the housing 708, such that rotation of the slide body 784 causes the slide body 784 to slide. The non-rotating portion of the slide body 784 may prevent the ring 783 from rotating as slide body 784 slides upon the housing 708.

The lock control mechanism 781 may include a stop 785. The stop 785 may be configured to stop the movement of the receiver 782 along the outer surface of the housing 708. The stop 785 may be configured to be variably positioned on the housing 708. The stop 785 may comprise a ring body that may threaded to threading on the outer surface of the housing 708. The stop 785 may abut the receiver 782 along the outer surface of the housing 708 to stop movement of the receiver 782.

The lock control mechanism 781 may operate, as a lock retainer member 856 may pass from the anchor through the lumen 720, 730. The lock retainer member 856 may then pass through an opening 786 in a wall of the housing 708 and couple to ring 783. As the receiver 782 is moved towards the distal end 742 of the housing 706 and away from the opening 786, the lock retainer member 856 may be pulled through the lumen 720, 730 and away from the anchor to move a lock of an anchor to an unlocked state. The receiver 782 may be moved away from the distal end 742 of the housing 706 and towards the opening 786 to slide the lock retainer member 856 through the lumen 720, 730 and towards the anchor to move a lock of an anchor to a locked state. The movement of the receiver 782 accordingly controls the operation of a lock of an anchor.

The lock control mechanism 781 may include the lock retainer member 856. FIG. 8A illustrates the lock retainer member 856. The lock retainer member 856 may comprise a tether, and may be in the form of a cord, or other form of lock retainer member. The lock retainer member 856 may be looped around the ring 783 of the receiver 782, and may pass through the opening 786 and through the lumen 720, 730 and through the opening 718 to the anchor. In other embodiments, other forms of lock retainer members may be utilized.

The deployment apparatus 700 may include a control mechanism for controlling rotation of the retainer 712. The control mechanism may include the housing 708 and the rotation device 756. The housing 708 may be coupled to the lumen 730 such that the rotation of the housing 708 rotates the lumen 730 within the outer sheath 736 of the elongate neck 704. The lumen 703 may be coupled to the retainer 712 such that the rotation of the housing 708 rotates the portion of the head 702 comprising the retainer 712 in position relative to the connection portion 713 of the head 702. FIG. 7D, for example, illustrates the portion of the head 702 comprising the retainer 712 rotating in position relative to the connection portion 713 of the head 702. The housing 706 may remain non-rotational during such movement. The housing 708 may be configured to rotate relative to the housing 706 due to the rotation of the rotation device 756 in the housing 706, as previously described. In other embodiments, a separate control device, similar to the control device 163 discussed in regard to the access apparatus 100 of FIGS. 1A and 1B, may be utilized to rotate the retainer 712 in position.

The control mechanism for controlling rotation of the receiver 712 may operate together with the control mechanism 747 to comprise a control mechanism for controlling the deflection of the elongate neck 704 and controlling the rotation of the retainer 712. In such a manner, the user may be able to control the deflection of the elongate neck 704 and the rotation of the retainer 712 independently, to position an anchor in a desired position on the patient's heart.

The deployment apparatus 700 may include the snare 722. The snare 722 may include a proximal end 788 and a distal end 789 and a body extending between the proximal end 788 and the distal end 789. The snare 722 may include a snare device 790 at the distal end 789 of the snare 722. The snare device 790 may comprise a loop, or may have another form as desired. The snare device 790 may be configured to couple to a tension member of an anchor (such as tension member 286 shown in FIG. 2G). A handle 791 may be positioned at the proximal end 788 of the snare 722. The handle 791 may be configured for a user to pull the snare 722 through the lumen 720, 730, 770. The snare 722 may be pulled through the lumen 720, 730, 770 upon a tension member of an anchor being coupled to the snare device 790, so that the tension member is drawn through the lumen 720, 730, 770. The tension member drawn through the lumen 720, 730, 770 may be engaged with the lock 750 and tensioned with the tension mechanism 749.

The deployment apparatus 700 may be configured to deploy an anchor at a desired orientation due to the deflection of the elongate neck 704 and the rotation of the retainer 712. The snare 722 may be utilized to pass a tension member of an anchor through the lumen of the deployment apparatus 700. The tension mechanism 749 may be used to tension the tension member positioned within the lumen of the deployment apparatus 100. The lock control mechanism 781 may be configured to set the lock of the anchor in a locked state upon the tension mechanism 749 tensioning the tension member to a desired degree. The deployment apparatus 700 may then be released from the anchor, which may be in position on a portion of a patient's heart. In other embodiments, the configuration of the deployment apparatus 700 may vary from the configuration shown in FIGS. 7A and 7B.

FIG. 8A illustrates an embodiment of a heart anchor 800 that may be used in the systems and methods disclosed herein. The heart anchor 800 may be utilized in a heart splint (for example the splint 3100 shown in FIG. 31, or other splints).

The heart anchor 800 may include a first support pad 802 and a second support pad 804. The anchor 800 may include a bridge 806 coupling the first support pad 802 to the second support pad 804.

The support pads 802, 804 may each be configured to press against a surface of the heart. The support pads 802, 804 may each include respective pressing surfaces 808, 810 for pressing against the surface of the heart. The pressing surface 808, 810 may be configured to be planar, or may have another shape as desired. The first support pad 802 may include a side wall 812 that extends away from the pressing surface 808 to a coupling surface 814 (marked in FIG. 8C) that faces opposite the pressing surface 808. The second support pad 804 may similarly include a side wall 816 that extends away from the pressing surface 810 to a coupling surface 818 (marked in FIG. 8C) that faces opposite the pressing surface 810.

Figure 8B:
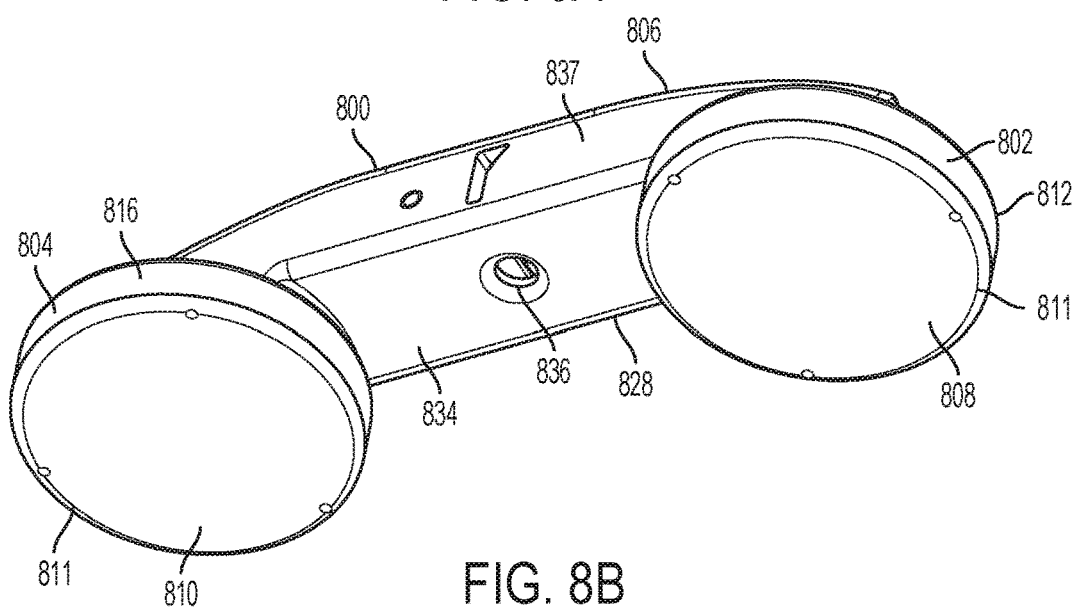
FIG. 8B illustrates a bottom perspective view of the heart anchor shown in FIG. 8A according to an embodiment of the present disclosure.

The support pads 802, 804 may include respective covers 820, 822 that form the outer surface of the respective support pads 802, 804. The covers 820, 822 may be made of a cloth or other material, and the material of the covers may be suitable for contacting a portion of a patient's heart. In other embodiments, the covers 820, 822 may not be utilized. FIG. 8B for example, shows the support pads 802, 804 without the covers 820, 822 such that the outer surface of the support pads 802, 804 comprise the pressing surfaces 808, 810. The support pads 802, 804 may include location markers 811 that may allow the position of the anchor 800 in the patient's body to be determined and verified. The location markers 811 may be radio-opaque markers that may extend around an outer periphery of the support pads 802, 804 and may be constructed as part of the support pads 802, 804.

The support pads 802, 804 may have a circular shape, or in other embodiments may have a different shape as desired. The support pads 802, 804 may be configured to be sufficiently firm to apply a force to a portion of a patient's heart. The support pads 802, 804 may be sized to distribute the force to a relatively large portion of the outer surface of the patient's heart.

The bridge 806 may extend from the first support pad 802 to the second support pad 804. The bridge 806 may comprise a laterally extending body. The bridge 806 may comprise a bar that extends between the first support pad 802 and the second support pad 804. The bridge 806 may include a first end portion 824 and a second end portion 826, and a central portion 828 positioned between the end portions 824, 826. The bridge 806 may have a top surface 830 (marked in FIG. 8C) that has a curved profile. The curved profile may allow the shape of the bridge 806 to be atraumatic to the surrounding portion of the patient's body when the anchor 800 is implanted.

Figure 8C:
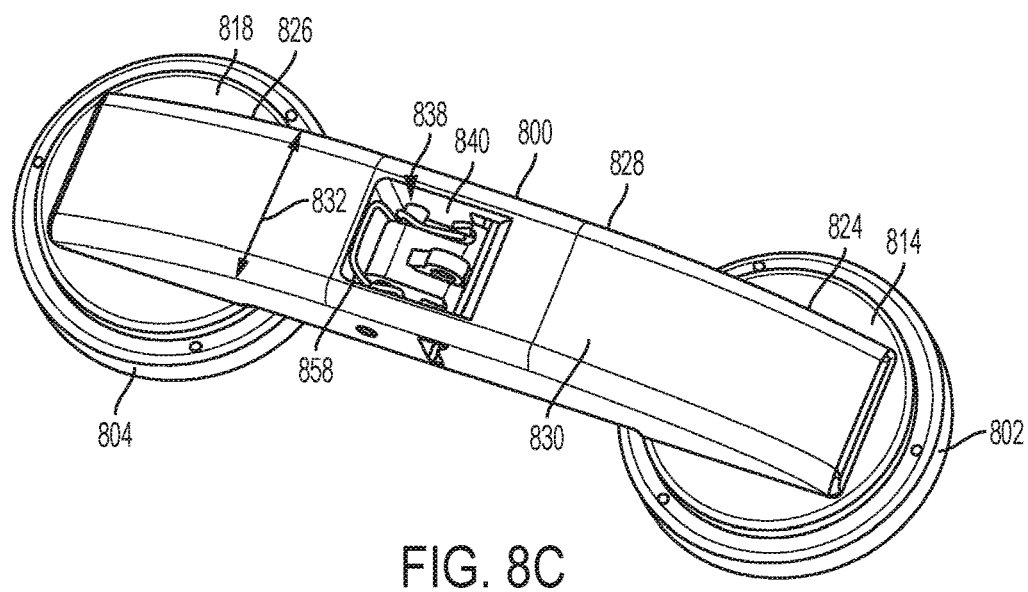
FIG. 8C illustrates a top perspective view of the heart anchor shown in FIG. 8A according to an embodiment of the present disclosure.

The bridge 806 may couple to the first support pad 802 at the first end portion 824 of the bridge 806 and may couple to the second support pad 804 at the second end portion 826 of the bridge 806. The bridge 806 may couple to central portions of the respective support pads 802, 804. The bridge 806 may couple to the support pads 802, 804 such that the support pads 802, 804 face the same direction and may each apply a force to the same surface. The bridge 806 may be offset from the support pads 802, 804. Referring to FIG. 8C, a width 832 of the bridge may be less than the diameter of each support pad 802, 804.

The bridge 806 may have a strength sufficient to firmly press both the support pad 802, 804 upon a tension member 286 being tensioned at the central portion 828 of the bridge 806. The bridge 806 may comprise a rigid body.

FIG. 8B illustrates a bottom perspective view of the anchor 800. The covers 820, 822 are not shown in FIG. 8B. The bottom surface 834 of the bridge 806 is visible including opening 836. The bridge 806 may include one or more side walls 837 extending from the bottom surface 834 to the top surface 830. Another side wall 839 is visible in FIG. 8F.

FIG. 8C illustrates a top perspective view of the anchor 800. A lock 838 is visible within a receiver 840 of the anchor 800.

Figure 8D:
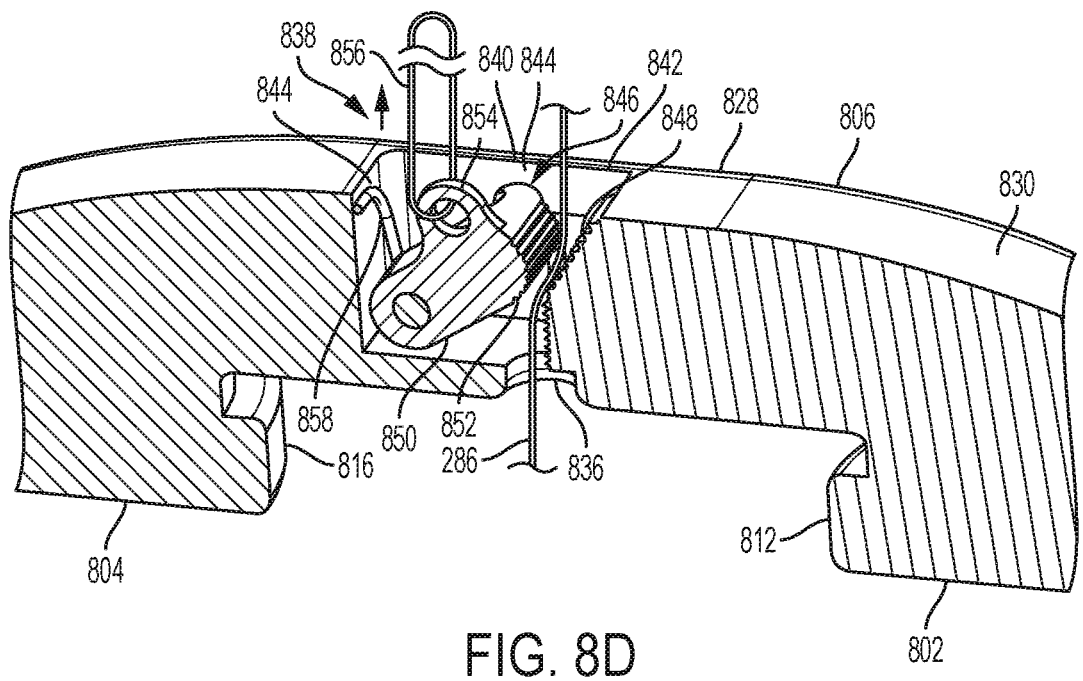
FIG. 8D illustrates a cross sectional view of the heart anchor shown in FIG. 8A according to an embodiment of the present disclosure.

FIG. 8D illustrates a cross sectional view of the anchor 800. A cross sectional view of the lock 838 and the receiver 840 is provided. The receiver 840 may be coupled to the bridge 806 and configured to receive the tension member 286.

The receiver 840 may include an opening 842 in the top surface 830 of the bridge 806 and may include the opening 836 in the bottom surface 834 of the bridge 806. The receiver 840 may include one or more side walls 844 that define a cavity 846 in the bridge 806. One of the side walls 844 may include a locking surface 848. The locking surface 848 may comprise a surface for the tension member 286 to be pressed against upon operation of the lock 838. The locking surface 848 may include a grip surface, which may include ridges or another gripping structure that may improve a grip of the locking surface 848.

The lock 838 may be positioned within the receiver 840. The lock 838 may be coupled to the bridge 806. The lock 838 may be configured to vary from an unlocked state in which the tension member 286 is unlocked in the receiver 840 to a locked state in which the tension member 286 is locked in the receiver 840. The lock 838 may be configured to move from the locked state to the unlocked state.

The lock 838 may include a rotatable body 850, which may be configured to rotate about a pivot. The pivot may comprise an axle extending through the rotatable body 850, or another form of pivot. The rotatable body 850 may be configured to rotate within the cavity 846 of the receiver 840. The rotatable body 850 may comprise a cam body with a surface of the body 850 comprising a locking surface 852. The cam body may allow the force from the lock 838 against the tension member 286 to increase as tension is increased upon the tension member 286. The locking surface 852 may comprise a surface to press against the tension member 286, and press the tension member 286 against the locking surface 848, to lock the tension member 286 in position within the receiver 840. The locking surface 852 may include a grip surface, which may include ridges or another gripping structure that may improve a grip of the locking surface 852.

The lock 838 may include a connector 854 for coupling with the lock retainer member 856. The connector 854 may include an aperture for the lock retainer member 856 to be passed through.

The lock 838 may include a biasing device 858. The biasing device 858 may bias the lock 838 to a locked state, in which the rotatable body 850 is pressed towards the locking surface 848. The rotatable body 850 in the locked state may press the tension member 286 against the locking surface 848 to prevent movement of the tension member 286 and to lock the tension member 286 to the anchor 800. The biasing device 858 may comprise a spring, or other form of biasing device as desired.

The lock retainer member 856 may be pulled to oppose the biasing force of the biasing device 858 and may retain the lock 838 in an unlocked state. The lock retainer member 856 may be configured to couple to the rotatable body 850 to hold the rotatable body 850 in the unlocked state. Such an unlocked state is shown in FIG. 8D. The locking surface 852 of the rotatable body 850 is pulled away from the locking surface 848 of the receiver 840 and the tension member 286 may slide within the receiver 840 and through the openings 836, 842.

The tension member 286 may be slid within the receiver 840 to tension the tension member 286 before the lock 838 is moved to the locked state. The tension member 286 may be tensioned with a mechanism such as the tension mechanism 749 of the deployment apparatus 700, while the anchor 800 is coupled to the retainer 712 of the deployment apparatus 700. Upon a desired amount of tension being reached, the lock retainer member 856 may be moved towards the anchor 800 with a mechanism such as the lock control mechanism 781 of the deployment apparatus 700. The movement of the lock retainer member 856 towards the anchor 800 may allow the biasing device 858 to move the lock 838 to the locked state.

Figure 8E:
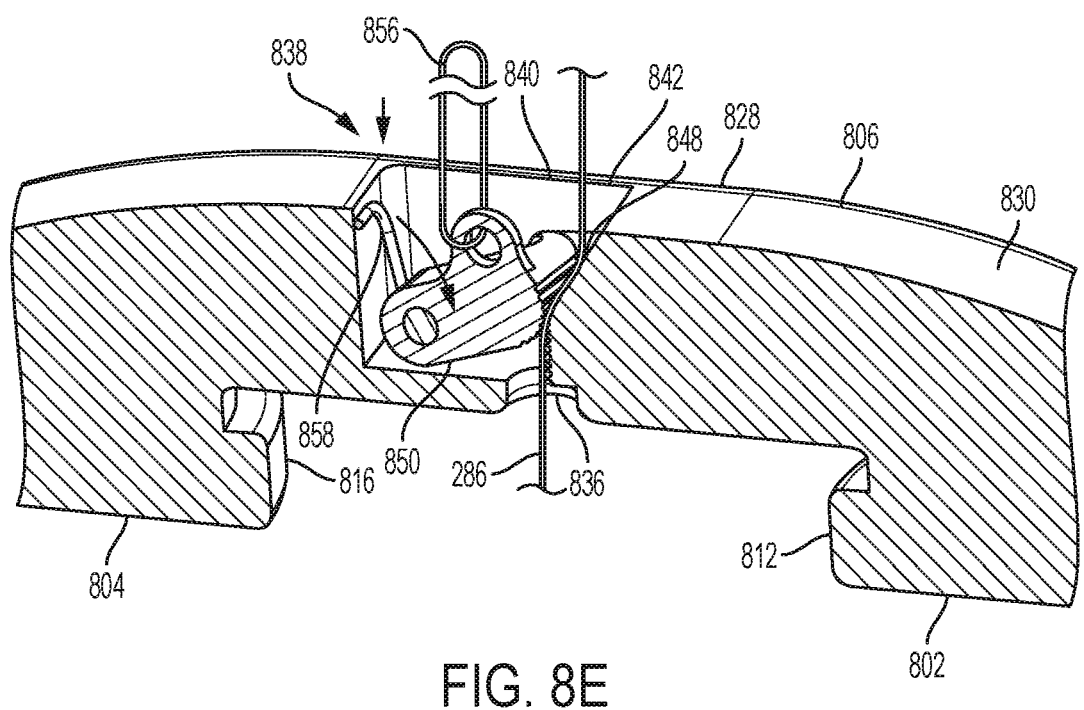
FIG. 8E illustrates a cross sectional view of the heart anchor shown in FIG. 8A according to an embodiment of the present disclosure.

FIG. 8E illustrates the lock 838 in the locked state. The biasing device 858 has moved the rotatable body 850 to press against the tension member 286 against the locking surface 848 (the ridges in the locking surface 848 are not shown for clarity). The lock 838 in the locked state presses the tension member 286 against a wall of the receiver 840. The tension member 286 is locked in position. If desired, the lock 838 may again be moved to the unlocked state by the lock retainer member 856 being pulled away from the anchor 800. The lock 838 may move to an unlocked state as shown in FIG. 8D.

The position of the lock 838 and the receiver 840 may be varied as desired. For example, the lock 838 and receiver 840 may be positioned in a support pad or other location of the anchor 800, yet remain coupled to the bridge 806. Multiple receivers 840 and locks 838 may be utilized if multiple tension members are utilized.

Figure 8F:
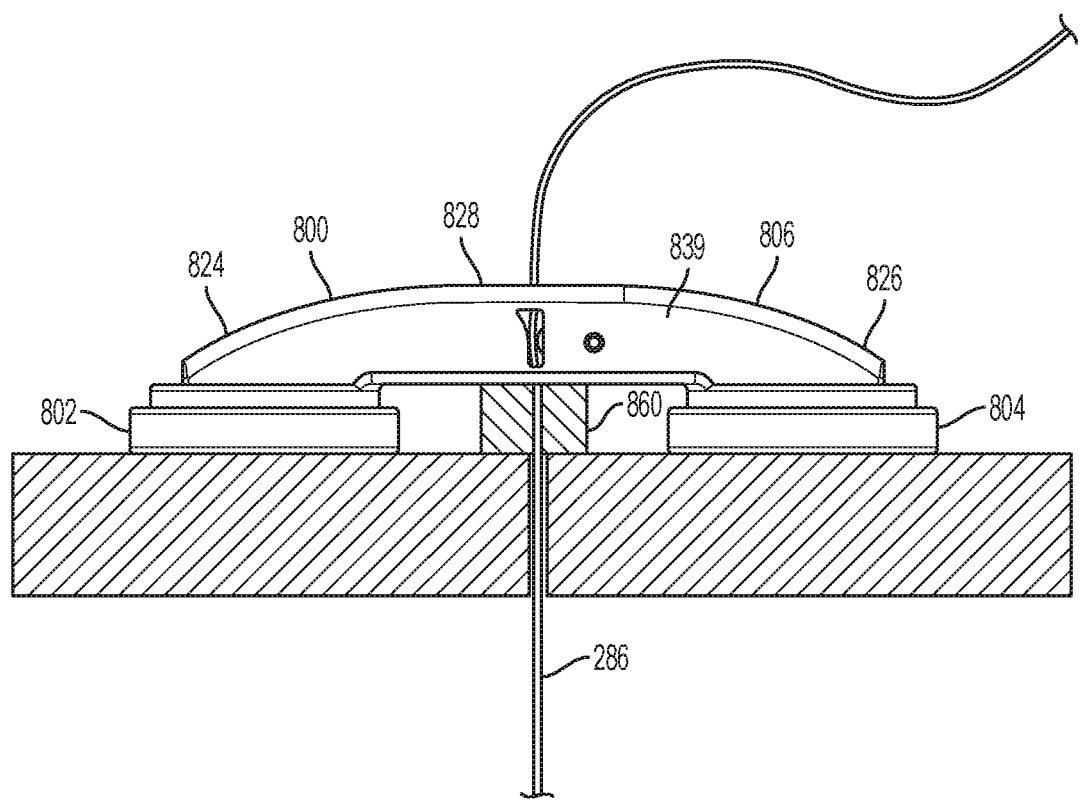
FIG. 8F illustrates a side view of the heart anchor shown in FIG. 8A according to an embodiment of the present disclosure.

FIG. 8F illustrates an embodiment of the anchor 800 in which a seal 860 may be positioned between the bridge 806 and the portion of the patient's heart being supported. The seal 860 may comprise a body that is positioned at the central portion 828 of the bridge 806 and may plug the opening of the heart that the tension member 286 passes through. The tension member 286 may pass through the central portion 828 of the bridge 806 and through the seal 860. The seal 860 may reduce the possibility of bleeding through the opening of the heart and may comprise a biocompatible material for sealing the opening of the heart. In other embodiments, the seal 860 may not be utilized.

The anchor 800 may be configured to beneficially support a portion of the patient's heart in two positions, utilizing the two support pads 802, 804. In other embodiments, a greater number of support pads may be utilized, including three or possibly more pads. A bridge may connect the pads. The anchor 800 beneficially includes the lock 838 that may be movable between the locked state and the unlocked state. As such, the tension member 286 may be tensioned at the anchor 800 and the tension member 286 may be locked in position at the anchor 800.

The apparatuses and other components disclosed herein may comprise one or more systems. The systems may be utilized in a variety of methods. The methods may include the methods disclosed herein. The methods may include a method for treating ventricular dilation and/or mitral regurgitation. The methods may include deploying a heart splint.

The steps disclosed herein are illustrative, and may be modified, varied, reordered, or excluded as desired. The "steps" referred to herein may include multiple steps, or may comprise portions of steps.

Figure 9:
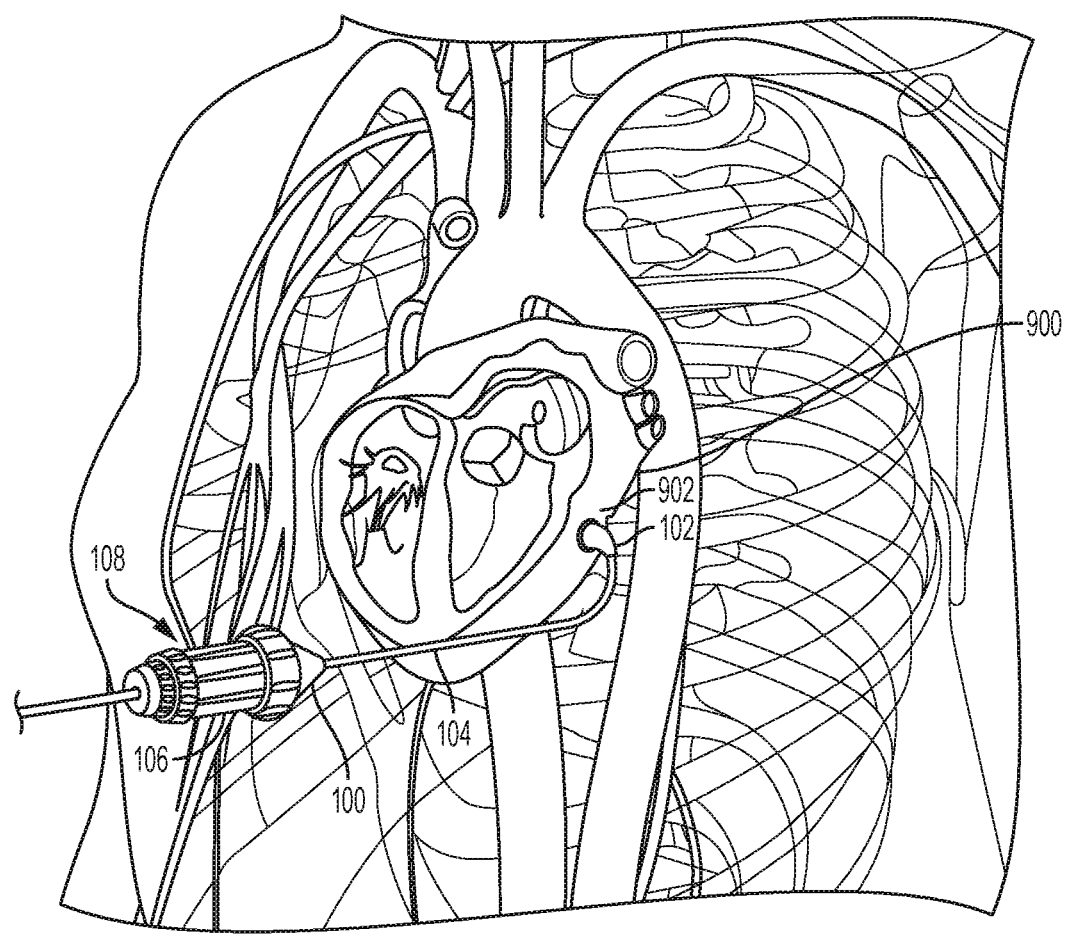
FIG. 9 illustrates a perspective view of an access apparatus being gripped to a portion of a patient's heart according to an embodiment of the present disclosure.
Figure 31:
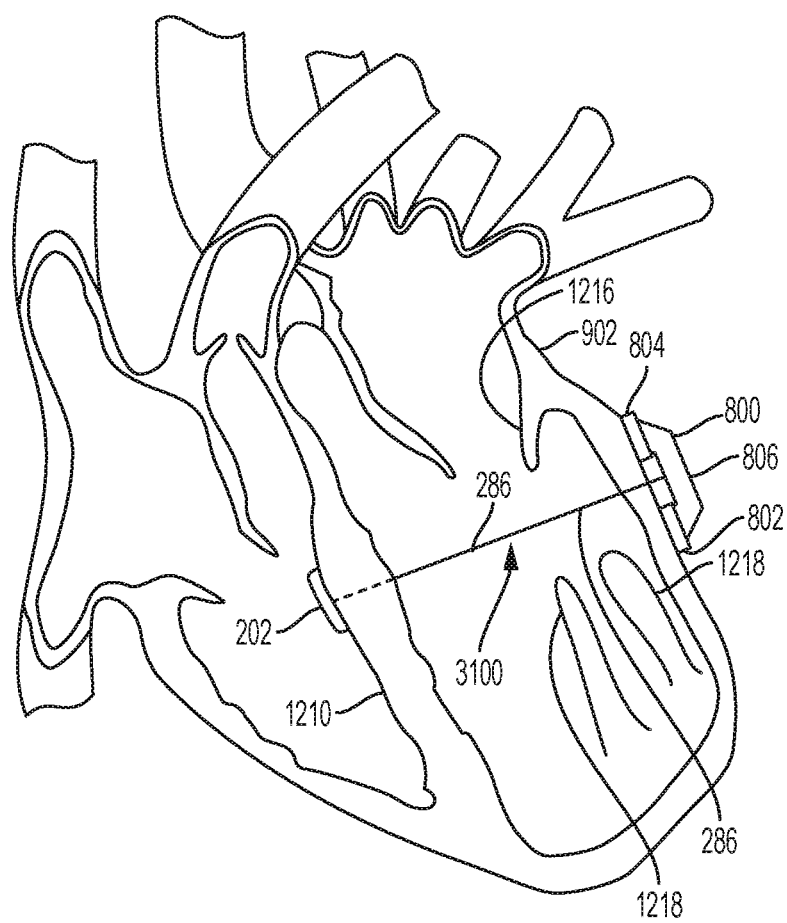
FIG. 31 illustrates a cross sectional view of a patient's heart with a heart anchor deployed according to an embodiment of the present disclosure.

FIG. 9 illustrates a step in a method of deploying a heart splint to a patient's heart 900. The resulting heart splint 3100 is shown in FIG. 31. The method may be for treating a dilated heart condition or functional heart valve regurgitation of a patient. The method may be for treating ventricular dilation and/or mitral regurgitation. The method may include reshaping a ventricle of the heart by applying pressure to the heart to reshape the geometry of heart. The method may include supporting a ventricle of the heart to reduce the presence of ventricular dilation and prevent further dilation.

The step may include accessing the patient's heart 900. An access apparatus, such as the access apparatus 100 may be inserted through a small sub-xiphoid incision into the patient's body or thoracotomy incision or intercostal incision, or possibly a more invasive incision such as a sternotomy. The access apparatus 100 may be passed through the patient's body and towards the desired portion of the external surface 902 of the patient's heart. As discussed previously, the elongate neck 104 may be configured to deflect to place the head 102 in position proximate a posterior portion of the patient's heart 900. The elongate neck 104 may be configured to wrap around a portion of the patient's heart 900 such that the posterior portion of the heart 900 is accessible even with a frontal entry of the patient's body. FIG. 9, for example, illustrates the elongate neck 104 wrapping around the patient's heart 900 and positioning the head 102 on the desired posterior portion of the heart 900. The application portion 114 of the head 102 may additionally be rotated, in a manner discussed previously, to place the head 102 in the desired position. The control mechanism 108 may be utilized to deflect the elongate neck 104 and rotate the head 102 to place the head 102 in the desired position, as discussed previously.

A user may utilize the location marker 136 (marked in FIG. 1C) to determine the location of the head 102 within the patient's body and to identify the correct position of the head 102 against the external surface 902 of the patient's heart. For example, the user may utilize an imaging system to visualize the radio-opaque location marker 136 to visualize the position of the head 102. Echo guidance or fluoroscopic guidance or both may be utilized to guide the head 102, and/or guide other components in the systems and methods disclosed herein.

Figure 10:
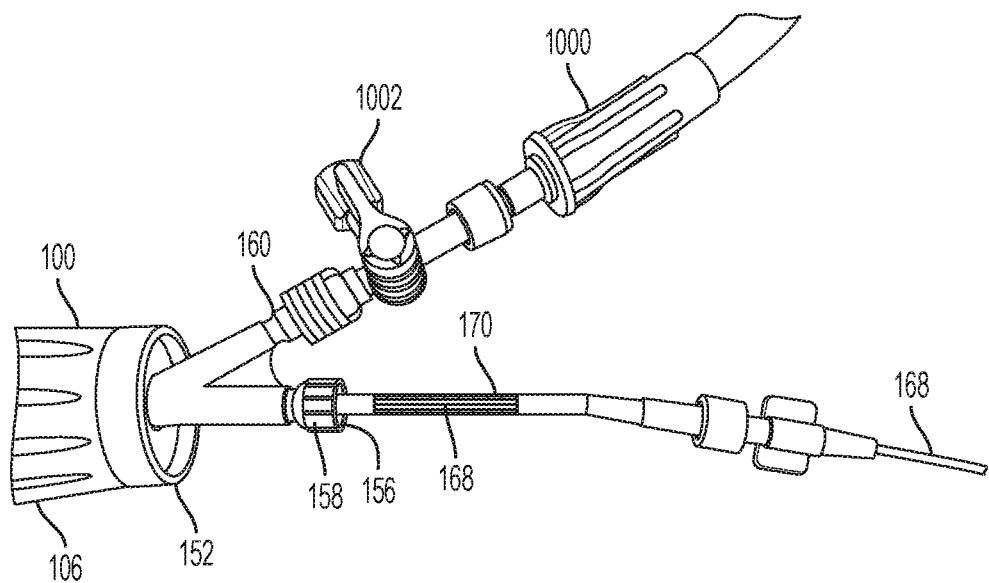
FIG. 10 illustrates a side view of the proximal end of the access apparatus shown in FIG. 1A.

The application portion 114 (marked in FIG. 1C) of the head 102 may be placed against the external surface 902 of the patient's heart via movement of the elongate neck 104 and the head 102. The application portion 114 may pass through the pericardium and contact the myocardium (the external surface 902). The application portion 114 may rest upon the myocardium. Upon the application portion 114 being placed in the desired position, vacuum suction may be applied by the head 102 to grip the head 102 to the external surface 902 of the patient's heart. The vacuum suction may be provided by the vacuum lumen 128 (marked in FIG. 1D) in the head 102. The vacuum suction may be provided in a manner discussed previously. For example, as shown in FIG. 10, a vacuum hose 1000 may be coupled to the vacuum port 160, and a valve 1002 may be opened to allow vacuum suction to be conveyed through the vacuum lumen 128 (marked in FIG. 1D) and the lumen 142 (marked in FIG. 1B). The application portion 114 may be positioned on the desired external surface 902 of the patient's heart, with the opening 126 (marked in FIG. 1C) adjacent the desired external surface 902 of the patient's heart.

If the user determines that the head 102 is gripped to an undesired position on the patient's heart 900, the vacuum suction may be released and the head 102 may be repositioned on the external surface 902 of the patient's heart as desired, and gripped again to the patient's heart 900. For example, if the user determines that the head 102 is gripped to a coronary or the like, the head 102 may be removed from that position so that the puncture device does not puncture a coronary. The location marker 136 may be utilized to confirm the head 102 is in the correct position on the patient's heart. The position may be verified through fluoroscopy.

Figure 12:
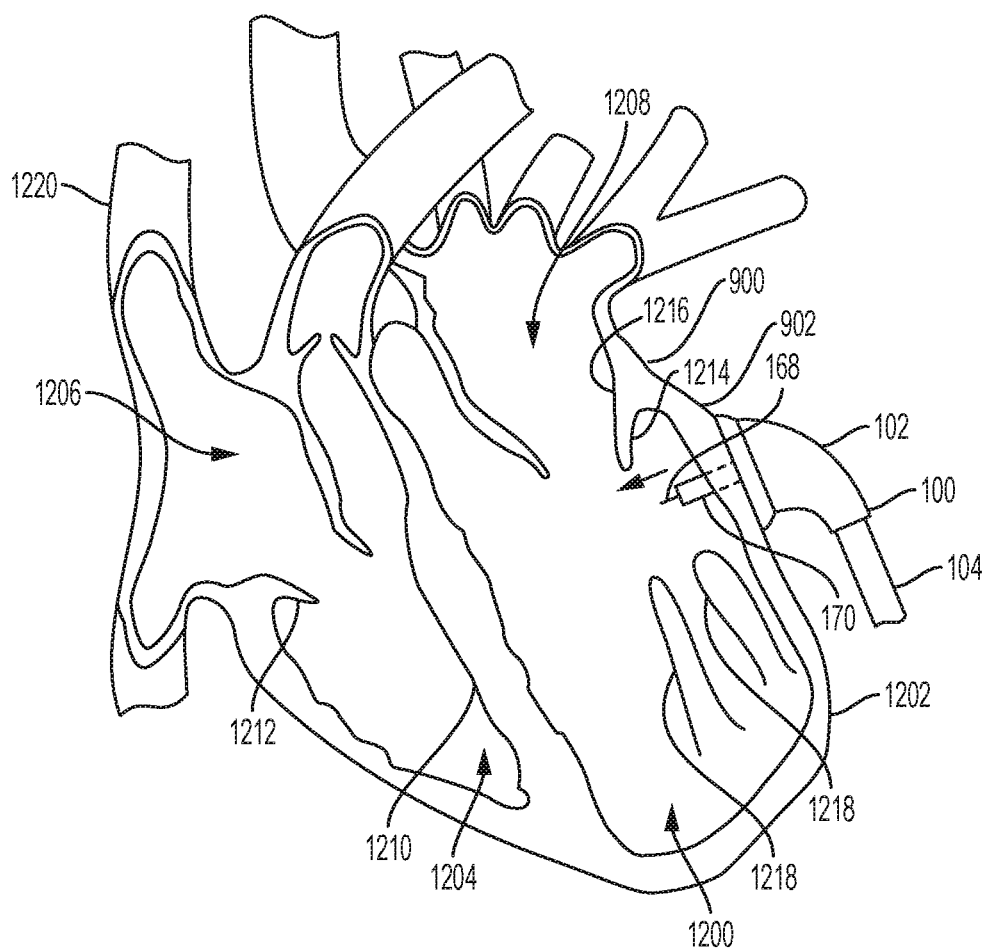
FIG. 12 illustrates a cross sectional view of a patient's heart with a sheath and puncture device being passed into the heart according to an embodiment of the present disclosure.

The head 102 may be positioned on a portion of the patient's heart 900 that is exterior of the left ventricle of the heart 900 and between the position of the mitral annulus and the papillary heads of the left ventricle. Such a position is shown in FIG. 12. In other embodiments, the head 102 may be positioned on a different portion of the patient's heart 900 as desired.

FIG. 10 illustrates a view of the proximal end 152 of the housing 106 of the access apparatus 100. The head 102 is gripped to the external surface 902 of the patient's heart. As discussed, vacuum suction may be provided by a vacuum hose 1000 to provide the vacuum suction for the head 102. A puncture device 168 and sheath 170 may be locked in position to the port 156. Upon the head 102 being gripped to the external surface 902 of the patient's heart, a puncture device 168 and sheath 170 may be passed through the port 156 to pass through the lumen 142 and the lumen 124 of the head 102 (marked in FIG. 1B). The puncture device 168 may be positioned within the sheath 170 and may be locked to the sheath 170.

FIG. 11 illustrates a view of the puncture device 168 and sheath 170 passing through the opening 126 of the head 102. At this step in the process, the head 102 may be gripped to the external surface of the patient's heart, which is not shown in FIG. 11. The puncture device 168 and sheath 170 may be passed through the port 156 shown in FIG. 10 and passed through the lumens 142, 124 of the elongate neck 104 (marked in FIG. 1B) and head 102 to exit the opening 126 as shown in FIG. 11. The puncture device 168 may protrude slightly from the sheath 170, such that the puncture device 168 is exposed for puncturing a wall of the patient's heart.

FIG. 12 illustrates a cut-away portion of the patient's heart 900 illustrating the puncture device 168 and sheath 170 advancing into the left ventricle 1200 of the patient's heart 900 from the head 102. The puncture device 168 and sheath 170 pass through the myocardium. The head 102 is shown gripped to the external surface 902 of the patient's heart 900. The puncture device 168 and sheath 170 pass through an outer wall 1202 of the patient's heart 900 comprising the myocardium. Additional portions of the patient's heart 900 are illustrated, including the right ventricle 1204, the right atrium 1206, the left atrium 1208, and the interventricular septum 1210. The tricuspid valve 1212, the mitral valve 1214 and mitral annulus 1216 and the papillary heads 1218 of the left ventricle 1200 are additionally shown. The superior vena cava 1220 is also shown.

The puncture device 168 and sheath 170 may be advanced into the left ventricle 1200 to a desired amount. For example, the puncture device 168 and sheath 170 may be advanced to a distance of about two centimeters, although other distances may be utilized as desired. The advance of the puncture device 168 and the sheath 170 may be controlled by sliding the puncture device 168 and the sheath 170 locked together through the port 156 at the proximal end 152 of the housing 106 as shown in FIG. 10.

Figure 13:
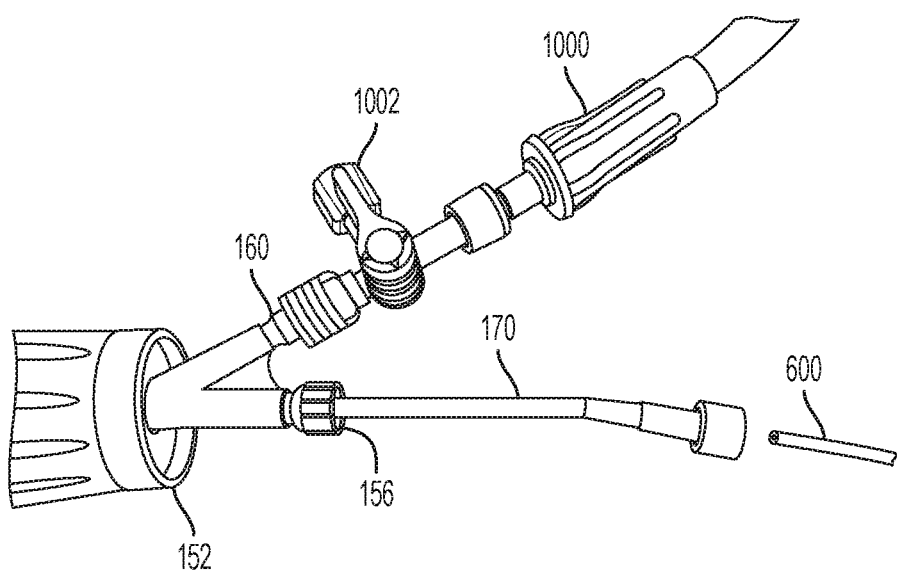
FIG. 13 illustrates a side view of the proximal end of the access apparatus shown in FIG. 1A.

Upon the puncture device 168 and sheath 170 reaching the desired position within the left ventricle 1200, the puncture device 168 may be withdrawn from the sheath 170 entirely by being pulled proximally out of the end of the sheath 170 shown in FIG. 10. The puncture device 168 may be unlocked from the sheath 170 in this procedure. Referring to FIG. 13, a snare, such as snare 600 may be inserted through the sheath 170 from the proximal end of the sheath. The snare 600 may extend through the lumen of the sheath 170 and pass through the head 102 to reach the left ventricle 1200.

Figure 14:
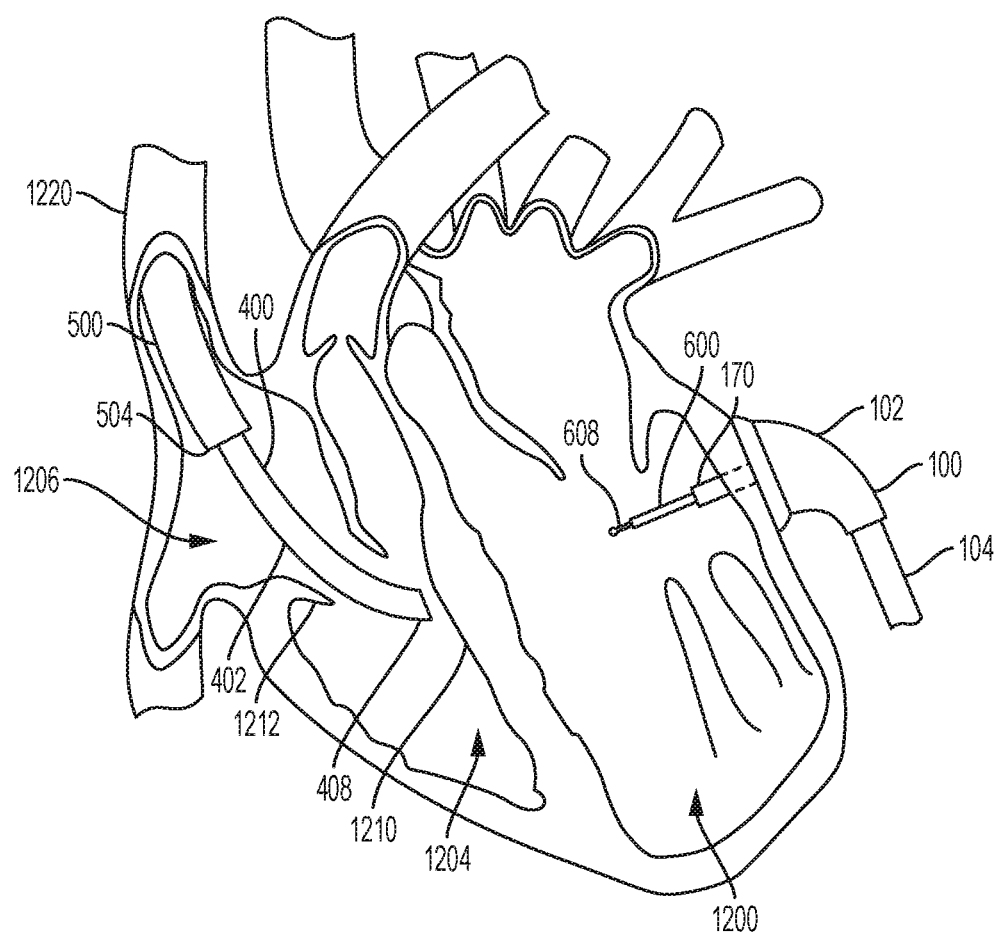
FIG. 14 illustrates a cross sectional view of a patient's heart with a snare and delivery apparatus being passed into the heart according to an embodiment of the present disclosure.

FIG. 14 illustrates the snare 600 positioned within the left ventricle 1200 and passing through the sheath 170. The snare device 608 may protrude slightly from the end of the snare 600.

An introducer sheath, such as introducer sheath 500, may be introduced into the patient's body for access to the right ventricle 1204. The introducer sheath 500 may be introduced in a neckline access procedure and pass through the superior vena cava 1220. The introducer sheath 500 may be entered into the patient's body through endovascular entry. In other embodiments, other access points and methods may be utilized.

The distal end 504 of the introducer sheath 500 may be positioned in the right atrium 1206. In other embodiments, the distal end 504 may be positioned in an alternate position.

A delivery apparatus, such as the delivery apparatus 400, may be inserted into the sheath 500. The sheath 402 of the delivery apparatus 400 may be passed through the lumen of the introducer sheath 500.

Upon the delivery apparatus 400 being passed through the sheath 500, the distal end 408 of the delivery apparatus 400 may be positioned or moved to the right ventricle 1204. The sheath 402 of the delivery apparatus 400 may extend through the tricuspid valve 1212 to reach the right ventricle 1204. The distal end 408 of the delivery apparatus 400 may be controlled to deflect to a position proximate the interventricular septum 1210. A control mechanism, such as the control mechanism 406 (marked in FIG. 4B), may be utilized to deflect the sheath 402 to the position proximate the interventricular septum 1210. The sheath 402 may be deflected such that a device passing through the lumen 412 of the sheath 402 and exiting the opening 414 (marked in FIG. 4B) will contact the interventricular septum 1210.

Figure 14A:
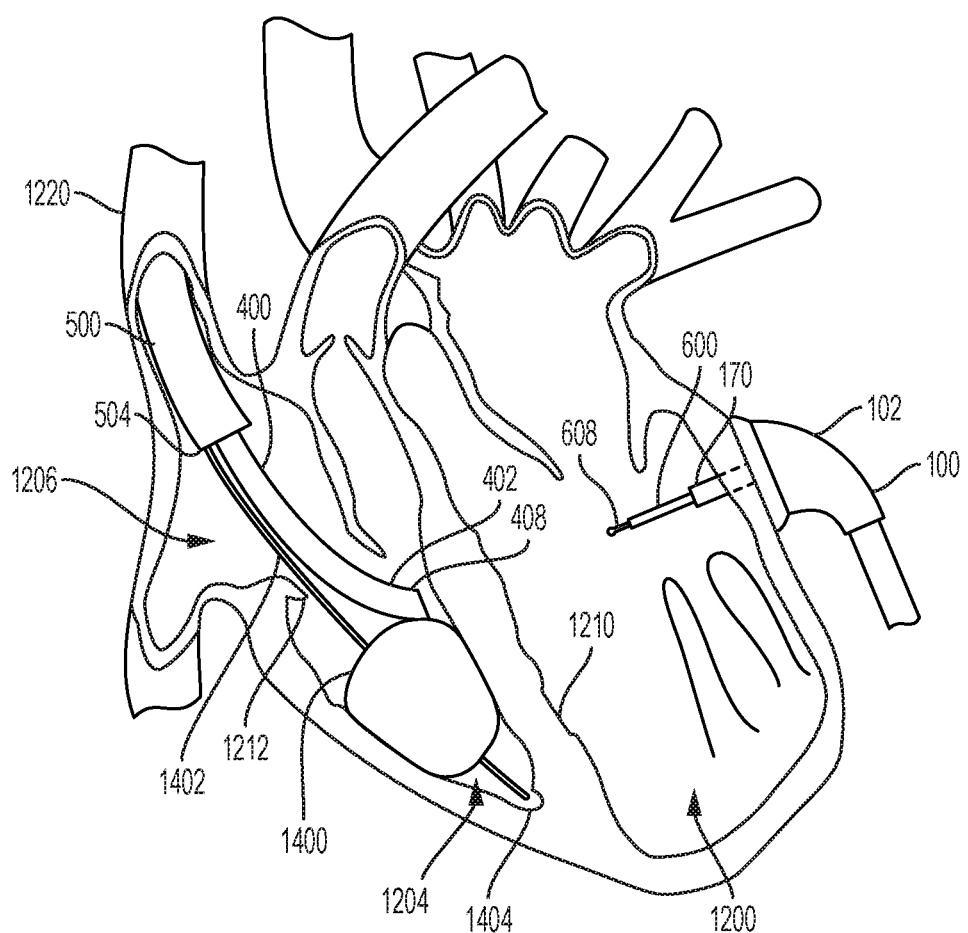
FIG. 14A illustrates a cross sectional view of a patient's heart with a snare, and a delivery apparatus being passed into the heart adjacent a spacer, according to an embodiment of the present disclosure.

In one embodiment, a spacer may be utilized to assist with the positioning of the delivery apparatus 400. Referring to FIG. 14A, a spacer 1400 may be positioned within the right ventricle 1204, and may be positioned between the apex 1404 of the right ventricle 1204 and the desired puncture point of the interventricular septum 1210 or the location of the interventricular septum 1210 that the heart anchor will be positioned upon. The spacer 1400 may be utilized to take up volume within the right ventricle 1204, which may block the distal end 408 of the delivery apparatus 400 from extending into the apex 1404 of the right ventricle 1204, and accordingly may assist to position the distal end 408 of the delivery apparatus 400 adjacent to the position of the spacer 1400 and at a desired location proximate the interventricular septum 1210.

The spacer 1400 may have a variety of forms. As shown in FIG. 14A, the spacer 1400 may comprise a balloon that may be inflated within the right ventricle 1204 to take up volume within the right ventricle 1204. The balloon may have a variety of shapes, including frustoconical as shown in FIG. 14A, or round, or a variety of other shapes. The balloon may be shaped to contour to the shape of the right ventricle 1204, and may have a shape that is specifically contoured to the shape of the patient's right ventricle 1204. The balloon may be configured for the distal end 408 of the delivery apparatus 400 to contact, in order to position the distal end 408 of the delivery apparatus 400 at the desired location proximate the interventricular septum 1210. The balloon may be coupled to a catheter 1402 that is configured to provide fluid to and from the balloon to inflate and deflate the balloon respectively. In one embodiment, one or more balloons may be utilized as the spacer 1400.

The spacer 1400 in one embodiment may comprise a frame that is configured to take up volume within the right ventricle 1204. The frame may include a plurality of supports that may be configured to bound a volume. The frame may be configured to be moved between an unexpanded state and an expanded state. The frame may move from the unexpanded state to the expanded state to increase the volume of the frame. The frame may be configured for the distal end 408 of the delivery apparatus 400 to contact, in order to position the distal end 408 of the delivery apparatus 400 at the desired location proximate the interventricular septum 1210. An example of a frame that may be utilized is an Amplatzer™ Septal Occluder, by Abbott Laboratories, Abbott Park, Illinois, in which the occluder may be expanded within the right ventricle (and not necessarily within a septal hole) to block off and take up volume within the right ventricle 1204. An example of such a device is disclosed in U.S. Pat. No. 5,944,738, the entire disclosure of which is incorporated by reference. Other forms of frames may be utilized as desired. The frame may be made of a shape memory material such as nitinol or another shape-memory material, or another material as desired. The frame may be coupled to a catheter 1402 that is configured to deploy the frame to the expanded state, and to collapse the frame to the unexpanded state for removal from the right ventricle 1204.

In use, the spacer 1400 may be deployed to the right ventricle 1204 in an unexpanded state. Referring to FIG. 14A, the spacer 1400 may be coupled to the catheter 1402 that may be passed through a sheath, such as the introducer sheath 500, to a desired location in the right ventricle 1204. For example, as shown in FIG. 14A, the catheter 1402 may be inserted into the right ventricle 1204 until it contacts the wall of the apex 1404 of the right ventricle 1204. The spacer 1400 may then be expanded to a desired expanded size.

The spacer 1400 may be located within the right ventricle 1204 and expanded to a desired size such that the distal end 408 of the delivery apparatus 400 will be placed at the desired location proximate the interventricular septum 1210 when contacting the spacer 1400. For example, a user may visualize the location of the spacer 1400 and the expansion of the spacer 1400 to determine if a position adjacent the spacer 1400 will be the desired location of puncture of the interventricular septum 1210. In an embodiment in which the spacer 1400 is a balloon, the balloon may be inflated. In an embodiment in which the spacer 1400 is a frame, the frame may be expanded to a desired size. In one embodiment, a distance of the spacer 1400 from the end of the catheter 1402 may be set so that the length of the exposed end of the catheter 1402 (distal the spacer 1400) sets the height of the top of the spacer 1400.

In certain embodiments, the size or other configuration of the spacer 1400 may be selected based on the desired location of puncture of the interventricular septum 1210. For example, a series of sizes or configurations of the spacers 1400 may be provided, and a user may select the desired size or configuration based on the patient's particular anatomy and the desired position of puncture on the interventricular septum 1210.

With the spacer 1400 in the desired position in the right ventricle 1204, the distal end 408 of the delivery apparatus 400 will be placed at the desired location proximate the interventricular septum 1210 when contacting the spacer 1400. The spacer 1400 beneficially prevents the distal end 408 of the delivery apparatus 400 from dropping into the apex 1404 of the right ventricle 1204, which may be undesired. Upon the desired operation of the delivery apparatus 400 being performed, the spacer 1400 may be reduced to the unexpanded state, and then withdrawn from the right ventricle 1204 with the catheter 1402 being withdrawn.

The spacer 1400 may optionally be utilized with the steps of the methods disclosed herein, and may not be utilized in certain embodiments as desired. The spacer 1400 may be utilized in any embodiment in which a heart anchor is deployed to the interventricular septum 1210 within the right ventricle 1204, or any other embodiment as desired. A spacer may also be used in another heart chamber or body cavity, for example, a left ventricle, for assisting in positioning a delivery apparatus.

Figure 15:
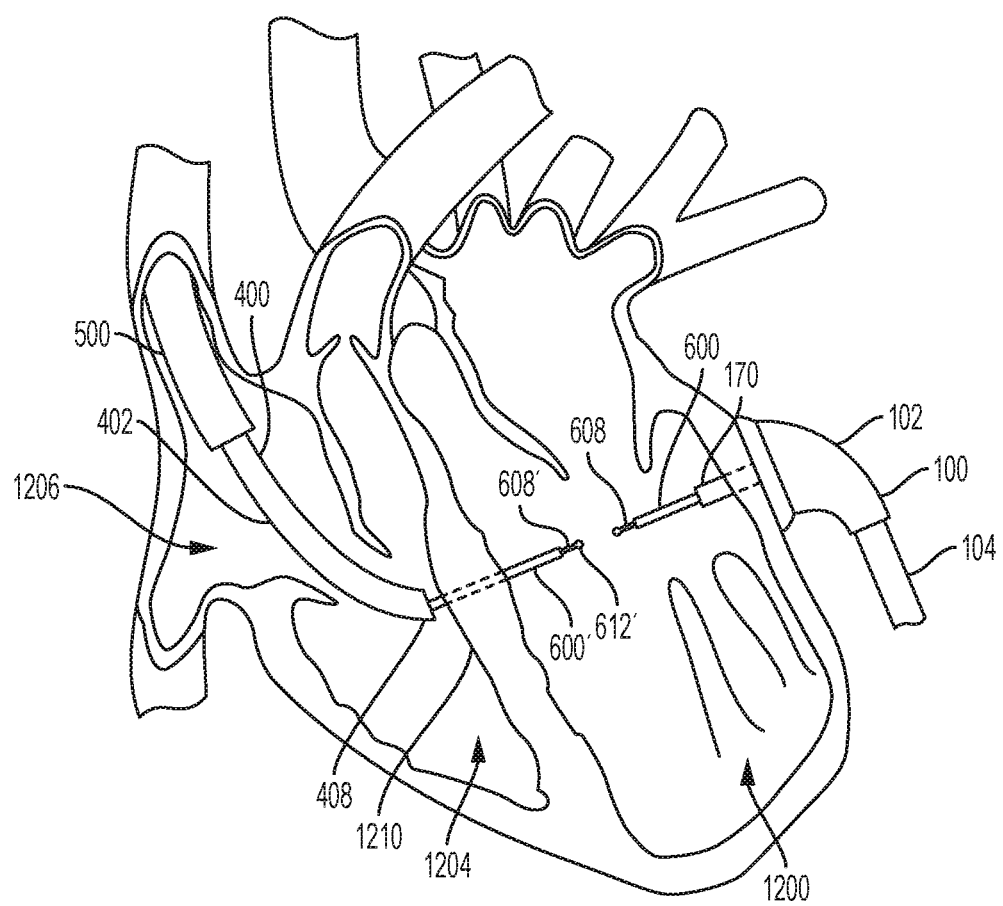
FIG. 15 illustrates a cross sectional view of a patient's heart with a snare entering the left ventricle according to an embodiment of the present disclosure.

Referring to FIG. 15, upon the distal end 408 of the delivery apparatus 400 being positioned proximate the interventricular septum 1210, a snare 600', which may be configured similarly as the snare 600, may be passed through the lumen 412 (marked in FIG. 4B) of the delivery apparatus 400 (and accordingly the lumen of the introducer sheath 500). The snare 600' may include a puncture device 612' at the end of the snare device 608'. The puncture device 612' and snare device 608' may be configured similarly as the respective puncture device 612 and snare device 608 shown in FIG. 6B. The snare 600' may be advanced through the lumen of the sheath 402 such that the puncture device 612' punctures through the interventricular septum 1210, as shown in FIG. 15. The snare 600' may be passed through the interventricular septum 1210 and into the left ventricle 1200. The snare 600 may be referred to as a left snare 600, and the snare 600' may be referred to as a right snare 600', for identification purposes.

Figure 16:
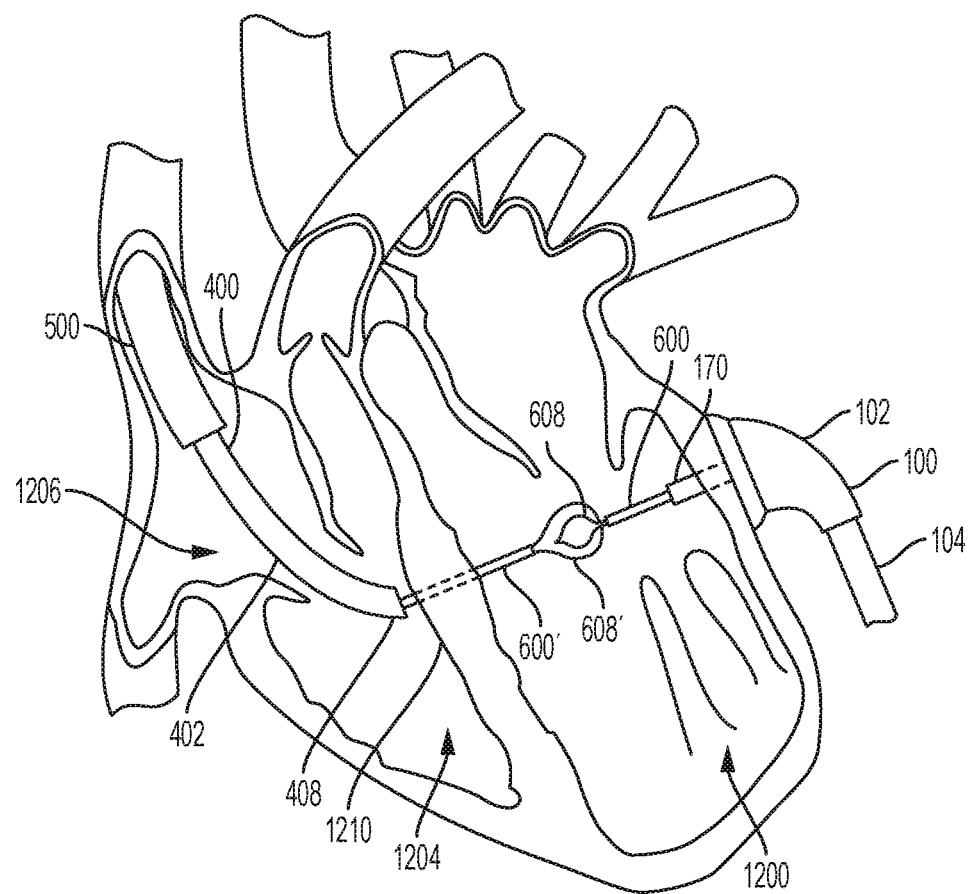
FIG. 16 illustrates a cross sectional view of a patient's heart with snares snaring each other according to an embodiment of the present disclosure.

Upon the right snare 600' and left snare 600 being positioned in the left ventricle 1200, the right snare 600' may snare the left snare 600. FIG. 16 illustrates the right snare 600' snaring the left snare 600. The snare device 608' of the right snare 600' may be deployed and may snare the snare device 608 of the left snare 600. The snare device 608 of the left snare 600 may also be deployed. In an embodiment in which the snare device 608' is a loop, the loop may extend around and capture the snare device 608 of the left snare 600. The snare device 608 may then be closed upon the snare device 608 of the left snare 600. In one embodiment, either the left snare 600 or right snare 600', or both, may snare the respective other snare. For example, the snare device 608 of the left snare 600 may be deployed and may snare the snare device 608' of the right snare 600'. Upon the snares 600', 600 being coupled together, the right snare 600' may be pulled and withdrawn from the delivery apparatus 400.

FIG. 17 illustrates the proximal end of the delivery apparatus 400 with the right snare 600' being withdrawn from the housing 404 of the delivery apparatus 400, and accordingly withdrawn from the right ventricle 1204. The snare device 608 of the left snare 600 is withdrawn from the delivery apparatus 400 and may be accessible by a user. The left snare 600 extends through the left ventricle 1200 and the right ventricle 1204. The delivery apparatus 400 may then be withdrawn from the introducer sheath 500, with the snare device 608 of the left snare 600 remaining accessible by a user.

FIG. 18 illustrates the left snare 600 being positioned exterior to the proximal end 502 of the introducer sheath 500 (as the delivery apparatus 400 has been withdrawn from the introducer sheath 500). The snare device 608 of the left snare 600 may couple to a tension member of a heart anchor, such as the tension member 286 of the heart anchor 202 (as shown in FIG. 2G).

Upon the left snare 600 coupling to the tension member 286, the left snare 600 may then be withdrawn in a distal direction through the introducer sheath 500 and may be withdrawn through the right ventricle 1204 and the left ventricle 1200 and withdrawn in a proximal direction through the access apparatus 100 while pulling the tension member 286 along with the snare 600. The tension member 286 accordingly may extend through the introducer sheath 500 and the right ventricle 1204, and may pass through the interventricular septum 1210, and may extend through the left ventricle 1200 and the lumen 124, 142 of the access apparatus 100 (marked in FIG. 1B). The tension member 286 may extend from the introducer sheath 500 to exit at the port 156 of the access apparatus 100 (marked in FIG. 1B). A portion of the tension member may extend exterior of the left ventricle of the patient's heart.

As or after the tension member 286 is pulled through the ventricles 1204, 1200, a deployment apparatus, such as the deployment apparatus 300 may be advanced towards the proximal end 502 of the introducer sheath 500. The deployment apparatus 300 may include an anchor, such as the heart anchor 202 (as shown in FIG. 2H) in a linearized configuration and positioned within the lumen 313 of the deployment apparatus 300, and specifically the lumen 313 of the deployment catheter 302 (for example in portion 321 as marked in FIG. 3B), with the tension member extending from the lumen 313. The tension member 286 may extend from the heart anchor 202 and distally from the tip 322 (marked in FIG. 3B) of the deployment apparatus 300.

Figure 19:
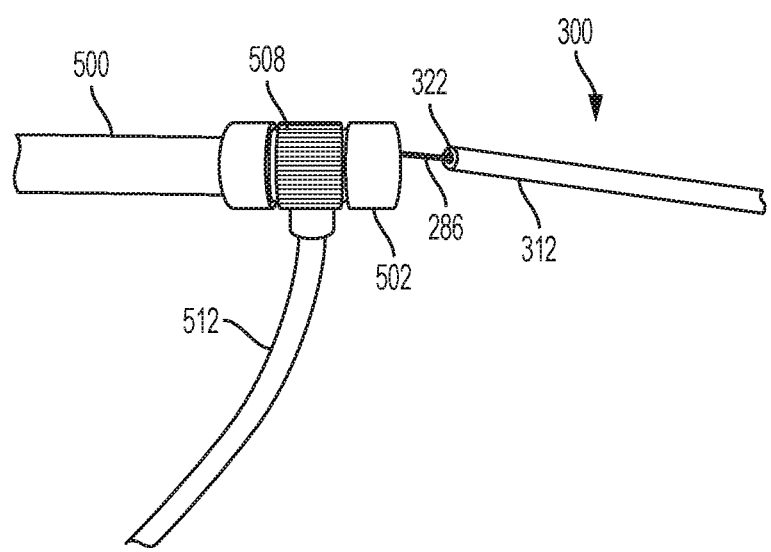
FIG. 19 illustrates a side view of a proximal end of an introducer sheath according to an embodiment of the present disclosure.

FIG. 19 illustrates the deployment apparatus 300 being advanced towards the proximal end 502 of the introducer sheath 500. The slack in the tension member 286 may be drawn through the ventricles 1204, 1200 and the access apparatus 100 as the deployment apparatus 300 advances towards the proximal end 502 of the introducer sheath 500 and passes through the lumen 506 of the introducer sheath 500 (marked in FIG. 5).

The deployment apparatus 300 may be advanced through lumen 506 of the introducer sheath 500 to a desired position. FIG. 20 illustrates the deployment apparatus 300 having been advanced until the housing 314 of the deployment apparatus 300 contacts the housing 508 at the proximal end 502 of the introducer sheath 500.

The deployment apparatus 300 may be configured with the lock 316 (marked in FIG. 3B) locking the push device 304 in position relative to the deployment catheter 302 (marked in FIG. 3B). The lock 316 may remain locked as the deployment apparatus 300 is advanced through the lumen 506 of the introducer sheath 500. The lock 316 may then be unlocked when the deployment apparatus 300 is in the desired position, to allow the push device 304 to slide relative to the deployment catheter 302 and push the heart anchor 202 out of the distal end of the deployment apparatus 300.

Upon the distal end 312 of the deployment apparatus 300 being in a desired position, the lock 316 (marked in FIG. 3B) may be unlocked and the push device 304 may be advanced through the lumen 313 of the deployment catheter 302 to push the heart anchor 202 out of the distal end 312 of the deployment catheter 302. FIG. 21 illustrates the heart anchor 202 exiting the distal end 312 of the deployment catheter 302. The ring 200 (marked in FIG. 2H) of the heart anchor 202 may automatically move to a ring-shaped configuration. The cover 212 of the anchor 202 has not yet been drawn towards its central opening 293 (marked in FIG. 2G).

The distal end 312 of the deployment catheter 302 may be positioned in the chambers of the patient's heart when the heart anchor 202 is pushed out of the distal end 312 of the deployment catheter 302. The distal end 312 of the deployment catheter 302 may be positioned in the right atrium 1206 (marked in FIG. 16). The right atrium 1206 may be selected for deployment of the heart anchor 202 so that the possibility of hooking the heart anchor 202 on one or more chordae in the right ventricle 1204 is reduced. In other embodiments, the heart anchor 202 may be deployed in a different location in the patient's heart.

Figure 22:
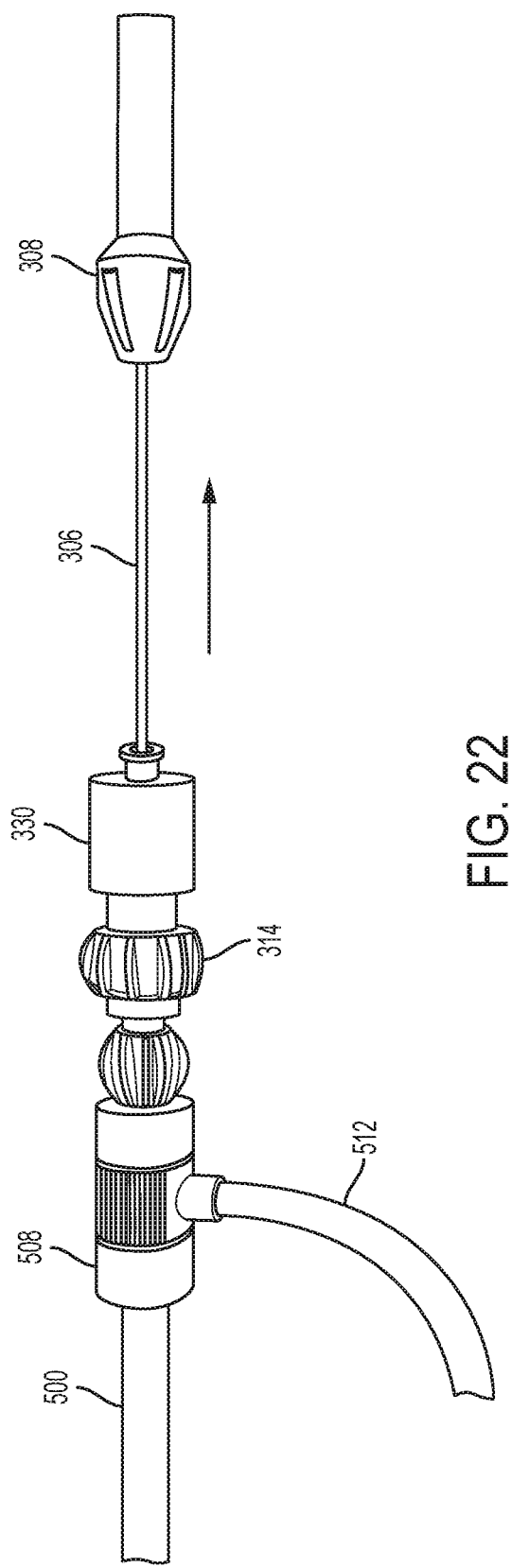
FIG. 22 illustrates a perspective view of a deployment member being withdrawn according to an embodiment of the present disclosure.

Upon the heart anchor 202 being pushed out of the deployment catheter 302, the deployment member 306 may be pulled to draw or cinch the cover 212 of the anchor 202 towards its central opening 293 (marked in FIG. 2G). FIG. 22 illustrates the deployment member 306 being pulled proximally to draw the cover 212 of the anchor 202 towards its central opening 293. The pull device 308 may be pulled in a direction away from the housing 330, in a manner discussed previously. The deployment member 306 may be routed through the cover 212 of the anchor 202 in a manner shown in FIG. 2H. As such, the proximal movement of the deployment member 306 may draw the cover 212 of the anchor 202 towards its central opening 293 and may close the central opening 293.

Figure 23:
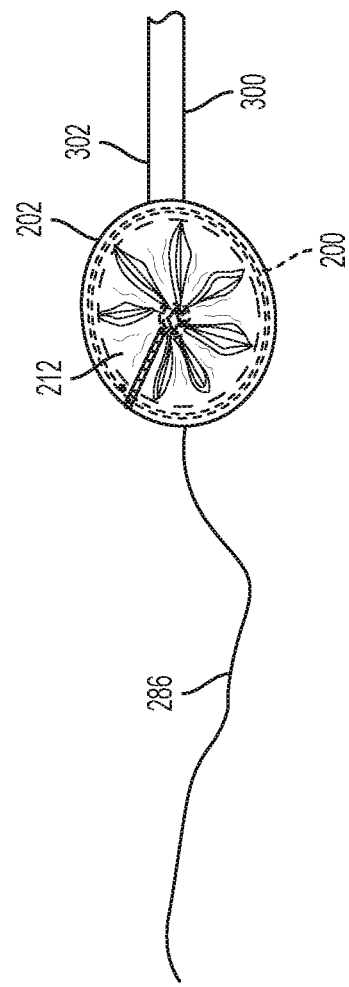
FIG. 23 illustrates a perspective view of a heart anchor in an expanded configuration according to an embodiment of the present disclosure.

FIG. 23 illustrates the cover 212 of the anchor 202 drawn towards its central opening 293 and the anchor 202 in its expanded configuration. The ring 200 is in its ring-shaped configuration. Portions of the ring 200 overlap each other in a manner discussed in regard to FIGS. 2A-2H. The anchor 202 may move from the unexpanded configuration to the expanded configuration adjacent the distal end of the deployment apparatus 300, to provide support to the anchor 202 as the cover 212 of the anchor 202 is drawn towards its central opening 293 (marked in FIG. 2G). The anchor 202 may be pressed against the tip 322 (marked in FIG. 3B) of the deployment apparatus 300 as the deployment member 306 is withdrawn to expand the cover 212.

Figure 24:
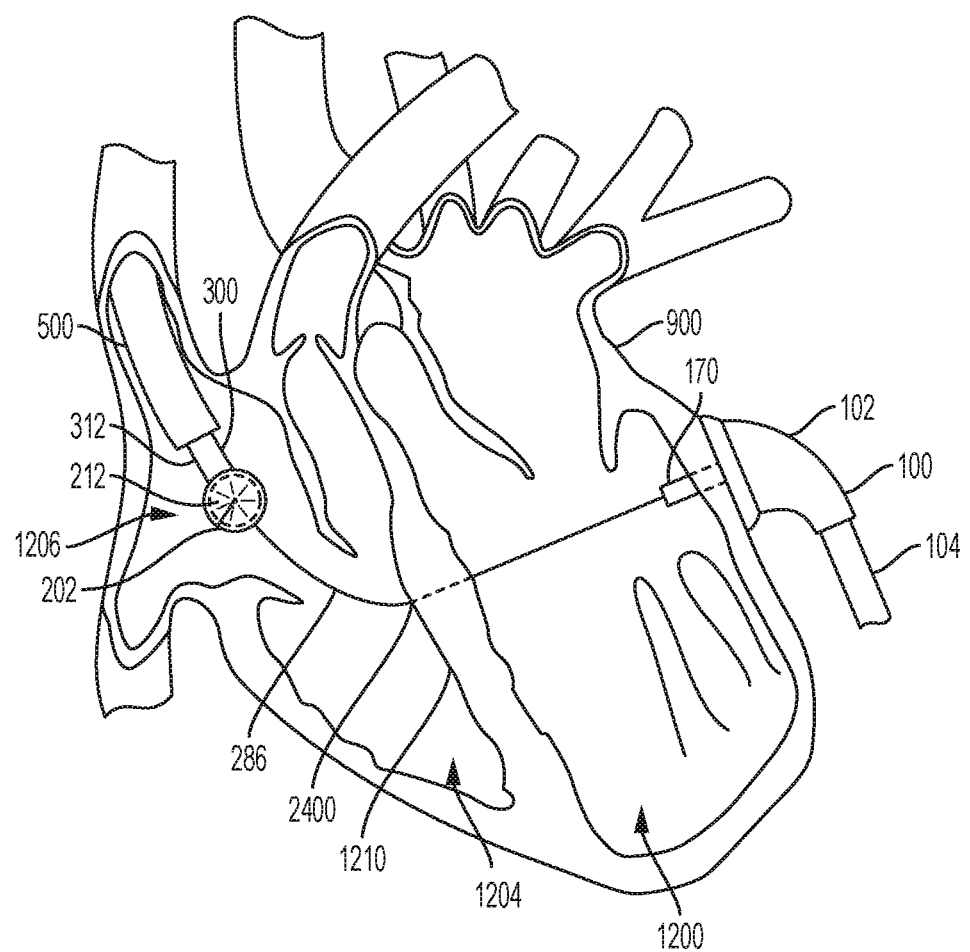
FIG. 24 illustrates a cross sectional view of a patient's heart with a heart anchor in an expanded configuration in the patient's right atrium according to an embodiment of the present disclosure.

FIG. 24 illustrates the position of the anchor 202 in the right atrium 1206 of the patient's heart 900 as the anchor 202 moves from the unexpanded configuration to the expanded configuration adjacent the distal end 312 of the deployment apparatus 300. With the anchor 202 in the position shown in FIG. 24, the deployment member 306 (marked in FIG. 22) may be released from the anchor 202. The deployment member 306 may then be pulled away from the anchor 202 and separated from the anchor 202. The deployment member 306 may be released by being cut along its length. Due to the looped configuration of the deployment member 306 (shown in FIG. 2H), the cut deployment member 306 may be pulled through the deployment apparatus 300 and entirely removed from the deployment catheter 302.

The deployment apparatus 300 may be withdrawn from the introducer sheath 500. The introducer sheath 500 may be withdrawn from the patient's body.

The tension member 286 may be pulled through the interventricular septum 1210 and the left ventricle 1200 and the lumen 142 (marked in FIG. 1B) of the access apparatus 100 further, to draw the free heart anchor 202 to the puncture position 2400 on the interventricular septum 1210. The heart anchor 202 may be pressed against the surface of the interventricular septum 1210 in the right ventricle.

Figure 25:
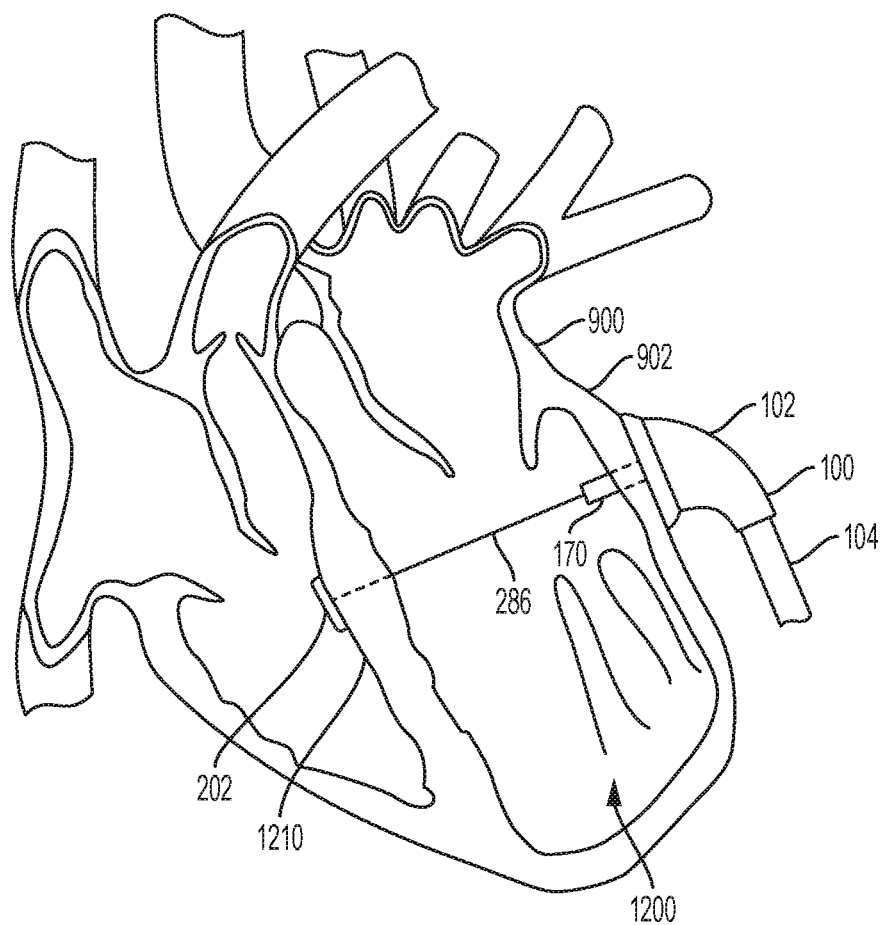
FIG. 25 illustrates a cross sectional view of a patient's heart with a heart anchor positioned on the patient's interventricular septum according to an embodiment of the present disclosure.

FIG. 25 illustrates the heart anchor 202 positioned against the surface of the interventricular septum 1210. The heart anchor 202 is accordingly deployed to a position on the interventricular septum 1210. The tension member 286 may seal the puncture in the interventricular septum 1210, and the cover 212 (marked in FIG. 24) may provide the strength to prevent the anchor 202 from passing through the interventricular septum 1210 or collapsing upon a tension force being applied to the tension member 286.

The sheath 170 may then be withdrawn from the left ventricle 1200 and the lumen 142 (marked in FIG. 1B) of the access apparatus 100. The access apparatus 100 may have its grip on the external surface 902 of the patient's heart 900 released by the vacuum suction of the head 102 being removed or reduced. The access apparatus 100 may be withdrawn from the external surface 902 of the patient's heart 900 and may be deflected in a manner discussed herein to avoid interfering with the patient's heart 900 upon withdrawal. The portion of the tension member 286 extending exterior of the patient's heart 900 remains accessible by a user.

Figure 26:
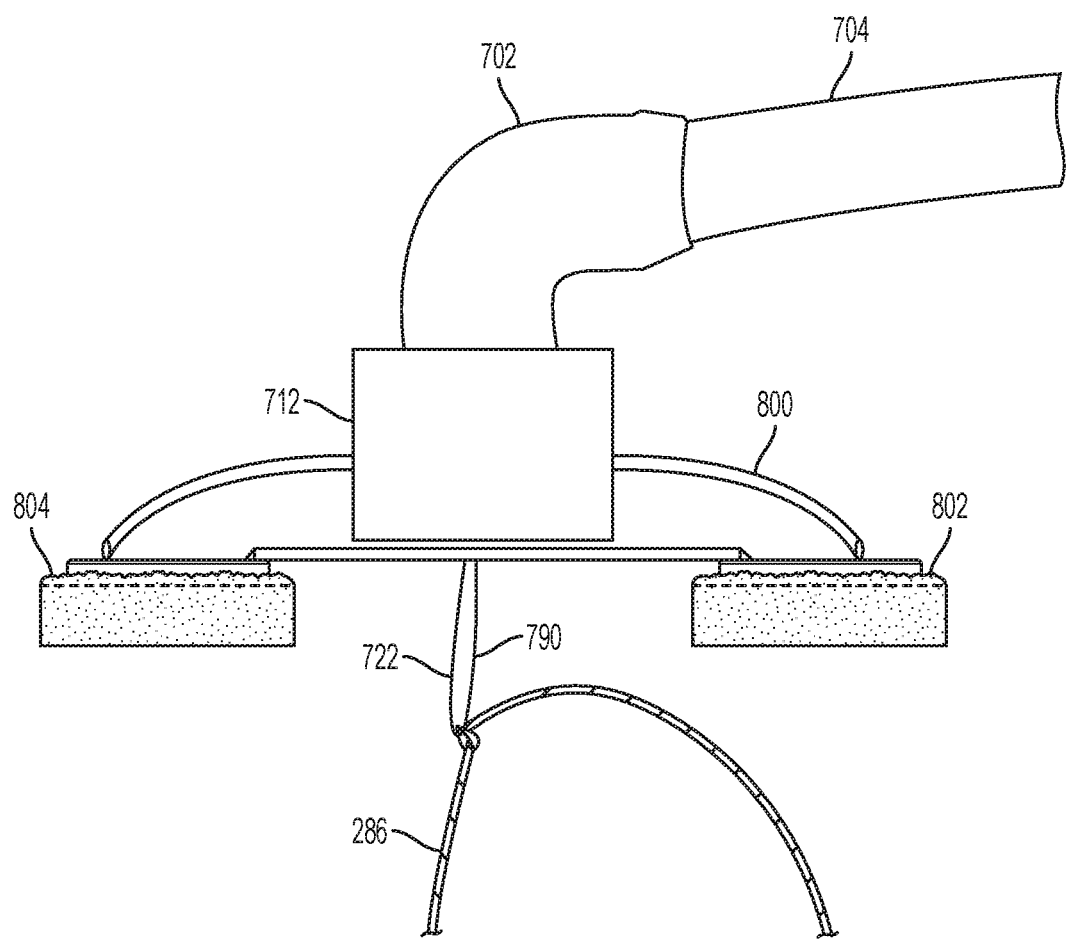
FIG. 26 illustrates a side view of a heart anchor coupled to a deployment apparatus according to an embodiment of the present disclosure.

FIG. 26 illustrates the portion of the tension member 286 extending exterior of the patient's heart 900 coupled to a snare of a deployment apparatus, such as deployment apparatus 700. The tension member 286 may be coupled to the snare device 790 of the snare 722 with a knot or other form of coupling.

An anchor, such as anchor 800, may be coupled to the receiver 712. The anchor 800 may be positioned between the side walls 714 (marked in FIG. 7B) of the receiver 712 and within gap 716.

The snare 722 may extend through the receiver 840 (shown in FIG. 8D) of the anchor 800, and may pass through the lumen 720, 730, 770 of the deployment apparatus 700 in a manner shown in FIG. 7B. The snare 722 may be locked to lock 750 (shown in FIG. 7B) in a manner discussed herein. The lock 838 of the anchor 800 may be in an unlocked state, to allow the snare 722 to slide within the receiver 840 (shown in FIG. 8D). The lock retainer member 856 may retain the lock 838 in the unlocked state, and may be coupled to the receiver 782 of the lock control mechanism 781 (shown in FIG. 7B). The connection of the lock retainer member 856 with the anchor 800 may additionally assist to secure the anchor 800 to the retainer 712.

FIG. 27 illustrates the proximal end of the deployment apparatus 700. The snare 722 is coupled to the tension member 286 as shown in FIG. 26 and is locked in the lumen 720, 730, 770 (marked in FIG. 7B) of the deployment apparatus 700. The unlock ring 780 may be slid over the housing 710 to press the rotatable body 774 of the lock 750 and unlock the snare 722.

Figure 28:
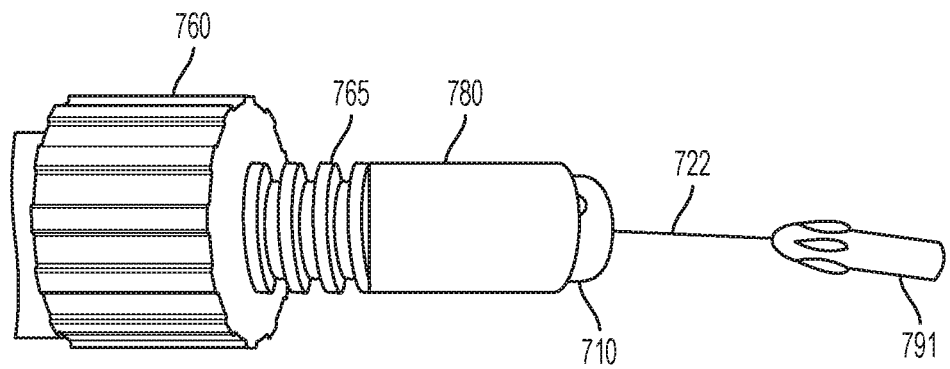
FIG. 28 illustrates a side view of a proximal end of a deployment apparatus with an unlock ring coupled thereto according to an embodiment of the present disclosure.

FIG. 28 illustrates the unlock ring 780 positioned around the housing 710 to unlock the snare 722. The handle 791 may then be withdrawn from the deployment apparatus 700, drawing the snare 722 through the lumen 720, 730, 770 (marked in FIG. 7B) of the deployment apparatus 700 and drawing the tension member 286 through the lumen 720, 730, 770 as well. The tension member 286 may then be positioned within the lumen 720, 730, 770 of the deployment apparatus.

The deployment apparatus 700, with the anchor 800 coupled thereto, may then be advanced to the position on the external surface 902 of the patient's heart 900 where the tension member extends therethrough. The portion of the tension member 286 extending exterior of the patient's heart 900 may be withdrawn through the receiver 840 of the anchor 800 and the lumen 720, 730, 770 of the deployment apparatus, to remove slack as the deployment apparatus 700 is advanced.

Figure 29:
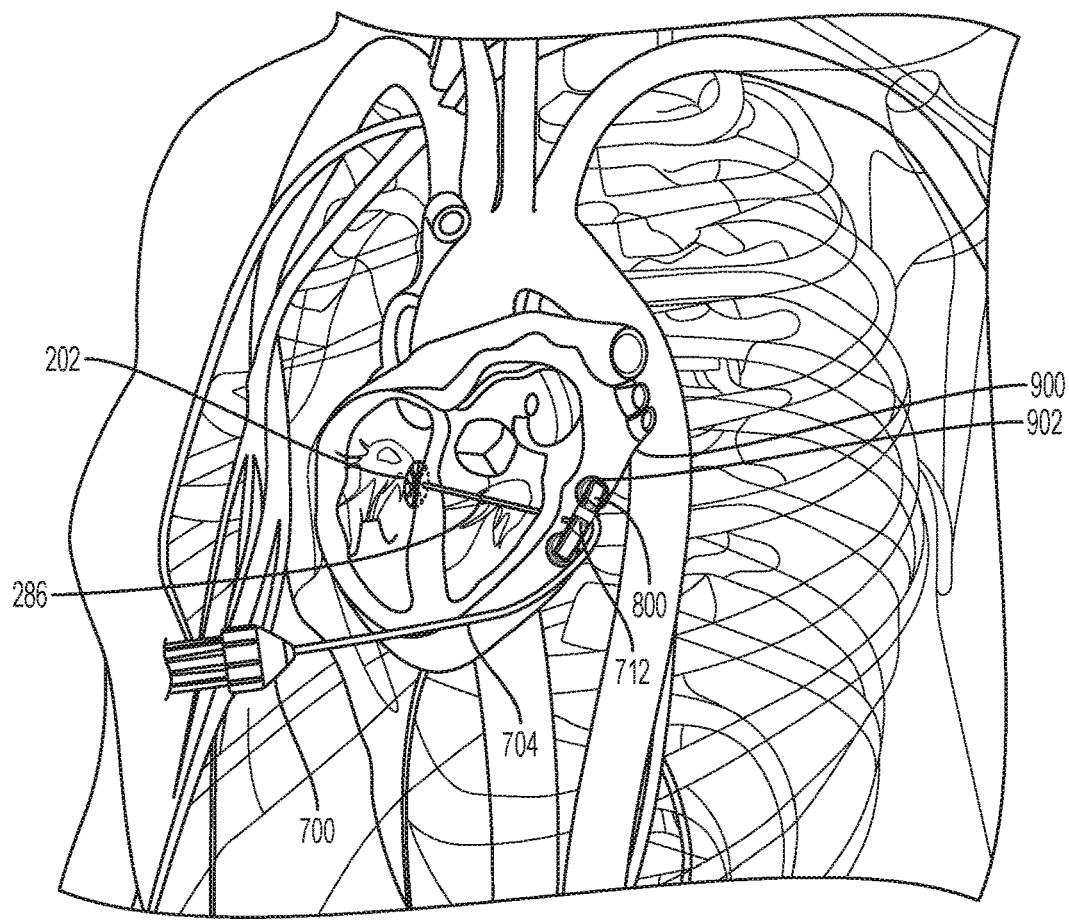
FIG. 29 illustrates a perspective view of a deployment apparatus being moved to a portion of a patient's heart according to an embodiment of the present disclosure.

The deployment apparatus 700 may be passed through the patient's body in a similar manner of entry as discussed with the access apparatus 100. As discussed previously, the elongate neck 704 may be configured to deflect to place the anchor 800 in position at a posterior portion of the patient's heart 900. The elongate neck 704 may be configured to wrap around a portion of the patient's heart 900 such that the posterior portion of the heart 900 is accessible even with a frontal entry of the patient's body. FIG. 29, for example, illustrates the elongate neck 704 wrapping around the patient's heart 900 and positioning the anchor 800 on the desired posterior portion of the heart 900. The retainer 712 may additionally be rotated, in a manner discussed previously, to place the anchor 800 in the desired position. The control mechanism of the elongate neck 704 and retainer 712 may be utilized to deflect the elongate neck 704 and rotate the retainer 712 to place the anchor 800 in the desired position, as discussed previously.

The anchor 800 may be positioned at the puncture point of the external surface 902 of the patient's heart 900. The anchor 800 may be oriented as desired, and may have a pad 804 positioned adjacent the mitral annulus 1216 (as shown in FIG. 31), and may have a pad 802 positioned adjacent the papillary muscle head origins 1218. The anchor 800 may be deployed to the left ventricle free wall. The anchor 800 may be positioned on the posterior surface of the heart on the external surface 902. The location markers 811 of the anchor 800 may be utilized to verify the position of the anchor 800 on the correct position of the patient's body.

Upon the anchor 800 being positioned on the desired position of the patient's heart, the tension member 286 for coupling the heart anchors 800, 202 may be tensioned to a desired amount. The tensioning may include applying a force to the external surface of the patient's heart and accordingly applying a force to the interventricular septum (via the resisting force of the anchor 202). The tension mechanism 749 (marked in FIG. 7B) of the deployment apparatus 700 may be utilized to tension the tension member 286 to a desired amount. The tension mechanism 749 may operate with the lock 750 of the tension mechanism 749 locking the tension member 286 in position. The unlock ring 780 shown in FIG. 27 may be removed from the housing 710 to allow the biasing device 776 to rotate the rotatable body 774 against the tension member 286 positioned in lumen 770 (marked in FIG. 7B). The tension member 286, locked in the lumen 770, may then be tensioned by the tension mechanism 749 in a manner discussed herein. The control device 760 (shown in FIG. 27) of the tension mechanism 749 may be operated to pull the locked tension member 286 relative to the housing 706 and relative to the head 702 and anchor 800. The control device 760 may be controlled by the user to set a precise desired amount of tension in the tension member 286.

The tension member 286 may be tensioned to a desired amount with the user simultaneously verifying proper hemodynamics and left ventricle reduction. The user may monitor the ventricular diameter and mitral regurgitation.

Upon the desired tension being reached, the lock control mechanism 781 may be released to lock the lock 838 (marked in FIG. 8E) of the anchor 800 in the locked state in a manner discussed herein with the tension member 286 in tension between the anchors 800, 202. Upon the lock 838 moving to the locked state, the tension of the tension mechanism 749 may be released slightly to confirm that proper tension is maintained in the heart splint. If the tension is incorrect, the lock 838 may be unlocked again, and the tension of the tension member 286 may be reset.

Figure 30:
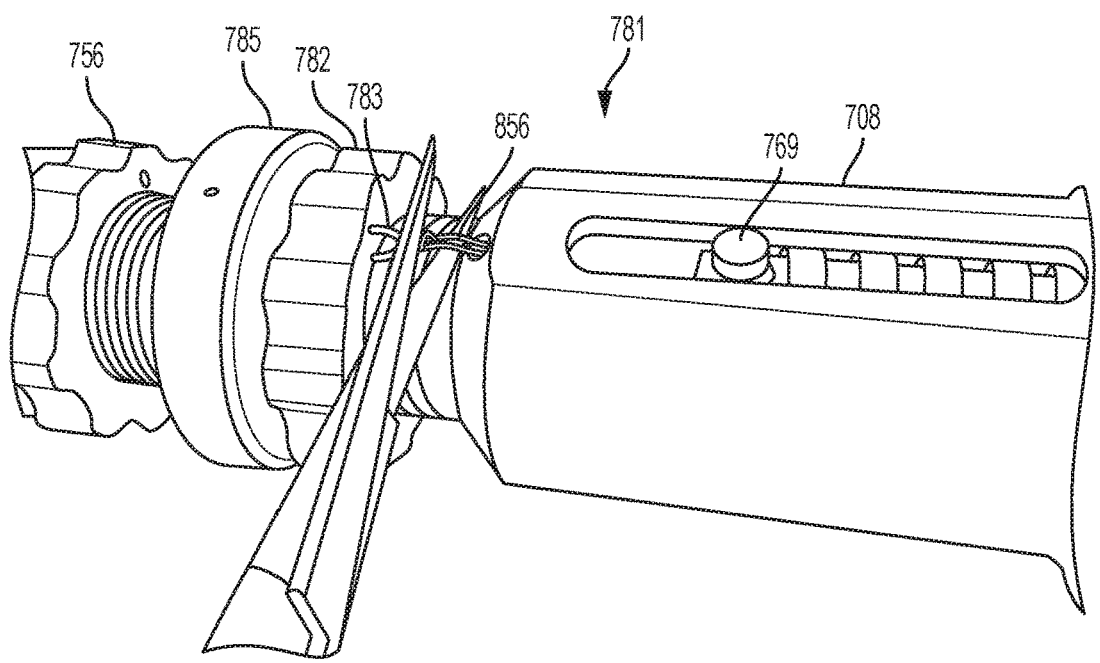
FIG. 30 illustrates a perspective view of a lock retainer member being cut according to an embodiment of the present disclosure.

Referring to FIG. 30, upon the desired tension being reached, the lock retainer member 856 may be cut from the receiver 782 and withdrawn from the lumen 720, 730 of the deployment apparatus 700. Due to the double cord structure of the lock retainer member 856, the lock retainer member 856 may be entirely pulled away from the anchor 800 and the lumen 720, 730 of the deployment apparatus 700 when cut.

The deployment apparatus 700 may then be withdrawn from the patient's body and may be deflected in a manner discussed herein to avoid interfering with the patient's heart 900 upon withdrawal. The portion of the tension member 286 extending exterior of the anchor 800 may then be cut.

FIG. 31 illustrates the anchor 800 in position on the external surface 902 of the patient's heart, and the anchor 202 in position on the interventricular septum 1210. The tension member 286 extends through the interventricular septum 1210 and between the anchor 202 and the anchor 800. The anchors 202, 800 and the tension member 286 together form a splint 3100 for treating ventricle dilation and/or mitral regurgitation. The anchor 800 may apply a supporting force to the patient's heart to reduce the possibility of regurgitation and support the papillary heads 1218 and reshape the ventricle.

The methods disclosed in regard to FIGS. 9-31 may beneficially provide for treating a dilated ventricle of the heart, while providing a minimally invasive procedure. Under the methods disclosed in regard to FIGS. 9-31, a full sternotomy may not be required, and entry into the right ventricle may comprise an endovascular entry into the patient's heart. The application of the splint may comprise a beating-heart repair of the left ventricle. The method may include reshaping a ventricle of the heart by applying pressure to the heart to reshape the geometry of heart. Endovascular or transcatheter methods may be utilized. Percutaneous entry of the patient's body may occur. In one embodiment, a full sternotomy may be performed if desired. The anchor 800 may beneficially provide two support locations for supporting the heart, in a configuration that is believed to provide enhanced therapeutic effects for the patient. The anchor 202 may be configured to easily deploy to the expanded configuration, and may be moved to the unexpanded or linearized configuration with a low force. The cover 212 of the anchor 202 may bear the majority of the force against the anchor 202 while the overlapping portions of the ring 200 may provide support to the ring 200.

Figure 32:
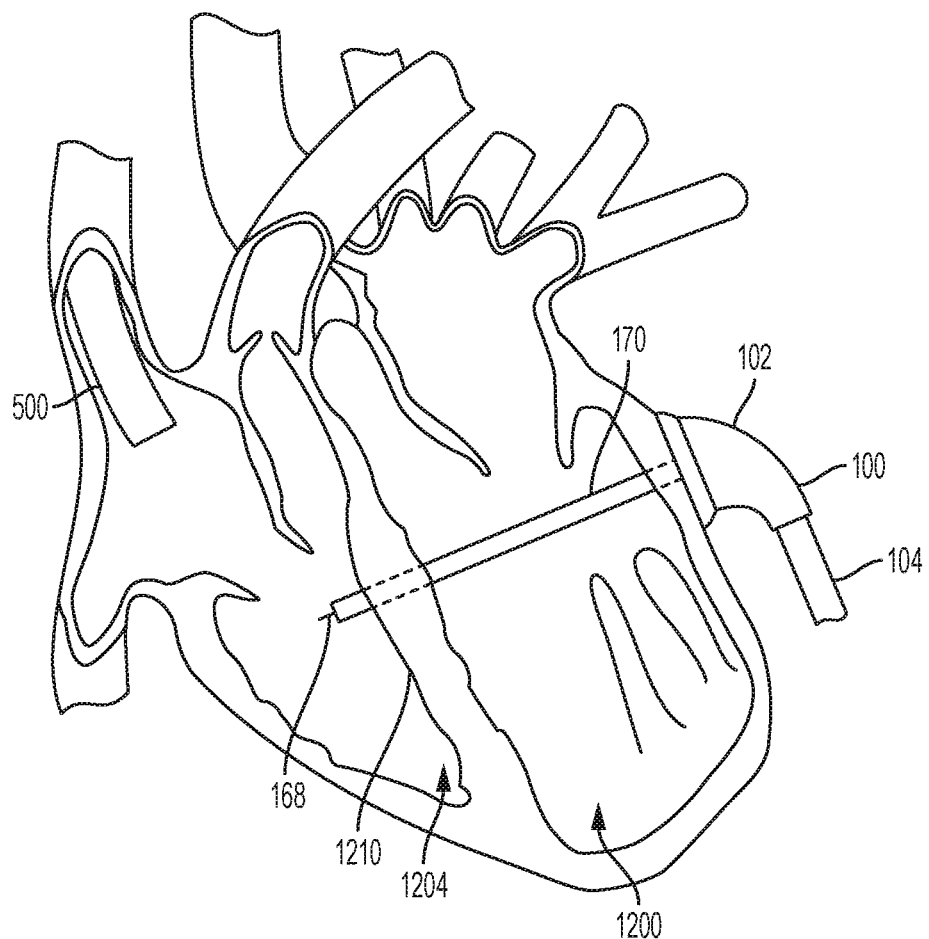
FIG. 32 illustrates a cross sectional view of a patient's heart with a puncture device and sheath being passed through the interventricular septum according to an embodiment of the present disclosure.
Figure 33:
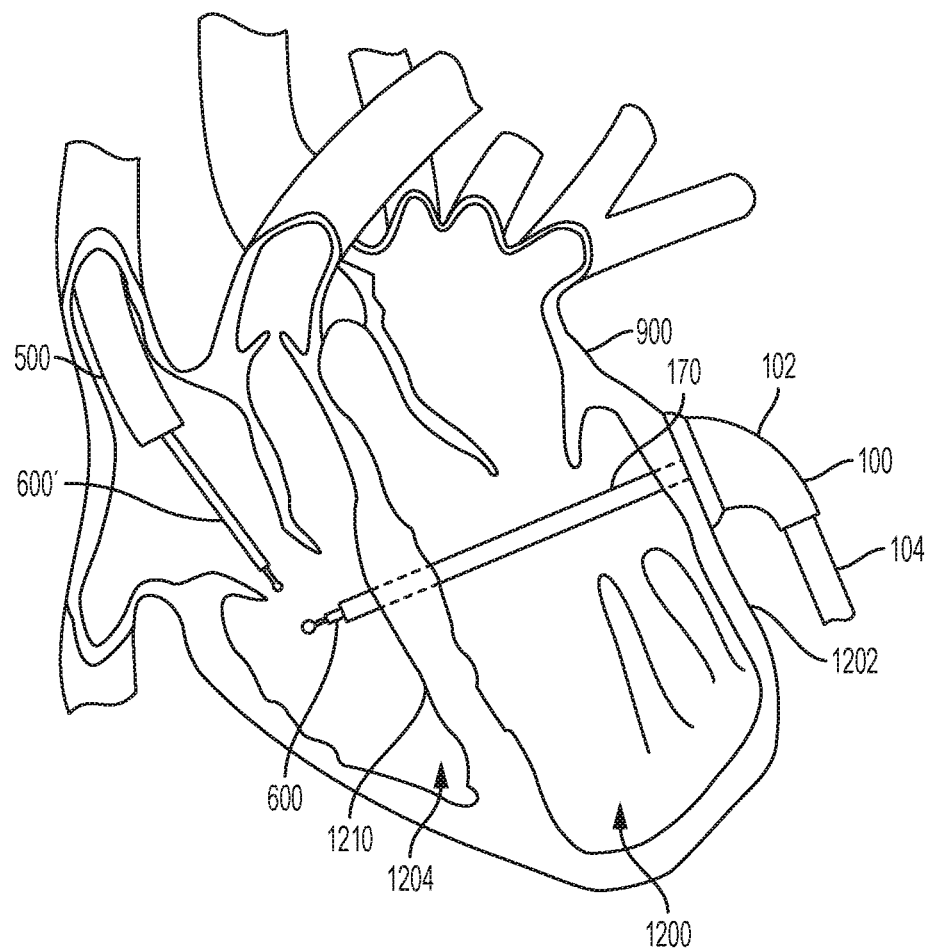
FIG. 33 illustrates a cross sectional view of a patient's heart with snares extending towards each other in the right ventricle according to an embodiment of the present disclosure.

FIGS. 32 and 33 illustrate an alternative method for deploying the heart splint 3100. In this method, the snaring of the snares 600, 600' may occur in the right ventricle 1204. The method is similar to steps discussed in regard to FIGS. 9-12, however, the sheath 170 and the puncture device 168, upon entering the left ventricle 1200 (as shown in FIG. 12) may continue to advance through the interventricular septum 1210 and into the right ventricle 1204. FIG. 32 illustrates the puncture device 168 and sheath 170 extending through the interventricular septum 1210 and into the right ventricle 1204. The puncture device 168 and sheath 170 may be advanced slowly to reach the interventricular septum 1210 and the position of the puncture device 168 and sheath 170 may be tracked with echo and/or fluoroscopic guidance. The puncture location in the interventricular septum 1210 may be approximately halfway between the right ventricular apex and the tricuspid annulus and centered laterally. If needed, the access apparatus 100 may be moved for the puncture device 168 to reach the desired position.

After puncturing the interventricular septum 1210, the puncture device 168 may be withdrawn in a proximal direction from the sheath 170 and access apparatus 100.

The introducer sheath 500 may be introduced into the patient's body in a similar manner as discussed in regard to FIG. 14.

Referring to FIG. 33, the left snare 600' may be passed through the introducer sheath 500 until positioned in the right ventricle 1204. The right snare 600 may be passed through the sheath 170 until positioned in the right ventricle 1204. The snaring may occur in a similar manner as discussed in regard to FIG. 16 (although in the right ventricle 1204), and the left snare 600' may be withdrawn from the sheath 500 in a similar manner as discussed in regard to FIGS. 16 and 17. The anchor 202 may be deployed utilizing the deployment apparatus 300 and the processes discussed in regard to FIGS. 17-23. The introducer sheath 500 may then be withdrawn. The anchor 202 may be drawn to the tip of the sheath 170 in the right ventricle 1204, and then the sheath 170 may be removed from the patient's body via the access apparatus 100. The remaining steps of FIGS. 25-31 may then occur.

In an embodiment in which snaring occurs in the right ventricle 1204, the path of the puncture device 168 may beneficially provide a straighter line extending through the outer wall 1202 of the patient's heart 900 and the interventricular septum 1210 than may occur with snaring in the left ventricle 1200. This is because the puncture device 168 may pass straight from the outer wall 1202 of the patient's heart through the interventricular septum 1210. The straighter path may result in less bending of the tension member 286 when coupled between the anchors 800, 202. However, in an embodiment in which snaring occurs in the left ventricle 1200, the user may have greater precision in the location of the interventricular septum puncture (as shown in FIG. 15), because the distal end 408 of the delivery apparatus 400 may be better controlled to be proximate a desired position on the interventricular septum 1210.

Figure 34:
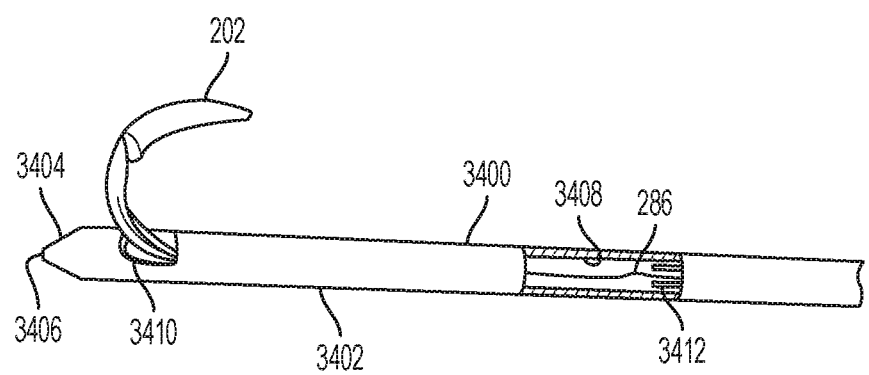
FIG. 34 illustrates a side view of a deployment apparatus with an anchor partially extending out of a deployment apparatus according to an embodiment of the present disclosure.
Figure 37:
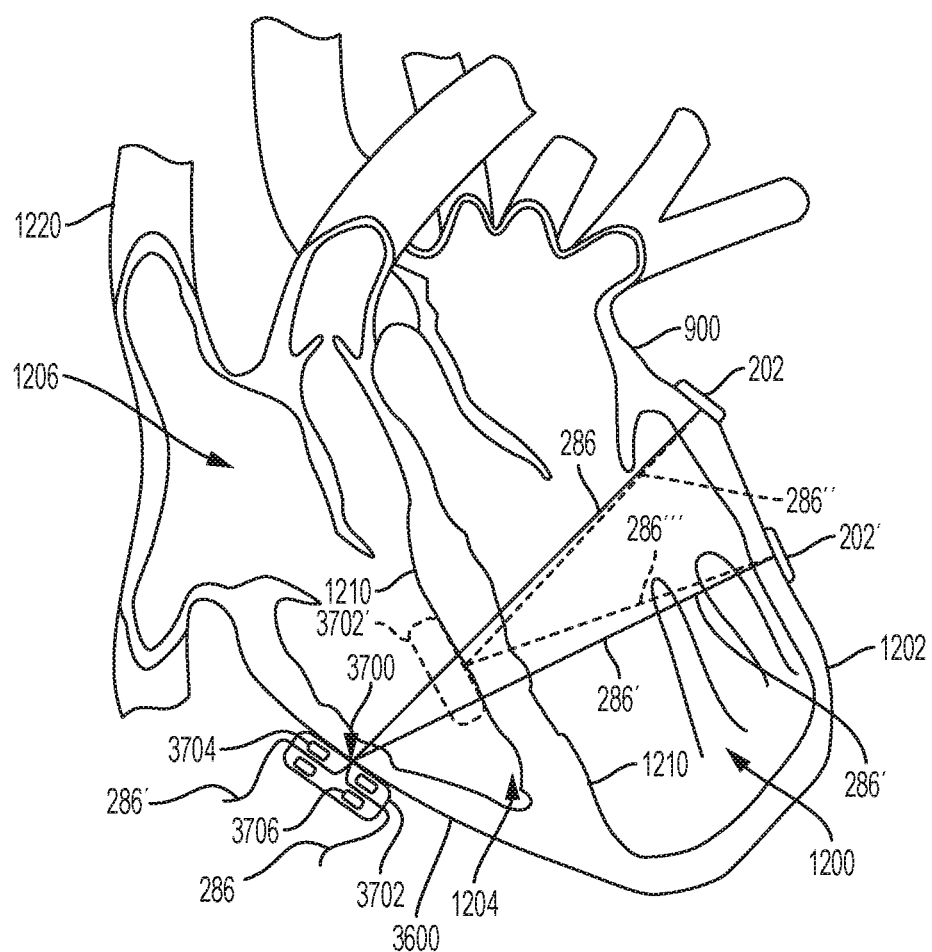
FIG. 37 illustrates a cross sectional view of a patient's heart with a heart splint being deployed to the heart according to an embodiment of the present disclosure.

FIG. 34 illustrates an embodiment of a deployment apparatus 3400 including a body portion 3402 and a distal end 3404. The deployment apparatus 3400 may be utilized in a method of applying heart anchors to a patient's heart. The method may be for treating a dilated heart condition or functional heart valve regurgitation of a patient. The method may be for treating ventricular dilation and/or mitral regurgitation. The method may include reshaping a ventricle of the heart by applying pressure to the heart to reshape the geometry of heart. The method may include supporting a ventricle of the heart to reduce the presence of ventricular dilation and prevent further dilation. The method may include deploying a heart splint to a patient's heart 900. The resulting heart splints are shown in FIG. 37.

The distal end 3404 of the deployment apparatus 3400 may include a puncture device 3406. The deployment apparatus 3400 may include an internal lumen 3408 and may include an opening 3410 along the body portion 3402 positioned adjacent the puncture device 3406. The deployment apparatus 3400 may include a push device 3412 for passing through the lumen 3408 for pushing anchor 202 out of the opening 3410. The push device 3412 may be configured similarly as the push device 304 discussed in regard to FIGS. 3A and 3B.

The body portion 3402 may have the shape of an elongate rod. The body portion 3402 may be sufficiently rigid to withstand the force of penetrating through a portion of a patient's heart.

The push device 3412 may be configured to pass through the lumen 3408 with an internal lumen to allow the tension member 286 to pass through the lumen 3408 and the internal lumen, and be accessible for tensioning by a user.

The lumen 3408 may be configured to retain the anchor 202 in the unexpanded or linearized configuration within the lumen 3408. The anchor 202 may be positioned within the lumen 3408 such that as the anchor 202 is pushed out of the lumen 3408 with the push device 3412, the tension member 286 remains in the lumen 3408 and a portion of the tension member 286 remains accessible to be pulled to move the cover 212 towards the central opening 293 of the cover 212 as discussed herein. The ring 200 (marked in FIG. 2G) of the anchor 202 may be configured to automatically move to the ring-shaped configuration, as discussed herein.

The anchor 202 may be configured to move from the unexpanded configuration to the expanded configuration adjacent the opening 3410. In one embodiment, multiple anchors 202 may be positioned within the lumen 3408 and may be pushed out in sequence.

Figure 35:
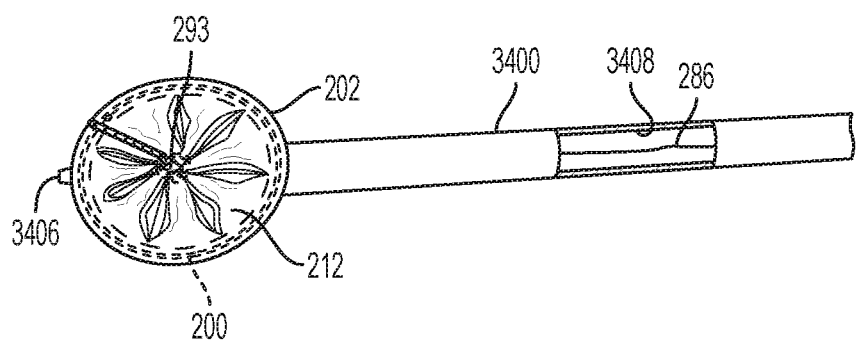
FIG. 35 illustrates a side view of a deployment apparatus with an anchor extending out of a deployment apparatus according to an embodiment of the present disclosure.

FIG. 35 illustrates the anchor 202 passed out of the opening 3410 and in the expanded configuration in which the ring 200 (marked in FIG. 2G) of the anchor 202 is in the ring-shaped configuration.

Figure 36:
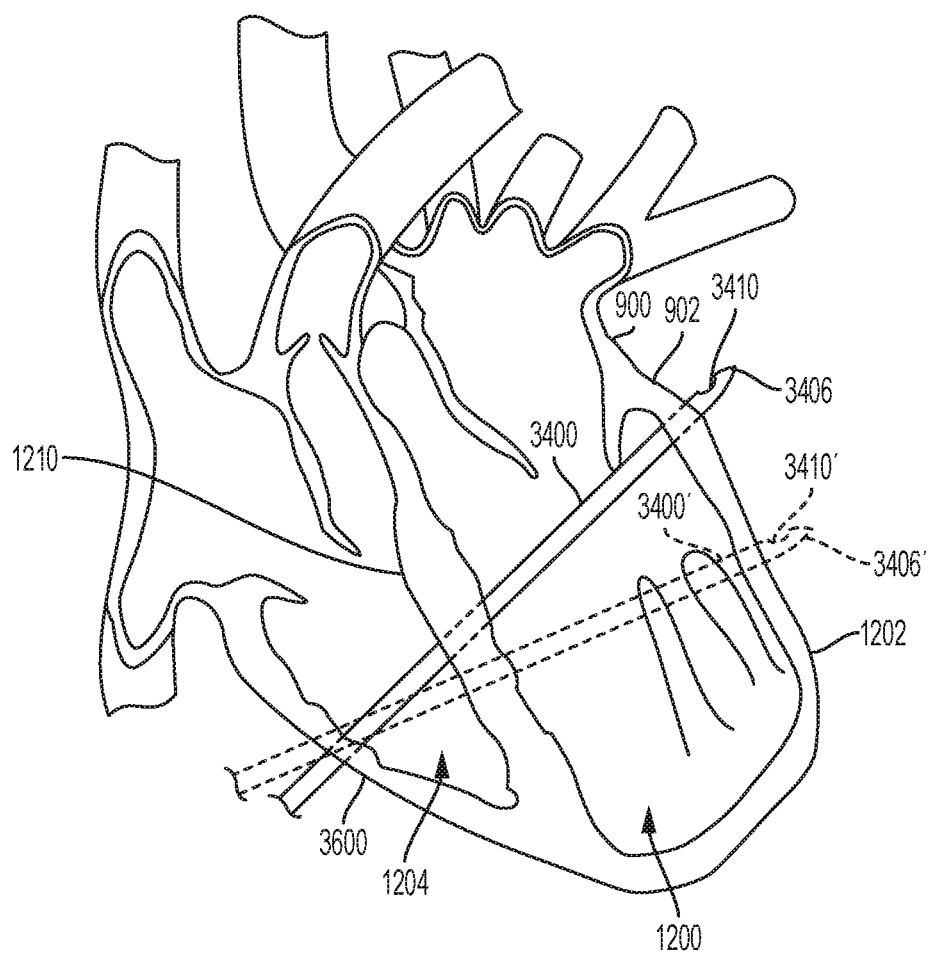
FIG. 36 illustrates a cross sectional view of a patient's heart with a deployment apparatus passing through the patient's heart according to an embodiment of the present disclosure.

FIGS. 36 and 37 illustrate one or more methods of deploying the anchor 202 utilizing the deployment apparatus 3400. As shown in FIG. 36, the deployment apparatus 3400 may be passed in a direction through the outer wall 3600 of the right ventricle 1204 and through the interventricular septum 1210 to the left ventricle 1200. The deployment apparatus 3400 may then be passed through the outer wall 1202 of the left ventricle 1202 and may position the opening 3410 exterior of the left ventricle 1200. The puncture device 3406 may penetrate through the portions of the patient's heart 900. With the opening 3410 exterior of the left ventricle 1202, the push device 3412 (shown in FIG. 34) may be utilized to push the anchor 202 out of the deployment apparatus 3400. The anchor 202 may move from the unexpanded configuration to the expanded configuration, and the tension member 286 (shown in FIG. 37) may be withdrawn to expand the cover 212 of the anchor 202. The anchor 202 may be deployed to a position on an external surface of the patient's heart and adjacent the left ventricle. Referring to FIG. 37, the deployment apparatus 3400 may be withdrawn from the puncture points with the tension member 286 trailing from the deployment apparatus 3400. The tension member 286 may pass out of the opening 3410 to pass the tension member 286 through the puncture point 3700 of the outer wall 3600 and leave a portion of the tension member 286 exterior of the patient's heart at the puncture point 3700 of the outer wall 3600.

Referring back to FIG. 36, an additional puncture of the patient's heart 900 may be made by the deployment apparatus 3400', with like elements as deployment apparatus 3400 marked with a prime symbol. The deployment apparatus 3400' may comprise the same deployment apparatus as deployment apparatus 3400 or may comprise a separate deployment apparatus. In an embodiment in which the same deployment apparatus is utilized, the anchor 202' may be positioned in series in the deployment apparatus 3400' with the deployment apparatus 3400. The deployment apparatus 3400' is marked in dashed lines to distinguish from the movement of the deployment apparatus 3400. The deployment apparatus 3400' may similarly be passed in a direction through the outer wall 3600 of the right ventricle 1204 and through the interventricular septum 1210 to the left ventricle 1200. The deployment apparatus 3400' may then be passed through the outer wall 1202 of the left ventricle 1200 and may position the opening 3410' exterior of the left ventricle 1200. With the opening 3410' exterior of the left ventricle 1200, a push device may be utilized to push the anchor 202' (which may be configured similarly as anchor 202) out of the deployment apparatus 3400'. The anchor 202' may be deployed in the same manner as anchor 202. The anchor 202' may be deployed to a position on an external surface of the patient's heart and adjacent the left ventricle. Referring to FIG. 37, the deployment apparatus 3400' may be withdrawn from the patient's heart 900 with the tension member 286' (which may be configured similarly as tension member 286) trailing, to leave a portion of the tension member 286' exterior of the patient's heart at the puncture point 3700 of the outer wall 3600.

In other embodiments, the position of deployed anchors 202, 202' may be varied as desired. A different number of anchors may be deployed, such as three or four or more as desired. For example, an anchor may be deployed adjacent each papillary head muscle, with a third anchor deployed adjacent the mitral annulus.

The portions of the tension members 286, 286' positioned exterior of the patient's heart at the puncture point 3700 may be coupled to an anchor 3702. The anchor 3702 may be configured to support the portion of the patient's heart to which it is applied. The anchor 3702 may comprise a pad configured to press against the patient's heart. The anchor 3702 may include one or more locks for locking a tension member coupled to the anchor 3702. The one or more locks may include a first lock 3704 and a second lock 3706 that may be configured similarly as the first lock 3704. The locks 3704, 3706 may be configured to press a tension member to hold the tension member in position, or may comprise other forms of locks. The one or more locks may be configured to move from an unlocked state to a locked state for locking the respective tension members to the anchor 3702.

The anchor 3702 may be configured to independently control the tension of the tension member 286 and the tension member 286'. One of the locks 3704 may be configured to lock the tension of the tension member 286 while the other lock 3706 may be configured to independently lock the tension member 286'. In this manner, the tension of the tension member 286 and the tension member 286' may be set independently and locked independently. The force applied to the different portions of the heart by anchor 202 and 202' may accordingly be independently set and may be varied depending on the therapeutic effect desired for the patient. The resulting heart splint (anchors 3702, 202, 202' and tension members 286, 286') may have different tension on each tension member 286, 286'.

Figure 38:
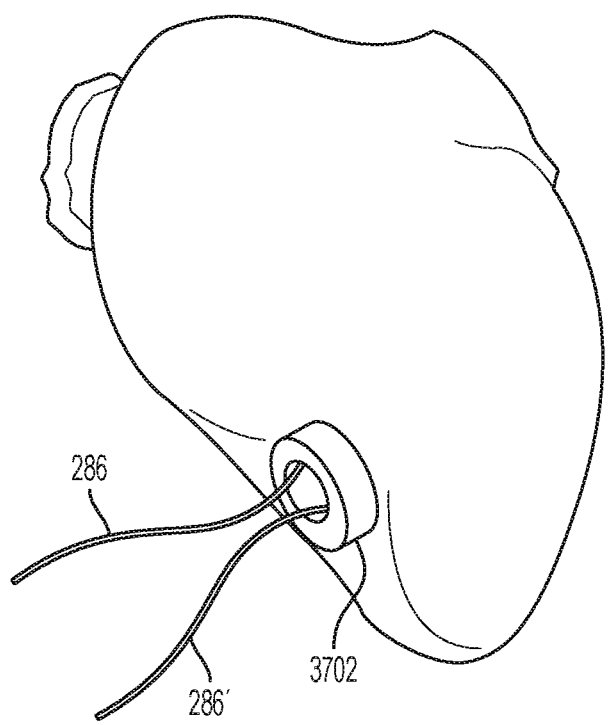
FIG. 38 illustrates a perspective view of a heart anchor positioned on an external surface of the patient's heart according to an embodiment of the present disclosure.

FIG. 38 illustrates the anchor 3702 positioned on the external surface of the patient's heart adjacent the right ventricle, coupled to tension members 286 and 286'.

In an embodiment shown in dashed lines in FIG. 37, the anchor 3702' (which may be configured similarly as anchor 3702) may be positioned on the interventricular septum 1210 of the patient's heart. The anchors 202, 202' in this configuration may be positioned on the outer wall 1202 of the left ventricle 1200 utilizing a deployment apparatus 3400 passed endovascularly into the right ventricle 1204 (for example via the superior vena cava 1220 and the right atrium 1206) and then puncturing the interventricular septum 1210 and the outer wall 1202 of the left ventricle 1200. The deployment apparatus 3400 may be configured to have a flexible body portion to allow for movement within the patient's vasculature. The anchors 202, 202' may be deployed in sequence to the external surface of the left ventricle 1200 in a similar manner as discussed in regard to the embodiment shown in solid lines in FIG. 37. The portions of the tension members 286" and 286''' (which each may be configured similarly as tension members 286 and 286') passing through the interventricular septum 1210 may be coupled to the anchor 3702' and may be independently tensioned as discussed in regard to anchor 3702. The anchor 3702' may be deployed endovascularly to the right ventricle 1204 and the portions of the tension members 286" and 286''' passing through the interventricular septum 1210 may be coupled to the anchor 3702'. The anchor 3702 thus may be either deployed to a position on the external surface of the patient's heart adjacent the right ventricle or may be deployed to a position that is on the interventricular septum. The tension members may be tensioned and locked in tension between the respective anchor 3702, 3702' and the anchors on the external surface of the left ventricle. The respective tension members may be tensioned independently, and locked in tension.

In one embodiment, the anchors 202 and 202' may be separately deployed to the interventricular septum 1210 utilizing the methods of FIGS. 9-33. Separate deployments of the anchors 202 and 202' to the side of the interventricular septum 1210 in the right ventricle 1204 may be made. The portions of the tension members 286, 286' extending through the outer wall 1202 of the left ventricle 1200 may be coupled to separate anchors 3702, 3702' that may be positioned where the anchors 202, 202' are shown to be positioned in FIG. 37. The tension members 286, 286' may be independently tensioned at the anchors 3702, 3702'. In this manner, the force applied to the outer wall 1202 of the left ventricle 1200 by anchors 3702, 3702' may accordingly be independently set and may be varied depending on the therapeutic effect desired for the patient.

The methods discussed in regard to FIGS. 36 and 37 may beneficially allow for the force applied to portions of the patient's heart to be independently set based on the therapeutic effect desired for the patient. The resulting heart splints (anchors and tension members) may have different tension on each tension member. The methods of FIGS. 36 and 37 are not limited to the number of anchors shown in FIGS. 36 and 37, but may extend to a variety of numbers of anchors, and a variety of positions of anchors. A variety of numbers of anchors may have tension members with tension independently set.

The use of the heart anchors disclosed herein may not be limited to use for heart splints, but may be utilized to seal an opening between chambers of a patient's heart. The opening may be in a septum, which may comprise the patient's interventricular septum 1210. However, in other embodiments, the opening may be in any septum, and between any chambers of the heart. The opening may comprise a ventricular septal defect (VSD), an atrial septal defect (ASD), or a patent foramen ovale (PFO). Here, the opening is referred to as an opening in the interventricular septum as an example, although the apparatuses and methods may apply to any opening between chambers of the heart. The method may result in a plug 4100 shown in FIG. 44 extending through and sealing the opening in the septum.

Figure 39:
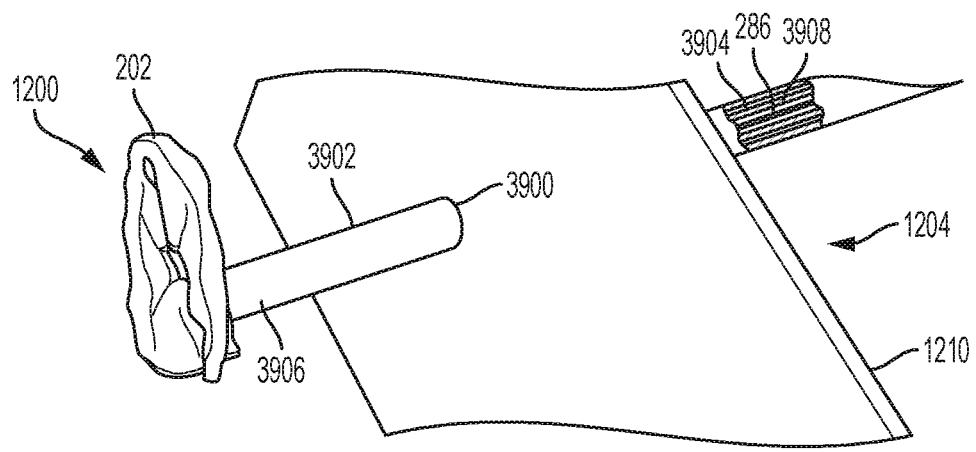
FIG. 39 illustrates a perspective view of a representation of a heart anchor being deployed to a chamber of the patient's heart according to an embodiment of the present disclosure.

FIG. 39 illustrates a representation of the patient's interventricular septum 1210 and right ventricle 1204 and left ventricle 1200. The interventricular septum 1210 may include an opening 3900, which may have been caused by various maladies of the patient or another cause.

A deployment apparatus 3902 may include a lumen 3904 and an opening at a distal end 3906 of the deployment apparatus 3902. The deployment apparatus 3902 may include a push device 3908 configured to push an anchor 202 through the lumen 3904 with a tension member 286 trailing from the heart anchor 202, in a similar manner as discussed in regard to deployment apparatus 3400. The push device 3908 may be configured similarly as the push device 304 discussed in regard to FIGS. 3A and 3B. The deployment apparatus 3902 may be configured to deploy multiple anchors 202, 202' from the lumen 3904.

The deployment apparatus 3902 may be configured to pass through the opening in the interventricular septum 1210 and push an anchor 202 into a chamber of the patient's heart. The anchor 202 may deploy in a similar manner as discussed in regard to the anchor 202 in FIGS. 36 and 37. FIG. 39 illustrates the anchor 202 deployed in a left ventricle 1200 of the patient.

Figure 42:
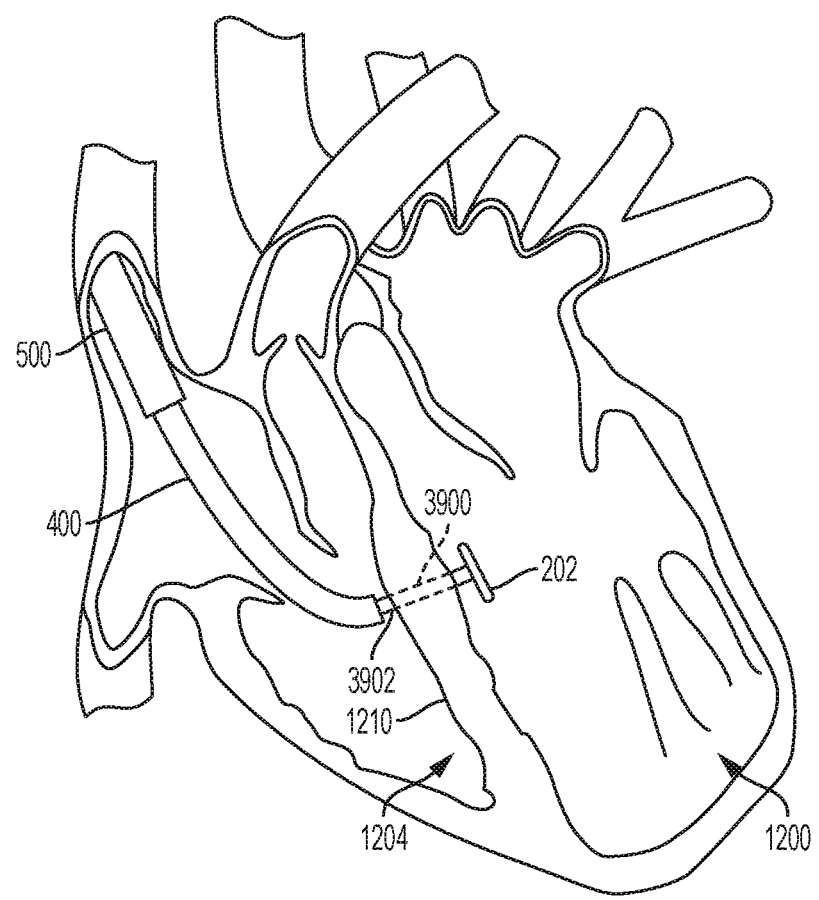
FIG. 42 illustrates a cross sectional view of a patient's heart with an anchor being deployed in a chamber of the heart according to an embodiment of the present disclosure.

FIG. 42, for example, illustrates an embodiment of the anchor 202 being deployed in the left ventricle 1200 of the patient's heart with the deployment apparatus 3902 passing through the opening 3900 in the interventricular septum 1210. The introducer sheath 500 and the delivery apparatus 400 may additionally be utilized to position the deployment apparatus 3902 in the desired position. The deployment apparatus 3902 may be advanced to the interventricular septum 1210 endovascularly (for example via the superior vena cava 1220 and the right atrium 1206). A spacer such as the spacer disclosed in regard to FIG. 14A may be utilized as desired.

Figure 40:
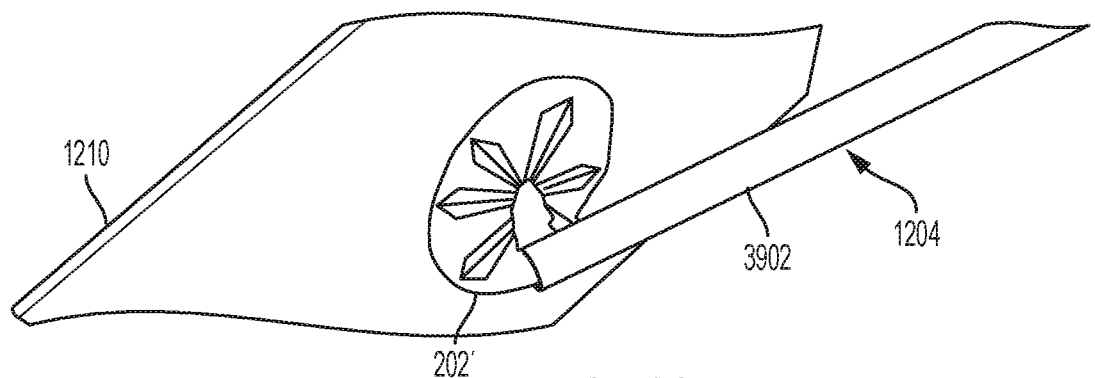
FIG. 40 illustrates a perspective view of a representation of a heart anchor being deployed to another chamber of the patient's heart according to an embodiment of the present disclosure.

Upon the anchor 202 being deployed to a position on the septum 1210 adjacent the opening 3900 and in a chamber of the heart, the deployment apparatus 3902 may be retracted through the interventricular septum 1210 with the tension member 286 trailing from the deployment apparatus 3902. The heart anchor 202' may then be deployed from the deployment apparatus 3902 in the chamber of the heart on the opposite side of the interventricular septum 1210 (the right ventricle 1204 as shown in FIG. 40). The heart anchor 202' may be deployed to a position on the septum 1210 and in a chamber of the heart on an opposite side of the septum 1210 and adjacent the opening 3900. FIG. 40 illustrates the anchor 202' deployed to the interventricular septum 1210 in the right ventricle 1204. The anchors 202, 202' may have a cloth positioned on one or more side to aid in sealing and to promote tissue attachment.

The deployment apparatus 3902 may then be withdrawn with the tension member 286 trailing from the deployment apparatus 3902. The tension member 286 may couple the anchors 202, 202' to each other and may extend through the opening 3900. The tension member 286 may then be pulled to tension the tension member 286 and draw the anchors 202, 202' towards each other. Forces may be applied to opposite sides of the septum 1210.

Figure 43:
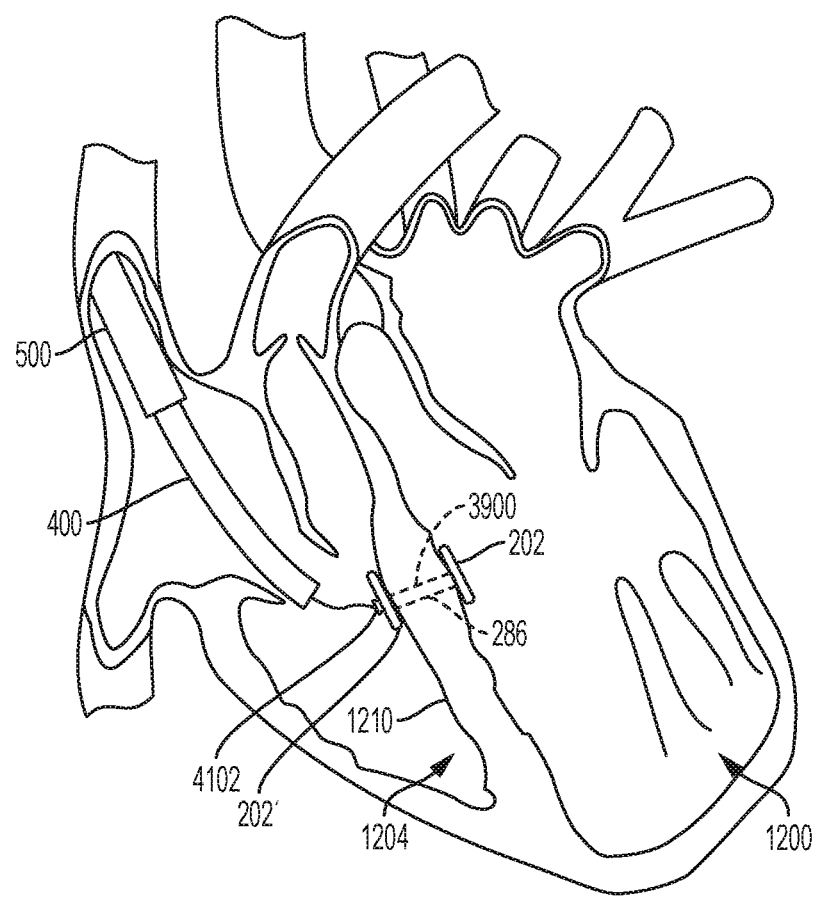
FIG. 43 illustrates a cross sectional view of a patient's heart with a plug deployed to the heart according to an embodiment of the present disclosure.

FIG. 43, for example, illustrates the deployment apparatus 3902 withdrawn from the left ventricle 1200 with the anchor 202' positioned in the right ventricle 1204 on the interventricular septum 1210. The tension member 286 may extend exterior of the patient's heart for tensioning.

Figure 41:
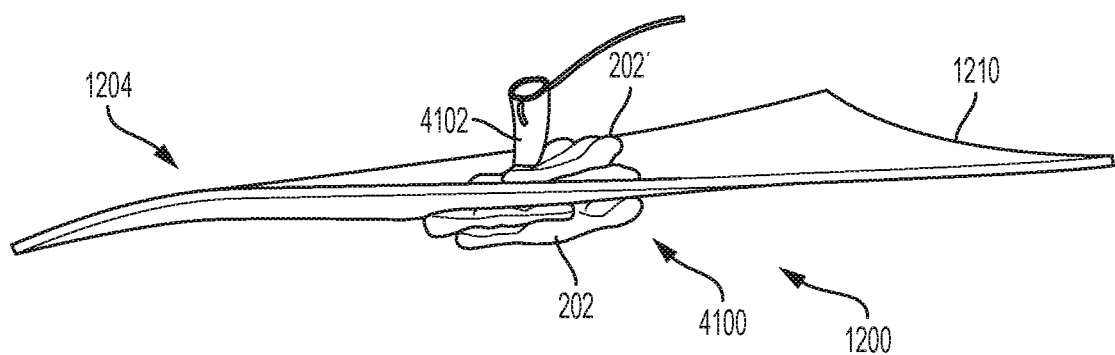
FIG. 41 illustrates a perspective view of a representation of a plug being deployed to a patient's septum according to an embodiment of the present disclosure.

FIG. 41 illustrates the anchors 202, 202' positioned on opposite sides of the intraventricular septum 1210 and drawn together to seal the opening in the intraventricular septum 1210. The combination of anchors 202, 202' and tension member 286 may form a plug of the opening.

A lock 4102 may extend from the anchors 202, 202' to prevent the tension member 286 from slipping after being set. The lock may comprise a clip, autoknotter device, or another form of lock (for example, as described in U.S. Pat. No. 9,498,202 or 7,628,797, the entire disclosures of which are incorporated by reference). The remaining portion of the tension member 286 may then be cut and the deployment apparatus 3902 withdrawn from the patient's body, leaving the plug 4100 in position sealing the opening in the intraventricular septum 1210.

Figure 44:
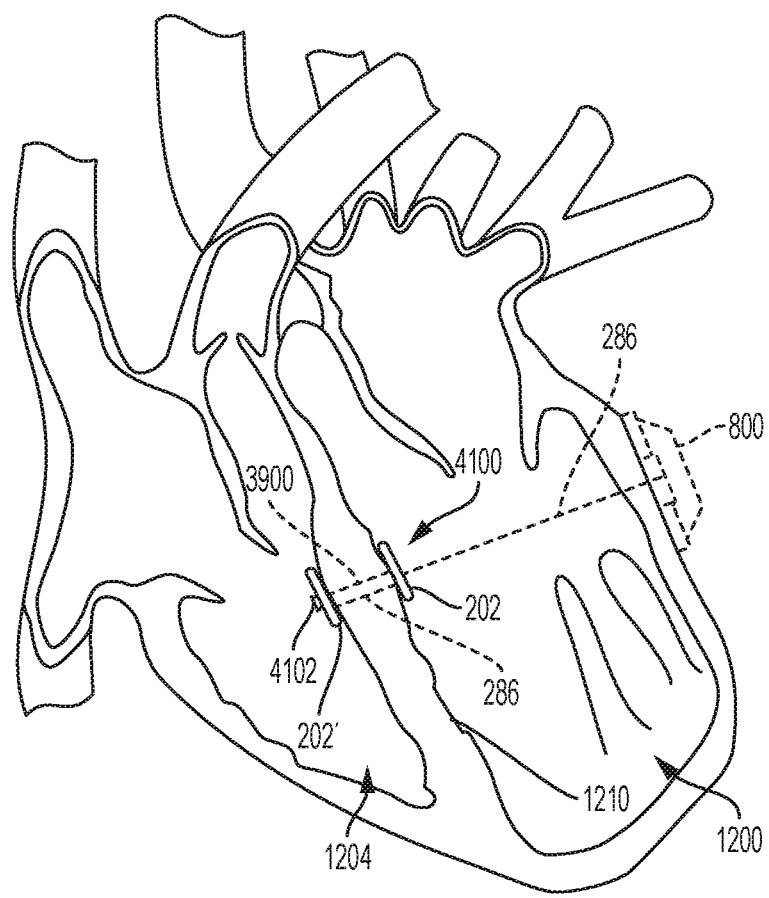
FIG. 44 illustrates a cross sectional view of a patient's heart with a plug deployed to the heart according to an embodiment of the present disclosure.

FIG. 44 illustrates the deployed plug 4100 plugging the opening 3900 in the interventricular septum 1210.

FIG. 44 illustrates an embodiment shown in dashed lines in which the anchor 800 may be coupled to the plug 4100. In this embodiment, the plug 4100 may be deployed in a manner similar to the procedure shown in FIG. 32. For example, a puncture device 168 and sheath 170 as shown in FIG. 32 may be passed through the right ventricle 1200 and to the opening 3900 in the interventricular septum 1210. The puncture device 168 may be withdrawn, and the deployment apparatus 3902 may be passed through the sheath 170 and opening 3900. The deployment apparatus 3902 may first deploy the anchor 202' in the right ventricle 1204 and then deploy the anchor 202 in the left ventricle 1200. The deployment apparatus 3902 and sheath 170 and access apparatus 100 may then be withdrawn with the tension member 286 extending out of the puncture in the external surface of the patient's left ventricle 1200. The anchor 800 may then be deployed in a similar manner as discussed in regard to FIGS. 26-31. The tension member 286 may be tensioned at the anchor 800 and locked in position, as discussed herein. The tensioned tension member 286 may tension and seal the plug 3900.

The methods discussed in regard to FIGS. 39-44 may beneficially utilize the anchors 202, 202' to treat an opening in a septum positioned between chambers of the heart, and may provide an anchoring system for the anchor 800.

Figure 45:
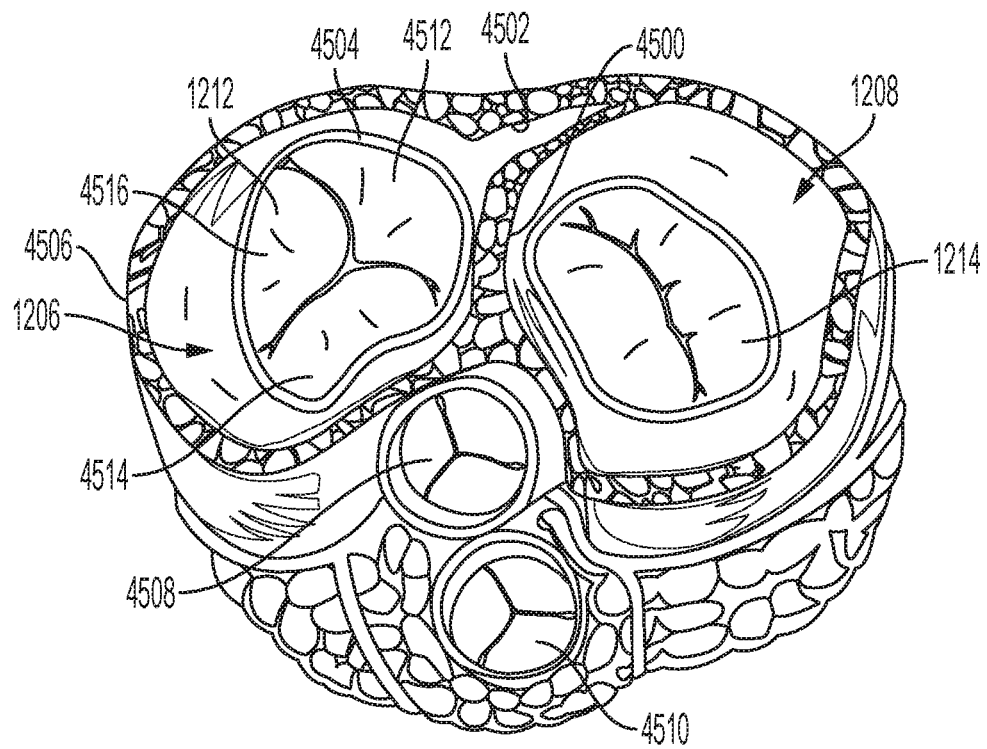
FIG. 45 illustrates a cross sectional view of a patient's heart showing the tricuspid and mitral valves.

Heart anchors may be utilized to reshape an annulus of a tricuspid valve of a patient's heart. FIG. 45 illustrates a cross sectional view of a heart showing a right atrium 1206, a left atrium 1208, the tricuspid valve 1212, and the mitral valve 1214. The interatrial septum 4500, the coronary sinus 4502, the annulus 4504 of the tricuspid valve 1212 and the free wall 4506 of the right atrium are also shown. The aortic valve 4508 and pulmonary valve 4510 are also visible.

The tricuspid valve 1212 includes three leaflets. The three leaflets include the septal leaflet 4512, the anterior leaflet 4514, and the posterior leaflet 4516. A condition that may affect the tricuspid valve 1212 is expansion of the tricuspid valve annulus 4504. This condition may occur for a variety of reasons, including general poor health of the patient as well as dilation of one or more of the right chambers 1206, 1204 of the patient's heart.

The expansion of the tricuspid valve annulus 4504 may lead to functional heart valve regurgitation of the tricuspid valve 1212.

Figure 46:
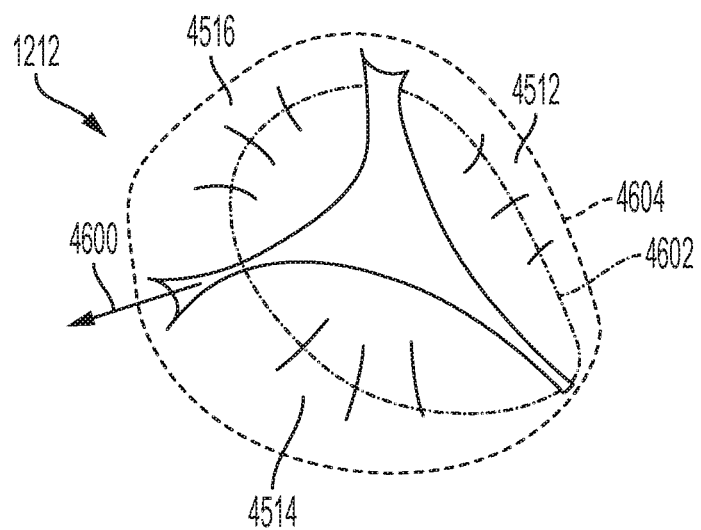
FIG. 46 illustrates a representation of expansion of a tricuspid valve.

FIG. 46 illustrates a representation of a tricuspid valve 1212 that is affected by expansion of the tricuspid valve annulus 4504. The direction of expansion is represented by the arrow 4600 and may be in a direction from septal to lateral. The expansion may be in a direction towards the anterior and posterior commissure of the tricuspid valve 1212. The inner dot-dash line 4602 in FIG. 46 may represent the original size of the tricuspid valve annulus 4504. The outer dash-dash line 4604 may represent an expanded size of the annulus 4504 due to expansion of the tricuspid valve annulus 4504. The size of the leaflets 4512, 4514, 4516 does not significantly increase during expansion of the tricuspid valve annulus 4504, which may lead to areas of poor coaptation between the leaflets as shown in FIG. 46. The poor coaptation may cause functional heart valve regurgitation of the tricuspid valve 1212 (functional tricuspid regurgitation (FTR)).

A heart splint may be utilized that is configured to reshape the annulus 4504 of the tricuspid valve 1212 of the patient's heart. The heart splint may utilize components disclosed herein, including heart anchors and a tension member for coupling the heart anchors together. A heart splint may be deployed to exert a force that opposes a direction of expansion. For example, a heart splint may be deployed to exert a force that is opposite the direction of expansion (marked by arrow 4600) shown in FIG. 46. The resulting force may serve to reshape the tricuspid valve annulus 4504 and improve coaptation of the valve leaflets 4512, 4514, 4516. The improved coaptation may reduce the functional heart valve regurgitation of the tricuspid valve 1212.

The heart splint, or any of the components of the heart splint (e.g., a heart anchor), may be deployed in a less invasive, or minimally invasive manner, and may utilize techniques previously disclosed in this application. For example, a heart anchor may be deployed endovascularly and another heart anchor may be deployed via a small surgical access to the patient's heart. In embodiments, both heart anchors may be deployed endovascularly, via a neckline access procedure or the like.

Figure 47:
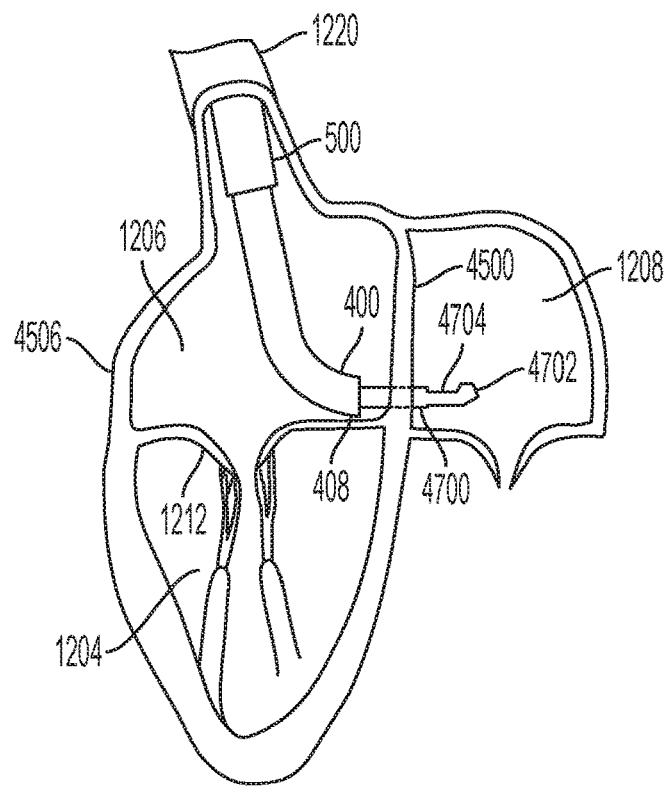
FIG. 47 illustrates a cross sectional view of a patient's heart showing a deployment apparatus passing through an interatrial septum according to an embodiment of the present disclosure.

FIGS. 47-51 illustrate steps in a method for reshaping an annulus 4504 of a tricuspid valve 1212 of a patient's heart. FIG. 47 illustrates a side cross sectional view of a patient's heart showing the right atrium 1206, the left atrium 1208, and the right ventricle 1204. The interatrial septum 4500 and the free wall 4506 of the right atrium 1206 are also shown. A side view of the tricuspid valve 1212 is shown, with poor coaptation between leaflets of the tricuspid valve 1212.

A heart anchor 202 (marked in FIG. 48) may be deployed to the interatrial septum 4500. The heart anchor 202 may be configured to be positioned on the interatrial septum 4500 of the patient's heart. The heart anchor 202 may comprise the heart anchor shown and discussed in regard to FIG. 2A-2H. The heart anchor 202 as shown in FIGS. 2A-2H includes a ring 200 having two ends (204, 206) and configured to move from a linearized configuration to a ring-shaped configuration. A cover 212 is coupled to the ring 200 and extends inward from the ring 200 in the ring-shaped configuration. The ring 200 includes a first portion and a second portion 214, 216, and the first portion overlaps the second portion in the ring-shaped configuration.

The heart anchor 202 may be deployed through use of a deployment apparatus 4700. The deployment apparatus 4700 may be configured similarly as the deployment apparatus 3400 shown in FIG. 34. The deployment apparatus 4700 may be configured to deploy the heart anchor 202 to the interatrial septum 4500 of the patient's heart. The deployment apparatus 4700 may be configured to flex and curve to allow for endovascular passage into the right atrium 1206 and to allow for direction to the interatrial septum 4500 as shown in FIG. 47. The deployment apparatus 4700 may include a puncture device 4702 (which may be configured similarly as puncture device 3406) and may include an opening 4704 (which may be configured similarly as opening 3410). The opening 4704 may be configured to pass the anchor 202 through the opening 4704. The deployment apparatus 4700 may include an internal lumen (which may be configured similarly as lumen 3408) configured to retain the anchor 202 in the unexpanded or linearized configuration within the lumen. A push device (which may be configured similarly as push device 3412) may be configured to pass through the lumen of the deployment apparatus 4700 for pushing anchor 202 out of the opening 4704, in a similar manner as push device 3412.

The deployment apparatus 4700 may be passed into the right atrium endovascularly, for example, via a neckline introduction into the patient's blood vessels, and particularly through the patient's superior vena cava 1220 as shown in FIG. 47. An introducer sheath 500, similar to the introducer sheath disclosed in regard to FIG. 5 may be utilized for access to the patient's blood vessels. A delivery apparatus 400, similar to the delivery apparatus disclosed in regard to FIG. 4 may be utilized to direct the deployment apparatus 4700 to a desired position. For example, the distal end 408 of the delivery apparatus 400 may be controlled to deflect to a position proximate the interatrial septum 4500.

The deployment apparatus 4700 may be passed through the interatrial septum 4500 to reach the left atrium 1208. The puncture device 4702 may be used to puncture the interatrial septum 4500. In other embodiments, a separate puncture device may be utilized to puncture the interatrial septum 4500, among other methods of accessing the left atrium 1208. In certain embodiments, passing through the interatrial septum 4500 may occur through the foramen ovale if the foramen ovale is in the desired location.

The heart anchor 202 may be deployed to the interatrial septum 4500 by being passed out of the opening 4704. The heart anchor 202 may be deployed in a similar manner as discussed in regard to FIGS. 34-37. For example, the heart anchor 202 may be positioned in a lumen of the deployment apparatus 4700 in an unexpanded configuration, with the ring of the heart anchor 202 linearized. The heart anchor 202 may be pushed out of the opening 4704 with a push device or other device. The heart anchor 202 may be configured to automatically move from the unexpanded configuration to the expanded configuration, with the ring of the heart anchor 202 having a ring-shaped configuration. A tension member 286 (shown in FIG. 37) may be withdrawn to expand the cover of the anchor 202. In other embodiments, a deployment member or the like (as shown in FIG. 2H as deployment member 306) may be utilized to expand the cover of the anchor 202.

The heart anchor 202 may be deployed to the interatrial septum 4500 at a desired location that serves to oppose a direction of expansion of the tricuspid annulus 4504 (such as a direction represented by the arrow 4600 in FIG. 46). The deployment apparatus 4700 may be passed through the interatrial septum 4500 at this location. The heart anchor 202 may be deployed on the interatrial septum 4500 in the left atrium 1208 at this location. The heart anchor 202 may be securely pressed against the interatrial septum 4500 by the user pulling the tension member 286 or a deployment member or the like.

Figure 48:
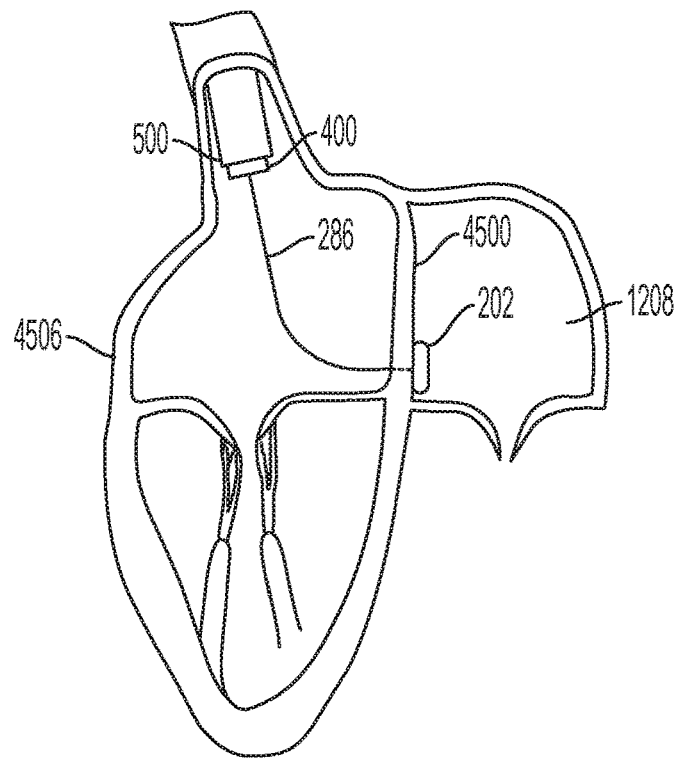
FIG. 48 illustrates a cross sectional view of a patient's heart with a heart anchor positioned on an interatrial septum according to an embodiment of the present disclosure.

FIG. 48 illustrates the heart anchor 202 having been deployed to the interatrial septum 4500. The deployment apparatus 4700 may be withdrawn, with the tension member 286 trailing from the deployment apparatus 4700 (and extending through the sheath 500).

The tension member 286 may be brought to the corresponding desired position in the free wall 4506 of the right atrium 1206 in a variety of methods.

Figure 49:
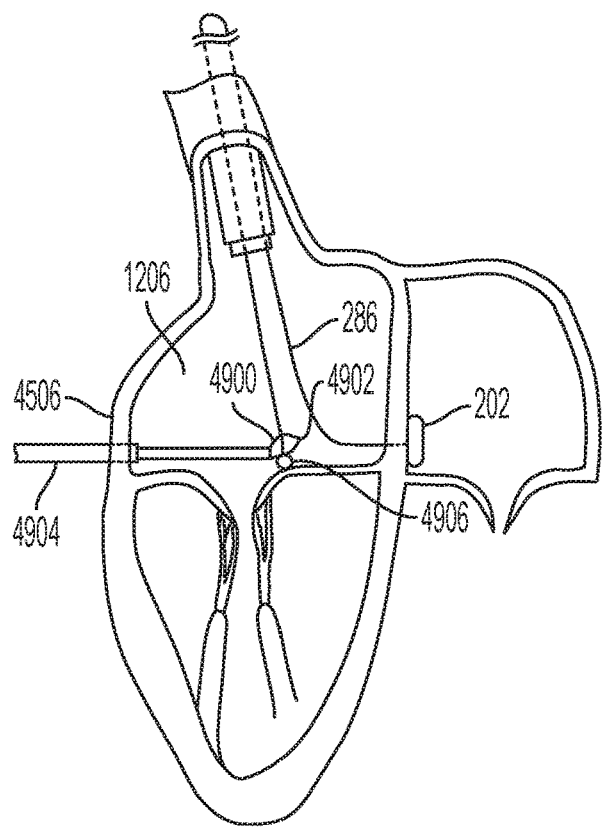
FIG. 49 illustrates a cross sectional view of a patient's heart with a heart anchor positioned on an interatrial septum and a snare passing into the right atrium according to an embodiment of the present disclosure.

FIG. 49 illustrates a method of bringing the tension member 286 to a corresponding desired position in the free wall 4506 of the right atrium 1206 utilizing external access of the right atrium 1206. The method may utilize a snare 4900 or other method of drawing the tension member 286 to the free wall 4506 of the right atrium 1206.

As shown in FIG. 49, a puncture of the free wall 4506 of the right atrium 1206 may be made. A puncture device 4902 at the tip of a snare 4900, or other form of puncture device may be utilized to enter the right atrium 1206 through the free wall 4506. The puncture may be made at a desired location to position the heart anchor 5100 (marked in FIG. 51) on the external surface of the free wall 4506. The puncture may be made at a location that the tension member 286 is drawn through to define the direction of force between the heart anchor 202 and the heart anchor 5100.

Upon the puncture of the free wall 4506 being made, the snare 4900 may be advanced into the right atrium 1206. The snare 4900 may pass through a sheath 4904 or other device for allowing smooth entry into the right atrium 1206. The snare 4900 may be utilized to snare the tension member 286, either directly or by snaring another snare 4906 as shown in FIG. 49. The snare 4906 may be coupled to the tension member 286, as represented by the loop at the top of FIG. 49.

Figure 50:
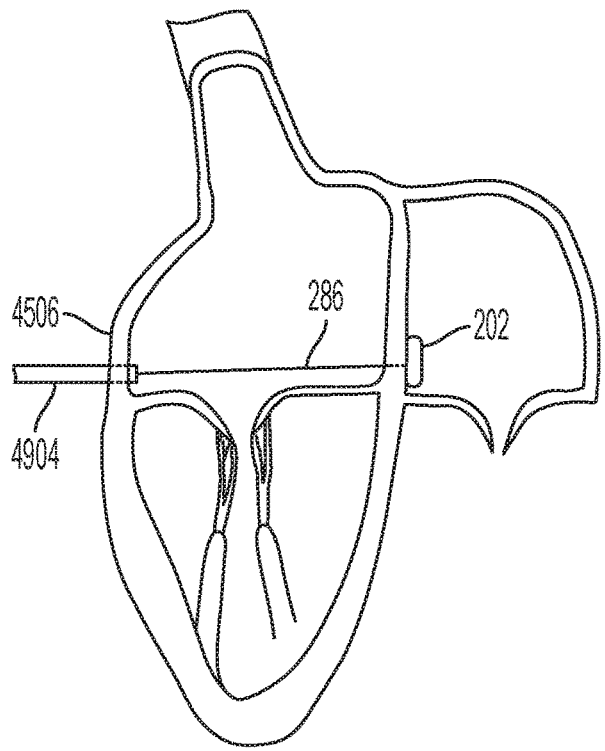
FIG. 50 illustrates a cross sectional view of a patient's heart with a tension member extending across the right atrium according to an embodiment of the present disclosure.
Figure 51:
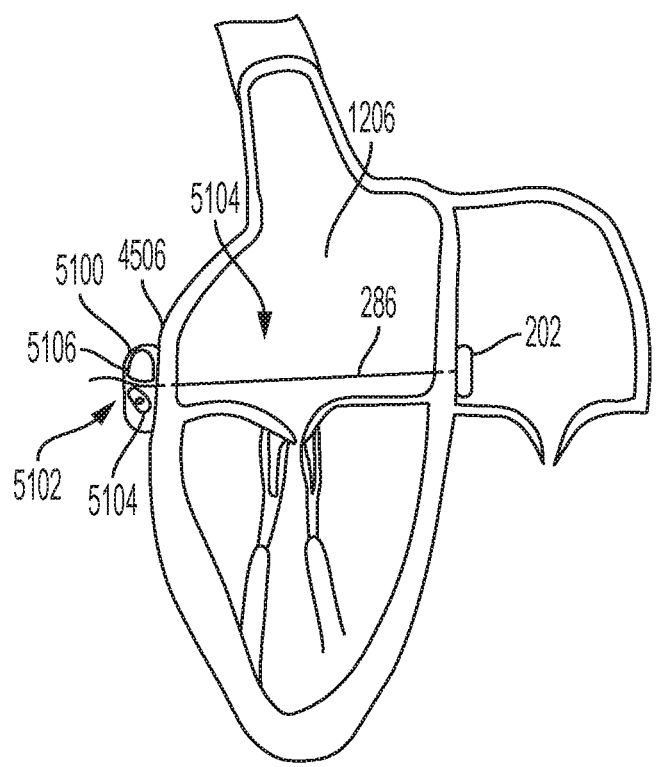
FIG. 51 illustrates a cross sectional view of a patient's heart with a heart splint deployed to the heart according to an embodiment of the present disclosure.

Upon the tension member 286 being snared, the tension member 286 may be withdrawn through the puncture in the free wall 4506 of the right atrium 1206 in a configuration shown in FIG. 50. In an embodiment in which the tension member 286 is coupled to a snare 4906, then the snare may be withdrawn through the puncture as well. The tension member 286 may be brought outside of the patient's body or may otherwise be accessible for coupling to a heart anchor such as the heart anchor 5100 shown in FIG. 51. The heart anchor 5100 may be coupled to the tension member 286 and deployed to the free wall of the right atrium 1206 as shown in FIG. 51. The heart anchor 5100 may be deployed to the external surface of the patient's heart on the free wall 4506. The heart anchor 5100 may be deployed adjacent to the tricuspid annulus.

FIG. 51 illustrates the heart anchor 5100 in position on the free wall 4506 of the right atrium 1206. The heart anchor 5100 is configured to be positioned on the free wall 4506 of the right atrium 1206. The heart anchor 5100 may include a lock 5102. The lock 5102 may be configured similarly as the lock 838 shown in FIG. 8D, and may be configured to set a locked or unlocked state of the heart anchor 5100. The lock 5102 may be for locking the tension member 286 to the heart anchor 5100. The lock 5102 may include a rotatable body 5104 and a locking surface 5106 that operate similarly as the respective rotatable body 850 and locking surface 848 of the lock 838. The rotatable body 5104 may comprise a cam body that operates similarly as the rotatable body 850 discussed in regard to FIGS. 8D and 8E. The heart anchor 5100 may comprise a pad, as shown in FIG. 38 with anchor 3702, or may have another configuration as desired.

The user may tension the tension member 286 for coupling the heart anchor 202 to the heart anchor 5100. The user may set a tension of the tension member 286 by pulling the tension member 286 through the lock 5102 of the heart anchor 5100 to a desired amount. The user accordingly may set a length of the tension member 286 between the heart anchors 202, 5100 and a distance between the heart anchors 202, 5100. The tension member 286 may be tensioned to a desired amount with the user simultaneously verifying proper hemodynamics. The user may monitor the diameter of the tricuspid annulus and tricuspid regurgitation. The tensioning and monitoring may occur in real-time.

Preferably, the tensioning of the tension member 286 counteracts the expansion of the tricuspid valve annulus and improves coaptation of the tricuspid valve leaflets. The diameter of the tricuspid valve annulus may be reduced. The tricuspid valve annulus may be moved in a septal direction (from lateral). Upon the tension member 286 having the desired amount of tension, the user may lock the tension member 286 in tension between the heart anchor 202 and the heart anchor 5100. The lock 5102 may be locked to secure tension member 286 to the heart anchor 5100. The remaining portion of the tension member 286 may be cut by the user as desired. The resulting heart splint 5104 may be left in position to therapeutically counteract the expansion of the tricuspid valve annulus.

Figure 52:
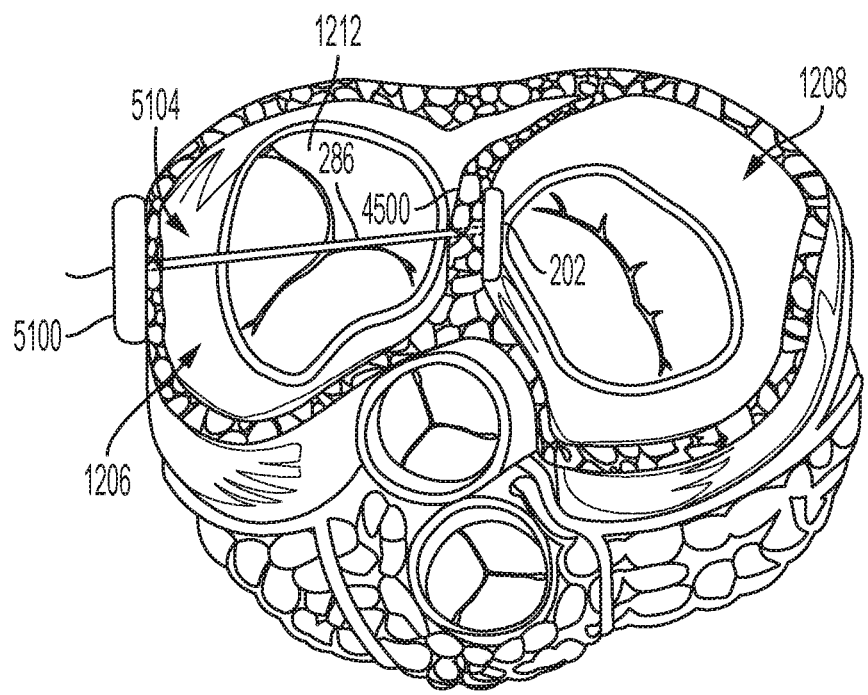
FIG. 52 illustrates a cross sectional view of a patient's heart with a heart splint deployed to the heart according to an embodiment of the present disclosure.

FIG. 52 illustrates a top cross-sectional view of the patient's heart with the heart splint 5104 in position. The heart splint 5104 extends across the right atrium 1206. The tension member 286 couples the heart anchor 202 to the heart anchor 5100 and extends within the right atrium 1206 and extends over at least a portion of the tricuspid valve 1212. As shown in FIG. 52, preferably the tension member 286 extends in a direction that counteracts the direction of expansion of the tricuspid valve annulus.

The heart splint 5104 may be deployed in a variety of methods that are not limited to the method shown in FIGS. 47-51. In addition, the components comprising the heart splint may vary in other embodiments.

Figure 53:
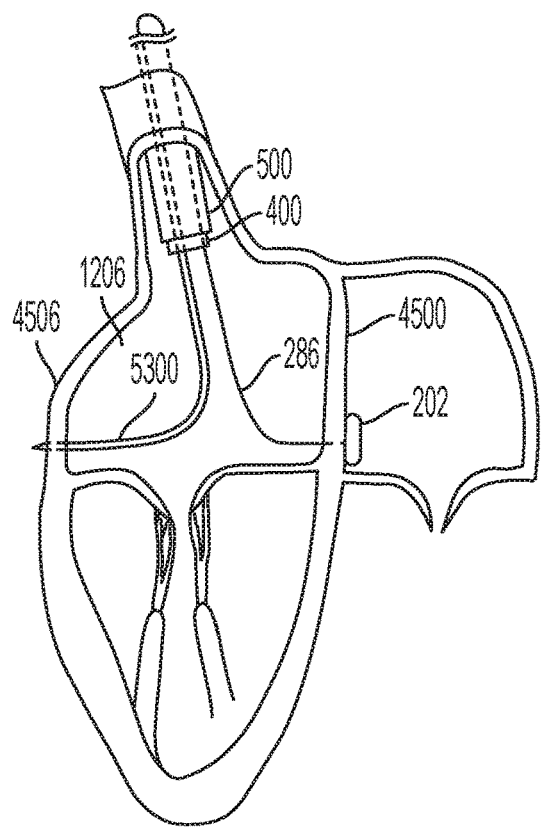
FIG. 53 illustrates a cross sectional view of a patient's heart with a heart anchor positioned on an interatrial septum and a puncture device penetrating the free wall of the right atrium according to an embodiment of the present disclosure.
Figure 54:
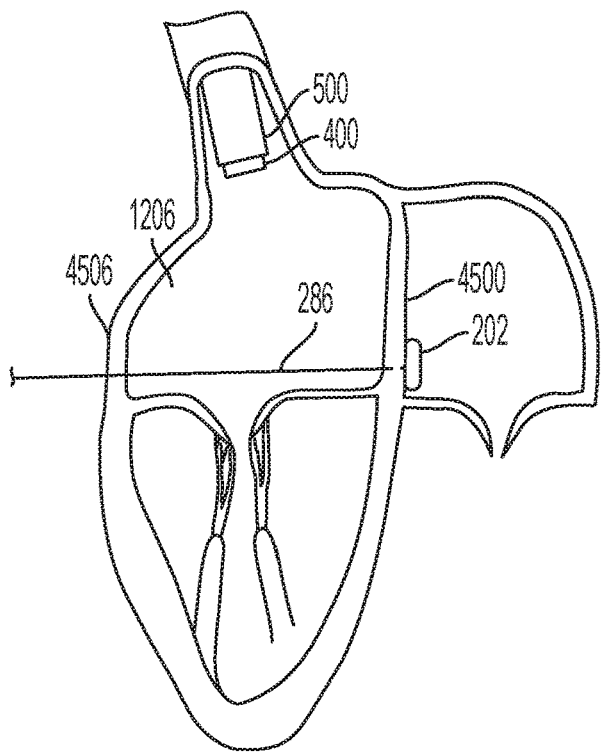
FIG. 54 illustrates a cross sectional view of a patient's heart with a tension member extending across the right atrium according to an embodiment of the present disclosure.
Figure 55:
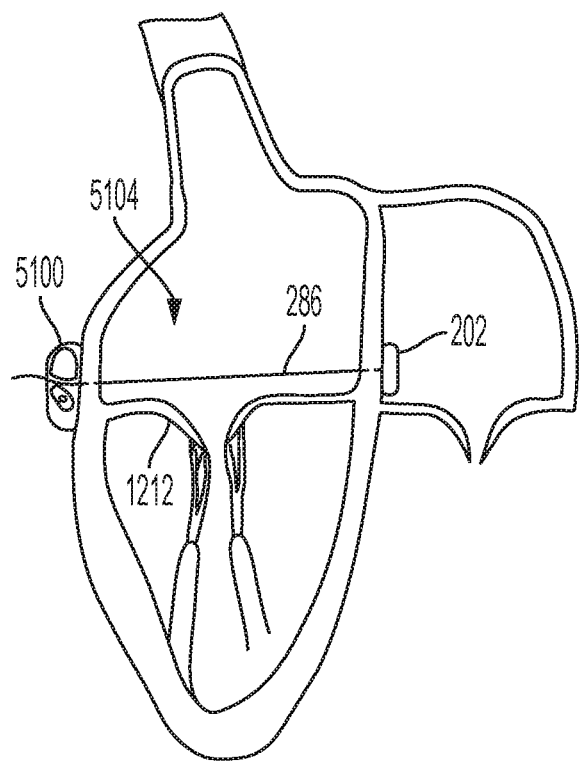
FIG. 55 illustrates a cross sectional view of a patient's heart with a heart splint deployed to the heart according to an embodiment of the present disclosure.

FIGS. 53-55 illustrate an embodiment in which the heart splint 5104 is deployed in a method in which the free wall 4506 of the right atrium 1206 is punctured from inside the right atrium 1206. FIG. 53 illustrates a configuration in which the heart anchor 202 has been deployed to the interatrial septum, for example, in a manner as shown in FIGS. 47 and 48. A puncture may then be made of the free wall 4506 of the right atrium 1206 from inside the right atrium 1206.

FIG. 53 illustrates a puncture device 5300 that may be used to puncture the free wall 4506 of the right atrium 1206 from inside the right atrium 1206. The puncture device 5300 may comprise a curved or directable needle device that may puncture the free wall 4506 at the desired location. In other embodiments, other forms of puncture devices may be utilized. The puncture device 5300 may be coupled to the tension member 286, as represented by the loop shown at the top of FIG. 53. The puncture device 5300 may then be drawn through the free wall 4506 of the right atrium 1206 and may be accessed via surgical access of the exterior of the patient's heart. The puncture device 5300 may exit the patient's heart with the tension member 286 trailing, to allow the user to access the tension member 286.

Figure 60:
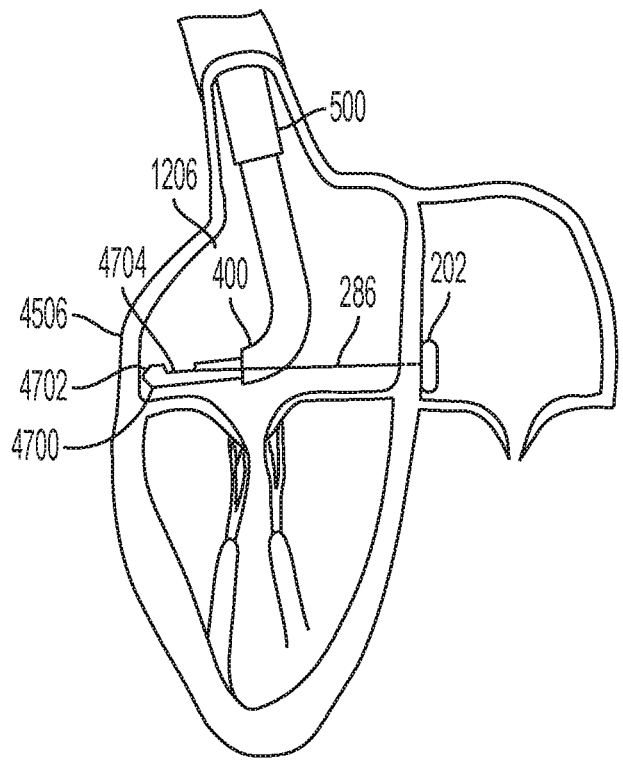
FIG. 60 illustrates a cross sectional view of a patient's heart with a heart anchor positioned on an interatrial septum and a deployment apparatus directed towards the free wall of the right atrium according to an embodiment of the present disclosure.

In one embodiment, the deployment apparatus 4700 shown in FIG. 47 may be utilized to puncture the free wall 4506 from inside the right atrium 1206. For example, after the interatrial septum 4500 is punctured as shown in FIG. 47 and the heart anchor 202 is deployed to the interatrial septum 4500, then the deployment apparatus 4700 may be rotated to puncture the free wall 4506 from inside the right atrium 1206 (in a similar manner as shown in FIG. 60). A puncture device 4702 at the tip of the deployment apparatus 4700 may be utilized to puncture the free wall 4506 from inside the right atrium 1206. The deployment apparatus 4700 may be passed outside of the patient's heart with the tension member 286 trailing, to allow the user to access the tension member 286.

The tension member 286 extends outside of the patient's heart, as shown in FIG. 54. The heart anchor 5100 may then be coupled to the tension member 286 and deployed to the free wall of the right atrium 1206 in a similar manner as discussed in regard to FIGS. 50-51. FIG. 55 illustrates the heart splint 5104 in position, with the tension member 286 extending across the tricuspid valve 1212.

Figure 56:
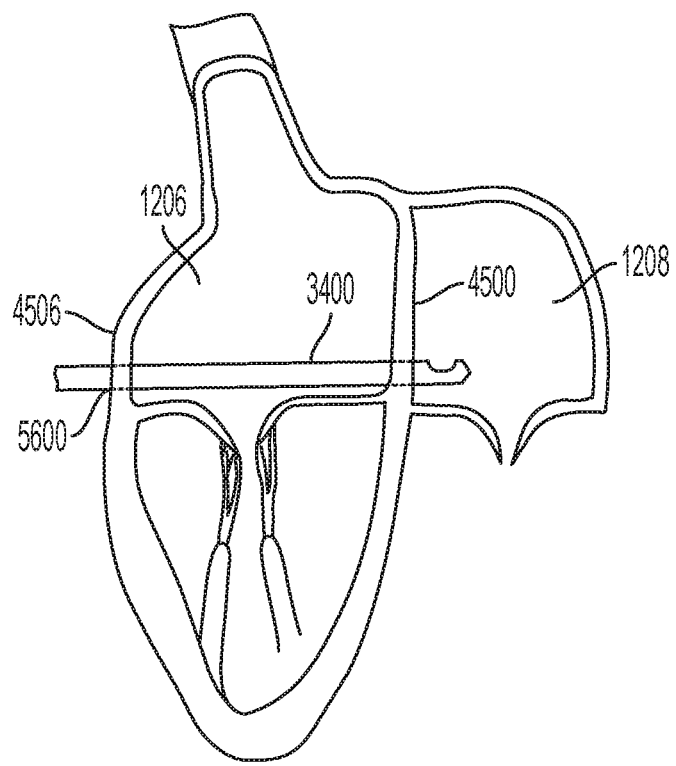
FIG. 56 illustrates a cross sectional view of a patient's heart with a deployment member passing through the free wall of the right atrium and the interatrial septum according to an embodiment of the present disclosure.
Figure 57:
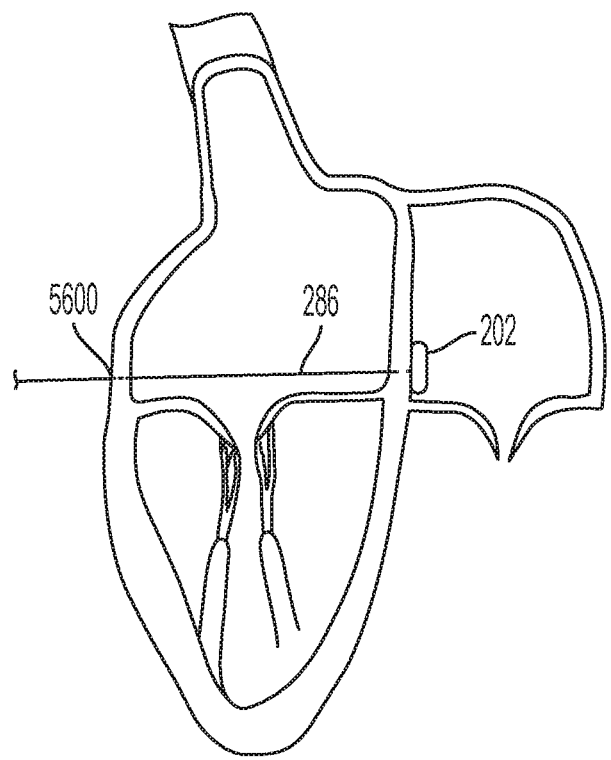
FIG. 57 illustrates a cross sectional view of a patient's heart with a tension member extending across the right atrium according to an embodiment of the present disclosure.
Figure 58:
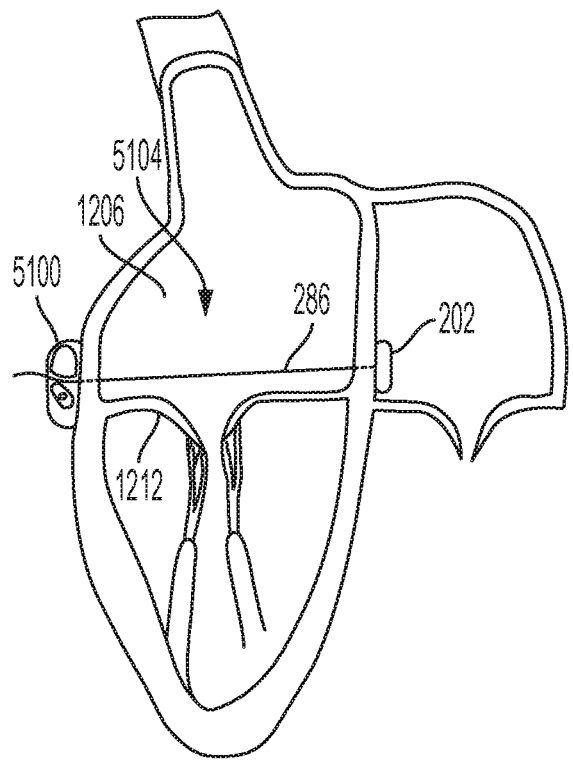
FIG. 58 illustrates a cross sectional view of a patient's heart with a heart splint deployed to the heart according to an embodiment of the present disclosure.

FIGS. 56-58 illustrate an embodiment in which the heart splint 5104 is deployed in a method in which the free wall 4506 of the right atrium 1206 is punctured from outside the right atrium 1206 and the interatrial septum 4500 is punctured in a direction from the right atrium 1206 to the left atrium 1208. The free wall 4506 and the interatrial septum 4500 may each be punctured by a deployment apparatus 3400 passing through both the free wall 4506 and the interatrial septum 4500.

FIG. 56 illustrates the deployment apparatus 3400 having entered the right atrium 1206 from outside the free wall 4506 of the right atrium and passing through the interatrial septum 4500 into the left atrium 1208. The heart anchor 202 may be deployed to the interatrial septum 4500 in a similar manner as described in regard to FIGS. 34-37. The deployment apparatus 3400 may then be withdrawn from the right atrium 1206 with the tension member 286 trailing out of the puncture 5600 of the free wall 4506 of the right atrium 1206. A configuration as shown in FIG. 57 may result. The heart anchor 5100 may then be coupled to the tension member 286 and deployed to the free wall of the right atrium 1206 in a similar manner as discussed in regard to FIGS. 50-51. FIG.

58 illustrates the heart splint 5104 in position, with the tension member 286 extending across the tricuspid valve 1212.

Figure 59:
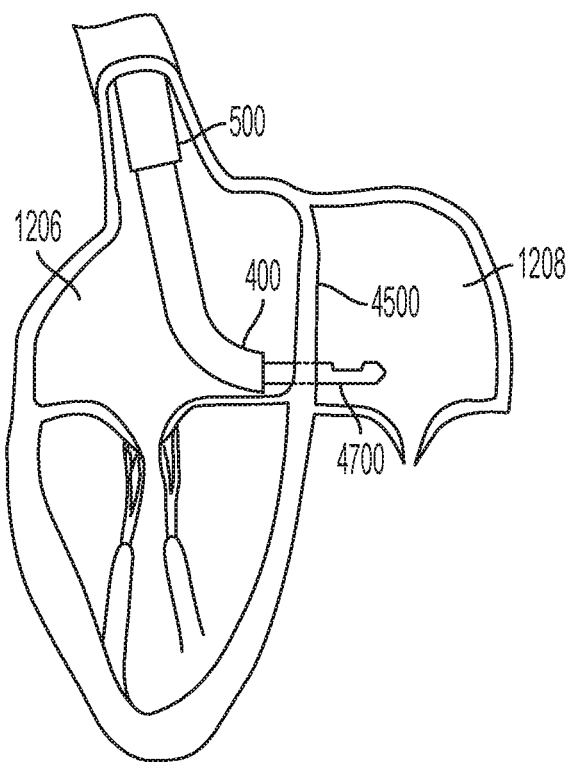
FIG. 59 illustrates a cross sectional view of a patient's heart showing a deployment apparatus passing through an interatrial septum according to an embodiment of the present disclosure.

FIGS. 59-63 illustrate an embodiment in which a heart splint 6300 is deployed that uses multiple of the heart anchors 202 (the second heart anchor is configured similarly as heart anchor 202 and is designated as heart anchor 202'). FIG. 59 illustrates that the deployment apparatus 4700 may be utilized to puncture the interatrial septum 4500 in a similar manner as discussed regarding FIG. 47. The deployment apparatus may deploy the heart anchor 202 to the interatrial septum 4500 in the left atrium 1208.

The deployment apparatus 4700 may be loaded with at least two heart anchors 202, 202' or otherwise configured to deploy at least two heart anchors 202, 202'. The heart anchors 202, 202' may be connected with a common tension member 286.

FIG. 60 illustrates the deployment apparatus 4700 may be passed to the free wall 4506 of the right atrium 1206 with the tension member 286 trailing the opening 4704 of the deployment apparatus 4700. The deployment apparatus 4700 may puncture the free wall 4506 of the right atrium 1206 with the puncture device 4702. The deployment apparatus 4700 may deploy the heart anchor 202' to the external surface of the free wall 4506 of the right atrium 1206. The deployment apparatus 4700 may then be withdrawn from the right atrium 1206 with the tension member 286 trailing.

Figure 61:
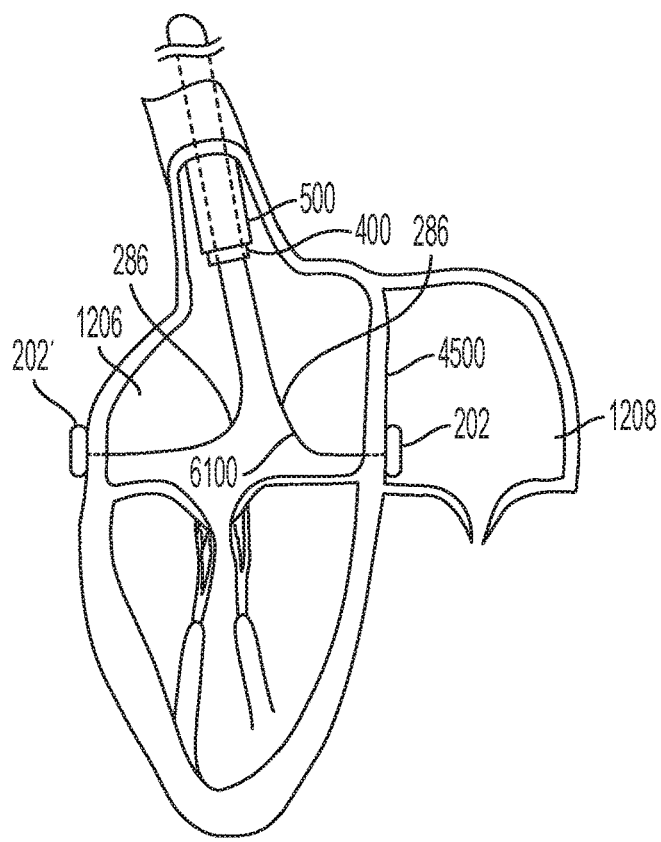
FIG. 61 illustrates a cross sectional view of a patient's heart with a heart anchor positioned on an interatrial septum and a heart anchor positioned on the free wall of the right atrium according to an embodiment of the present disclosure.

FIG. 61 illustrates the deployment apparatus 4700 having been withdrawn from the right atrium 1206 with the tension member 286 trailing. The tension member 286 may then be tensioned to a desired amount by a user. Multiple methods of tensioning the tension member 286 may be utilized. The tensioning may include drawing the portions of the tension member 286 coupled to the respective heart anchors 202, 202' towards each other. A lock 6200 as shown in FIG. 62 may be placed along the tension member 286 and may allow a central portion 6100 of the tension member 286 to be withdrawn to draw the heart anchors 202, 202' towards each other.

Figure 62:
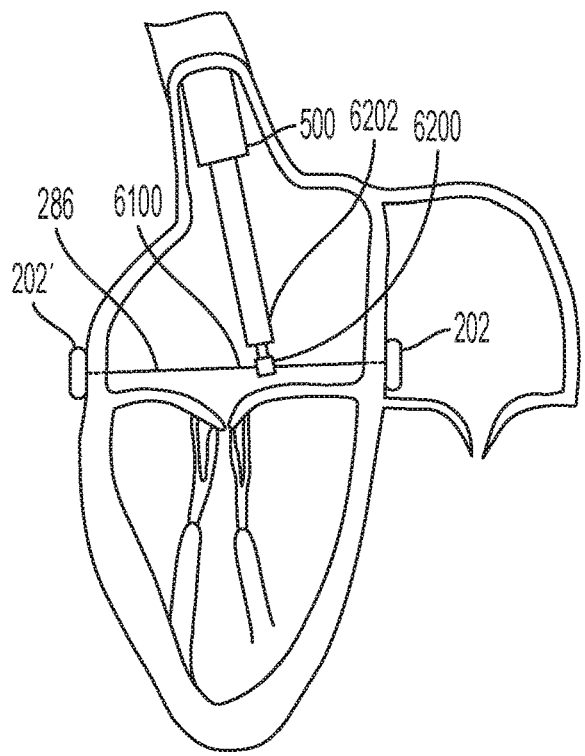
FIG. 62 illustrates a cross sectional view of a patient's heart with a lock positioned between a heart anchor positioned on an interatrial septum and a heart anchor positioned on the free wall of the right atrium according to an embodiment of the present disclosure.

FIG. 62 illustrates a lock 6200 in position on the tension member 286 between the heart anchors 202, 202'. A sheath 6202 or other device may hold the lock 6200 in position while the central portion 6100 of the tension member 286 is withdrawn to draw the heart anchors 202, 202' towards each other. The lock 6200 may comprise a releasable lock, and may be configured similarly as the lock 5102, to allow for the lock 6200 to be set once the tension in the tension member 286 is set to the desired amount. The tension member 286 may be tensioned to a desired amount with the user simultaneously verifying proper hemodynamics. The user may monitor the diameter of the tricuspid annulus and tricuspid regurgitation. The tensioning and monitoring may occur in real-time.

Figure 63:
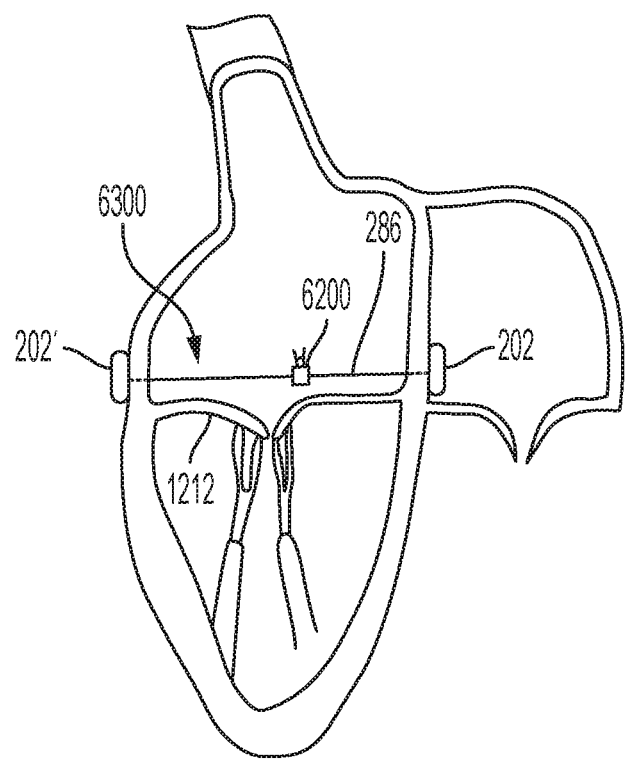
FIG. 63 illustrates a cross sectional view of a patient's heart with a heart splint deployed to the heart according to an embodiment of the present disclosure.

Upon the desired tension being provided in the tension member 286, the remaining portion of the tension member 286 may be cut. FIG. 63 illustrates the heart splint 6300 in position, with the tension member 286 extending across the tricuspid valve 1212. The lock 6200 may be positioned centrally as shown in FIG. 63, or may be positioned proximate one of the heart anchors 202, 202' in other embodiments. The lock 6200 in certain embodiments may be positioned out of the flow path of the tricuspid valve 1212 to reduce the possibility of disrupting the flow through the tricuspid valve 1212.

Figure 64:
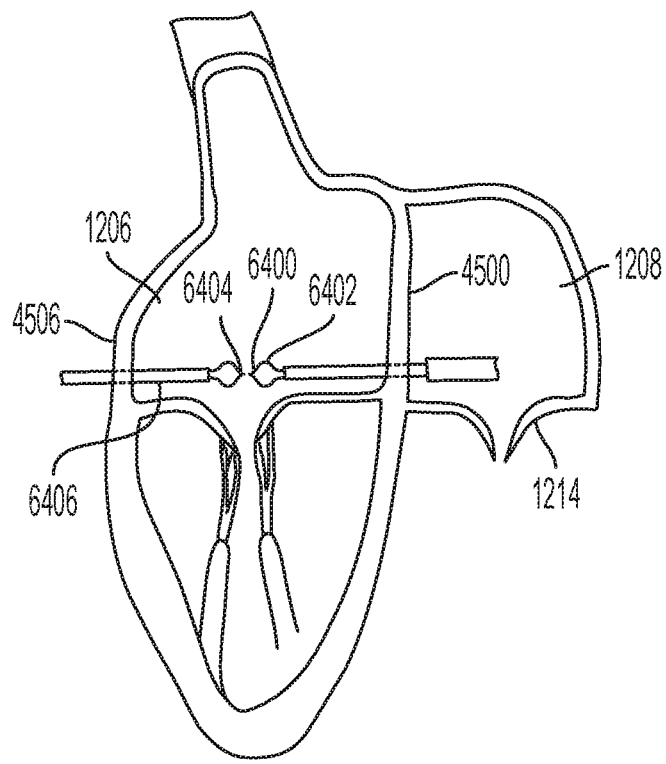
FIG. 64 illustrates a cross sectional view of a patient's heart with a snare passing through the interatrial septum and a snare passing through the free wall of the right atrium according to an embodiment of the present disclosure.
Figure 65:
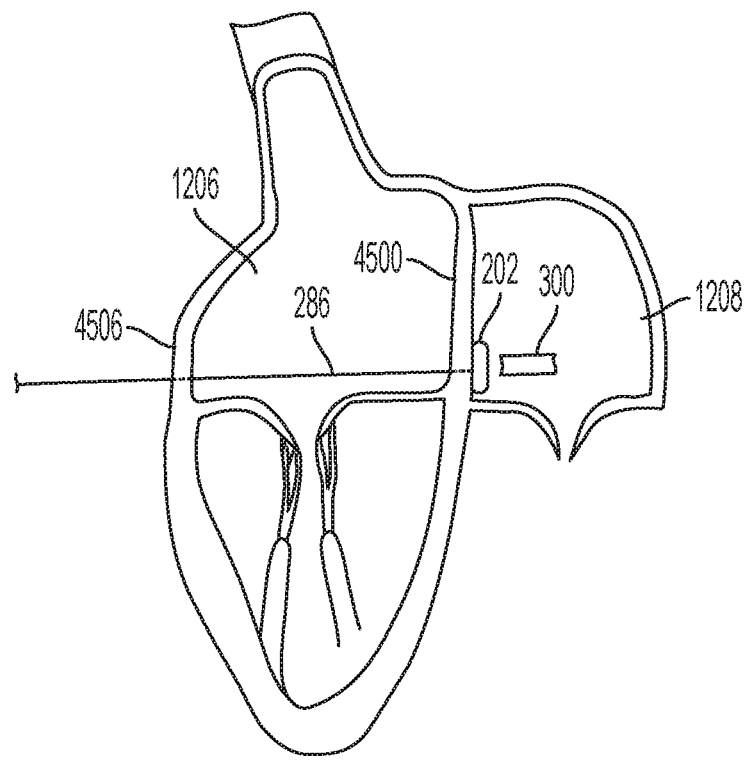
FIG. 65 illustrates a cross sectional view of a patient's heart with a tension member extending across the right atrium according to an embodiment of the present disclosure.
Figure 66:
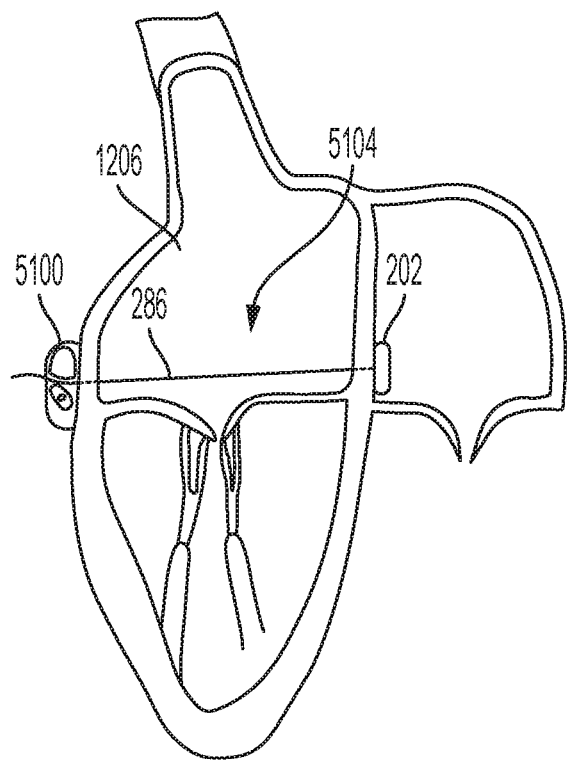
FIG. 66 illustrates a cross sectional view of a patient's heart with a heart splint deployed to the heart according to an embodiment of the present disclosure.

FIGS. 64-66 illustrate an embodiment in which a puncture is made in the interatrial septum 4500 from the left atrium 1208 to the right atrium 1206. The left atrium 1208 may be accessed in a variety of methods. Such methods may include puncture of the left atrium 1208 from outside the patient's heart as well as vascular access. Such vascular access may be provided through the mitral valve 1214 for example.

FIG. 64 illustrates a puncture device 6400 may be passed from the left atrium 1208 to the right atrium 1206 through the interatrial septum 4500. The puncture device 6400 may comprise a portion of a snare 6402. A puncture may be made of the free wall 4506 of the right atrium 1206 via a puncture device 6404. The puncture device may comprise a portion of a snare 6406. The snares 6402, 6406 may snare each other, and may both be withdrawn outside the patient's body through the puncture in the free wall 4506 of the right atrium 1206. The snare 6402 may be coupled to a tension member 286 that is drawn through the puncture in the free wall 4506 of the right atrium 1206 for access by a user. The opposite end of the tension member 286 may be coupled to the anchor 202, which may be deployed at the interatrial septum 4500 in the left atrium 1208 using a deployment apparatus such as the deployment apparatus 300.

FIG. 65 illustrates the anchor 202 having been deployed at the interatrial septum 4500 in the left atrium 1208, with the tension member 286 extending through the right atrium 1206 and the free wall 4506 of the right atrium 1206. The user may then access the tension member 286. The heart anchor 5100 may then be coupled to the tension member 286 and deployed to the free wall of the right atrium 1206 in a similar manner as discussed in regard to FIGS. 50-51. The resulting heart splint 5104 is shown in FIG. 66.

Figure 67:
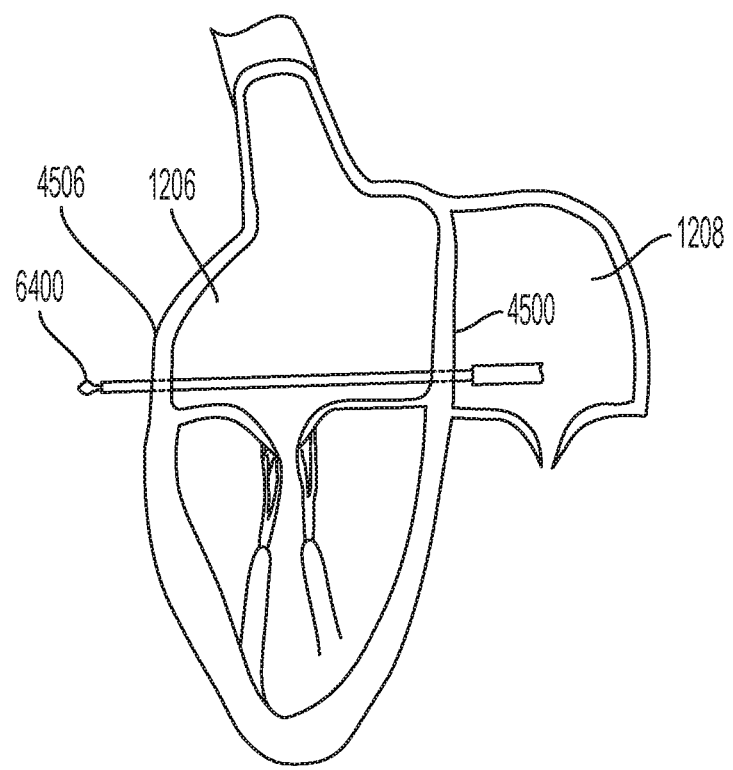
FIG. 67 illustrates a cross sectional view of a patient's heart with a snare passing through the interatrial septum and through the free wall of the right atrium according to an embodiment of the present disclosure.

FIG. 67 illustrates a similar method as shown in FIGS. 64-66, however, here the puncture device 6400 passes from the left atrium 1208 through the interatrial septum 4500 and through the free wall 4506 of the right atrium 1206. A user may access the puncture device 6400 that may be coupled to a tension member 286. The user may withdraw the puncture device 6400 and tension member 286 outside the patient's body through the puncture in the free wall 4506 of the right atrium 1206. The opposite end of the tension member 286 may be coupled to the anchor 202, which may be deployed at the interatrial septum 4500 in the left atrium 1208 using a deployment apparatus such as the deployment apparatus 300. The configuration shown in FIG. 65 may result. The heart anchor 5100 may then be coupled to the tension member 286 and deployed to the free wall of the right atrium 1206 in a similar manner as discussed in regard to FIGS. 50-51. The heart splint 5104 shown in FIG. 66 may result.

Figure 68:
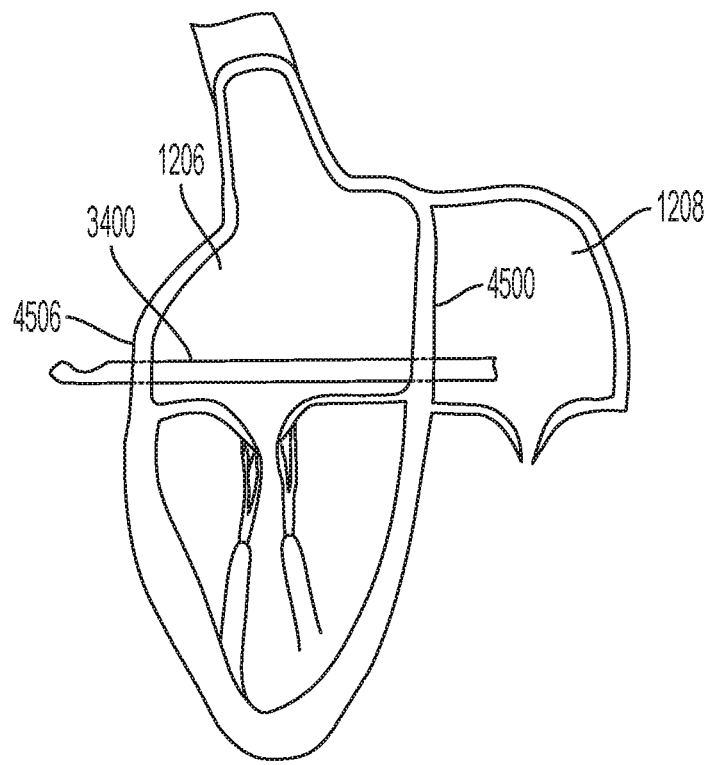
FIG. 68 illustrates a cross sectional view of a patient's heart with a deployment apparatus passing through the interatrial septum and through the free wall of the right atrium according to an embodiment of the present disclosure.

FIG. 68 illustrates an embodiment in which a heart splint 6900 is deployed that uses multiple of the heart anchors 202 (the second heart anchor is configured similarly as heart anchor 202 and is designated as heart anchor 202'). A deployment apparatus 3400 may be passed from the left atrium 1208 through the interatrial septum 4500 and through the free wall 4506 of the right atrium 1206. The deployment apparatus 3400 may deploy the heart anchor 202 to the external surface of the free wall of the right atrium 1206 in a similar manner as described in regard to FIGS. 34-37. The deployment apparatus 3400 may then be withdrawn into the right atrium 1206 with the tension member 286 trailing out of the puncture 6800 of the free wall 4506 of the right atrium 1206. The deployment apparatus 3400 may then be withdrawn into the left atrium 1208 and may deploy the anchor 202' to the interatrial septum 4500. The tension member 286 may be cinched between the two anchors 202, 202' until a desired tension of the tension member 286 is reached. The tension member 286 may be tensioned to a desired amount with the user simultaneously verifying proper hemodynamics. The user may monitor the diameter of the tricuspid annulus and tricuspid regurgitation. The tensioning and monitoring may occur in real-time.

Figure 69:
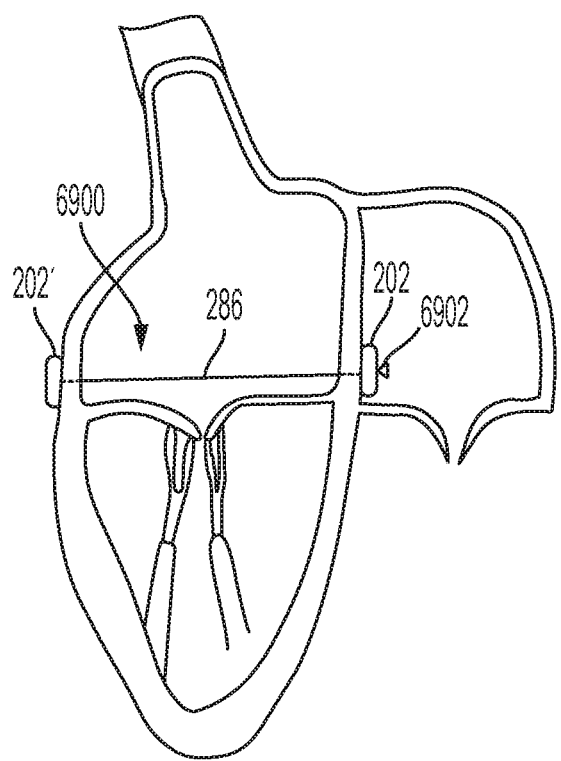
FIG. 69 illustrates a cross sectional view of a patient's heart with a heart splint deployed to the heart according to an embodiment of the present disclosure.

A resulting heart splint 6900 is shown in FIG. 69. A lock 6902 may be set at the anchor 202 to lock the tension of the tension member 286. The lock 6902 may comprise a clip, autoknotter device, or another form of lock (for example, as described in U.S. Pat. No. 9,498,202 or 7,628,797, the entire disclosures of which are incorporated by reference). The remaining portion of the tension member 286 may then be cut.

FIGS. 70-73 illustrate an embodiment of deploying a heart splint 7300 (marked in FIG. 73) that utilizes a heart anchor 7000 configured to be positioned within the coronary sinus 4502 of the patient's heart. The position of the coronary sinus 4502 is represented in FIG. 45. The coronary sinus 4502 may comprise an anchoring point for the heart anchor 7000 of the heart splint 7300.

The heart anchor 7000 may comprise a stent configured to be positioned within the coronary sinus 4502. In other embodiments, other forms of heart anchors configured to be positioned within the coronary sinus 4502 may be utilized, including barbs, prongs, hooks, or other forms of heart anchors.

Figure 70:
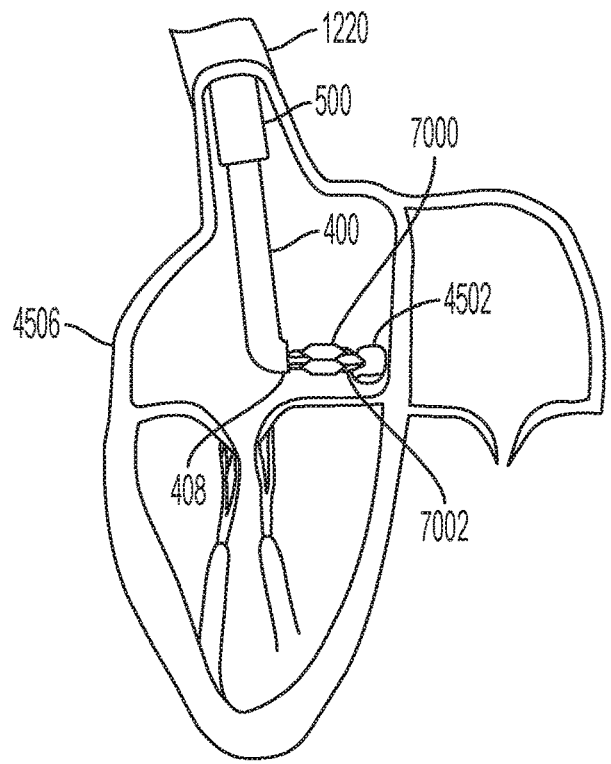
FIG. 70 illustrates a cross sectional view of a patient's heart with a heart anchor directed to a coronary sinus according to an embodiment of the present disclosure.

FIG. 70 illustrates the heart anchor 7000 as a stent that may be deployed to the coronary sinus 4502. The stent may be an expandable stent and may be configured to move from an unexpanded configuration to an expanded configuration. The unexpanded configuration may be a configuration in which the outer profile of the stent is reduced until the stent is deployed in the coronary sinus 4502. FIG. 70 illustrates that the stent may be positioned on a deployment apparatus 7002 in the form of an expandable body such as a balloon or the like that the stent may extend over. The expandable body may expand to move the stent from the unexpanded configured to the expanded configuration.

The deployment apparatus 7002 may be passed into the right atrium endovascularly, for example, via a neckline introduction into the patient's blood vessels, and particularly the patient's superior vena cava 1220 as shown in FIG. 70. An introducer sheath 500, similar to the introducer sheath disclosed in regard to FIG. 5 may be utilized for access to the patient's blood vessels. A delivery apparatus 400, similar to the delivery apparatus disclosed in regard to FIG. 4 may be utilized to direct the deployment apparatus 7002 to a desired position. For example, the distal end 408 of the delivery apparatus 400 may be controlled to deflect to a position proximate the coronary sinus 4502.

The heart anchor 7000 may have a tension member 286 (marked in FIG. 71) coupled to the heart anchor 7000. The heart anchor 7000 may be deployed within the coronary sinus 4502 and then have the delivery apparatus 400 withdrawn to leave the tension member 286 trailing.

The tension member 286 may be brought to the corresponding desired position in the free wall 4506 of the right atrium 1206 in a variety of methods.

Figure 71:
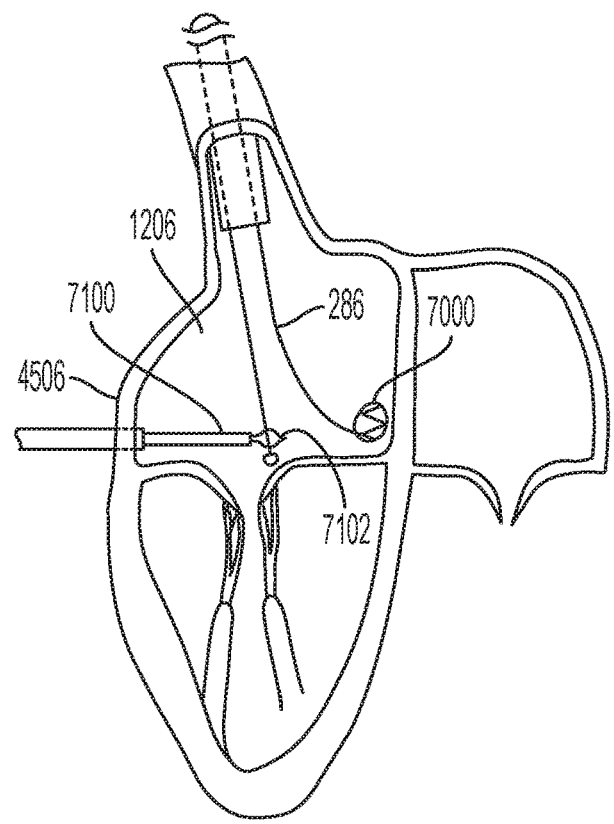
FIG. 71 illustrates a cross sectional view of a patient's heart with a heart anchor positioned within a coronary sinus and a snare passing through the free wall of the right atrium according to an embodiment of the present disclosure.

FIG. 71 illustrates a method of bringing the tension member 286 to a corresponding desired position in the free wall 4506 of the right atrium 1206 utilizing external access of the right atrium 1206. The method may utilize a snare 7100 or other method of drawing the tension member 286 to the free wall 4506 of the right atrium 1206.

Figure 72:
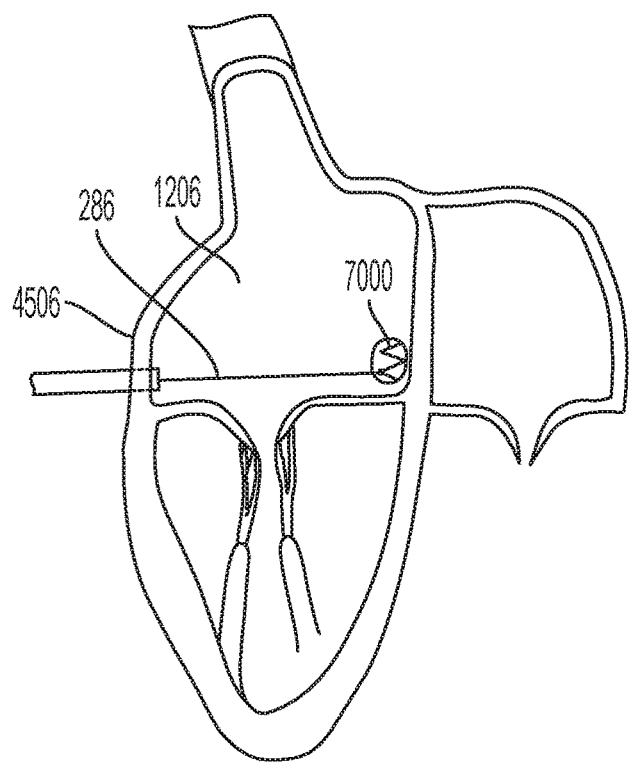
FIG. 72 illustrates a cross sectional view of a patient's heart with a heart anchor positioned within a coronary sinus and a tension member extending across the right atrium according to an embodiment of the present disclosure.
Figure 73:
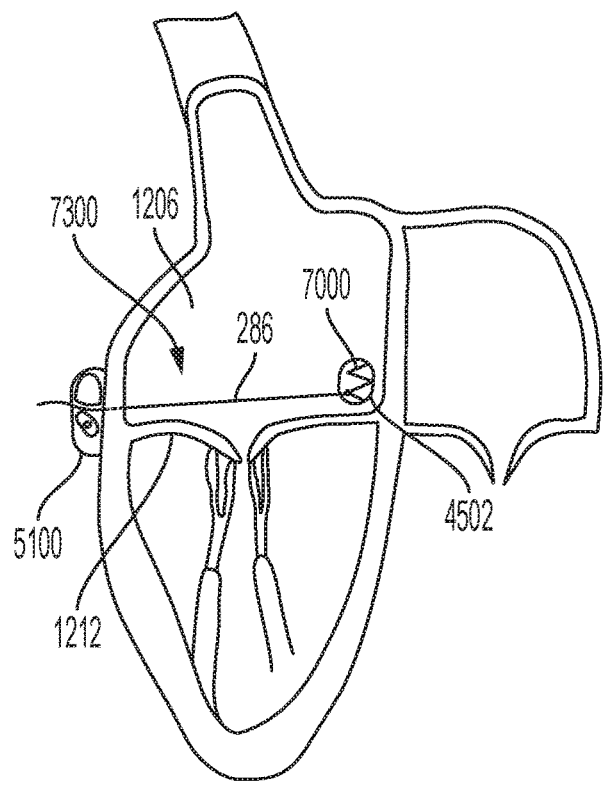
FIG. 73 illustrates a cross sectional view of a patient's heart with a heart splint deployed to the heart according to an embodiment of the present disclosure.

As shown in FIG. 71, a puncture of the free wall 4506 of the right atrium 1206 may be made. A puncture device 7102 at the tip of a snare 7100, or other form of puncture device may be utilized to enter the right atrium 1206 through the free wall 4506 in a similar manner as discussed in regard to FIG. 49. FIG. 72 illustrates the tension member 286 being drawn outside of the patient's heart, in a similar manner as discussed in regard to FIG. 50. The heart anchor 5100 may then be coupled to the tension member 286 and deployed to the free wall of the right atrium 1206 in a similar manner as described in regard to FIG. 51. The heart splint 7300 is shown in FIG. 73.

Figure 74:
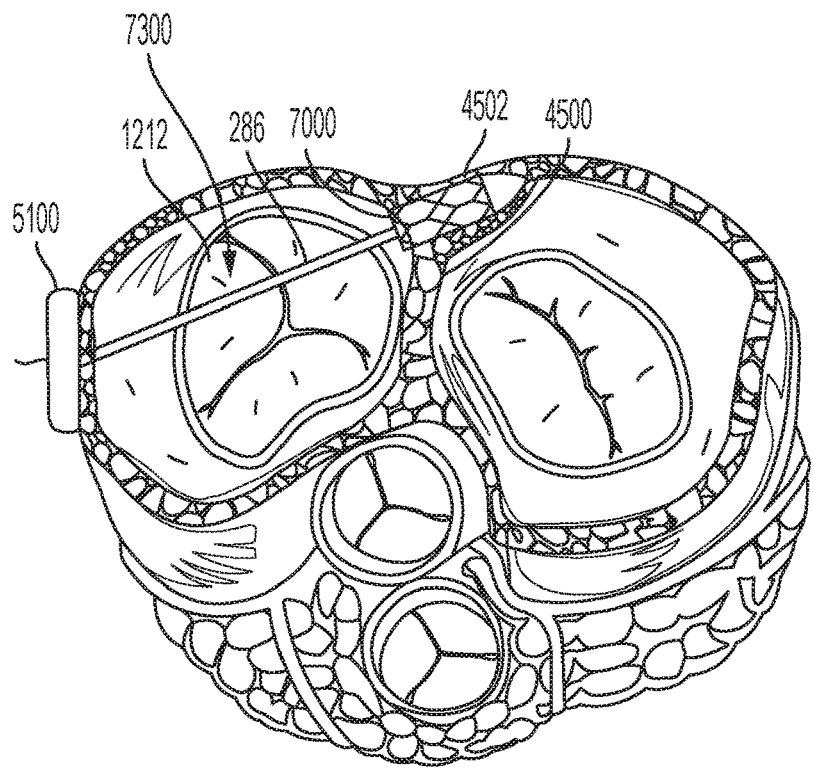
FIG. 74 illustrates a cross sectional view of a patient's heart with a heart splint deployed to the heart according to an embodiment of the present disclosure.

The position of the heart anchor 7000 within the coronary sinus 4502 may vary the direction that the tension member 286 has over the tricuspid valve 1212. FIG. 74 illustrates a top cross-sectional view of the patient's heart. The heart anchor 7000 in the form of a stent is shown positioned within the coronary sinus 4502.

Figure 75:
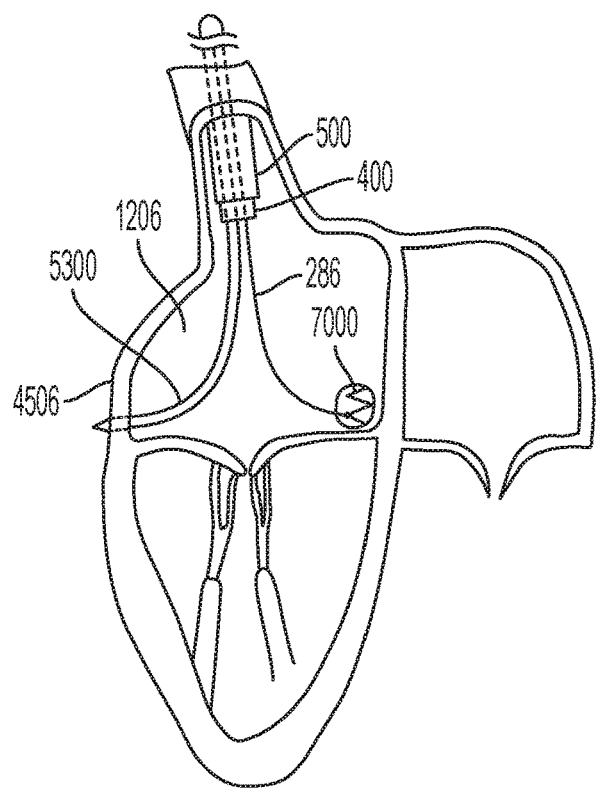
FIG. 75 illustrates a cross sectional view of a patient's heart with a heart anchor positioned within a coronary sinus and a puncture device passing through the free wall of the right atrium according to an embodiment of the present disclosure.

FIG. 75 illustrates an embodiment in which a puncture device 5300 may be used to puncture the free wall 4506 of the right atrium 1206 from inside the right atrium 1206. The puncture device 5300 may be used to pass the tension member 286 outside the right atrium in a similar manner as discussed in regard to FIGS. 53-55. The heart anchor 5100 may then be coupled to the tension member 286 and deployed to the free wall of the right atrium 1206 in a similar manner as described in regard to FIG. 51. The resulting heart splint 7300 is shown in FIG. 73.

Figure 76:
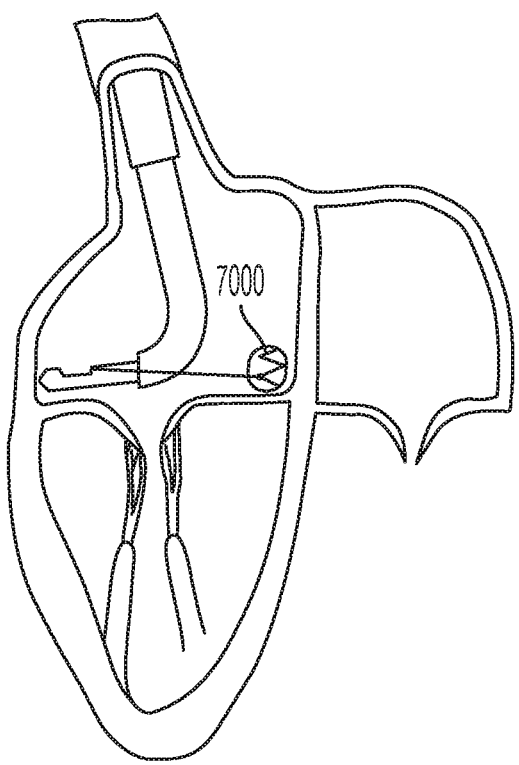
FIG. 76 illustrates a cross sectional view of a patient's heart with a heart anchor positioned within a coronary sinus and a deployment apparatus directed to the free wall of the right atrium according to an embodiment of the present disclosure.
Figure 77:
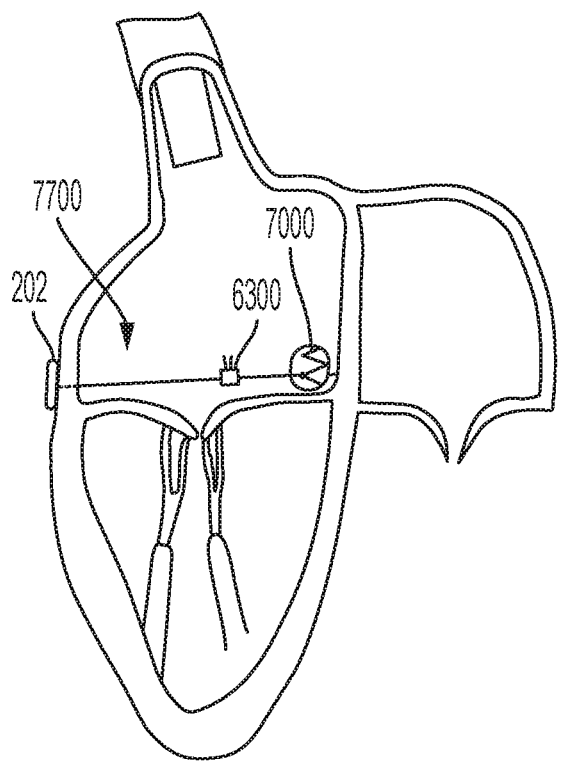
FIG. 77 illustrates a cross sectional view of a patient's heart with a heart splint deployed to the heart according to an embodiment of the present disclosure.

FIGS. 76-77 illustrate an embodiment in which a heart splint 7700 is deployed that uses the heart anchor 202. The heart anchor 202 may be deployed in a similar manner as the heart anchor 202' described in regard to FIGS. 59-63. The resulting splint 7700 is shown in FIG. 77, with a lock 6300 positioned between the heart anchor 202 and anchor 7000.

The heart splints of the embodiments of FIGS. 45-77, or any of the components of the heart splint (e.g., a heart anchor), may be deployed in a less invasive, or minimally invasive manner, and may utilize techniques previously disclosed in this application. For example, in the embodiments of FIGS. 47-52, 53-55, 56-58, 64-66, 67, 70-74, and 75, a small surgical access may be made to the patient's body (such as through a thoracotomy, including a small right anterior thoracotomy, or mini-thoracotomy) to deploy the anchor 5100. In the embodiments of FIGS. 59-63, 68-69, and 76-77, both heart anchors 202, 202' may be deployed endovascularly. Endovascular deployment may include access through the jugular or femoral vein. Transcatheter and percutaneous deployment may be utilized. Other forms of deployment may be utilized as desired. The reshaping of the heart valve annulus may include a beating heart reshaping.

The heart splints of the embodiments of FIGS. 45-77 may beneficially serve to reshape an annulus of a tricuspid valve of the patient's heart. In an embodiment in which a heart anchor 202 (or 202') is utilized, the heart anchor may beneficially distribute the force applied to the heart anchor over a relatively large area. The cover 212 may bear a majority of the force applied to the heart anchor 202. In an embodiment in which anchor 5100 is utilized, the anchor 5100 may beneficially distribute the force applied to the heart anchor 5100 over a relatively large area. In other embodiments, other forms of heart anchors may be utilized as desired (e.g., barbs, prongs, hooks, or other forms of heart anchors).

The position of the heart anchors (including heart anchors 202, 5100) may be set to provide a desired direction of force applied to the tricuspid valve annulus. The direction of force preferably opposes the direction of expansion of the tricuspid annulus. The direction of force may be in a septal direction.

The sizes of the heart anchors utilized may be set at desired. In one embodiment a heart anchor 202 deployed on an interatrial septum may have a diameter of between about 10 mm and about 20 mm, and may have a diameter of about 15 mm. In one embodiment, a heart anchor 5100 for positioning on the free wall of the right atrium may have a diameter of between about 20 and about 25 mm, and may be about 23 mm in certain embodiments.

Although the embodiments of FIGS. 45-77 are described in relation to reshaping an annulus of a tricuspid valve of the patient's heart, it is contemplated that the devices, systems, and methods may be utilized to reshape other heart annuluses or other portions of the heart or body generally. The devices, systems, and methods may be utilized to treat functional heart valve regurgitation and other valve incompetencies. The devices disclosed herein may comprise systems for reshaping an annulus of a tricuspid valve of the patient's heart.

Figure 78:
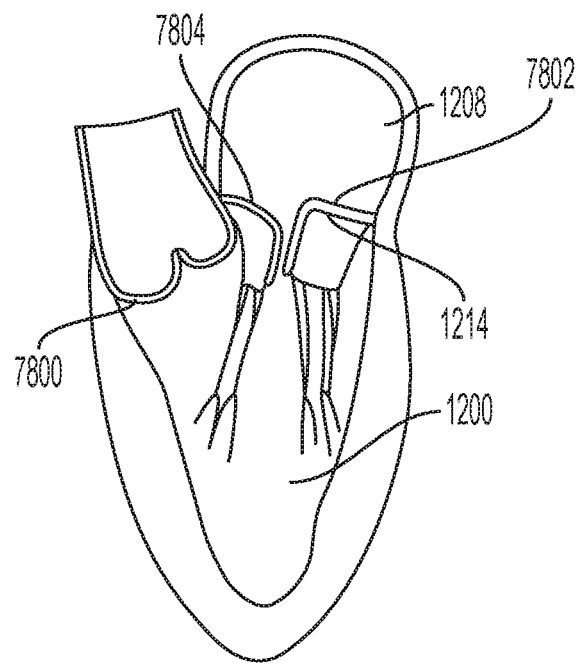
FIG. 78 illustrates a cross sectional view of a patient's heart showing a prolapsing leaflet of a heart valve according to an embodiment of the present disclosure.

Heart anchors may be utilized to reposition a valve leaflet of a mitral valve of a patient's heart. FIG. 78 illustrates a cross sectional view of a left ventricle 1200, a left atrium 1208 and a mitral valve 1214 of a patient's heart. The aortic valve 7800 is also visible.

The mitral valve 1214 may be suffering from prolapse, in which the leaflet 7802 is bulging into the left atrium 1208. The leaflet 7802 may bulge relative to the position of the leaflet 7804, which may result in functional heart valve regurgitation of the mitral valve 1214. It may be beneficial to reposition the leaflet 7802, to bring the leaflet 7802 to the plane of the leaflet 7804 and improve the coaptation of the leaflets 7802, 7804.

A heart splint may be utilized to reposition the leaflet 7802. The heart splint may utilize heart anchors disclosed herein, including the anchor 202 shown and discussed in regard to FIG. 2A-2H. The heart anchor may be configured to be positioned on a leaflet of a valve in a patient's heart. The heart anchor 202 as shown in FIGS. 2A-2H includes a ring 200 having two ends (204, 206) and configured to move from a linearized configuration to a ring-shaped configuration. A cover 212 is coupled to the ring 200 and extends inward from the ring 200 in the ring-shaped configuration. The ring 200 includes a first portion and a second portion 214, 216, and the first portion overlaps the second portion in the ring-shaped configuration.

Figure 79:
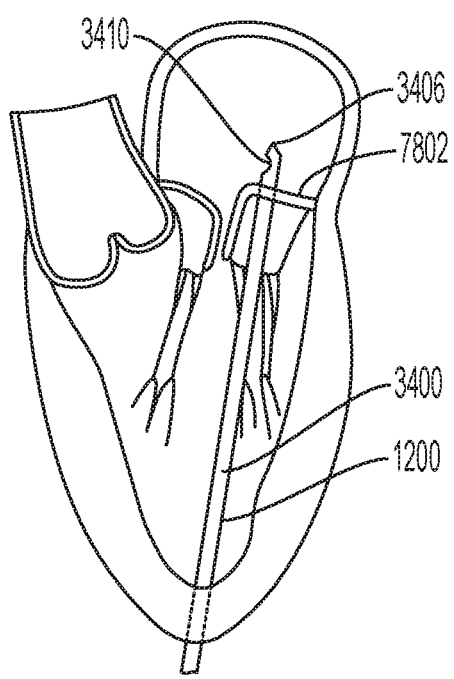
FIG. 79 illustrates a cross sectional view of a patient's heart showing a deployment apparatus passing through a prolapsing leaflet according to an embodiment of the present disclosure.
Figure 80:
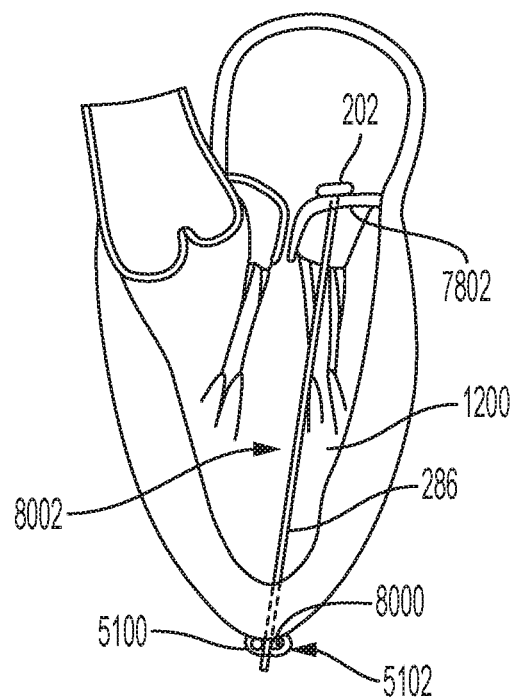
FIG. 80 illustrates a cross sectional view of a patient's heart showing a heart splint deployed to the heart according to an embodiment of the present disclosure.

FIGS. 79-80 illustrate steps in a method for repositioning a heart valve leaflet. In FIG. 79, a deployment apparatus 3400 may be passed through the left ventricle 1200 and may puncture the leaflet 7802. The deployment apparatus 3400 may be configured similarly as shown in FIGS. 34 and 35 and may include a puncture device 3406 and an opening 3410 for passing the heart anchor 202 out of a central lumen. The heart anchor 202 may be deployed in a similar manner as described in regard to FIGS. 34 and 35.

The deployment apparatus 3400 may be passed into the left ventricle 1200 by being passed through the outer wall of the left ventricle 1200. The puncture device 3406 of the deployment apparatus 3400 may be used to puncture the outer wall of the left ventricle 1200. The deployment apparatus 3400 may puncture the outer wall of the left ventricle 1200 at a desired position for a heart anchor to be deployed. The position may be determined based on the desired angle that a resulting tension member will have between the heart anchor 202 and the heart anchor on the outer wall of the left ventricle 1200. In one embodiment, the position may be near the left ventricle apex, adjacent the papillary muscles.

The deployment apparatus 3400 may puncture the leaflet 7802 with the puncture device 3406 of the deployment apparatus 3400. In other embodiments, other methods of puncturing the outer wall of the left ventricle 1200 and puncturing the leaflet 7802 may be utilized.

Upon the deployment apparatus 3400 puncturing the leaflet 7802, the heart anchor 202 may be deployed to the leaflet 7802. The heart anchor 202 may be deployed to the leaflet such that it rests against the surface of the leaflet 7802. The deployment apparatus 3400 may then be withdrawn with the tension member 286 trailing out of the opening 3410 in the deployment apparatus 3400.

Referring to FIG. 80, the deployment apparatus 3400 may continue to be withdrawn from the left ventricle 1200 and out of the puncture 8000 in the left ventricle 1200 with the tension member 286 trailing out of the puncture 8000. The tension member 286 positioned outside of the left ventricle 1200 may be accessible by a user. The heart anchor 5100 may then be coupled to the tension member 286 and deployed to a portion of the patient's heart. The portion may comprise the exterior surface of the left ventricle 1200 as shown in FIG. 80.

The heart anchor 5100 may be configured to be positioned on a portion of a patient's heart. The heart anchor 5100 may include a pad configured to be positioned on an exterior surface of the patient's heart and may include lock 5102 for locking the tension member 286 to the heart anchor 5100. The tension member 286 may be configured to couple the heart anchor 202 to the heart anchor 5100 and provide a tension that repositions the leaflet.

The tension member 286 may be tensioned to a desired amount with the user simultaneously verifying proper hemodynamics. The user may monitor the position of the leaflet 7802 and the mitral valve regurgitation. The tensioning and monitoring may occur in real-time. The user may pull the prolapsing leaflet 7802 to a desired state of coaptation by tensioning the tension member 286 to reposition the leaflet.

The prolapse of the leaflet may be reduced. Upon the tension in the tension member 286 being set to the desired amount, the lock 5102 may be set to lock the tension member 286 to the heart anchor 5100 and set the length of the heart anchor 202 from the heart anchor 5100 to a length that repositions the leaflet 7802. The resulting heart splint 8002 is shown in FIG. 80.

Figure 81:
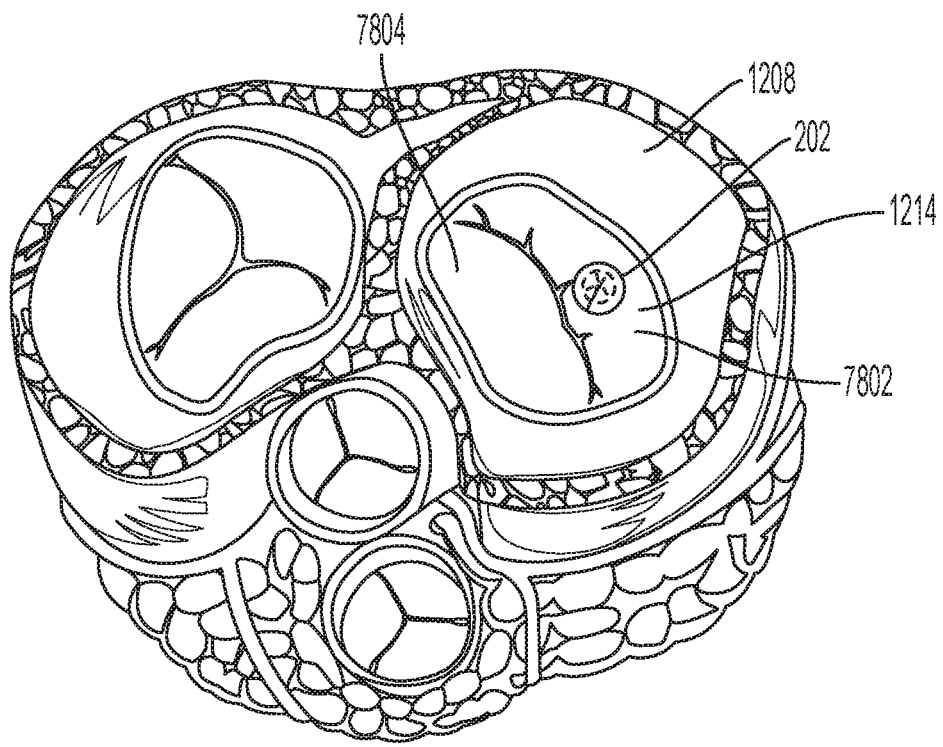
FIG. 81 illustrates a cross sectional view of a patient's heart with an anchor deployed to a heart valve leaflet according to an embodiment of the present disclosure.

FIG. 81 shows a top cross-sectional view of the patient's heart with the heart splint 8002 in position. The heart anchor 202 is shown in position on the leaflet 7802. The position of the heart anchor 202 on the leaflet 7802 may be varied in other embodiments.

Figure 82:
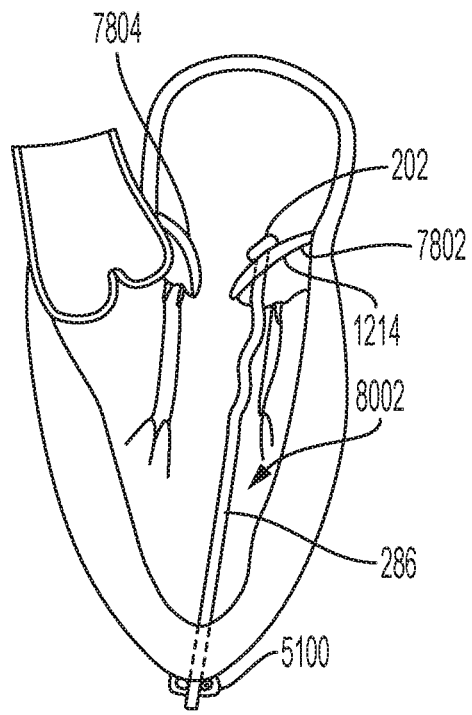
FIG. 82 illustrates a cross sectional view of a patient's heart showing a heart splint deployed to the heart according to an embodiment of the present disclosure.

The heart splint 8002, and particularly the tension member 286, may be configured to allow the mitral valve 1214 to open and function substantially similar to its normal operation. FIG. 82, for example, illustrates that the tension member 286 may be flexible, to allow the tension member 286, the heart anchor 202, and the leaflet 7802 to move towards the heart anchor 5100. Thus, during diastole, the mitral valve 1214 may open due to the flexible configuration of the tension member 286. During systole, the tension member 286 may resist movement of the leaflet 7802 beyond a desired state of coaptation of the leaflets 7802, 7804. The tension member 286 may resist movement of the tension member 286 in a direction towards the heart anchor 202 and may resist movement of the leaflet 7802 in a direction away from the tension member in order to reduce the prolapse of the leaflet 7802. The heart splint 8002 during systole may have a configuration as shown in FIG. 80.

Figure 83:
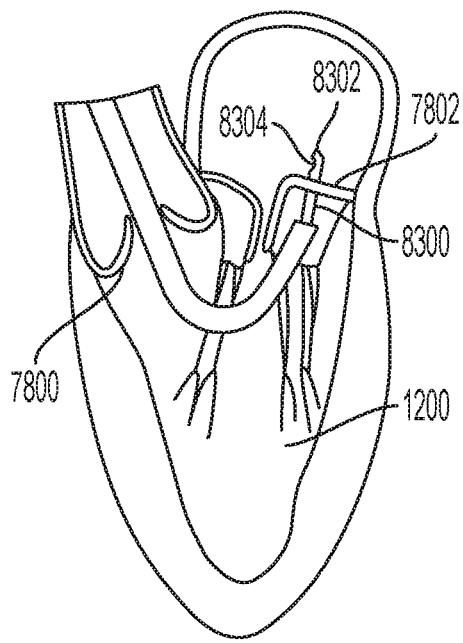
FIG. 83 illustrates a cross sectional view of a patient's heart with a deployment apparatus passing through a prolapsing leaflet according to an embodiment of the present disclosure.
Figure 84:
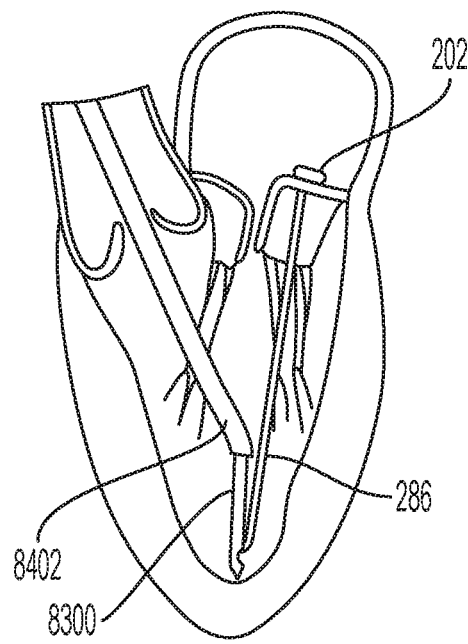
FIG. 84 illustrates a cross sectional view of a patient's heart with a deployment apparatus directed to a wall of the patient's heart according to an embodiment of the present disclosure.
Figure 85:
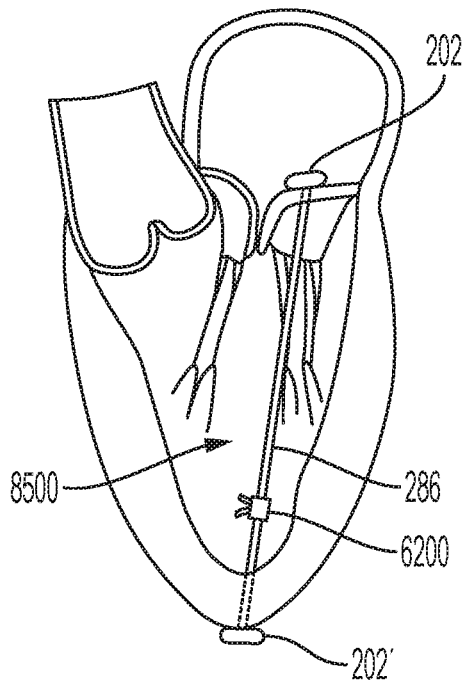
FIG. 85 illustrates a cross sectional view of a patient's heart with a heart splint deployed to the heart according to an embodiment of the present disclosure.

FIGS. 83-85 illustrate an embodiment that uses multiple of the heart anchors 202 (the second heart anchor is configured similarly as heart anchor 202 and is designated as heart anchor 202'). Both heart anchors 202, 202' may be deployed endovascularly. The entry to the patient's left ventricle 1200 may be via the aortic valve 7800.

Referring to FIG. 83, a deployment apparatus 8300 may be utilized that is configured similarly as the deployment apparatus 3400 shown in FIG. 34. The deployment apparatus 8300 may be configured to flex and curve to allow for endovascular passage into the left ventricle 1200 and to allow for direction to the mitral valve leaflet 7802 and the wall of the left ventricle 1200. The deployment apparatus 8300 may include a puncture device 8302 (which may be configured similarly as puncture device 3406) and may include an opening 8304 (which may be configured similarly as opening 3410). The opening 8304 may be configured to pass the anchor 202 through the opening 8304. The deployment apparatus 8300 may include an internal lumen (which may be configured similarly as lumen 3408) configured to retain the anchor 202 in the unexpanded or linearized configuration within the lumen. A push device (which may be configured similarly as push device 3412) may be configured to pass through the lumen of the deployment apparatus 8300 for pushing anchor 202 out of the opening 8304, in a similar manner as push device 3412.

The deployment apparatus 8300 may be loaded with at least two heart anchors 202, 202'. The heart anchors 202, 202' may be connected with a common tension member 286.

As shown in FIG. 83, the deployment apparatus 8300 may be directed to puncture the leaflet 7802 and deploy the heart anchor 202 to the leaflet 7802 in a similar manner as discussed in regard to FIGS. 79 and 80.

Referring to FIG. 84, upon deployment of the heart anchor 202 to the leaflet 7802, the deployment apparatus 8300 may be directed to puncture the outer wall of the left ventricle 1200. The tension member 286 may trail from the opening 8304 as the deployment apparatus 8300 punctures the outer wall of the left ventricle 1200. The deployment apparatus 8300 may puncture the outer wall of the left ventricle 1200 in the desired location. The deployment apparatus 8300 may then deploy the second heart anchor 202' to a position on the outer wall of the left ventricle 1200.

The tension member 286 may then be tensioned. Referring to FIG. 85, multiple methods of tensioning the tension member 286 may be utilized. For example, a method may be utilized similar to the method disclosed in regard to FIGS. 62 and 63. The tensioning may include drawing the portions of the tension member 286 coupled to the respective heart anchors 202, 202' towards each other. A lock 6200 may be placed along the tension member 286 and may allow a central portion of the tension member 286 to be withdrawn to draw the heart anchors 202, 202' towards each other. The tension member 286 may be tensioned to a desired amount with the user simultaneously verifying proper hemodynamics. A sheath 8402 or other device may hold the lock 6200 in position while the central portion of the tension member 286 is withdrawn to draw the heart anchors 202, 202 towards each other. The user may monitor the monitor the position of the leaflet 7802 and the mitral valve regurgitation. The lock 6200 may comprise a releasable lock, and may be configured such as the lock 5800, to allow for the lock 6200 to be set once the tension in the tension member 286 is set to the desired amount.

FIG. 85 illustrates a lock 6200 in position on the tension member 286 between the heart anchors 202, 202'. Upon the desired tension being provided in the tension member 286, the remaining portion of the tension member 286 may be cut. The heart splint 8500 is shown in position in FIG. 85, with the tension member 286 extending through the left ventricle 1200.

In the embodiments of FIGS. 78-85, the location of the heart anchor that is not deployed to the leaflet may be positioned as desired for the desired therapeutic effect. For example, the location may be set to provide a particular direction of the tension applied to the tension member 286. Although the anchoring location is shown as the wall of the left ventricle in FIGS. 78-85, other locations may be utilized as desired such as the interventricular septum. Other anchoring locations are contemplated as well.

In the embodiments of FIGS. 78-85, preferably a single heart anchor 202 may be deployed to the leaflet to be repositioned. The configuration of the heart anchor 202 may beneficially distribute the force applied to the heart anchor over a relatively large area, thus allowing only one heart anchor 202 to be deployed to the leaflet and reposition the leaflet. This is in contrast to other known anchoring systems that may utilize multiple (e.g., three or more) anchors to reposition the leaflets. A single tension member 286 may be utilized to set the position of the leaflet, which would simplify the process over tensioning multiple tension members to set the position of the leaflet. Further, a single tension member 286 may allow for more precise tensioning of the tension member 286. In other embodiments, multiple heart anchors 202 may be deployed to the heart valve leaflet as desired.

Although a single leaflet of the mitral valve is shown to be repositioned in FIGS. 78-85, in other embodiments heart anchors may be applied to both leaflets as desired. In addition, although the embodiments of FIGS. 78-85 are discussed in regard to the mitral valve, repositioning of other leaflets of valves or other portions of the heart or body are contemplated. For example, one or more leaflets of the tricuspid valve may be repositioned in certain embodiments. The devices, systems, and methods may be utilized to treat functional heart valve regurgitation and other valve incompetencies.

The heart splints of the embodiments of FIGS. 78-85, or any of the components of the heart splint (e.g., a heart anchor), may be deployed in a less invasive, or minimally invasive manner, and may utilize techniques previously disclosed in this application. For example, in the embodiments of FIGS. 78-81 a small surgical access may be made to the patient's body (through a thoracotomy, or mini-thoracotomy) to deploy the anchor 5100. In the embodiments of FIGS. 83-85, both heart anchors 202, 202' may be deployed endovascularly. Transcatheter and percutaneous deployment may be utilized. Other forms of deployment may be utilized as desired. The devices disclosed herein may comprise systems for repositioning a leaflet of a heart valve.

Figure 86:
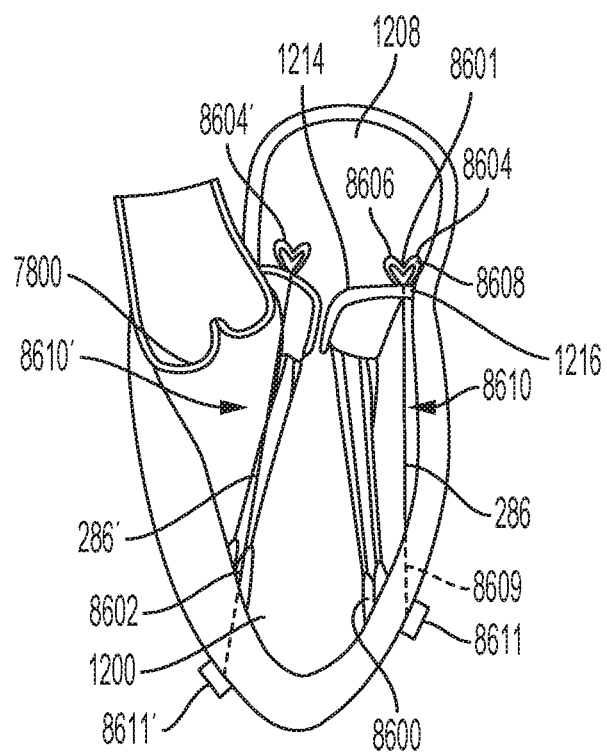
FIG. 86 illustrates a cross sectional view of a patient's heart with multiple heart splints deployed to the heart according to an embodiment of the present disclosure.

Heart anchors may be utilized to reposition one or more papillary muscles of a patient's heart, including the papillary muscles of the left ventricle. FIG. 86 illustrates a cross sectional view of a left ventricle 1200, a left atrium 1208, and a mitral valve 1214 of a patient's heart. The mitral annulus 1216 and papillary muscle head bases 8600, 8602 are also depicted in FIG. 86. The aortic valve 7800 is also visible.

The left ventricle 1200 may be suffering from dilation, which may have resulted from a medical condition such as an ischemic event. The ischemic event may have produced structural changes in the myocardium, which may include the wall of the left ventricle 1200 expanding in the posteriolateral and apical directions which in turn increases the distance of the papillary muscles from the mitral valve 1214. Such an increase in distance may cause chordae of the left ventricle 1200 to exert a force on the mitral valve 1214 leaflets to the point where the leaflets can no longer coapt properly during systole. Such failure of coaptation may result in functional mitral valve regurgitation (FMR). It may be beneficial to reposition the papillary muscles such that the papillary muscles are drawn towards the mitral valve 1214, thus reducing the tension of the chordae, improving coaptation, and reducing functional mitral valve regurgitation.

A heart splint may be utilized to reposition the one or more papillary muscles. The heart splint may utilize heart anchors that are utilized to draw the papillary muscles towards the mitral valve 1214. Referring to FIG. 86, a heart anchor 8604 may include two lobes 8606, 8608 that are each formed by a loop of material. The heart anchor 8604 may be configured similarly as, and may comprise, the heart anchor referred to as a bulky knot implant 131 (or 131') in U.S. Pat. No. 9,681,864, titled Method and Apparatus for Transapical Procedures on a Mitral Valve, filed Dec. 29, 2014, the entire contents of which are incorporated herein for all purposes. The lobes 8606, 8608 may comprise the lobes of the implant 131' shown in FIG. 3 of U.S. Pat. No. 9,681,864. The lobes 8606, 8608 may extend outward from a central portion 8601 to provide a width of the heart anchor 8604. The lobes 8606, 8608 may support the heart anchor 8604 on the portion of the heart to which it is applied, and may prevent the heart anchor 8604 from passing back through a puncture hole that the heart anchor 8604 has been passed through. The looped material may include a cloth material or other form of flexible material that allows the heart anchor 8604 to be flexed into a smaller profile to be deployed via a catheter or the like, before expanding after deployment. The heart anchor 8604 may be larger in diameter than the implant 131' shown in FIG. 3 of U.S. Pat. No. 9,681,864, and may be made of a material such as ultra-high-molecular-weight polyethylene (UHMwPE) (for example, DYNEEMA® fabric or laminate, Koninklijke DSM, the Netherlands). The looped material may form a knotted structure as shown in FIG. 3 of U.S. Pat. No. 9,681,864. The heart anchor 8604 may be configured to be positioned on a mitral annulus of a patient's heart and may include two or more lobes 8606, 8608 that extend outward from the central portion 8601 of the heart anchor 8604.

The anchor 8604 may be deployed by a deployment apparatus that is utilized to deploy the heart splint and the heart anchor 8604, to draw the papillary muscles towards the mitral valve 1214. The deployment apparatus may comprise an apparatus for deploying an implant 131 as disclosed in U.S. Pat. No. 9,681,864, and similar methods may be utilized to deploy the heart anchor 8604. A deployment apparatus may be passed through the left ventricle 1200 and may include a puncture device and an opening for passing the heart anchor 8604 out of a central lumen.

The deployment apparatus may be passed into the left ventricle 1200 by being passed through the outer wall of the left ventricle 1200. A puncture device of the deployment apparatus may be used to puncture the outer wall of the left ventricle 1200. The deployment apparatus may puncture the outer wall of the left ventricle 1200 at a desired position for a heart anchor to be deployed. The position may be adjacent a papillary muscle head base 8600. A puncture 8609 adjacent a papillary muscle head base 8600 is shown in FIG. 86. In other embodiments, other locations of puncture may be utilized.

The deployment apparatus may be advanced to puncture the mitral annulus 1216. The ipsilateral mitral annulus may be punctured near the fibrous trigone. Other locations of puncture may be utilized in other embodiments. Upon the deployment apparatus puncturing the mitral annulus 1216, the heart anchor 8604 may be deployed to the mitral annulus 1216 as shown in FIG. 86. Methods of deployment may include those disclosed in U.S. Pat. No. 9,681,864. The heart anchor 8604 may expand outward with the lobes 8606, 8608 extending radially outward to increase the width and contact surface area of the heart anchor 8604. The heart anchor 8604 may be deployed to the mitral annulus 1216 such that it rests against the surface of the mitral annulus 1216. The deployment apparatus may then be withdrawn with the tension member 286 trailing out of the opening in the deployment apparatus. The tension member 286 may be configured to couple the heart anchor 8604 to the heart anchor 8611 and extend within the left ventricle. The tension member 286 may couple to the central portion 8601 of the heart anchor 8604.

The deployment apparatus may continue to be withdrawn from the left ventricle 1200 and out of the puncture 8609 in the left ventricle 1200 with the tension member 286 trailing out of the puncture 8609. The tension member 286 positioned outside of the left ventricle 1200 may be accessible by a user. The heart anchor 8611 may then be coupled to the tension member 286 and deployed to a portion of the patient's heart. The heart anchor 8611 may be deployed to a location on an external wall portion of the patient's heart and proximate the papillary muscle base 8600. The heart anchor 8611 may be deployed to a portion of a patient's heart such that the heart anchor 8611 is configured to apply a force to one or more of the papillary muscles. The portion may comprise the exterior surface of the left ventricle 1200 as shown in FIG. 86, and may be proximate the papillary muscle as shown in FIG. 86. The heart anchor 8611 may take a variety of forms and may comprise a pledget or the like. The heart anchor 8611 may be configured to apply a force to one or more of the papillary muscles of the left ventricle of the patient's heart.

Prior to or after the tension member 286 being coupled to the heart anchor 8611, the tension member 286 may be tensioned to a desired amount with the user simultaneously verifying proper hemodynamics. The user may monitor the position of the mitral annulus 1216 and the papillary muscle adjacent the puncture of the left ventricle 1200 and the mitral valve regurgitation. The tensioning and monitoring may occur in real-time. Such measurement may occur as the patient's heart is beating. The user may pull the tension member to draw the papillary muscle and mitral valve annulus 1216 towards each other to a desired state of coaptation of the mitral valve leaflets, and a desired distance between the papillary muscle and mitral valve annulus 1216, by tensioning the tension member 286. The papillary muscle may be repositioned. A distance between one or more of the papillary muscles and the mitral annulus may be reduced.

The mitral valve regurgitation may be reduced. Upon the tension in the tension member 286 being set to the desired amount, the tension may be set by locking the tension member 286 to heart anchor 8611, which may occur by tying the tension member 286 in position to the heart anchor 8611 or another form of securement. The resulting heart splint 8610 is shown in FIG. 86.

Figure 87:
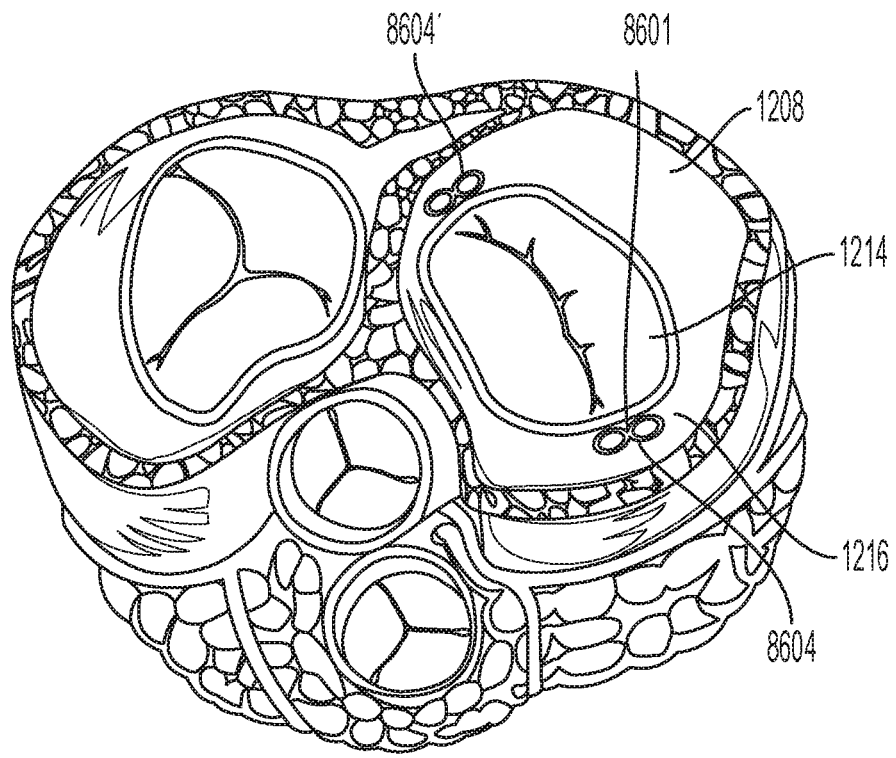
FIG. 87 illustrates a cross sectional view of a patient's heart with multiple heart splints deployed to the heart according to an embodiment of the present disclosure.

FIG. 87 shows a top cross-sectional view of the patient's heart with the heart splint 8610 in position. The heart anchor 8604 is shown in position on the mitral annulus 1216. The position of the heart anchor 8604 on the mitral annulus 1216 may be varied in other embodiments.

Another heart splint may be deployed in a similar manner as the heart splint 8610. Referring back to FIG. 86, a second heart splint 8610' may be deployed by puncturing the left ventricle 1200 adjacent a contralateral papillary muscle head base 8602. A heart anchor 8604' configured similarly as heart anchor 8604 may be positioned on the mitral annulus 1216 on an opposite side of the mitral annulus 1216 than the heart anchor 8604, or at a different location as desired. A heart anchor 8611' may be configured similarly as the heart anchor 8611 and positioned on the left ventricle wall. The resulting heart splint 8610' may be tensioned similarly as the heart splint 8610, to reduce the mitral valve regurgitation. The tension in the tension member 286' may be set and locked between the anchors 8604', 8611'.

FIG. 87 shows a top cross-sectional view of the patient's heart with the heart splint 8610' in position. The heart anchor 8604' is shown in position on the mitral annulus 1216 opposite the mitral valve 1214 from the heart anchor 8604. The position of the heart anchor 8604' on the mitral annulus 1216 may be varied in other embodiments.

The number of heart splints and heart anchors utilized may be varied as desired. For example, multiple heart splints may be applied to each of the papillary heads, or each papillary head may include its own heart splint. In one embodiment, a single heart anchor may reposition one or more papillary muscles. The location of the heart anchors and heart splints may be varied as desired to achieve the desired therapeutic effect.

Figure 88:
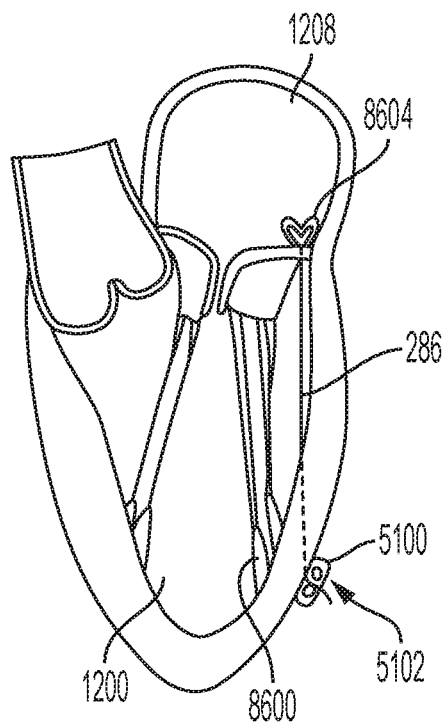
FIG. 88 illustrates a cross sectional view of a patient's heart with a heart splint deployed to the heart according to an embodiment of the present disclosure.

The type of heart anchor utilized with the heart splints may be varied as desired. For example, referring to FIG. 88, a heart anchor positioned to support the papillary muscle head base 8600 may comprise a heart anchor 5100 in the form of a pad configured to be positioned on an exterior surface of the patient's heart and may include lock 5102 for locking the tension member 286 to the heart anchor 5100. The heart anchor 5100 may be configured to apply a force to one or more of the papillary muscles of the left ventricle of the patient's heart. The tension member 286 may be configured to couple the heart anchor 8604 to the heart anchor 5100 and provide a tension that draws the papillary muscle head base 8600 to the mitral annulus 1216. The lock 5102 may be set to lock the tension member 286 to the heart anchor 5100 and set the length of the heart anchor 8604 from the heart anchor 5100 to a length that repositions the papillary muscle head base 8600.

Figure 89:
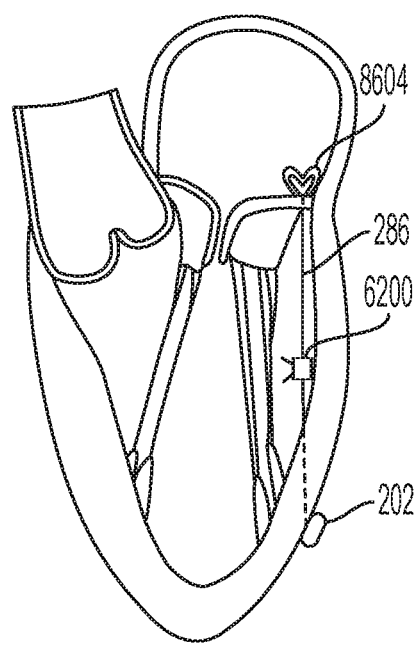
FIG. 89 illustrates a cross sectional view of a patient's heart with a heart splint deployed to the heart according to an embodiment of the present disclosure.

FIG. 89 illustrates an embodiment in which a heart anchor positioned to support the papillary muscle head base 8600 may comprise a heart anchor 202 shown and discussed in regard to FIG. 2A-2H. The heart anchor may be configured to be positioned to support and reposition a papillary muscle head base 8600. The heart anchor 202 may be configured to apply a force to one or more of the papillary muscles of the left ventricle of the patient's heart. The heart anchor 202 as shown in FIGS. 2A-2H includes a ring 200 having two ends (204, 206) and configured to move from a linearized configuration to a ring-shaped configuration. A cover 212 is coupled to the ring 200 and extends inward from the ring 200 in the ring-shaped configuration. The ring 200 includes a first portion and a second portion 214, 216, and the first portion overlaps the second portion in the ring-shaped configuration.

The heart anchor 202 shown in FIG. 89 may be deployed to the surface of the left ventricle in a similar manner as shown in FIGS. 84-85, which may include use of a lock 6200 that may be placed along the tension member 286 and may allow a central portion of the tension member 286 to be withdrawn to draw the heart anchors 202, 8604 towards each other.

Figure 90:
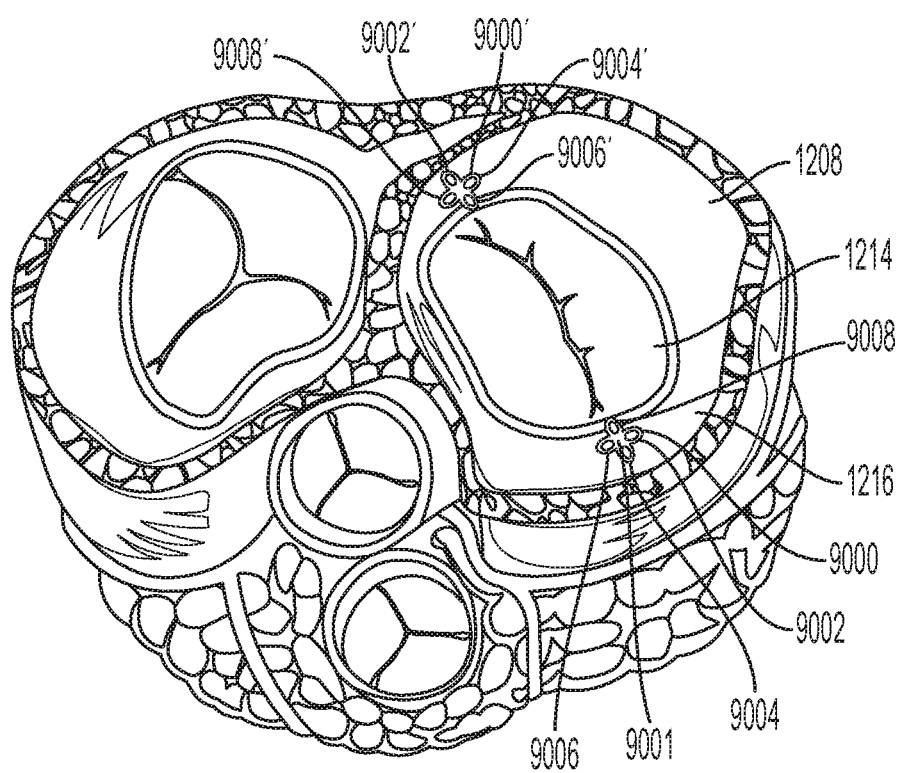
FIG. 90 illustrates a cross sectional view of a patient's heart with multiple heart splints deployed to the heart according to an embodiment of the present disclosure.
Figure 91:
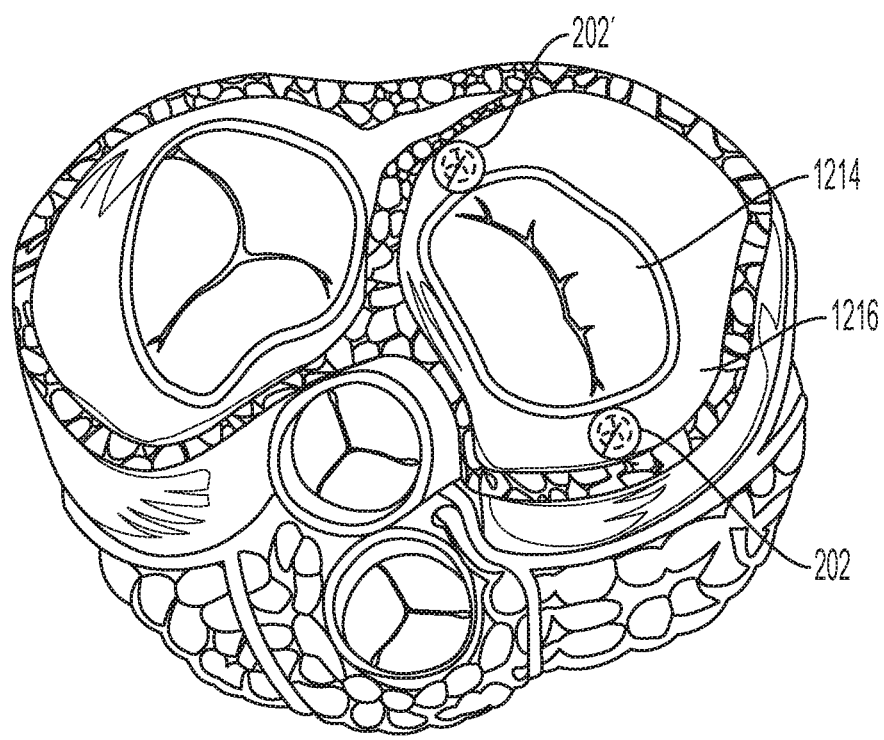
FIG. 91 illustrates a cross sectional view of a patient's heart with multiple heart splints deployed to the heart according to an embodiment of the present disclosure.

Other forms of heart anchors may be utilized on the mitral annulus 1216. FIG. 90, for example, illustrates an embodiment of a heart anchor 9000 that is similar as the heart anchor 8604, but includes four lobes 9002, 9004, 9006, 9008 that are each formed by a loop of material. The lobes 9002, 9004, 9006, 9008 may extend radially outward from a central portion 9001 to provide a width of the heart anchor 9000 in transverse dimensions. The tension member 286 may couple to the central portion 9001 of the heart anchor 9000. The lobes 9002, 9004, 9006, 9008 may extend radially outward from the central connection portion in different directions and may form an "X" or clover pattern. The lobes 9002, 9004, 9006, 9008 may support the heart anchor 9000 on the portion of the heart to which it is applied, and may prevent the heart anchor 9000 from passing back through a puncture hole that the heart anchor 9000 has been passed through. The looped material may include a cloth material or other form of flexible material that allows the heart anchor 9000 to be flexed into a smaller profile to be deployed via a catheter or the like, before expanding after deployment. The heart anchor 9000' may be configured similarly as heart anchor 9000, and may include similarly configured lobes 9002', 9004', 9006', 9008'. In other embodiments, a different number of lobes (e.g., 3, 5, 6, or more) may be utilized as desired. The heart anchor 9000 may be configured to be positioned on a mitral annulus of a patient's heart and may include at least four lobes 9002, 9004, 9006, 9008 (or four or more lobes) that extend outward from a central portion 9001 of the heart anchor 9000.

FIGS. 91-94 illustrate embodiments in which heart anchors utilized on the mitral annulus 1216 comprise a heart anchor 202 shown and discussed in regard to FIG. 2A-2H. The heart anchor 202 may be configured to be positioned upon a mitral annulus. The heart anchor 202 as shown in FIGS. 2A-2H includes a ring 200 having two ends (204, 206) and configured to move from a linearized configuration to a ring-shaped configuration. A cover 212 is coupled to the ring 200 and extends inward from the ring 200 in the ring-shaped configuration. The ring 200 includes a first portion and a second portion 214, 216, and the first portion overlaps the second portion in the ring-shaped configuration. The heart anchor 202' may be configured similarly as the heart anchor 202.

Figure 92:
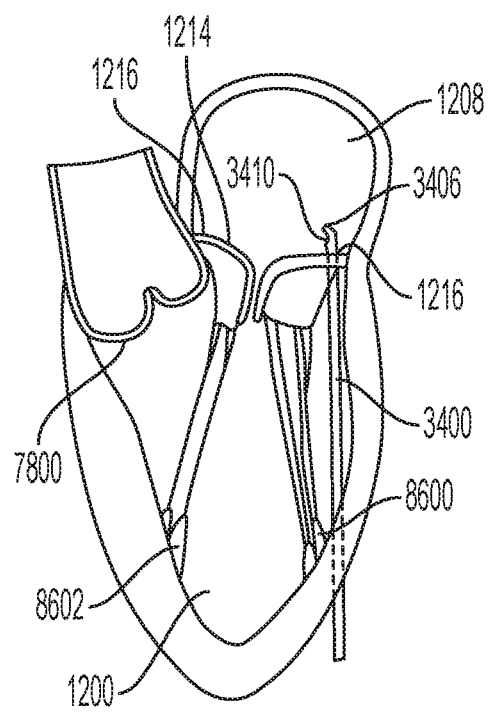
FIG. 92 illustrates a cross sectional view of a patient's heart with a deployment apparatus passing through a mitral annulus of the patient's heart according to an embodiment of the present disclosure.

FIG. 92 illustrates that the heart anchor 202 may be deployed to the mitral annulus via a deployment apparatus 3400 that may be passed into the left ventricle 1200 by being passed through the outer wall of the left ventricle 1200 in a similar manner as shown in FIG. 79. The puncture device 3406 of the deployment apparatus 3400 may be used to puncture the outer wall of the left ventricle 1200. The deployment apparatus 3400 may puncture the outer wall of the left ventricle 1200 at a desired position for a heart anchor to be deployed, and may puncture the mitral annulus at the location for deployment of the heart anchor 202.

Figure 93:
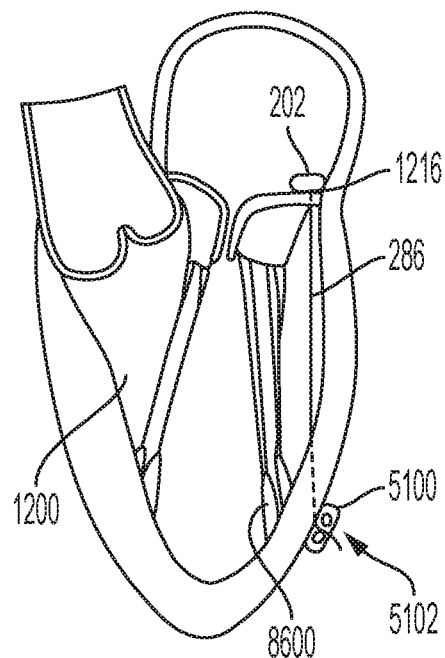
FIG. 93 illustrates a cross sectional view of a patient's heart with a heart splint deployed to the heart according to an embodiment of the present disclosure.

Referring to FIG. 93, a heart anchor 5100 on an exterior surface of the left ventricle 1200 may be utilized with a heart anchor 202 to form a heart splint for treating mitral valve regurgitation in the same manner as the heart splints shown in FIGS. 86-90. The heart anchor 5100 may be in the form of a pad configured to be positioned on an exterior surface of the patient's heart and may include lock 5102 for locking the tension member 286 to the heart anchor 5100. The tension member 286 may be configured to couple the heart anchor 202 to the heart anchor 5100 and provide a tension that draws the papillary muscle head base 8600 to the mitral annulus 1216. The lock 5102 may be set to lock the tension member 286 to the heart anchor 5100 and set the length of the heart anchor 202 from the heart anchor 5100 to a length that repositions the papillary muscle head base 8600.

Figure 94:
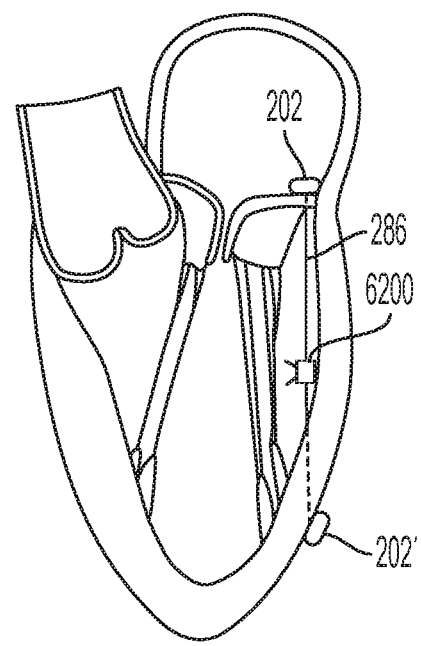
FIG. 94 illustrates a cross sectional view of a patient's heart with a heart splint deployed to the heart according to an embodiment of the present disclosure.

FIG. 94 illustrates a heart anchor 202' on an exterior surface of the left ventricle 1200 that may be utilized with heart anchor 202 to form a heart splint for treating mitral valve regurgitation in the same manner as the heart splints shown in FIGS. 86-90. The heart anchor 202' may be configured to apply a force to one or more of the papillary muscles of the left ventricle of the patient's heart. The heart anchor 202' may be deployed to the surface of the left ventricle in a similar manner as shown in FIGS. 84-85, which may include use of a lock 6200 that may be placed along the tension member 286 and may allow a central portion of the tension member 286 to be withdrawn to draw the heart anchors 202, 202' towards each other.

The systems, devices, apparatuses, and methods shown in FIGS. 86-94 may provide improved methods of treating functional mitral valve regurgitation. The methods utilized to reposition the papillary muscles towards the mitral valve annulus may provide a therapeutic effect for the patient, and the heart anchors disclosed may distribute the tension force of the heart splints along a relatively wide surface of the mitral annulus and outer surface of the left ventricle. In addition, although the embodiments of FIGS. 86-94 are discussed in regard to the mitral valve, repositioning of other leaflets of valves, or papillary muscles, or other portions of the heart or body are contemplated. For example, one or more leaflets of the tricuspid valve, or papillary muscles of the tricuspid valve, may be repositioned in certain embodiments. The devices, systems, and apparatuses and methods may be utilized to treat other valve incompetencies.

The heart splints of the embodiments of FIGS. 86-94, or any of the components of the heart splint (e.g., a heart anchor), may be deployed in a less invasive, or minimally invasive manner, and may utilize techniques previously disclosed in this application. For example, in the embodiments of FIGS. 86-94 a small surgical access may be made to the patient's body (through a thoracotomy, or minithoracotomy) to deploy the anchor 5100. In the embodiments of FIGS. 86-94, both the heart anchors may be deployed endovascularly. Transcatheter and percutaneous deployment may be utilized. Other forms of deployment may be utilized as desired. The devices disclosed herein may comprise systems for repositioning one or more papillary muscles of a heart valve.

FIGS. 95-100 illustrate an embodiment of a head 9500 of an access apparatus, which may comprise an access apparatus 100 as shown in FIGS. 1A-1F. The head 9500 may be utilized in lieu of the head 102, or in substitution with the head 102, shown in FIGS. 1A-1F, and may be positioned at a distal end of the elongate neck 104. The head 9500 may be utilized in other embodiments with other types of apparatuses, including catheters. Such apparatuses may be utilized to provide a suction force to a surface of a patient's body.

Figure 95:
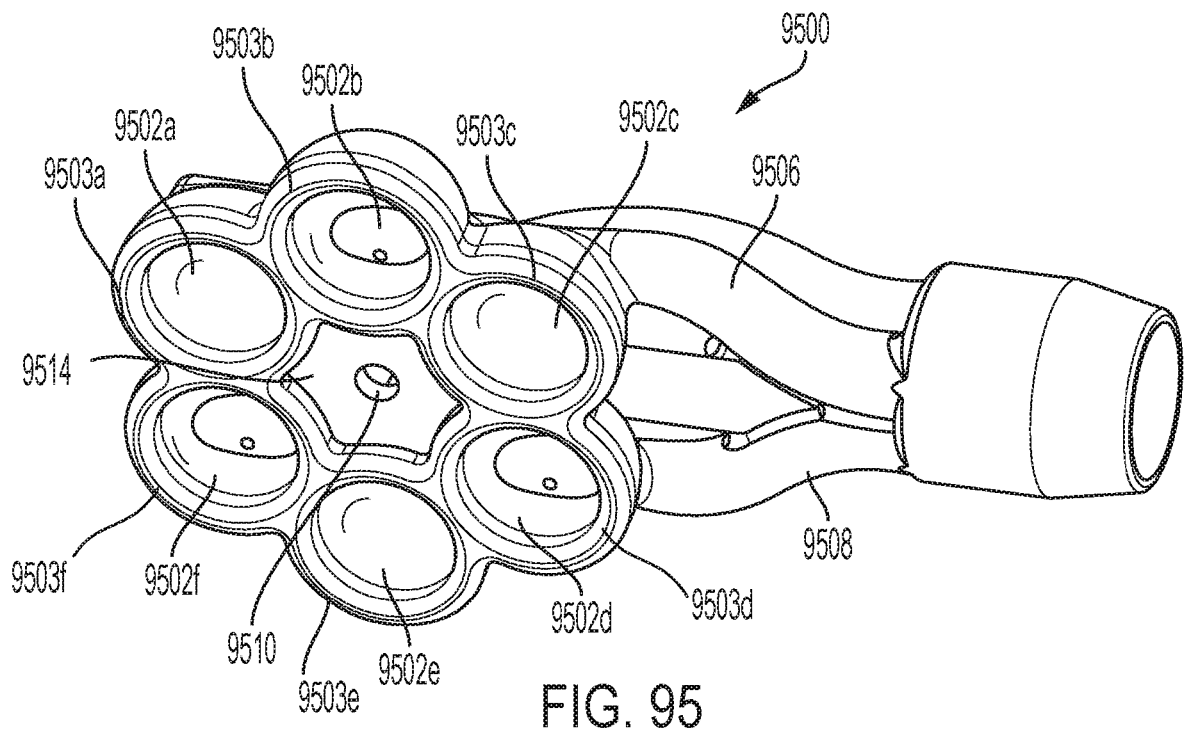
Figure 96:
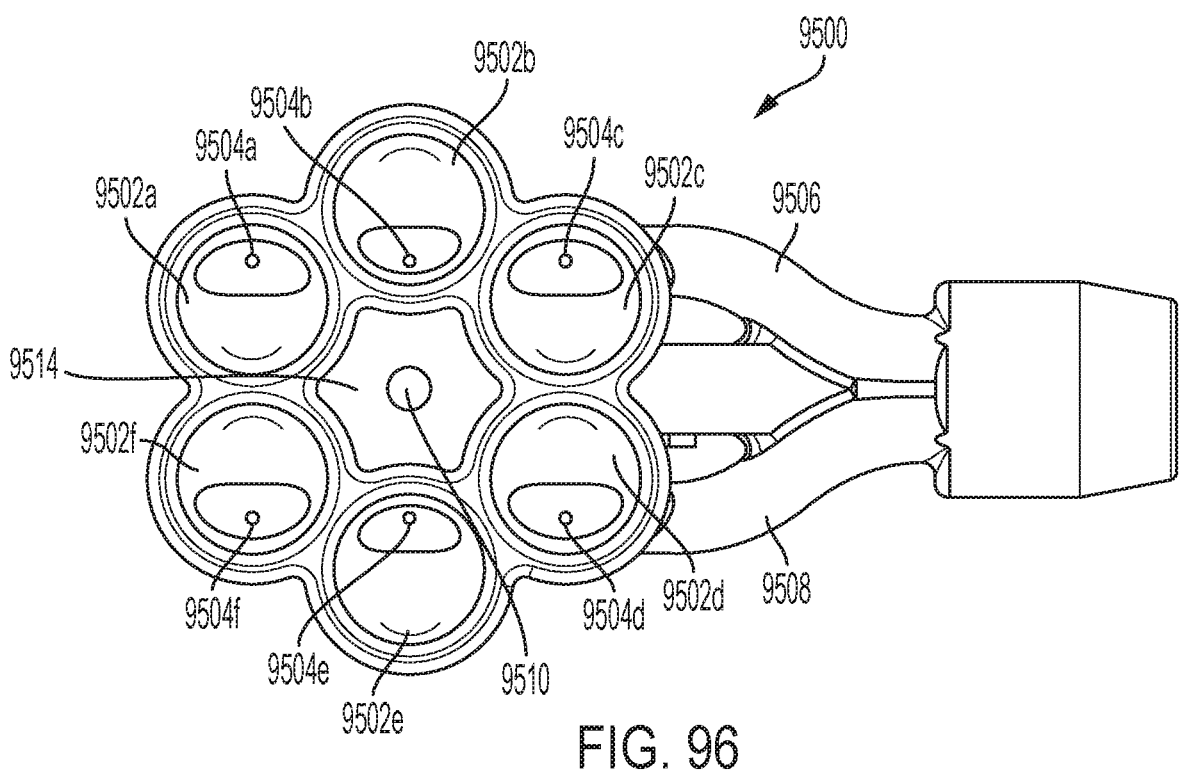

Referring to FIG. 95, the head 9500 includes a plurality of chambers 9502*a-f* that are each configured to contact a portion of the patient's body (such as an external surface of the patient's heart) and apply a suction force to a surface of a patient's body (such as the external surface of the patient's heart). Each chamber 9502*a-f* may include a front face surface or contact surface 9503*a-f*, for contacting the portion of the patient's body and forming the contact surface of the head 9500. The contact surfaces 9503*a-f* may form a planar contact surface for the head 9500, with each contact surface 9503*a-f* extending in the same plane. The plurality of chambers 9502*a-f* may form an application portion of the head 9500. The front face surfaces or contact surfaces 9503*a-f* may extend circumferentially about the respective chamber 9502*a-f*, forming the outer perimeter of the respective chamber.

Figure 97:
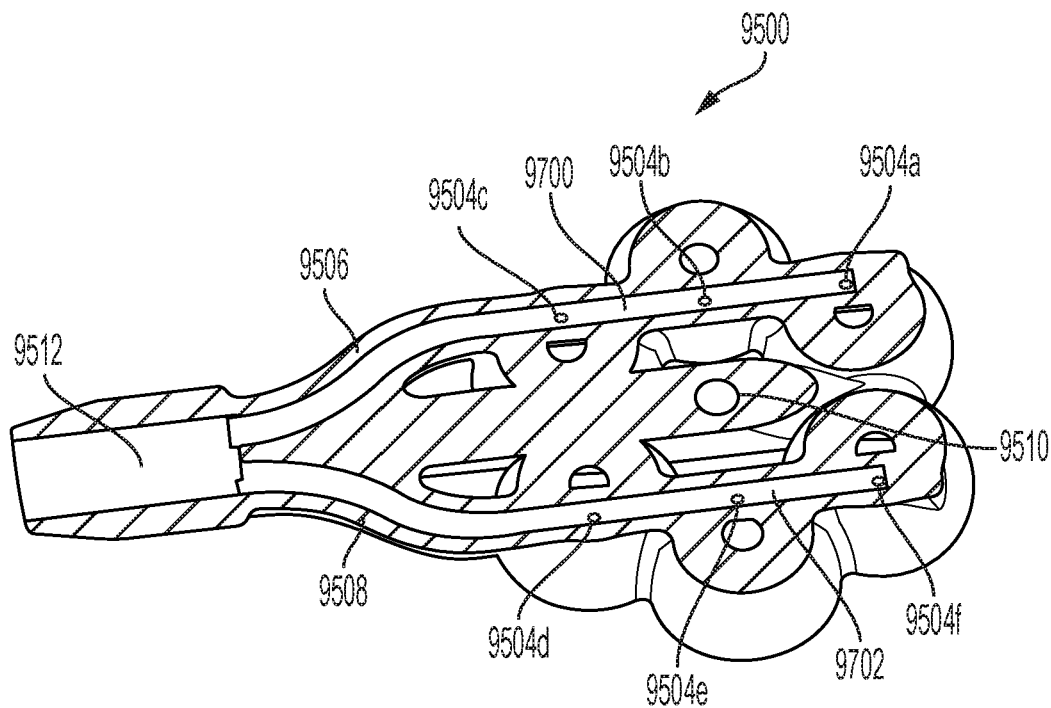

Each chamber may have a dome-shape, or a half sphere shape. Each chamber may form an internal dome-shaped volume that allows vacuum suction to be applied to the surface of the patient's heart. In other embodiments, other shapes of chambers may be utilized. Each chamber 9502*a-f* may include a respective opening 9504*a-f* (marked in FIGS. 96 and 97) that allows vacuum suction to be applied by the respective chambers 9502*a-f*. The respective openings 9504*a-f* connect the interior cavity of the chambers 9502*a-f* to lumens or suction channels 9700, 9702 (marked in FIG. 97) that allow suction to be provided from the suction channel 9700 to openings 9504*a*, 9504*b*, 9504*c*, and allow suction to be provided from the suction channel 9702 to openings 9504*f*, 9504*e*, 9504*d* as shown in FIG. 97. Each suction channel 9700, 9702 accordingly couples to openings of multiple chambers 9502*a-f*. The set of chambers 9502*a-c* accordingly forms a set of chambers that applies the vacuum suction from the suction channel 9700 and the set of chambers 9502*d-f* accordingly forms a set of chambers that applies the vacuum suction from the suction channel 9702. Each of the plurality of openings 9504*a-f* couples one of the respective plurality of chambers 9502*a-f* to the respective suction channel 9700, 9702 and is configured to pass the vacuum suction through the opening to allow the respective one of the plurality of chambers 9502*a-f* to apply the vacuum suction from the respective suction channel 9700, 9702. The suction channels 9700, 9702 may be positioned within respective manifolds 9506, 9508 (marked in FIGS. 95-97) of the head 9500 that couple to the chambers 9502*a-f*.

Each suction channel 9700, 9702 may couple to a suction lumen 9512 (marked in FIGS. 97 and 98), which may exert a suction force through the suction channel 9700, 9702. Such a lumen 9512 may be positioned within an elongate neck of the device to which the head 9500 is coupled to, which may comprise the elongate neck 104. Such a lumen may be positioned within another structure to which the head 9500 couples.

Referring to FIG. 97, each opening 9504*a-f* may have a diameter that is smaller than a diameter of the respective lumen or suction channel 9700, 9702 to which it is coupled. Such a feature may allow the suction channel 9700, 9702 to exert a greater suction force than would be provided through a single one of the openings 9504*a-f*, or that would be lost if a single one of the chambers 9502*a-f* lost its seal with the surface of the patient's body. As such, the plurality of openings 9504*a-f* is sized such that a loss of vacuum suction by one of the plurality of chambers 9502*a-f* allows another of the plurality of chambers 9502*a-f* to allow the vacuum suction from the respective suction channel 9700, 9702. Such a feature may provide a benefit of allowing the head 9500 to remain suctioned to the surface of the patient's body even if a suction seal between one of the chambers 9502*a-f* and the surface of the patient's body was lost. Multiple of the chambers 9502*a-f* may lose a suction force, and the respective suction channel 9700, 9702 may continue to exert a suction force great enough to secure the head 9500 to the patient's body with at least one of the chambers 9502*a-f*. This feature may reduce the possibility of the head 9500 undesirably and inadvertently detaching from the surface of the patient's body if one or more of the chambers 9502*a-f* lost its seal with the surface of the patient's body.

Referring to FIG. 95, the head 9500 may include a central lumen 9510 for allowing a puncture device to pass therethrough to pass through an external surface of the patient's heart. The lumen 9510 may be positioned within a central portion 9514 of the head 9500 or may be positioned in another location as desired. The lumen 9510 may be positioned such that the chambers 9502*a-f* are positioned around the lumen 9510, which may be radially positioned as shown in FIG. 95. The chambers 9502*a-f* may be spaced radially from the central portion 9514 of the head 9500. The chambers 9502a-f may be positioned around the lumen 9510 such that securement around the lumen 9510 is provided by the suction force of the chambers 9502a-f, so that when the puncture device passes through the lumen 9510 into a portion of the patient's body, the puncture device is supported on multiple sides or all sides of the lumen 9510.

In other embodiments, other configurations of the chambers 9502a-f may be utilized, including extending linearly along both sides of the central lumen 9510, or in another configuration. The number of the chambers 9502a-f and the number of suction channels to which each of the chambers couple may be varied as desired (e.g., a greater or lesser number may be utilized). For example, a single suction channel may couple to at least two of the chambers, or a different number a desired. A single suction channel may be utilized, or a greater number of suction channels may be utilized. Although six chambers are shown in FIGS. 95-100, a greater or lesser number may be utilized as desired. The openings 9504a-f may have a diameter of 0.5 millimeters in certain embodiments, although in other embodiments the size may vary as desired.

Figure 98:
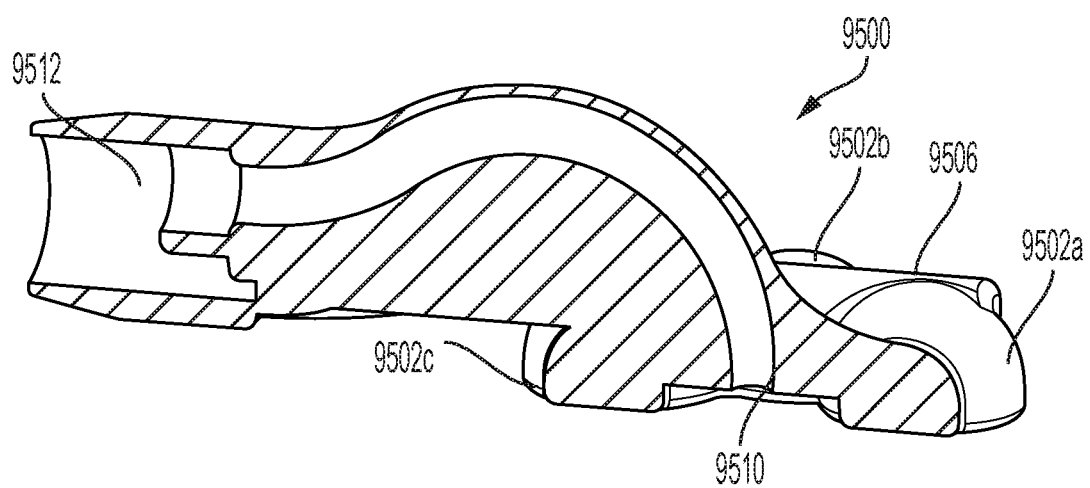

FIG. 98 illustrates that the lumen 9510 may extend upward from the head 9500 in a curve to allow the puncture device to smoothly transition at a 90-degree angle, or other angle to puncture the portion of the patient's body.

Figure 99:
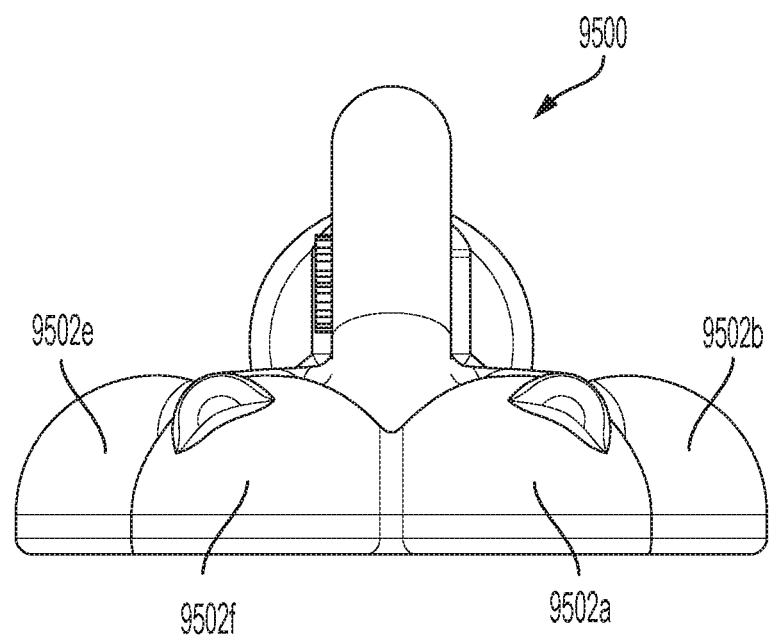
Figure 100:
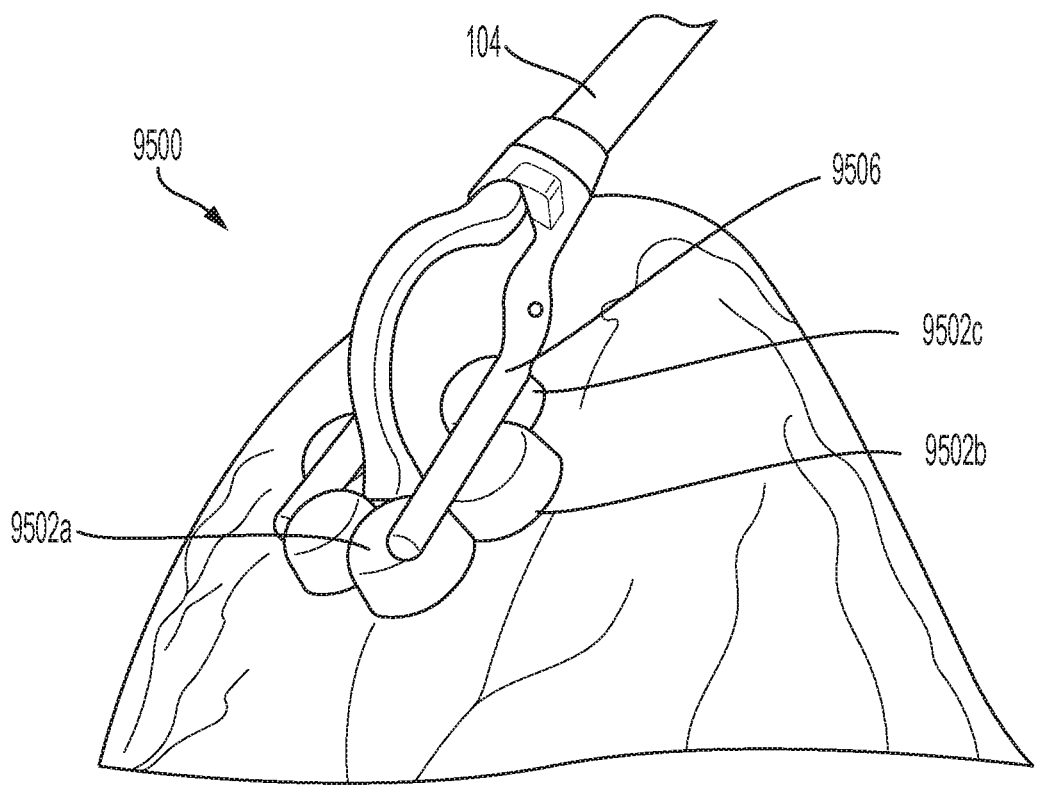

FIG. 99 illustrates a front view of the head 9500. FIG. 100 illustrates the head 9500 being suctioned to a portion of a patient's body. The head 9500 may be compliant to allow for flexibility upon placement on the portion of the patient's body, and to conform to irregularities. The head 9500 may be compliant such that a flexible skirt or the like is not needed in certain embodiments.

The head 9500 may be utilized according to methods disclosed herein in a similar manner as the head 102 shown in FIGS. 1A-1F. The apparatus 100 shown in FIGS. 1A-1F may be modified to allow for a vacuum port to provide the suction through the head 9500. The head 9500 may be utilized to access a portion of a patient's heart for deployment of a heart splint as disclosed herein, with a puncture device passing through the lumen 9510 for access to the interior of the patient's heart. The head 9500 may be utilized for other purposes, and may be utilized with other devices other than access apparatuses.

FIGS. 101-112 illustrate embodiments of apparatuses that provide a combination of functions, including serving to secure the apparatus to a portion of a patient's body, and providing access to a portion of a patient's body, and deploying a heart anchor to a patient's body. Securing the apparatus to a portion of a patient's body may include applying a suction force to the portion of the patient's body.

The apparatuses shown in FIGS. 101-112 may provide combined functionality of the access apparatus 100 shown in FIGS. 1A-1F and the deployment apparatus 700 shown in FIGS. 7A-7D, and may be used in similar manners as described herein for the access apparatus 100 and the deployment apparatus 700. The apparatuses shown in FIGS. 101-112 may comprise a modification of the deployment apparatus 700 shown in FIGS. 7A-7D, and may be utilized in lieu of, or in substitution of the head 702 of the deployment apparatus 700, with the remainder of the deployment apparatus 700 being utilized to serve the functions of the deployment apparatus 700 (e.g., tensioning of a tension member and deployment of a heart anchor, among other functions). In other embodiments, the apparatuses shown in FIGS. 101-112 may be utilized for other purposes.

Figure 101:
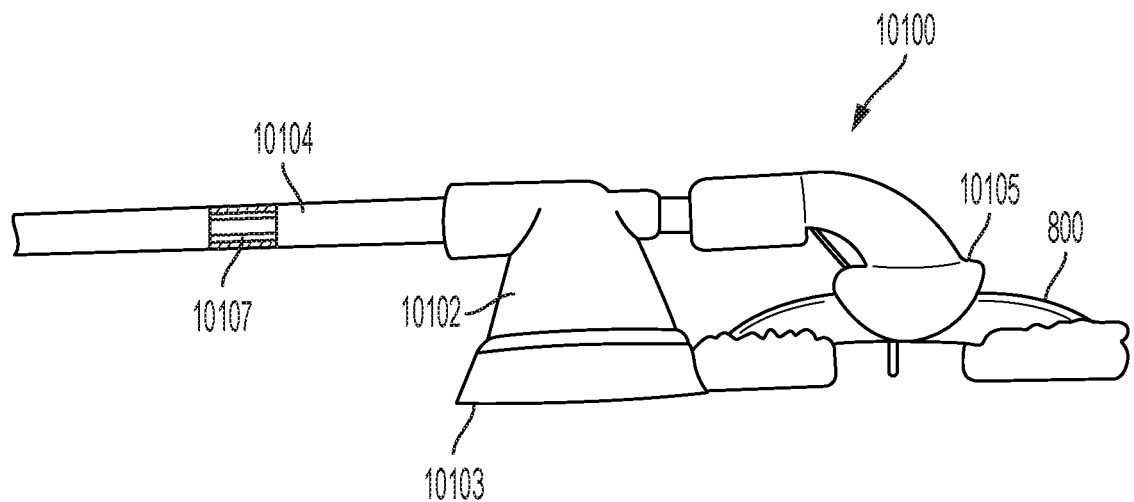

Each of the embodiments of FIGS. 101-112 illustrates an embodiment including a suction device that is configured to apply vacuum suction to an external surface of a patient's heart to grip the external surface of the patient's heart. FIG. 101 illustrates an embodiment in which an apparatus 10100 includes a suction device 10102 coupled to a shaft 10104 of the apparatus 10100 (which may comprise the neck 704 shown in FIGS. 7A-7D). The suction device 10102 may comprise a suction head that is configured to contact the external surface of the patient's heart to apply the vacuum suction to the external surface of the patient's heart. The suction head may be configured similarly as the head 102 shown in FIG. 1A, although the suction device 10102 may lack a lumen for passing a puncture device therethrough. The suction device 10102 may include a pliant skirt 10103 that may enhance the suction coupling between the device 10102 and the portion of the patient's body. The suction device 10102 may receive suction via a suction lumen 10107 contained within the shaft 10104.

A heart anchor retainer 10105 may be positioned at a distal portion of the shaft 10104 and distal of the suction device 10102. The heart anchor retainer 10105 may be coupled to the shaft 10104 at a position adjacent to the suction device 10102. The heart anchor retainer 10105 may couple to the heart anchor 800, which may be configured as shown in FIGS. 8A-8F. The heart anchor retainer 10105 may include a central lumen (similar to lumen 720 of FIGS. 7A-7D) that may allow a puncture device to pass therethrough, and may allow a tether such as tension member 286 to pass therethrough, as shown in FIG. 29 for example. The heart anchor retainer 10105 may be configured to be rotatable, and rotate the heart anchor 800, in a similar manner as disclosed regarding the retainer 712. The rotation of the heart anchor retainer 10105 may allow the orientation of the heart anchor 800 to be varied as desired. The heart anchor 800 may extend longitudinally in line with the longitudinal axis of the shaft 10104.

Figure 102:
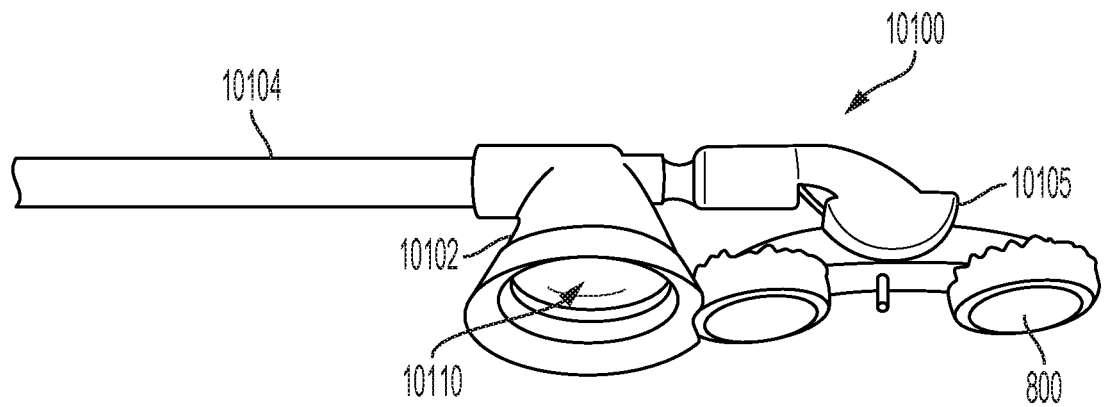

FIG. 102 illustrates a perspective view of the apparatus 10100, displaying the interior chamber 10110 of the suction device 10102.

Figure 103:
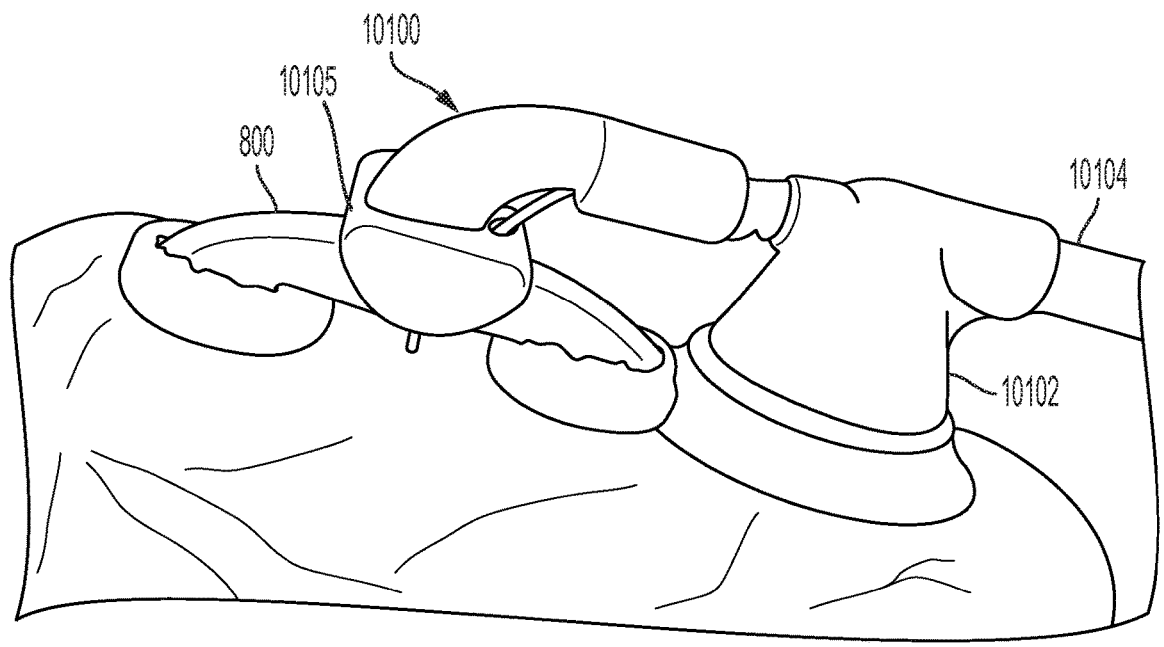

FIG. 103 illustrates the apparatus 10100 suctioned onto a portion of a patient's body, with the anchor 800 in position to be deployed.

FIG. 104 illustrates an embodiment in which an apparatus 10400 includes a suction device 10402 (marked in FIG. 105) positioned within a heart anchor 10404 for deployment to a surface of a patient's heart. The apparatus 10400 may include a shaft 10406 and a heart anchor retainer 10408 positioned at a distal portion of the shaft 10406. The heart anchor retainer 10408 may be configured similarly as the retainer 10105 shown in FIG. 101, and may include a central lumen for passing a puncture device therethrough and may be configured to rotate according to certain embodiments.

The heart anchor 10404 may be configured similarly as the heart anchor 800, but may include a suction device 10402 in the form of two suction heads or chambers 10409 that form the pads of the heart anchor 10404. The suction chambers 10409 may include pliant skirts 10411 extending around the suction chambers 10409. The suction chambers 10409 may be configured to apply a supporting force to a portion of the patient's body as well, and may provide the same functionality as the pads of the heart anchor 800. The heart anchor 10404 may include an interior suction lumen 10410 (marked in FIG. 105). The interior suction lumen 10410 may be configured to transmit a suction force through the suction chambers 10409, which may include a plurality of openings 10412 that provide support for the suction chambers 10409 but also allow a suction force to pass therethrough. The interior suction lumen 10410 may couple to a suction lumen 10414, shown in FIGS. 104 and 105 as a tube, that may allow suction force to be transmitted from a suction lumen of the shaft 10406 to the interior suction lumen 10410 of the heart anchor 10404.

The suction channel 10414 may be configured to removably couple from the heart anchor 10404, such that as the heart anchor 10404 is fixed in position via a tension member 286 or the like, the suction lumen 10414 may be removed to separate from the heart anchor 10404.

Figure 106:
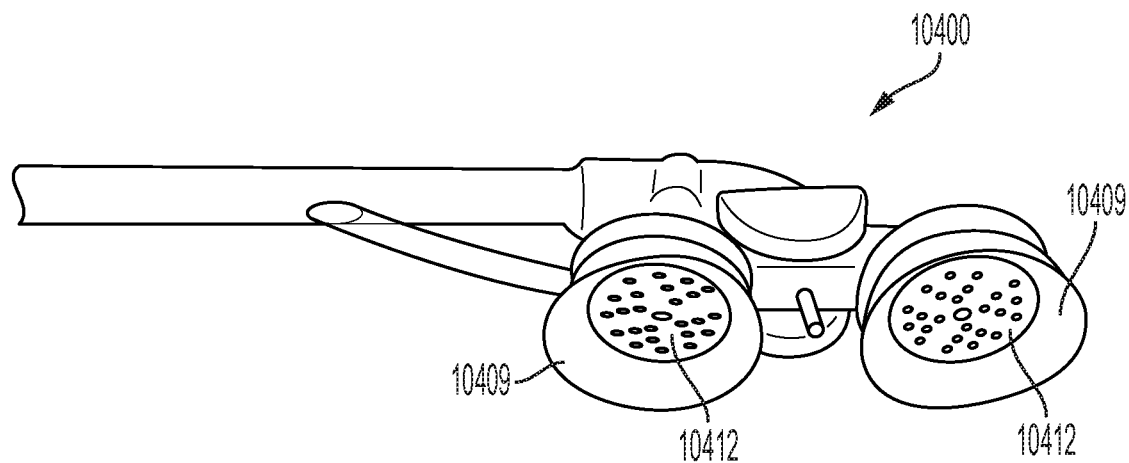

FIG. 106 illustrates a perspective view of the apparatus 10400, showing the plurality of openings 10412 of the suction chambers 10409.

FIG. 107 illustrates the apparatus 10400 suctioned onto a portion of a patient's body.

FIG. 108 illustrates an embodiment in which an apparatus 10800 includes a suction device 10802 comprising a suction head in the form of a hood positioned around a head 10805 of the apparatus including a heart anchor retainer 10804 and a heart anchor 800. The head 10805 of the apparatus may be configured similarly as the head 702 shown in FIGS. 7A-7D. The apparatus 10800 may include a shaft 10806 and the heart anchor retainer 10804 positioned at a distal portion of the shaft 10806. The heart anchor retainer 10804 may be configured similarly as the retainer 10105 shown in FIG. 101, and may include a central lumen for passing a puncture device therethrough and may be configured to rotate according to certain embodiments.

The suction device 10802 may cover the heart anchor retainer 10804 and a heart anchor 800, and may include an interior suction cavity 10808 (marked in FIG. 109) that allows the suction force to be transmitted along a suction lumen 10810 of the shaft 10806. The suction device 10802 may form the head of the apparatus 10800.

FIG. 110 illustrates a perspective view of the apparatus 10800 showing the heart anchor 800 positioned within the hood of the suction device 10802.

FIG. 111 illustrates the apparatus 10800 suctioned onto a portion of a patient's body.

FIG. 112 illustrates an embodiment in which an apparatus 11200 includes a suction device configured as the suction head 9500 shown in FIGS. 95-100. The apparatus 11200, however, includes a heart anchor retainer 11204 that retains the heart anchor 800 therein. Chambers 11202a-f of the suction device may operate similarly as the chambers 9502a-f of FIGS. 95-100, and may operate in a similar manner. The chambers 11202a-f may be positioned around the heart anchor 800, and the apparatus 11200 may include a central lumen similar to lumen 9510 of FIGS. 95-100 that allows a puncture device to pass therethrough and through the heart anchor 800. The number and configuration of the chambers 11202a-f may be varied from the number and configuration shown in FIG. 112.

The apparatuses disclosed in FIGS. 101-112 may operate in a manner in which the apparatuses are directed to an outer surface of a patient's heart, with the suction device then applying suction to secure the apparatuses to the outer surface. The suction device may serve a similar purpose as the head 102 shown in FIG. 1A, which provides a suction force to secure an apparatus to an outer surface of a patient's heart. The interior lumens of the apparatuses may allow a puncture device to pass therethrough, to allow for similar functionality as the head 102 shown in FIG. 1A.

The interior lumens may then pass one or more snares therethrough, to allow a tension member 286 to pass through the interior lumens for securing to the heart anchor coupled to the respective apparatuses, in a similar manner as the apparatus 700. Upon the tension member 286 being tensioned, the tension may be locked by the heart anchor coupled to the apparatuses, and the heart anchor may be deployed from the apparatus, in a similar manner as with the apparatus 700. The suction force provided by the apparatuses may be reduced to allow the apparatuses to separate from the heart anchors. As such, the apparatuses disclosed in FIGS. 101-112 may provide combined functionality of the access apparatus 100 shown in FIGS. 1A-1F and the deployment apparatus 700 shown in FIGS. 7A-7D, and may be used in similar manners as described herein for the access apparatus 100 and the deployment apparatus 700. The number of apparatuses inserted into the patient's body accordingly may be reduced in the procedures disclosed herein. In other embodiments, the apparatuses shown in FIGS. 101-112 may be utilized for other purposes.

FIG. 113 illustrates a distal portion of an embodiment of a delivery apparatus 11300 having a heart anchor retainer 11302 that rotates. The delivery apparatus 11300 may be utilized in a similar manner and for similar purposes as the delivery apparatus 700 shown in FIGS. 7A-7D. The delivery apparatus 11300, however, has a head 11304 that provides a lower height profile than the head of the delivery apparatus 700 shown in FIGS. 7A-7D. The apparatus shown in FIGS. 113-118 may comprise a modification of the deployment apparatus 700 shown in FIGS. 7A-7D, and may be utilized in lieu of, or in substitution of the head 702 of the deployment apparatus 700, with the remainder of the deployment apparatus 700 being utilized to serve the functions of the deployment apparatus 700 (e.g., tensioning of a tension member and deployment of a heart anchor, among other functions). The pulley assembly disclosed herein may be integrated with the deployment apparatus 700 shown in FIGS. 7A-7D, or may be utilized with a different apparatus as desired.

The delivery apparatus 11300 may include a pulley assembly configured to rotate a heart anchor retainer 11302 that is configured to retain a heart anchor and is positioned on the head 11304 of the delivery apparatus 11300. FIG. 114 illustrates a portion of a pulley assembly that may allow the head 11304 to have a lower height profile than the head of the delivery apparatus 700 shown in FIGS. 7A-7D. The pulley assembly may include a pulley wheel 11306 that may be positioned to rotate in a plane that the heart anchor retainer 11302 rotates in. FIG. 115 illustrates a close-up perspective view of the pulley wheel 11306 and the heart anchor retainer 11302. Referring to FIG. 115, the pulley wheel 11306 may include a channel 11307 (marked in FIG. 115) that one or more cables 11303a, b may extend along, to couple to a pin 11305 that may be held in a pin support 11312. The pin 11305 may couple to the distal portions or ends of the one or more cables 11303a, b, such that cables 11303a, b extend around both sides of the channel 11307 on both sides of the pulley wheel 11306. In one embodiment a single cable may be looped around the pulley wheel 11306 to form two cables extending from the pulley wheel 11306. In other embodiments two or more separate cables may be utilized with distal portions or ends coupled to the pin 11305.

The pulley wheel 11306 may be coupled to the heart anchor retainer 11302 (which may be configured similarly as the retainer 712 shown in FIGS. 7A-7D) and walls 11311, 11313 of the heart anchor retainer 11302 may extend from the pulley wheel 11306 perpendicular to the plane that the pulley wheel 11306 extends in. The pulley wheel 11306 may include a central lumen 11309 (similar to lumen 720 of FIGS. 7A-7D) that tension members, snares, puncture devices, or other devices disclosed in regard to the apparatus 700 may pass through, to pass through the anchor 800.

Referring back to FIG. 114, the pulley wheel 11306 may be positioned within the head 11304 of the apparatus 11300. The pulley wheel 11306 may be positioned within an interior chamber of the head, which may include a rotation gimbal 11315 that may allow the pulley wheel 11306 to rotate within the head.

FIG. 116 illustrates a side view of the apparatus 11300 illustrating the handle 11314 coupled to a proximal portion of an elongate shaft 11316 that the cables from the pulley wheel 11306 extend within. The apparatus 11300 may include a pulley control mechanism that may include a control knob 11318 coupled to the handle 11314 that couples to proximal portions of the cables and allows movement of the control knob 11318 to cause movement of the cables and thus rotate the pulley wheel 11306 and the heart anchor retainer 11302. Distal portions of the cables 11303a, b may couple to the pulley wheel 11306 and proximal portions of the cables 11303a, b may couple the pulley wheel 11306 to the pulley wheel control mechanism. The cables 11303a, b, may extend along the elongate shaft 11316 or elongate neck of the apparatus 11300.

FIG. 117 illustrates a close-up perspective view of the control knob 11318 and a pulley wheel 11320 that is coupled to the control knob 11318. The pulley wheel 11320 may be configured to rotate with the rotation of the control knob 11318. The pulley wheel 11320 may include a channel 11322 that the proximal portions of the cables 11303a, b extend in and extend along to couple to a pin (similar to pin 11305) that may be held in a pin support 11324. The pin may couple to the ends of one or more cables, such that the proximal portions of the cables extend around both sides of the channel 11322 on both sides of the pulley wheel 11320. With distal portions of the cables coupled to the pulley wheel 11306 in the head of the apparatus, and proximal portions of the cables coupled to the pulley wheel 11320 in the handle of the apparatus, the movement of the pulley wheel 11320 may cause movement of the other pulley wheel 11306 via the forces transmitted by the cables 11303a, b. The pulley assembly is configured to allow the retainer 11302 to rotate about an axis transverse to a longitudinal axis of the elongate shaft 11316 or elongate neck of the apparatus 11300, to accordingly rotate the heart anchor 800.

The pulley wheels 11306, 11320 may be configured to have the same diameters, such that a one-to-one ratio of rotation of one pulley wheel causes the same rotation of the other pulley wheel. Such a one-to-one ratio may provide for improved control of rotation of the heart anchor retainer 11302 by a user. In other embodiments, the pulley wheels 11306, 11320 may have different diameters to produce a desired scaling of control of rotation between the two pulley wheels 11306, 11320.

Detents may be utilized to maintain a position of the control knob 11318 yet allow for rotation of the control knob 11318. FIG. 118, for example, illustrates a portion of the handle 11314 shown in FIG. 117 with the control knob 11318 excluded from view. Detents 11326 may be positioned circumferentially around a supporting surface 11327, with the control knob 11318 engaging the detents 11326 via spring supported pins 11328 or other biased structures. As such, the biased structures may hold the control knob 11318 and the pulley wheel 11320 in position, until a user applies sufficient force to move the control knob 11318 relative to the detents 11326 to allow the control knob 11318 and pulley wheel 11320 to rotate.

The apparatus shown in FIGS. 113-118 may be utilized in methods disclosed herein, and may be utilized in a similar manner as the apparatus 700 disclosed in regard to FIGS. 7A-7D. The use of the pulley system may reduce the profile of the head of the apparatus 11300 from the head shown in FIGS. 7A-7D, and may allow for improved control of rotation of the heart anchor retainer of the apparatus 11300. The pulley system disclosed in FIGS. 113-118 may be utilized in any embodiment disclosed herein in which a head or heart anchor retainer or other portion of an apparatus is configured to rotate.

FIG. 119 illustrates an embodiment of a tension member 11900 that may be utilized in lieu of, or in substitution with, the tension members 286 disclosed in this application. The tension member 11900 may include a spring 11902. All or a portion of the tension member 11900 may comprise the spring 11902. The spring 11902 may be configured to produce a linear force upon movement of the spring, or, as shown in FIG. 119, may be configured to produce a non-linear force upon movement of the spring. The spring 11902 may be configured to produce variable, non-linear, tension as the spring 11902 is extended. A tension of the spring 11902 may be configured to increase non-linearly as the spring 11902 is extended.

Such variable, non-linear, tension may be utilized to accommodate for a variety of properties, including movement of the patient's heart. For example, during diastole, as the left ventricle fills with blood, the spring 11902 may be configured to extend with a lesser tension force produced, to allow the left ventricle to more easily fill with blood. At the end of diastole (peak distention) the spring 11902 may be configured to apply a greater tension force that aids the left ventricle to eject blood during systole. The transition of the lesser force to the greater force may be non-linear and may increase significantly at the end of diastole. The spring 11902 may be configured to compress in phase with systolic contraction, to possibly provide a more complete ejection of blood. The variable, non-linear, tension produced by the spring 11902 accordingly may accommodate a movement of the patient's heart, and may assist with desired movement of the patient's heart. A variety of configurations of tension strength of the spring 11902 may be provided according to various movements of the patient's heart or other properties.

A force profile of one or more of the anchors to which the spring 11902 is coupled to may be set by setting a non-linear tension force of the spring 11902, based on the desired force profile to by applied to the patient's heart by the anchors during one or more of diastole or systole. For example, the times at which certain forces are to be applied during diastole or systole may be determined and set in the spring 11902.

The spring 11902 may be tuned to match the desired profile of expansion and contraction of the patient's heart, and may be specific for the particular patient having the heart splint. The force applied by the spring 11902 may be set by varying a property of the spring 11902 according to the desired expansion and contraction profile. The property of the spring 11902 may comprise one or more of material properties of the spring or a shape of the spring. For example, the shape of the spring, such as the shape of loops of the spring, or another feature of loops of a spring may be set to produce the desired non-linear force. For example, as shown in FIG. 119, a spring 11902 may have a larger outer diameter at a central portion of the spring 11902, with smaller outer diameters at end portions of the spring 11902. The spring 11902 may taper in profile down from a central portion to end portions. Further, the shape of the spring may also be varied by varying the wire outer diameter at different locations of the spring, thinning the wire to reduce the spring constant and thickening the wire to increase the constant. In certain embodiments, the material properties of the spring 11902 may be set by altering a selection of materials comprising the spring. The spring 11902 may comprise a composite of different types of materials having different spring constants.

The spring 11902 may be utilized to match a profile of expansion and contraction, or in other embodiments may generally be utilized to dampen the loading of the heart anchors (e.g., anchor 202 and anchor 800) to which the spring 11902 is coupled.

In certain embodiments, the spring may have uniform characteristics along the length of the spring, and may be configured to have a linear force produced according to the movement of the spring. FIG. 120, for example, illustrates an embodiment of a tension member 12000 that includes a spring 12002 having a linear tension force as the spring 12002 is extended. Further, the spring 12002 may be covered by a sheath 12004 that may prevent the spring from interfering with portions of the patient's heart, which may comprise chordae or other structures.

Although the springs of FIGS. 119 and 120 are shown as coils, in other embodiments the springs may have any other shape or configuration as desired. The spring may be made of a shape memory material such as nitinol or another shape-memory material, or another material as desired, for example, spring steel or stainless steel. The spring may also include an elastomer, for example, a silicone, a polyurethane, or a thermoplastic elastomer.

The springs of FIGS. 119 and 120 may be deployed by being compressed in an unexpanded or undeployed configuration within a delivery apparatus, which may include a lumen as disclosed herein. For example, a delivery apparatus 400 as shown in FIG. 14 may be brought proximate the interventricular septum 1210. A spacer such as disclosed in regard to FIG. 14A may be utilized if desired. The springs of FIGS. 119 and 120 may be positioned within the delivery apparatus 400. The heart anchor 202 may be deployed proximate the interventricular septum 1210 and the springs of FIGS. 119 and 120 may be deployed through the interventricular septum 1210 into the left ventricle 1200, and expanded within the left ventricle 1200.

In one embodiment, the springs of FIGS. 119 and 120 may be positioned such that at least a portion of the spring is disposed within the anchor 800. Such a position may allow the springs to provide their desired force profiles, yet also not necessarily need to be deployed into the left ventricle 1200 (whether deployed partially or wholly into the left ventricle 1200). The tension member may provide a linear or non-linear force with the spring positioned exterior of the left ventricle 1200.

The springs may be utilized in any embodiment of tension member disclosed herein.

FIG. 121 illustrates an embodiment of a heart anchor 12101 that may be configured similarly as the heart anchor 202 shown in FIGS. 2A-2H. The heart anchor 12101, however, may include a cover 12100 composed of a knitted material that may allow a puncture device 12102 to pass therethrough, between the openings of the knitted material. The cover 12100 may thus be puncturable by a puncture device. Such a feature may allow a puncture device 12102 to be able to penetrate through the cover 12100 if passage through the cover 12100 is desired. For example, if the heart anchor 12101 occludes an area of the patient's heart such as foramen ovale, or another area that may require additional penetration at a later time for medical purposes, then the cover 12100 may be configured to be penetrated by such a puncture device 12102 to allow passage through the cover (and the area of the patient's heart to which the heart anchor 12101 is deployed). A knitted material may include a cloth or a knitted polymer, and may include knitted polytetrafluoroethylene (PTFE) or another polymer as desired. The cover 12100 may be made of polyethylene terephthalate (PET) if desired. The cover may be tearable to allow for other access through the cover.

FIG. 122 illustrates a cross sectional view of an embodiment of layers of a heart anchor, which may be configured similarly as the heart anchor 202 shown in FIGS. 2A-2H, but may include an additional mesh layer 12204 coupled to membrane layers 12200, 12202 that form the cover of the heart anchor. The cover may be formed of a membrane that may be puncturable by a puncture device 12102, and may be made of a cloth or a polymer. The mesh layer 12204 may support the membrane layers 12200, 12202 and may include openings that allow a puncture device to pass therethrough. As such, the configuration of layers shown in FIG. 122 serves a similar purpose as the configuration of the heart anchor shown in FIG. 121, to allow a puncture device to pass therethrough. The configuration of layers may be tearable to allow for other access through the heart anchor.

The features shown in FIGS. 121 and 122 may be utilized with any embodiment of heart anchor disclosed herein.

The embodiments of methods disclosed herein may be performed manually by a user, yet in other embodiments a robot, such as a surgical robot may be utilized to perform such methods. FIGS. 123 and 124 illustrate a variation of the heart anchor 800, in which the heart anchor 800' includes a flange 12300 that is configured for grasping by a grasper of a surgical robot. Such a flange 12300 may be positioned on and extend outward from a dorsal surface of the heart anchor 800' or another surface as desired. The robotic graspers may be able to more easily manipulate and place the heart anchor 800' in position.

FIG. 125, for example, illustrates a representation of a grasper 12500 of a surgical robot that may be configured to grasp the grasping flange 12300 shown in FIGS. 123 and 124. The grasper may include arms 12501, 12503 having grip surfaces 12505, 12507 that allow the arms 12501, 12503 to better grasp apparatuses of the systems disclosed herein, including the grasping flange 12300. The arms 12501, 12503 may be configured to articulate to move towards and away from each other to facilitate grasping. The grasper 12500 may be coupled to a robotic arm 12502 via one or more pivots 12504, which may allow the grasper 12500 to move in various directions. The pivots 12504 may allow for rotation or other movement in the x- and y-dimensions and about the z-dimension relative to the robotic arm 12502. Other combinations of directions of articulation, or other directions of articulation may be produced as desired. In other embodiments, the configuration of the grasper 12500 may vary from the configuration shown in FIG. 125.

In operation, a robot, such as a surgical robot, such as Totally Endoscopic Coronary Artery Bypass (TECAB) surgical robot may access desired portions of the patient's heart with visualization provided by the robot. FIG. 126 for example, illustrates a representation of a robotic arm 12502 having a robotic grasper at a distal portion of the arm 12502. The grasper may be configured similarly as the grasper 12500 shown in FIG. 125. The robotic arm 12502 may be configured to have a greater variety of access points to the patient's heart, including access points closer to the desired location of the heart anchor 800'. The robotic arm 12502 may be utilized to perform the methods disclosed herein that would be manually performed by a user. The robotic arm 12502 may be configured to grasp the heart anchor 800' and hold it against the free wall of the left ventricle, for example, prior to entry of the patient's heart to simulate the therapeutic contraction of the left ventricle. A position for the anchor 800' may be determined based on the monitored therapeutic result provided by the anchor 800'. The robotic arm 12502 may be utilized to perform the other methods disclosed herein of applying a heart splint to a patient's heart, including entry of the left ventricle for implantation of the anchor 800'. Any method or portion of a method disclosed herein may be performed by a robot, such as a surgical robot, such as Totally Endoscopic Coronary Artery Bypass (TECAB) surgical robot.

The methods, apparatuses, and systems disclosed herein may be utilized with one or more heart implants, which may be utilized for heart valve replacement or repair. Heart valve replacement may include use of a heart valve prosthetic, such as a prosthetic mitral valve or a prosthetic tricuspid valve, among other prosthetics. Heart valve repair may be utilized to provide therapeutic effects for the heart valve, without entirely replacing the heart valve. Heart valve repair may include use of annuloplasty devices or other repair devices.

FIG. 127, for example, illustrates a heart valve prosthetic in the form of a prosthetic mitral valve 12700 that may be utilized with the methods, apparatuses, and systems disclosed herein. The prosthetic mitral valve 12700 may comprise an expandable prosthetic valve that is deployed within the patient's heart and positioned in place of the mitral valve. The prosthetic mitral valve 12700 may include one or more anchors 12702 that couple to leaflets of the mitral valve, to secure the prosthetic mitral valve 12700 in position within the mitral valve annulus.

FIG. 128 illustrates that the prosthetic mitral valve 12700 may be utilized in combination with a heart splint as disclosed herein. The heart splint may include the heart anchor 202, the heart anchor 800, and the tension member 286, as disclosed herein, for example in FIG. 31. The heart anchor 202 may be configured as the heart anchor 202 shown in FIGS. 2A-2H, and may include a ring 200 having two ends (204, 206) and configured to move from a linearized configuration to a ring-shaped configuration. A cover 212 is coupled to the ring 200 and extends inward from the ring 200 in the ring-shaped configuration. The ring 200 includes a first portion and a second portion 214, 216, and the first portion overlaps the second portion in the ring-shaped configuration. The heart anchor 800 may include support pads 802, 804 and a bridge 806 coupling the support pads 802, 804 together.

The heart anchors 202, 800 may both be configured to be positioned on a ventricular wall of the patient's heart (with the heart anchor 202 positioned on the interventricular septum 1210 and the heart anchor 800 positioned on the free wall of the left ventricle 1200). The tension member 286 may extend transventricular to couple the heart anchor 202 to the heart anchor 800 and may have a tension that is set to provide a therapeutic effect for the left ventricle 1200, as disclosed herein. The prosthetic mitral valve 12700, however, may include a tension member 12800. The tension member 12800 may couple to the frame of the prosthetic mitral valve 12700 (for example, three points of connection are shown, although in other embodiments a greater or lesser number of connection points may be utilized). The tension member 12800 may also couple to the tension member 286, to couple and anchor the prosthetic mitral valve 12700 to each of the heart anchors 202, 800. The tension member 12800 for example, may include a coupler 12802 at its end, such as a loop or a hook or other form of coupler for coupling the tension member 12800 to the tension member 286.

Coupling the prosthetic mitral valve 12700 to the heart splint including the heart anchor 202, the heart anchor 800, and the tension member 286, may beneficially allow for enhanced anchoring of the prosthetic mitral valve 12700 within the mitral valve annulus. The force upon the prosthetic mitral valve 12700 in the atrial direction during systole is particularly high, and as such additional anchoring of the prosthetic mitral valve 12700 to a location within the left ventricle 1200 that opposes the atrial direction of force during systole may be beneficial. The heart anchor 202, the heart anchor 800, and the tension member 286 may provide therapeutic effects for the patient's heart disclosed herein, and may also serve as an anchoring point for the prosthetic mitral valve 12700 within the left ventricle 1200.

A variety of methods may be utilized to anchor the prosthetic mitral valve 12700 to the heart splint and accordingly to the heart anchor 202 and the heart anchor 800. In an embodiment in which the prosthetic mitral valve 12700 is first deployed to the heart valve of the patient's heart, the tension member 12800 may be left as a tether positioned within the left ventricle 1200 or elsewhere within the patient's heart. The heart splint may then be deployed according to methods disclosed herein, which may additionally include snaring the tension member 12800 and passing the tension member 286 of the heart splint through the coupler 12802 of the tension member 12800. The heart anchors 202 and 800 may otherwise be deployed and tensioned according to the methods disclosed herein.

In an embodiment in which the heart splint is first deployed to the left ventricle 1200, the prosthetic mitral valve 12700 may be deployed to the mitral valve annulus with the tension member 12800 hooking or otherwise being coupled to the tension member 286 that extends transventricular. The tension member 12800 may be tensioned utilizing the deployment apparatus that deployed the prosthetic mitral valve 12700, or with another apparatus.

FIG. 129 illustrates an embodiment in which a single heart anchor 202 may be utilized as an anchor for the prosthetic mitral valve 12700. The heart anchor 202 may be positioned on a ventricular wall of the patient's heart, particularly the interventricular septum 1210. The tension member 12900 may couple to the heart anchor 202 to allow the heart anchor 202 to anchor the prosthetic mitral valve 12700 to the ventricular wall. As such, the heart anchor 202 serves as an anchoring point for the prosthetic mitral valve 12700 within the left ventricle 1200, to oppose the atrial direction of force upon the prosthetic mitral valve 12700 during systole.

A variety of methods may be utilized to anchor the prosthetic mitral valve 12700 to the heart anchor 202 positioned upon the ventricular wall of the patient's heart. In one embodiment, the deployment apparatus that deploys the prosthetic mitral valve 12700 within the mitral valve annulus may first be extended through the mitral valve annulus in a ventricular direction to puncture the interventricular septum 1210. The heart anchor 202 may be deployed in a similar manner as shown in FIGS. 34 and 35, by being passed out of an opening in the deployment apparatus on the right ventricle side of the interventricular septum 1210. The deployment apparatus may then be retracted from the puncture in the interventricular septum 1210, with the tension member 12900 trailing into the left ventricle 1200. The deployment apparatus may then deploy the prosthetic mitral valve 12700 to the mitral valve, with the tension member 12900 coupled to the heart anchor 202 positioned on the interventricular septum 1210 and coupled to the prosthetic mitral valve 12700. The deployment apparatus may then tension the tension member 12900 if desired to securely anchor the prosthetic mitral valve 12700 to the heart anchor 202.

In one embodiment, the heart anchor 202 may be deployed to the interventricular septum 1210 in a similar manner as shown in FIGS. 9-25. The tension member 286 provided in FIGS. 9-25 may comprise the tension member 12900 shown in FIG. 129. The tension member 12900 may be positioned within the left ventricle 1200 after deployment of the heart anchor 202, and may be snared by a deployment apparatus that deploys the prosthetic mitral valve 12700 to the mitral valve. The deployment apparatus may couple the tension member 12900 to the prosthetic mitral valve 12700, thus anchoring the prosthetic mitral valve 12700 to the heart anchor 202. The deployment apparatus may then tension the tension member 12900 if desired to securely anchor the prosthetic mitral valve 12700 to the heart anchor 202.

In one embodiment, the prosthetic mitral valve 12700 may be first deployed to the mitral valve, with the tension member 12900 left as a tether positioned within the left ventricle 1200 or elsewhere within the patient's heart. A snare such as snare 600' shown in FIG. 15 may be passed through the interventricular septum 1210 from the right ventricle 1204 and into the left ventricle 1200 as described herein. A spacer as described in regard to FIG. 14A may be utilized if desired. The snare 600' may snare the tension member 12900, which may be drawn back through the puncture of the interventricular septum 1210. The heart anchor 202 may be coupled to the tension member 12900, and may be deployed to the interventricular septum 1210 as shown in FIG. 129. The tension member 12900 may be tensioned by pulling the tension member 12900 through the interventricular septum 1210 further, to securely anchor the prosthetic mitral valve 12700 to the heart anchor 202. The tensioning may also occur at the prosthetic mitral valve 12700 if desired via a deployment apparatus for the prosthetic mitral valve 12700 or another device. In one embodiment, the heart anchor 202 may include a lock that may extend from the anchor 202 to prevent the tension member 12900 from slipping after being set. The lock may comprise a clip, autoknotter device, or another form of lock (for example, as described in U.S. Pat. No. 9,498,202 or 7,628,797, the entire disclosures of which are incorporated by reference). The remaining portion of the tension member 12900 may then be cut. In one embodiment, the heart anchor 202 may be deployed in a similar manner but may comprise a pad, similar to the heart anchor 5100 shown in FIG. 93, and configured to be positioned on a surface of the ventricular wall of the patient's heart. The heart anchor 5100 may include a lock 5102 for locking the tension member 12900 to the heart anchor 5100. The tension member 12900 may be tensioned, and the lock 5102 may be set to securely anchor the prosthetic mitral valve 12700 to the heart anchor 5100 positioned on the interventricular septum 1210.

In one embodiment, the heart anchor 202 and/or prosthetic mitral valve 12700 may be deployed in a similar manner as shown in FIGS. 83-85. For example, aortic entry of the left ventricle 1200 may occur, with a deployment apparatus puncturing the interventricular septum 1210 from the left ventricle 1200, and deploying the heart anchor 202 to the interventricular septum 1210 within the right ventricle 1204 in the location shown in FIG. 129. The deployment apparatus may also deploy the prosthetic mitral valve 12700 to the mitral valve, or may snare the tension member 12900 that may extend from a prosthetic mitral valve 12700 that is already deployed to the mitral valve. The deployment apparatus may couple the tension member extending from the heart anchor 202 to the tension member 12900 of the prosthetic mitral valve 12700, or such tension members may already be coupled to each other as shown, for example, with the tension member shown in FIGS. 84-85. The deployment apparatus may tension the tension member to securely anchor the prosthetic mitral valve 12700 to the heart anchor 202 positioned on the interventricular septum 1210 in the location shown in FIG. 129, and may set a lock 6200 (similar to the lock shown in FIG. 85) on the tension member to lock the tension between the prosthetic mitral valve 12700 and the heart anchor 202.

FIG. 130 illustrates an embodiment in which a single heart anchor 202 may be utilized as an anchor for the prosthetic mitral valve 12700, and may be positioned on the ventricular wall comprising the free wall of the left ventricle. As such, the heart anchor 202 serves as an anchoring point for the prosthetic mitral valve 12700 within the left ventricle 1200, to oppose the atrial direction of force upon the prosthetic mitral valve 12700 during systole. The heart anchor 202 may also provide a compressive force to the left ventricle 1200 to provide a therapeutic compression to the left ventricle 1200 as disclosed herein.

The methods that may be utilized to anchor the prosthetic mitral valve 12700 to the heart anchor 202 positioned upon the free wall of the left ventricle are similar to the methods disclosed in regard to FIG. 129. For example, the deployment apparatus that deploys the prosthetic mitral valve 12700 within the mitral valve annulus may first be extended through the mitral valve annulus in a ventricular direction to puncture the free wall of the left ventricle 1200. The heart anchor 202 may be deployed in a similar manner as shown in FIGS. 34 and 35, by being passed out of an opening in the deployment apparatus exterior of the left ventricle 1200. The deployment apparatus may then be retracted from the puncture in the free wall, with the tension member 12900 trailing into the left ventricle 1200. The deployment apparatus may then deploy the prosthetic mitral valve 12700 to the mitral valve, with the tension member 12900 coupled to the heart anchor 202 positioned on the free wall of the left ventricle 1200 and coupled to the prosthetic mitral valve 12700. The deployment apparatus may then tension the tension member 12900 if desired to securely anchor the prosthetic mitral valve 12700 to the heart anchor 202.

In one embodiment, the prosthetic mitral valve 12700 may be first deployed to the mitral valve, with the tension member 12900 left as a tether positioned within the left ventricle 1200 or elsewhere within the patient's heart. A snare such as snare 600 shown in FIG. 15 may be passed through a puncture in the free wall of the left ventricle 1200 (the location of puncture shown in FIG. 130) and into the left ventricle 1200 as described herein. The snare 600 may snare the tension member 12900, which may be drawn back through the puncture of the free wall of the left ventricle 1200. The heart anchor 202 may be coupled to the tension member 12900, and may be deployed to the free wall of the left ventricle 1200 as shown in FIG. 130. The tension member 12900 may be tensioned by pulling the tension member 12900 through the free wall further, to securely anchor the prosthetic mitral valve 12700 to the heart anchor 202. The tensioning may also occur at the prosthetic mitral valve 12700 if desired via a deployment apparatus for the prosthetic mitral valve 12700 or another device. In one embodiment, the heart anchor 202 may include a lock that may extend from the anchor 202 to prevent the tension member 12900 from slipping after being set. The lock may comprise a clip, autoknotter device, or another form of lock (for example, as described in U.S. Pat. No. 9,498,202 or 7,628,797, the entire disclosures of which are incorporated by reference). The remaining portion of the tension member 12900 may then be cut. In one embodiment, the heart anchor 202 may be deployed in a similar manner but may comprise a pad, similar to the heart anchor 5100 shown in FIG. 93, and configured to be positioned on a surface of the ventricular wall of the patient's heart. The heart anchor 5100 may include a lock 5102 for locking the tension member 12900 to the heart anchor 5100. The tension member 12900 may be tensioned, and the lock 5102 may be set to securely anchor the prosthetic mitral valve 12700 to the heart anchor 5100 positioned on the free wall of the left ventricle 1200.

In one embodiment, the heart anchor 202 and/or prosthetic mitral valve 12700 may be deployed in a similar manner as shown in FIGS. 83-85, and as described in regard to FIG. 129. For example, aortic entry of the left ventricle 1200 may occur. The deployment apparatus may tension the tension member to securely anchor the prosthetic mitral valve 12700 to the heart anchor 202 positioned on the free wall of the left ventricle 1200 in the location shown in FIG. 130, and may set a lock 6200 (similar to the lock shown in FIG. 85) on the tension member to lock the tension between the prosthetic mitral valve 12700 and the heart anchor 202.

FIG. 131 illustrates an embodiment in which multiple heart anchors 202, 202' are utilized as anchors for the prosthetic mitral valve 12700. The heart anchor 202 may be positioned on a ventricular wall comprising the interventricular septum 1210 and the heart anchor 202' may be positioned on a ventricular wall comprising the free wall of the left ventricle 1200. As such, the heart anchor 202 serves as an anchoring point for the prosthetic mitral valve 12700 within the left ventricle 1200, and the heart anchor 202' serves as an anchoring point with the tension member 12900' extending therefrom to the prosthetic mitral valve 12700, to oppose the atrial direction of force upon the prosthetic mitral valve 12700 during systole. The heart anchors 202, 202' may also provide a compressive force to the left ventricle 1200 to provide a therapeutic compression to the left ventricle 1200 as disclosed herein. In one embodiment, a transventricular tension member may couple the heart anchors 202, 202' together to enhance a compressive force applied by the heart anchors 202, 202' to the left ventricle 1200.

The heart anchor 202 may be deployed in a manner disclosed in regard to FIG. 129. The heart anchor 202' may be deployed in a manner disclosed in regard to FIG. 130.

Although the methods, systems, and apparatuses of FIGS. 127-131 are disclosed in regard to use of a prosthetic mitral valve 12700, other forms of heart implants may be utilized, including any heart implants for heart valve replacement or repair. For example, the methods, systems, and apparatuses of FIGS. 127-131 may include use of a heart valve repair implant, such as an annuloplasty device (e.g., an annuloplasty ring) that anchors to the heart anchors disclosed herein. A heart valve repair implant may have the form of the annuloplasty device shown in U.S. Pat. No. 4,917,698, the entire disclosure of which is incorporated by reference. Other forms of heart valve prosthetics or heart valve repair implants (or combinations of heart valve prosthetics or heart valve repair implants) may be utilized. One or more of a heart valve prosthetic or heart valve repair implant may be utilized.

In one embodiment, a prosthetic tricuspid valve, or a tricuspid heart valve repair implant, such as an such as an annuloplasty device (e.g., an annuloplasty ring), may be utilized. One or more heart anchors 202, 202' may be configured to be positioned on a ventricular wall of the patient's heart, which may comprise a free wall of the right ventricle or the interventricular septum, to anchor the prosthetic tricuspid valve, or the tricuspid heart valve repair implant, in a similar manner as disclosed in regard to FIGS. 127-131. The one or more heart anchors 202, 202' may serve as an anchoring point for the prosthetic tricuspid valve within the right ventricle 1204, to oppose the atrial direction of force upon the prosthetic tricuspid valve during systole.

The heart valve prosthetics and heart valve repair implants may be for other valves of the heart (e.g., aortic valve) in other embodiments. In other embodiments, one or more of a heart valve prosthetic or a heart valve repair implant may be utilized without coupling to a heart anchor. For example, a heart splint as shown in FIG. 128 may be utilized without coupling to the prosthetic mitral valve 12700. The heart splint and prosthetic mitral valve 12700 may both produce therapeutic effects without coupling to each other. Any combination of heart splints, heart valve prosthetics, heart valve repair implants, or other devices, systems, or apparatuses disclosed herein may be utilized as desired.

The "user" as discussed herein may comprise a user of the systems and apparatuses disclosed herein, which may include a surgeon, or another individual such as a medical professional who may operate the systems and apparatuses disclosed herein, without limitation.

The present disclosure offers numerous advantages over existing treatments for various heart conditions, including valve incompetencies. The devices disclosed herein do not require the highly invasive procedures of current surgical techniques. For instance, the treatments described herein do not require removing portions of heart tissue, nor do they necessarily require opening the heart chamber or stopping the heart during operation. The methods of the present disclosure may comprise beating-heart repair of or treatment of the patient's heart. For these reasons, the treatments and techniques for implanting the devices of the present disclosure convey a reduced risk to the patient as compared with other techniques. The less invasive nature of the treatments and techniques and tools of the present disclosure may further allow for earlier intervention in patients with heart failure and/or valve incompetencies. While often discussed herein in terms of mitral valve treatments, the systems, devices, methods, etc. may be used to treat other heart valves, heart conditions, enlargement of other organs, etc.

Although the present disclosure is discussed in connection with treating the mitral valve and tricuspid valve of the heart, the present disclosure may be applied to various chambers of the heart and for other valves of the heart for similar purposes. More broadly, the systems, apparatuses, methods, etc. disclosed herein may be used in other applications to change the geometries and/or stresses of other parts of the body (e.g., a stomach, bladder, or other part of the body). It also is contemplated that the present disclosure may be used to support an infarcted heart wall so as to prevent further dilatation, or to treat aneurysms in the heart. It is further contemplated that the present disclosure may be placed relative to the heart without altering the shape of the chamber, and only altering the shape of the valve itself.

The apparatuses and other devices disclosed herein may be practiced separately as desired. In addition, the methods herein are not limited to the methods specifically described, and may include methods of utilizing the systems, apparatuses, and devices disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A heart anchor comprising:
  a ring having two ends and configured to move from a linearized configuration to a ring-shaped configuration, the ring in the ring-shaped configuration having a thickness in an axial dimension and having a width in a radial dimension and having a length, the ring having a top surface and a bottom surface facing opposite the top surface in the axial dimension, the top surface and the bottom surface extending along an entirety of the length of the ring, and a first portion of the ring overlapping a second portion of the ring in the axial dimension in the ring-shaped configuration to form an overlapping portion at which the top surface faces towards the bottom surface, and the ring including a non-overlapping portion at which portions of the ring do not overlap, the thickness of the ring at the overlapping portion being at least double the thickness of the ring at the non-overlapping portion, and wherein the bottom surface and the top surface are each planar along the entirety of the length of the ring and each surface is placed respectively and entirely within its own plane in the linearized configuration and in the ring-shaped configuration; and
  a cover coupled to the ring and extending inward from the ring in the ring-shaped configuration.

2. The heart anchor of claim 1, wherein the two ends of the ring include a first end and a second end, and the first portion of the ring includes the first end of the ring.

3. The heart anchor of claim 1, wherein the first portion of the ring does not overlap the second portion of the ring in the linearized configuration.

4. The heart anchor of claim 1, wherein the ring is configured to automatically move from the linearized configuration to the ring-shaped configuration.

5. The heart anchor of claim 4, wherein the ring is made of a shape-memory material.

6. The heart anchor of claim 1, wherein the cover includes at least one cut-out portion.

7. The heart anchor of claim 1, wherein the cover includes a central portion and a peripheral portion when the ring is in the ring-shaped configuration.

8. The heart anchor of claim 7, wherein the cover includes overlapping material extending from the peripheral portion to the central portion.

9. The heart anchor of claim 8, wherein the overlapping material includes a first layer and a second layer, the first layer including a pattern of cut-outs and the second layer including a pattern of cut-outs having a different shape than the pattern of cut-outs of the first layer.

10. The heart anchor of claim 7, wherein the central portion includes a coupler for coupling to a tension member and the peripheral portion includes a coupler for coupling to the ring.

11. The heart anchor of claim 1, wherein the cover is configured to be puncturable by a puncture device.

12. The heart anchor of claim 11, wherein the cover includes a knitted material having openings for the puncture device to pass through.

13. The heart anchor of claim 1, further comprising a mesh layer coupled to the cover.

14. The heart anchor of claim 1, wherein the two ends of the ring include a first end and a second end, and the first portion of the ring is configured to overlap the second portion of the ring such that the first end is offset along the length of the ring from the second end.

15. The heart anchor of claim 1, wherein the first portion of the ring is configured to overlap the second portion of the ring to at least 10 degrees of the ring.

16. The heart anchor of claim 1, wherein the first portion of the ring is configured to overlap the second portion of the ring to at least 20 degrees of the ring.

17. The heart anchor of claim 1, wherein the first portion of the ring overlapping the second portion of the ring comprises a single overlap.

18. The heart anchor of claim 1, wherein edges of the first portion and the second portion are aligned with each other in the radial dimension at the overlapping portion.

19. The heart anchor of claim 1, wherein a thickness of the ring between the top surface and the bottom surface in the axial dimension is uniform along the entirety of the length of the ring in the linearized configuration and in the ring-shaped configuration.

20. The heart anchor of claim 2, wherein the ring is unitary from the first end to the second end.

* * * * *